(12) United States Patent
Wang et al.

(10) Patent No.: US 11,504,450 B2
(45) Date of Patent: Nov. 22, 2022

(54) DRUG-COATED BALLOON CATHETERS FOR BODY LUMENS

(71) Applicant: Urotronic, Inc., Plymouth, MN (US)

(72) Inventors: Lixiao Wang, Henderson, NV (US);
Peter Barnett, Shakopee, MN (US);
David Hendrickson, Coon Rapids, MN (US)

(73) Assignee: Urotronic, Inc., Plymouth, MN (US)

( * ) Notice: Subject to any disclaimer, the term of this patent is extended or adjusted under 35 U.S.C. 154(b) by 152 days.

(21) Appl. No.: 17/133,088

(22) Filed: Dec. 23, 2020

(65) Prior Publication Data

US 2021/0113742 A1   Apr. 22, 2021

Related U.S. Application Data

(60) Continuation-in-part of application No. 16/986,683, filed on Aug. 6, 2020, now Pat. No. 10,987,451, and
(Continued)

(51) Int. Cl.
*A61L 29/08* (2006.01)
*A61M 25/10* (2013.01)
(Continued)

(52) U.S. Cl.
CPC ............. *A61L 29/08* (2013.01); *A61L 29/06* (2013.01); *A61L 29/085* (2013.01); *A61L 29/16* (2013.01);
(Continued)

(58) Field of Classification Search
None
See application file for complete search history.

(56) References Cited

U.S. PATENT DOCUMENTS 5,171,299 A   12/1992   Heitzmann et al.
5,263,931 A   11/1993   Miller
(Continued)

FOREIGN PATENT DOCUMENTS

CN   101610798   12/2009
CN   104936629   9/2015
(Continued)

OTHER PUBLICATIONS

Declaration from U.S. Appl. No. 16/519,677, filed Jul. 23, 2019. (Year: 2019).*
(Continued)

*Primary Examiner* — Dominic Lazaro
(74) *Attorney, Agent, or Firm* — Schwegman Lundberg & Woessner, P.A.

(57) ABSTRACT

Various embodiments disclosed relate to drug-coated balloon catheters for treating, preventing, or reducing the recurrence of a stricture and/or cancer, or for treating benign prostatic hyperplasia (BPH), in a non-vascular body lumen and methods of using the same. A drug-coated balloon catheter for delivering a therapeutic agent to a target site of a body lumen stricture includes an elongated balloon having a main diameter. The balloon catheter includes a coating layer overlying an exterior surface of the balloon. The coating layer includes one or more water-soluble additives and an initial drug load of a therapeutic agent. In some embodiments, the balloon catheter includes a length-control mechanism which stretches and elongates the balloon when it is in a deflated state, giving the balloon a smaller cross-sectional deflated profile for tracking through the body lumen and for removal after treatment.

26 Claims, 6 Drawing Sheets

Related U.S. Application Data a continuation-in-part of application No. PCT/US2020/019274, filed on Feb. 21, 2020, said application No. 16/896,683 is a division of application No. 16/135,436, filed on Sep. 19, 2018, now Pat. No. 10,806,830, which is a continuation-in-part of application No. PCT/US2018/031083, filed on May 4, 2018, and a continuation-in-part of application No. 15/568,614, filed as application No. PCT/US2016/028652 on Apr. 21, 2016, now Pat. No. 10,888,640, said application No. 16/135,436 is a continuation-in-part of application No. 14/438,327, filed as application No. PCT/US2013/064842 on Oct. 14, 2013, now Pat. No. 10,668,188.

(60) Provisional application No. 62/859,396, filed on Jun. 10, 2019, provisional application No. 62/809,048, filed on Feb. 22, 2019, provisional application No. 62/502,212, filed on May 5, 2017, provisional application No. 62/152,559, filed on Apr. 24, 2015, provisional application No. 61/795,790, filed on Oct. 26, 2012.

(51) Int. Cl.
*A61L 29/16* (2006.01)
*A61L 29/06* (2006.01)
*A61M 29/02* (2006.01)
*A61B 1/307* (2006.01)

(52) U.S. Cl.
CPC .. *A61M 25/1002* (2013.01); *A61M 25/10185* (2013.11); *A61M 29/02* (2013.01); *A61B 1/307* (2013.01); *A61L 2300/416* (2013.01); *A61L 2300/426* (2013.01); *A61M 2025/105* (2013.01); *A61M 2025/1075* (2013.01); *A61M 2202/0488* (2013.01); *A61M 2205/0205* (2013.01); *A61M 2210/0681* (2013.01); *A61M 2210/105* (2013.01); *A61M 2210/106* (2013.01); *A61M 2210/1032* (2013.01); *A61M 2210/1039* (2013.01); *A61M 2210/1053* (2013.01); *A61M 2210/1057* (2013.01); *A61M 2210/1064* (2013.01); *A61M 2210/1078* (2013.01); *A61M 2210/1085* (2013.01); *A61M 2210/1096* (2013.01); *A61M 2210/166* (2013.01)

(56) References Cited

U.S. PATENT DOCUMENTS

| | | |
|---|---|---|
| 5,312,430 A | 5/1994 | Rosenbluth et al. |
| 5,314,443 A | 5/1994 | Rudnick |
| 5,419,763 A | 5/1995 | Hildebrand |
| 5,423,755 A | 6/1995 | Kesten et al. |
| 5,718,684 A | 2/1998 | Gupta |
| 5,752,522 A | 5/1998 | Murphy |
| 5,904,648 A | 5/1999 | Arndt et al. |
| 6,059,713 A | 5/2000 | Urick et al. |
| 6,268,390 B1 | 7/2001 | Kunz |
| 6,306,421 B1 | 10/2001 | Kunz et al. |
| 6,403,635 B1 | 6/2002 | Kinsella et al. |
| 6,495,579 B1 | 12/2002 | Hunter |
| 6,515,009 B1 | 2/2003 | Kunz et al. |
| 6,530,948 B1 | 3/2003 | Vrba |
| 6,663,881 B2 | 12/2003 | Kunz et al. |
| 6,730,064 B2 | 5/2004 | Ragheb et al. |
| 7,803,149 B2 | 9/2010 | Bates et al. |
| 7,811,622 B2 | 10/2010 | Bates et al. |
| 7,882,841 B2 * | 2/2011 | Aljuri ............... A61B 18/24 606/171 |
| 8,052,668 B2 | 11/2011 | Sih |
| 8,092,864 B2 | 1/2012 | Isch et al. |
| 8,241,249 B2 | 8/2012 | Wang |
| 8,244,344 B2 | 8/2012 | Wang |
| 8,257,305 B2 | 9/2012 | Speck et al. |
| 8,366,660 B2 | 2/2013 | Wang |
| 8,366,662 B2 | 2/2013 | Wang |
| 8,403,910 B2 | 3/2013 | Wang |
| 8,404,300 B2 | 3/2013 | Wang |
| 8,414,525 B2 | 4/2013 | Wang\ |
| 8,414,526 B2 | 4/2013 | Wang |
| 8,414,909 B2 | 4/2013 | Wang |
| 8,414,910 B2 | 4/2013 | Wang |
| 8,425,459 B2 | 4/2013 | Wang |
| 8,430,055 B2 | 4/2013 | Wang et al. |
| 8,439,868 B2 | 5/2013 | Speck et al. |
| 8,557,272 B2 | 10/2013 | Zhao |
| 8,586,125 B2 | 11/2013 | Hossainy et al. |
| 8,673,387 B2 | 3/2014 | Bates et al. |
| 8,722,132 B2 | 5/2014 | Labrecque et al. |
| 9,066,990 B2 | 6/2015 | Speck et al. |
| 9,242,081 B2 | 1/2016 | Drasler et al. |
| 9,728,840 B2 | 8/2017 | Shi et al. |
| 10,245,419 B2 | 4/2019 | Drasler et al. |
| 10,668,188 B2 | 6/2020 | Wang |
| 10,675,386 B2 | 6/2020 | Wang |
| 10,806,830 B2 | 10/2020 | Wang et al. |
| 10,850,076 B2 | 12/2020 | Wang et al. |
| 10,881,839 B2 | 1/2021 | Wang et al. |
| 10,888,640 B2 | 1/2021 | Wang et al. |
| 10,898,700 B2 | 1/2021 | Wang et al. |
| 10,987,451 B2 | 4/2021 | Wang et al. |
| 10,994,103 B2 | 5/2021 | Wang et al. |
| 10,994,104 B2 | 5/2021 | Wang et al. |
| 2003/0203991 A1 | 10/2003 | Schottman et al. |
| 2004/0098019 A1 | 5/2004 | Tomaschko et al. |
| 2004/0144387 A1 | 7/2004 | Amar |
| 2004/0267355 A1 | 12/2004 | Scott et al. |
| 2005/0054978 A1 | 3/2005 | Segal et al. |
| 2005/0196518 A1 | 9/2005 | Stenzel |
| 2005/0249770 A1 | 11/2005 | Hunter |
| 2006/0083768 A1 | 4/2006 | Labrecque et al. |
| 2007/0005094 A1 | 1/2007 | Eaton et al. |
| 2007/0009692 A1 | 1/2007 | Wang et al. |
| 2007/0027523 A1 | 2/2007 | Toner et al. |
| 2007/0031371 A1 | 2/2007 | Kozlowski |
| 2007/0088255 A1 | 4/2007 | Toner et al. |
| 2008/0025952 A1 | 1/2008 | Scheule et al. |
| 2008/0113035 A1 | 5/2008 | Hunter |
| 2008/0118544 A1 | 5/2008 | Wang |
| 2008/0175887 A1 | 7/2008 | Wang |
| 2008/0245375 A1 | 10/2008 | Trudel |
| 2008/0255508 A1 | 10/2008 | Wang |
| 2008/0255509 A1 | 10/2008 | Wang |
| 2008/0255510 A1 | 10/2008 | Wang |
| 2008/0276935 A1 | 11/2008 | Wang |
| 2009/0018565 A1 | 1/2009 | To et al. |
| 2009/0028920 A1 | 1/2009 | Hodges |
| 2009/0171241 A1 | 7/2009 | Garcia et al. |
| 2009/0283206 A1 | 11/2009 | Eskaros et al. |
| 2010/0015200 A1 | 1/2010 | McClain et al. |
| 2010/0030183 A1 | 2/2010 | Toner et al. |
| 2010/0049182 A1 | 2/2010 | Ryan et al. |
| 2010/0055294 A1 | 3/2010 | Wang et al. |
| 2010/0076402 A1 | 3/2010 | Mazzone et al. |
| 2010/0198150 A1 | 8/2010 | Michal et al. |
| 2010/0209472 A1 | 8/2010 | Wang |
| 2010/0233228 A1 | 9/2010 | Speck |
| 2010/0285085 A1 | 11/2010 | Stankus et al. |
| 2011/0008260 A1 | 1/2011 | Flanagan |
| 2011/0015664 A1 | 1/2011 | Kangas et al. |
| 2011/0098683 A1 | 4/2011 | Wiita et al. |
| 2011/0144578 A1 | 6/2011 | Pacetti et al. |
| 2011/0159169 A1 | 6/2011 | Wang |
| 2011/0160575 A1 | 6/2011 | Beyar et al. |
| 2011/0160658 A1 | 6/2011 | Wang |
| 2011/0160660 A1 | 6/2011 | Wang |
| 2011/0166548 A1 | 7/2011 | Wang |
| 2011/0196340 A1 | 8/2011 | Barry et al. |

(56) References Cited

U.S. PATENT DOCUMENTS

| | | |
|---|---|---|
| 2011/0029520 A1 | 12/2011 | Speck et al. |
| 2011/0295200 A1 | 12/2011 | Speck et al. |
| 2011/0300221 A1 | 12/2011 | Kunz et al. |
| 2012/0029426 A1 | 2/2012 | Wang |
| 2012/0035530 A1 | 2/2012 | Wang |
| 2012/0109105 A1 | 5/2012 | Cambronne |
| 2012/0172796 A1 | 7/2012 | Chappa |
| 2012/0231037 A1 | 9/2012 | Levi et al. |
| 2012/0239001 A1 | 9/2012 | Barry et al. |
| 2012/0296274 A1 | 11/2012 | Slager |
| 2012/0302954 A1 | 11/2012 | Zhao |
| 2012/0316633 A1 | 12/2012 | Flanagan et al. |
| 2013/0197434 A1 | 8/2013 | Wang |
| 2013/0231638 A1 | 9/2013 | Speck et al. |
| 2013/0245058 A1 | 9/2013 | Hoffmann et al. |
| 2013/0253466 A1 | 9/2013 | Campbell et al. |
| 2013/0253475 A1 | 9/2013 | Wang |
| 2013/0261603 A1 | 10/2013 | Wang |
| 2013/0304029 A1 | 11/2013 | Barry et al. |
| 2014/0005541 A1 | 1/2014 | Bates et al. |
| 2014/0228751 A1 | 8/2014 | Speck et al. |
| 2014/0228752 A1 | 8/2014 | Speck et al. |
| 2014/0378896 A1 | 12/2014 | Venturelli |
| 2015/0231375 A1 | 8/2015 | Kubo et al. |
| 2015/0273117 A1 | 10/2015 | Wang |
| 2016/0038648 A1 | 2/2016 | Gemborys |
| 2016/0082159 A1 | 3/2016 | Orlowski |
| 2016/0250388 A1 | 9/2016 | Wang |
| 2016/0338793 A1 | 11/2016 | Shohat et al. |
| 2017/0028105 A1 | 2/2017 | Ahlering et al. |
| 2017/0086929 A1 | 3/2017 | Moll et al. |
| 2018/0104383 A1 | 4/2018 | Wang et al. |
| 2019/0015639 A1 | 1/2019 | Wang et al. |
| 2019/0015640 A1 | 1/2019 | Wang et al. |
| 2019/0167854 A1 | 6/2019 | Wang |
| 2019/0344053 A1 | 11/2019 | Wang et al. |
| 2019/0374685 A1 | 12/2019 | Wang et al. |
| 2020/0254148 A1 | 8/2020 | Wang |
| 2020/0360571 A1 | 11/2020 | Wang et al. |
| 2021/0052862 A1 | 2/2021 | Wang et al. |
| 2021/0052863 A1 | 2/2021 | Wang et al. |
| 2021/0052864 A1 | 2/2021 | Wang et al. |
| 2021/0052865 A1 | 2/2021 | Wang et al. |
| 2021/0077666 A1 | 3/2021 | Wang et al. |
| 2021/0113823 A1 | 4/2021 | Wang et al. |
| 2021/0205502 A1 | 7/2021 | Wang et al. |
| 2021/0228780 A1 | 7/2021 | Wang et al. |
| 2021/0361918 A1 | 11/2021 | Wang et al. |

FOREIGN PATENT DOCUMENTS

| | | | |
|---|---|---|---|
| CN | 107635593 | 1/2018 | |
| CN | 109414528 | 3/2019 | |
| CN | 111166942 | 5/2020 | |
| CN | 113727750 | 11/2021 | |
| EP | 0474906 | 3/1992 | |
| EP | 1135165 | 9/2001 | |
| EP | 1143968 | 8/2003 | |
| EP | 1539266 | 4/2008 | |
| EP | 2292225 | 5/2012 | |
| EP | 2098230 | 6/2012 | |
| EP | 2262547 | 1/2013 | |
| EP | 2324866 | 6/2014 | |
| EP | 2324867 | 6/2014 | |
| EP | 2531229 | 12/2014 | |
| EP | 2451496 | 7/2015 | |
| EP | 2911711 | 9/2015 | |
| EP | 3442612 | 8/2020 | |
| JP | 2010540159 | 12/2010 | |
| JP | 2012502690 | 2/2012 | |
| JP | 2013523209 | 6/2013 | |
| JP | 2014523790 | 9/2014 | |
| JP | 2015536709 | 12/2015 | |
| JP | 2016503330 | 2/2016 | |
| JP | 2016036730 | 3/2016 | |
| JP | 2016518200 | 6/2016 | |
| JP | 2017507741 | 3/2017 | |
| JP | 2018517454 | 7/2018 | |
| JP | 2019523032 | 8/2019 | |
| JP | 2019218354 | 12/2019 | |
| JP | 2020049269 | 4/2020 | |
| JP | 2020075155 | 5/2020 | |
| JP | 2022521000 | 4/2022 | |
| WO | 9728840 | 8/1997 | |
| WO | 0025848 | 5/2000 | |
| WO | 0032238 | 6/2000 | |
| WO | 2011147407 | 12/2001 | |
| WO | 2009051614 | 4/2009 | |
| WO | WO-2009051614 A1 * | 4/2009 | .......... A61K 31/337 |
| WO | 2011008393 | 1/2011 | |
| WO | 2011119159 | 9/2011 | |
| WO | 2012122023 | 9/2012 | |
| WO | 2013015941 | 1/2013 | |
| WO | 2014066085 | 5/2014 | |
| WO | 2014087395 | 6/2014 | |
| WO | 2014177678 | 11/2014 | |
| WO | 2015136106 | 9/2015 | |
| WO | 2016073294 | 5/2016 | |
| WO | 2016118923 | 7/2016 | |
| WO | 2016172343 | 10/2016 | |
| WO | 2018204782 | 11/2018 | |
| WO | 2020172560 | 8/2020 | |

OTHER PUBLICATIONS

"U.S. Appl. No. 16/864,373, Final Office Action dated May 25, 2021", 44 pgs.

"U.S. Appl. No. 16/864,373, Examiner Interview Summary dated Jul. 12, 2021", 2 pgs.

"International Application Serial No. PCT US2020 019274, International Preliminary Report on Patentability dated Sep. 2, 2021", 9 pgs.

"U.S. Appl. No. 14/438,327, Preliminary Amendment filed Jul. 28, 2015", 9 pgs.

"U.S. Appl. No. 14/438,327, Restriction Requirement dated Jul. 12, 2016", 9 pgs.

"U.S. Appl. No. 14/438,327, Response filed Aug. 24, 2016 to Restriction Requirement dated Jul. 12, 2016", 9 pgs.

"U.S. Appl. No. 14/438,327, Non Final Office Action dated Oct. 6, 2016", 10 pgs.

"U.S. Appl. No. 14/438,327, Response filed Dec. 28, 2016 to Non Final Office Action dated Oct. 6, 2016", 13 pgs.

"U.S. Appl. No. 14/438,327, Final Office Action dated May 3, 2017", 10 pgs.

"U.S. Appl. No. 14/438,327, Response filed Jul. 27, 2017 to Final Office Action dated May 3, 2017", 13 pgs.

"U.S. Appl. No. 14/438,327, Non Final Office Action dated Sep. 29, 2017", 11 pgs.

"U.S. Appl. No. 14/438,327, Response filed Dec. 15, 2017 to Non Final Office Action dated Sep. 29, 2017", 16 pgs.

"U.S. Appl. No. 14/438,327, Final Office Action dated Apr. 2, 2018", 14 pgs.

"U.S. Appl. No. 14/438,327, Response filed Jun. 1, 2018 to Final Office Action dated Apr. 2, 2018", 16 pgs.

"U.S. Appl. No. 14/438,327, Advisory Action dated Jul. 18, 2018", 6 pgs.

"U.S. Appl. No. 14/438,327, Response filed Aug. 1, 2018 to Advisory Action dated Jul. 18, 2018 and Final Office Action dated Apr. 2, 2018", 17 pgs.

"U.S. Appl. No. 16/135,436, Restriction Requirement dated Nov. 2, 2018", 7 pgs.

"U.S. Appl. No. 16/135,436, Response filed Nov. 14, 2018 to Restriction Requirement dated Nov. 2, 2018", 10 pgs.

"U.S. Appl. No. 14/438,327, Non Final Office Action dated Jan. 28, 2019", 14 pgs.

"U.S. Appl. No. 15/568,614, Restriction Requirement dated Feb. 8, 2019", 9 pgs.

"U.S. Appl. No. 16/135,436, Notice of Non-Responsive Amendment dated Mar. 8, 2019", 2 pgs.

(56) References Cited

OTHER PUBLICATIONS

"U.S. Appl. No. 15/568,614, Response filed Mar. 20, 2019 to Restriction Requirement dated Feb. 8, 2019", 8 pgs.
"U.S. Appl. No. 16/135,436, Response filed Mar. 28, 2019 to Notice of Non-Responsive Amendment dated Mar. 8, 2019", 10 pgs.
"U.S. Appl. No. 14/438,327, Response filed Apr. 16, 2019 to Non Final Office Action dated Jan. 28, 2019", 29 pgs.
"U.S. Appl. No. 15/568,614, Notice of Non-Responsive Amendment dated Jul. 1, 2019", 2 pgs.
"U.S. Appl. No. 15/568,614, Response filed Jul. 9, 2019 to Non-Responsive Amendment dated Jul. 1, 2019 and Restriction Requirement dated Feb. 8, 2019", 8 pgs.
"U.S. Appl. No. 16/135,436, Non Final Office Action dated Jul. 29, 2019", 38 pgs.
"U.S. Appl. No. 14/438,327, Final Office Action dated Aug. 9, 2019", 20 pgs.
"U.S. Appl. No. 16/135,436, Response filed Aug. 21, 2019 to Non Final Office Action dated Jul. 29, 2019", 18 pgs.
"U.S. Appl. No. 15/568,614, Non Final Office Action dated Nov. 18, 2019", 22 pgs.
"U.S. Appl. No. 16/135,436, Final Office Action dated Nov. 29, 2019", 41 pgs.
"U.S. Appl. No. 14/438,327, Response filed Dec. 3, 2019 to Final Office Action dated Aug. 9, 2019", 32 pgs.
"U.S. Appl. No. 14/438,327, Non Final Office Action dated Jan. 7, 2020", 11 pgs.
"U.S. Appl. No. 16/135,436, Response filed Jan. 13, 2020 to Final Office Action dated Nov. 29, 2019", 22 pgs.
"U.S. Appl. No. 14/438,327, Response filed Feb. 7, 2020 to Non Final Office Action dated Jan. 7, 2020", 13 pgs.
"U.S. Appl. No. 15/568,614, Response filed Feb. 10, 2020 to Non Final Office Action dated Nov. 18, 2019", 17 pgs.
"U.S. Appl. No. 14/438,327, Examiner Interview Summary dated Feb. 12, 2020", 3 pgs.
"U.S. Appl. No. 16/135,436, Non Final Office Action dated Mar. 5, 2020", 48 pgs.
"U.S. Appl. No. 16/135,436, Response filed Apr. 6, 2020 to Non Final Office Action dated Mar. 5, 2020", 21 pgs.
"U.S. Appl. No. 16/135,436, Examiner Interview Summary dated Apr. 8, 2020", 3 pgs.
"U.S. Appl. No. 14/438,327, Notice of Allowance dated Apr. 22, 2020", 10 pgs.
"U.S. Appl. No. 14/438,327, Corrected Notice of Allowability dated May 5, 2020", 3 pgs.
"U.S. Appl. No. 15/568,614, Final Office Action dated May 15, 2020", 25 pgs.
"U.S. Appl. No. 16/135,472, Examiner Interview Summary dated May 19, 2020", 4 pgs.
"U.S. Appl. No. 16/135,436, Notice of Allowance dated Jul. 10, 2020", 10 pgs.
"U.S. Appl. No. 15/568,614, Response filed Jul. 14, 2020 to Final Office Action dated May 15, 2020", 23 pgs.
"U.S. Appl. No. 16/135,472, Final Office Action dated Aug. 21, 2020", 6 pgs.
"U.S. Appl. No. 16/135,436, Corrected Notice of Allowability dated Sep. 11, 2020", 7 pgs.
"U.S. Appl. No. 15/568,614, Notice of Allowance dated Sep. 30, 2020", 10 pgs.
"U.S. Appl. No. 15/568,614, Corrected Notice of Allowability dated Nov. 30, 2020", 8 pgs.
"U.S. Appl. No. 16/135,472, Corrected Notice of Allowability dated Nov. 30, 2020", 8 pgs.
"37 C.F.R. section 1.132 Declaration for U.S. Appl. No. 16/135,436, filed Jan. 13, 2020", (2020), 5 pgs.
"International Application Serial No. PCT US2013 064842, International Search Report dated Jan. 17, 2014", 3 pgs.
"European Application Serial No. 13848400.1, Extended European Search Report dated Apr. 28, 2016", 8 pgs.
"International Application Serial No. PCT US2013 064842, Written Opinion dated Jan. 17, 2014", 10 pgs.
"International Application Serial No. PCT US2013 064842, International Preliminary Report on Patentability dated May 7, 2015", 12 pgs.
"International Application Serial No. PCT US2016 028652, International Search Report dated Jul. 26, 2016", 2 pgs.
"International Application Serial No. PCT US2016 028652, Written Opinion dated Jul. 26, 2016", 8 pgs.
"European Application Serial No. 13848400.1, Response filed Oct. 19, 2015 to Communication pursuant to Rules 161(1) and 162 EPC dated Jun. 2, 2015", 17 pgs.
"European Application Serial No. 13848400.1, Response filed Oct. 14, 2016 to Extended European Search Report dated Apr. 28, 2016", 17 pgs.
"Chinese Application Serial No. 201380055869.X, Response filed Feb. 28, 2017 to Office Action dated Dec. 15, 2016", w English Claims, 21 pgs.
"Japanese Application Serial No. 2015-539651, Office Action dated Jul. 11, 2017", w English Translation, 10 pgs.
"Japanese Application Serial No. 2015-539651, Response filed Sep. 6, 2017 to Office Action dated Jul. 11, 2017", w English claims, 15 pgs.
"International Application Serial No. PCT US2016 028652, International Preliminary Report on Patentability dated Nov. 2, 2017", 10 pgs.
"Japanese Application Serial No. 2015-539651, Examiners Decision of Final Refusal dated Nov. 21, 2017", w English Translation, 13 pgs.
"Japanese Application Serial No. 2015-539651, Response filed Mar. 20, 2018 to Examiners Decision of Final Refusal dated Nov. 21, 2017", w English Claims, 34 pgs.
"Japanese Application Serial No. 2015-539651, Office Action dated May 15, 2018", w English Translation, 15 pgs.
"European Application Serial No. 13848400.1, Communication Pursuant to Article 94(3) EPC dated Apr. 9, 2018", 7 pgs.
"European Application Serial No. 16783856.4, Response filed Jun. 22, 2018 to Communication pursuant to Rules 161(2) and 162 EPC dated Dec. 13, 2017", 11 pgs.
"International Application Serial No. PCT US2018 031083, International Search Report dated Jul. 27, 2018", 4 pgs.
"International Application Serial No. PCT US2018 031083, Written Opinion dated Jul. 27, 2018", 33 pgs.
"European Application Serial No. 13848400.1, Response filed Sep. 14, 2018 to Communication Pursuant to Article 94(3) EPC dated Apr. 9, 2018", 42 pgs.
"Japanese Application Serial No. 2017-555548, Office Action dated Aug. 21, 2018", w English translation, 8 pgs.
"Japanese Application Serial No. 2017-555548, Response filed Nov. 20, 2018 to Office Action dated Aug. 21, 2018", w English Claims, 11 pgs.
"Japanese Application Serial No. 2018-052874, Office Action dated Jan. 29, 2019", w English translation, 15 pgs.
"Japanese Application Serial No. 2017-555548, Examiners Decision of Final Refusal dated Mar. 26, 2019", w English translation, 5 pgs.
"European Application Serial No. 16783856.4, Extended European Search Report dated Nov. 9, 2018", 7 pgs.
"Japanese Application Serial No. 2018-563611, Notification of Reasons for Refusal dated Apr. 23, 2019", w English translation, 7 pgs.
"Japanese Application Serial No. 2018-052874, Response filed May 14, 2019 to Office Action dated Jan. 29, 2019", w English Claims, 24 pgs.
"European Application Serial No. 18794752.8, Communication Pursuant to Article 94(3) EPC dated Apr. 10, 2019", 8 pgs.
"European Application Serial No. 16783856.4, Response filed May 28, 2019 to Extended European Search Report dated Nov. 9, 2018", 16 pgs.
"European Application Serial No. 18794752.8, Extended European Search Report dated Mar. 29, 2019", 5 pgs.
"European Application Serial No. 13848400.1, Communication Pursuant to Article 94(3) EPC dated Jun. 4, 2019", 9 pgs.

(56) References Cited

OTHER PUBLICATIONS

"Japanese Application Serial No. 2018-563611, Response filed Jul. 22, 2019 to Notification of Reasons for Refusal dated Apr. 23, 2019", w English Claims, 14 pgs.
"Japanese Application Serial No. 2017-555548, Respone filed Jul. 26, 2019 to Examiners Decision of Final Refusal dated Mar. 26, 2019", w English Claims, 19 pgs.
"European Application Serial No. 18794752.8, Response filed Aug. 5, 2019 to Communication Pursuant to Article 94(3) EPC dated Apr. 10, 2019", 55 pgs.
"Japanese Application Serial No. 2018-563611, Notification of Reasons for Refusal dated Aug. 20, 2019", w English translation, 7 pgs.
"Japanese Application Serial No. 2017-555548, Office Action dated Sep. 10, 2019", w English Translation, 2 pgs.
"Japanese Application Serial No. 2018-052874, Office Action dated Oct. 1, 2019", w English translation, 6 pgs.
"International Application Serial No. PCT US2018 031083, International Preliminary Report on Patentability dated Nov. 14, 2019", 35 pgs.
"European Application Serial No. 13848400.1, Response filed Dec. 16, 2019 to Communication Pursuant to Article 94(3) EPC dated Jun. 4, 2019", 30 pgs.
"Chinese Application Serial No. 201680029925.6, Office Action dated Feb. 21, 2020", w English translation, 15 pgs.
"European Application Serial No. 13848400.1, Communication Pursuant to Article 94(3) EPC dated Apr. 24, 2020", 8 pgs.
"Chinese Application Serial No. 201680029925.6, Response filed Jul. 6, 2020 to Office Action dated Feb. 21, 2020", w English Claims, 36 pgs.
"International Application Serial No. PCT US2020 019274, International Search Report dated Jun. 26, 2020", 6 pgs.
"International Application Serial No. PCT US2020 019274, Written Opinion dated Jun. 26, 2020", 7 pgs.
"Japanese Application Serial No. 2019-137680, Notification of Reasons for Rejection dated Jul. 21, 2020", W English Translation, 5 pgs.
"Chinese Application Serial No. 201680029925.6, Office Action dated Jul. 16, 2020", w English Translation, 22 pgs.
"Japanese Application Serial No. 2017-555548, Office Action dated Aug. 25, 2020", w English translation, 22 pgs.
"European Application Serial No. 13848400.1, Response filed Oct. 19, 2020 to Communication Pursuant to Article 94(3) EPC dated Apr. 24, 2020", 13 pgs.
"Chinese Application Serial No. 201680029925.6, Office Action dated Oct. 22, 2020", w English translation, 25 pgs.
"Chinese Application Serial No. 201380055869.X, Office Action dated May 26, 2016", w English Translation, 6 pgs.
"Chinese Application Serial No. 201380055869.X, Response filed Sep. 9, 2016 to Office Action dated May 26, 2016", (With English Translation), 18 pgs.
"Chinese Application Serial No. 201380055869.X, Office Action dated Dec. 15, 2016", with English Translation, 20 pgs.
"Chinese Application Serial No. 201380055869.X, Office Action dated Jun. 19, 2017", With English Translation, 13 pgs.
"Chinese Application Serial No. 201380055869.X, Response filed Sep. 4, 2017 to Office Action dated Jun. 19, 2017", w English Claims, 17 pgs.
"Chinese Application Serial No. 201380055869.X, Office Action dated Nov. 27, 2017", W English Translation, 13 pgs.
"Chinese Application Serial No. 201380055869.X, Respone filed Apr. 12, 2018 to Office Action dated Nov. 27, 2017", w English Claims, 17 pgs.
"U.S. Appl. No. 16/135,472, Restriction Requirement dated Nov. 2, 2018", 5 pgs.
"U.S. Appl. No. 16/135,472, Response filed Nov. 14, 2018 to Restriction Requirement dated Nov. 2, 2018", 10 pgs.
"U.S. Appl. No. 16/135,472, Notice of Non Responsive Amendment dated Mar. 8, 2019", 2 pgs.

"U.S. Appl. No. 16/267,434, Non Final Office Action dated Mar. 22, 2019", 11 pgs.
"U.S. Appl. No. 16/135,472, Response filed Mar. 28, 2019 to Notice of Non Responsive Amendment dated Mar. 8, 2019", 10 pgs.
"U.S. Appl. No. 16/267,434, Response filed Apr. 24, 2019 to Non-Final Office Action dated Mar. 22, 2019", 11 pgs.
"U.S. Appl. No. 16/267,434, Final Office Action dated Jun. 14, 2019", 15 pgs.
"U.S. Appl. No. 16/135,472, Non Final Office Action dated Jul. 30, 2019", 40 pgs.
"U.S. Appl. No. 16/135,472, Response filed Aug. 21, 2019 to Non Final Office Action dated Jul. 30, 2019", 23 pgs.
"U.S. Appl. No. 16/267,434, Response filed Sep. 11, 2019 to Final Office Action dated Jun. 14, 2019", 17 pgs.
"U.S. Appl. No. 16/519,720, Restriction Requirement dated Oct. 18, 2019", 5 pgs.
"U.S. Appl. No. 16/519,720, Response filed Oct. 31, 2019 to Restriction Requirement dated Oct. 18, 2019", 10 pgs.
"U.S. Appl. No. 16/267,434, Non Final Office Action dated Nov. 18, 2019", 19 pgs.
"Chinese Application Serial No. 201380055869.X, Notice of Reexamination dated Nov. 21, 2019", w English Translation, 8 pgs.
"U.S. Appl. No. 16/135,472, Final Office Action dated Nov. 29, 2019", 43 pgs.
"U.S. Appl. No. 16/519,677, Restriction Requirement dated Nov. 20, 2019", 5 pgs.
"U.S. Appl. No. 16/519,677, Response filed Dec. 13, 2019 to Restriction Requirement dated Nov. 20, 2019", 10 pgs.
"U.S. Appl. No. 16/135,472, Response filed Jan. 13, 2020 to Final Office Action dated Nov. 29, 2019", 27 pgs.
"U.S. Appl. No. 16/519,720, Non Final Office Action dated Feb. 6, 2020", 23 pgs.
"U.S. Appl. No. 16/267,434, Response filed Feb. 13, 2020 to Non Final Office Action dated Nov. 18, 2019", 17 pgs.
"U.S. Appl. No. 16/135,472, Non Final Office Action dated Mar. 19, 2020", 56 pgs.
"U.S. Appl. No. 16/519,677, Non Final Office Action dated Mar. 19, 2020", 31 pgs.
"U.S. Appl. No. 16/267,434, Final Office Action dated Mar. 30, 2020", 18 pgs.
"U.S. Appl. No. 16/267,434, Response filed Mar. 31, 2020 to Final Office Action dated Mar. 30, 2020", 8 pgs.
"U.S. Appl. No. 16/267,434, Notice of Allowance dated Apr. 22, 2020", 10 pgs.
"U.S. Appl. No. 16/519,720, Response filed May 6, 2020 to Non Final Office Action dated Feb. 6, 2020", 19 pgs.
"U.S. Appl. No. 16/267,434, Corrected Notice of Allowability dated May 13, 2020", 3 pgs.
"U.S. Appl. No. 16/135,472, Response filed May 15, 2020 to Non Final Office Action dated Mar. 19, 2020", 29 pgs.
"U.S. Appl. No. 16/519,677, Response filed Jun. 19, 2020 to Non Final Office Action dated Mar. 19, 2020", 19 pgs.
"U.S. Appl. No. 16/519,720, Final Office Action dated Aug. 21, 2020", 23 pgs.
"U.S. Appl. No. 16/135,472, Response filed Sep. 4, 2020 to Final Office Action dated Aug. 21, 2020", 12 pgs.
"U.S. Appl. No. 16/519,720, Response filed Sep. 4, 2020 to Final Office Action dated Aug. 21, 2020", 12 pgs.
"U.S. Appl. No. 16/519,677, Notice of Allowance dated Sep. 21, 2020", 10 pgs.
"U.S. Appl. No. 16/135,472, Notice of Allowance dated Oct. 7, 2020", 9 pgs.
"U.S. Appl. No. 16/519,720, Notice of Allowance dated Oct. 21, 2020", 8 pgs.
"U.S. Appl. No. 16/986,683, Non Final Office Action dated Oct. 29, 2020", 14 pgs.
"U.S. Appl. No. 16/864,373, Restriction Requirement dated Nov. 17, 2020", 5 pgs.
"U.S. Appl. No. 16/519,677, Corrected Notice of Allowability dated Nov. 30, 2020", 7 pgs.
"U.S. Appl. No. 16/986,683, Response filed Dec. 4, 2020 to Non Final Office Action dated Oct. 29, 2020", 9 pgs.

(56) References Cited

OTHER PUBLICATIONS

"U.S. Appl. No. 16/864,373, Response filed Dec. 10, 2020 to Restriction Requirement dated Nov. 17, 2020", 7 pgs.
"U.S. Appl. No. 16/986,683, Notice of Allowance dated Jan. 4, 2021", 9 pgs.
"PMA P130024: FDA Summary of Safety and Effectiveness Data (SSED)", Retrieved from the Internet:URL:https: www.accessdata.fda.gov cdrh_docs pdf13 P130024b.pdf, 44 pgs.
"Stricture", definition accessed online on Jun. 10, 2019, [Online] Retrieved from the internet:www.merriam-webster.com dictionary stricture, (2019), 1 pg.
"Japanese Application Serial No. 2019-137680, Response filed Oct. 6, 2020 to Notification of Reasons for Rejection dated Jul. 21, 2020", w English Translation, 5 pgs.
Aaron, Latayia, "Review of Prostate Anatomy and Embryology and the Etiology of BPH", Urol Clin North Am 43(3), (Aug. 2016), pp. 279-288.
Daughtry, "Balloon Dilation of the Ureter: A Means to Facilitate Passage of Ureteral and Renal Calculi", The Journal of Urology, vol. 136, (1986), 1063-1065.
Daughtry, "Balloon dilation of urethral strictures", Urology, vol. 31, (1988), 231-233.
Donatucci, Craig F, "Randomized Clinical Trial Comparing Balloon Dilatation to Transurethral Resection of Prostate for Benign Prostatic Hyperplasia", Adult Urology vol. 4 2, No. 1, (Jul. 1993), 42-49.
Goldenberg, S L, "Balloon Dilatation of the Prostate", Alternate Methods in the Treatment of Benign Prostatic Hyperplasia, (1993), 97-119.
Huang, Weigua, "Effect of transurethral split of the prostate using a double-columnar balloon catheter for benign prostatic hyperplasia", Medicine 95:40, (Mar. 1, 2016), 4 pgs.
Lukacs, B, "One-year follow-up of 2829 patients with moderate to severe lower urinary tract symptoms treated with alt uzosin in general practice according to IPSS and a health-related quality-of-life questionnaire", BPM Group in General Practice, Urology; 55(4), (2000), 7 pgs.
Milonas, Daimantas, "The effect of complete transurethral resection of the prostate on symptoms, quality of life, and voiding function improvement", Central European Journal of Urology, (2015), pp. 169-174.
Oesterling, Joseph E, "The Origin and Development of Benign Prostatic Hyperplasia An Age-Dependent Process", Journal of Andrology, vol. 12, No. 6,, (1991), 8 pgs.
Roehrborn, C G, "Pathology of benign prostatic hyperplasia", International Journal of Impotence Research 20, (2008), S11-S18.
Shiel Jr, William C, "Definition of stricture", [Online] Retrieved from the internet:https: www.medicinenet.com script main art.asp? articlekey= 166621, (2019), 1 pg.
Shin, "Tissue Hyperplasia: Influence of a Paclitaxel-eluting Covered Stent-Preliminary Study in a Canine Urethral Model", Radiology, (2005), 438-444.
Vale, J A, "Balloon dilatation of the prostate-should it have a place in the urologist's armamentarium?", Journal of the Royal Society of Medicine vol. 86, (Feb. 1993), pp. 83-86.
Van Loenhout, Rhiannon, "Prostate Cancer—PI-RADS v2", https: radiologyassistant.nl abdomen prostate-cancer-pi-rads-v2 Accessed on May 14, 2020, (Aug. 1, 2018), 19 pgs.
Yazdani, Saami K, "Vascular, Downstream, and Pharmacokinetic Responses to Treatment with a Low Dose Drug-Coated Balloon in a Swine Femoral Artery Model", Catheterization and Cardiovascular Interventions 83: 132-140, (2014), 132-140.
"U.S. Appl. No. 17/255,701, Preliminary Amendment filed Dec. 2, 2021", 9 pgs.
"U.S. Appl. No. 17/080,088, Non Final Office Action dated Mar. 3, 2022", 7 pgs.
"U.S. Appl. No. 17/080,114, Non Final Office Action dated Mar. 3, 2022", 7 pgs.
"U.S. Appl. No. 17/108,517, Non Final Office Action dated Mar. 3, 2022", 5 pgs.
"U.S. Appl. No. 17/107,136, Non Final Office Action dated Mar. 4, 2022", 6 pgs.
"U.S. Appl. No. 17/080,140, Non Final Office Action dated Feb. 19, 2021", 13 pgs.
"U.S. Appl. No. 17/080,199, Non Final Office Action dated Feb. 19, 2021", 17 pgs.
"U.S. Appl. No. 17/080,140, Response filed Mar. 9, 2021 to Non Final Office Action dated Feb. 19, 2021", 10 pgs.
"U.S. Appl. No. 17/080,199, Response filed Mar. 9, 2021 to Non Final Office Action dated Feb. 19, 2021", 8 pgs.
"U.S. Appl. No. 16/864,373, Non Final Office Action dated Mar. 18, 2021", 32 pgs.
"U.S. Appl. No. 16/986,683, Corrected Notice of Allowability dated Mar. 17, 2021", 6 pgs.
"U.S. Appl. No. 17/080,140, Notice of Allowance Base Issue Fee dated Mar. 18, 2021", 12 pgs.
"U.S. Appl. No. 17/080,140, Notice of Allowance dated Mar. 18, 2021", 12 pgs.
"U.S. Appl. No. 17/080,199, Notice of Allowance dated Mar. 19, 2021", 11 pgs.
"U.S. Appl. No. 16/135,472, May 15, 2020 Declaration. (Year: 2020)", 15 pgs.
"U.S. Appl. No. 15/568,614, Jul. 14, 2020 declaration. (Year: 2020)", 4 pgs.
"Pentaerythritol ethoxylate (15 4 EO OH) Sigma-Aldrich", Sigma-Aldrich, Accessed online on Mar. 13, 2021 at https: www.sigmaaldrich.com catalog product aidrich 418730?lang=enandregion=US. (Year: 2021), (2021).
"Pentaerythritol ethoxylate (3 4 EO OH)", Sigma-Aldrich, Accessed online on Mar. 13, 2021 at https: www.sigmaaldrich.com catalog product aldrich 416150?lang=enandregion=US. (Year: 2021), (2021).
"Definition of "stricture" Merriam-Webster", Accessed online on Mar. 13, 2021 at https: www.merriam-webster.com dictionary stricture, (2021).
"Meglumine", ChemSpider, Accessed online on Mar. 13, 2021 at https: www.chemspider.com Chemical-Structure.8249.html, (2021).
"Lactic Acid", ChemSpider, Accessed online on Mar. 13, 2021 at https: www.chemspider.com search.aspx?q=lactic+acid, (2021).
"Gentisic Acid", ChemSpider, Accessed online on Mar. 13, 2021 at https: www.chemspider.com Chemical-Structure.3350.html. (Year: 2021), (2021).
"Acetic Acid", ChemSpider, Accessed online on Mar. 13, 2021 at https: www.chemspider.com Search.aspx?q=acetic+acidl, (2021).
"Lactobionic Acid", ChemSpider, Accessed online on Mar. 13, 2021 at https: www.chemspider.com Chemical-Structure.7040,html. (Year: 2021), (2021).
"TWEEN 20", Sigma-Aldrich, Accessed online on Mar. 13, 2021 at https: www.sigmaaldrich.com catalog product sigma p9416?lang= enandregion=US. (Year: 2021), (2021).
"U.S. Appl. No. 16/864,373, Response filed Apr. 6, 2021 to Non Final Office Action dated Mar. 18, 2021", 25 pgs.
"U.S. Appl. No. 17/107,136, Response filed May 27, 2022 to Non Final Office Action dated Mar. 4, 2022", 9 pgs.
"U.S. Appl. No. 17/080,088, Response filed May 27, 2022 to Non Final Office Action dated Mar. 3, 2022", 12 pgs.
"U.S. Appl. No. 17/080,114, Response filed May 27, 2022 to Non Final Office Action dated Mar. 3, 2022", 9 pgs.
"U.S. Appl. No. 17/108,517, Response filed May 27, 2022 to Non Final Office Action dated Mar. 3, 2022", 7 pgs.
"U.S. Appl. No. 17/080,088, Notice of Allowance dated Jun. 14, 2022", 11 pgs.
"U.S. Appl. No. 17/080,114, Notice of Allowance dated Jun. 14, 2022", 12 pgs.
"U.S. Appl. No. 17/108,517, Notice of Allowance dated Jun. 14, 2022", 10 pgs.
"U.S. Appl. No. 17/107,136, Notice of Allowance dated Jun. 23, 2022", 11 pgs.
"Declaration Under 37 C.F.R 1.132", (Jul. 14, 2020), 4 pgs.
"U.S. Appl. No. 17/107,136, Corrected Notice of Allowability dated Jul. 12, 2022", 7 pgs.

(56) References Cited

OTHER PUBLICATIONS

"U.S. Appl. No. 17/080,088, Corrected Notice of Allowability dated Jul. 12, 2022", 8 pgs.
"U.S. Appl. No. 17/108,517, Corrected Notice of Allowability dated Jul. 12, 2022", 6 pgs.

* cited by examiner

DRUG-COATED BALLOON CATHETERS FOR BODY LUMENS

CROSS-REFERENCE TO RELATED APPLICATIONS

This application is a continuation-in-part and claims the benefit of priority to international Patent Application Serial No. PCT/US2020/019274, filed Feb. 21, 2020, published on Aug. 27, 2020 as WO 2020/172560A1, which application claims the benefit of priority to U.S. Provisional Patent Application Ser. No. 62/809,048 filed Feb. 22, 2019, and to U.S. Provisional Patent Application Ser. No. 62/859,396 filed Jun. 10, 2019, the disclosures of which are incorporated herein in their entirety by reference.

This application is also a continuation-in-part of and claims the benefit of priority to U.S. patent application Ser. No. 16/986,683, filed Aug. 6, 2020, which application is a division of U.S. patent application Ser. No. 16/135,436, which is a continuation-in-part of international Application No. PCT/US2018/031083 filed May 4, 2018, which claims the benefit of priority to U.S. Provisional Patent Application Ser. No. 62/502,212 filed May 5, 2017. U.S. patent application Ser. No. 16/135,436 is also a continuation-in-part of U.S. patent application Ser. No. 15/568,614 filed Oct. 23, 2017, which is a U.S. National Stage Filing under 35 U.S.C. 371 from International Application No. PCT/US2016/028652 filed Apr. 21, 2016, which claims the benefit of priority to U.S. Provisional Patent Application Ser. No. 62/152,559 filed Apr. 24, 2015. U.S. patent application Ser. No. 16/135,436 is also a continuation-in-part of U.S. patent application Ser. No. 14/438,327 filed Apr. 24, 2015, which is a U.S. National Stage Filing under 35 U.S.C. 371 from International Application No. PCT/US2013/064842 filed. Oct. 14, 2013, which claims the benefit of priority to U.S. Provisional Patent Application Ser. No. 61/795,790 filed Oct. 26, 2012. The disclosures of all the applications in this paragraph are incorporated herein in their entirety.

The disclosure of U.S. patent application Ser. No. 16/135,472 is incorporated herein in its entirety.

BACKGROUND

Benign prostatic hyperplasia is a non-cancerous enlargement of the prostate gland, affecting more than 50% percent of men over the age of 60. The prostate early in life is the size and shape of a walnut and weighs about 20 grams. Prostate enlargement appears to be a normal process. With age, the prostate gradually increases in size to twice or more its normal size. As the prostate grows, it presses against and narrows the urethra, causing prostatic urethra compression and urinary obstruction that makes voiding difficult or impossible.

Male urethral stricture disease occurs at a rate as high as 0.6% in some populations. Urethral stricture diseases appear to be more common in the elderly population. Patients with urethral strictures experience moderate to severe complications, such as lower urinary tract voiding symptoms or urinary retention, recurrent urinary tract infection and the need for repeat urethral procedures such as dilation, urethrotomy, or urethroplasty.

Ureteral strictures of the upper urinary tract are either congenital or acquired. Most congenital ureteral strictures are located at the ureteropelvic junction. Most ureteral strictures are acquired and usually are iatrogenic. The most common etiology of the ureteral strictures is injury during endoscopic, open, or laparoscopic surgical procedures.

Bladder neck strictures (e.g., stenosis or contracture) and urethral strictures are recognized complications of all treatments for prostate cancer. Recalcitrant bladder neck strictures are relatively rare overall; however, these are associated with significant morbidity, often requiring multiple interventions with associated complications and impact upon quality of life. Bladder neck strictures and urethral strictures are complications following treatment for prostate cancer such as radical prostatectomy (RP), radiotherapy, cryotherapy, and high intensity focused ultrasound (HIFU).

Strictures in the digestive body lumen or the gastrointestinal tracts include esophageal strictures, achalasia strictures, biliary strictures, stomach strictures, small intestine strictures, duodenum strictures, jejunum strictures, ileum strictures, colon strictures, rectum strictures, and large intestine strictures. The type of disease classifies a stricture into benign or malignant.

A biliary stricture, also referred to as a bile duct stricture, occurs when the bile duct gets smaller or narrower. The bile duct is the tube that takes bile from the liver to the small intestine. When the bile duct becomes narrow, it makes it difficult for food to digest. Biliary strictures can be caused by any injuries to the bile duct, swelling, pancreatitis, intestinal injuries, and cancers in the bile duct or pancreas. The symptoms of the biliary stricture include pain, chills and fever, itching, and nausea or vomiting.

Esophageal strictures are a problem commonly encountered in gastroenterological medicine and can be caused by malignant or benign lesions. Dysphagia is the symptom experienced by all patients. Most of these patients require palliative treatment to relieve the dysphagia.

Gastrointestinal strictures are a narrowing of a section of the intestine that causes problems by slowing or blocking the movement of food through the area. The strictures are caused by recurrent inflammations, cancer, Crohn's disease, and ulcerative colitis. The strictures include esophageal strictures, achalasia strictures, strictures in stents, biliary strictures, stomach strictures, small intestine strictures, duodenum strictures, jejunum strictures, ileum strictures, colon strictures, rectum strictures, and large intestine strictures.

Chronic obstructive pulmonary disease (COPD) is a term used to classify two major airflow obstruction disorders: chronic bronchitis and emphysema. Approximately 16 million Americans have COPD, 80-90% of them were smokers throughout much of their lives. COPD is a leading cause of death in the U.S. Chronic bronchitis is inflammation of the bronchial airways. The bronchial airways connect the trachea with the lungs. When inflamed, the bronchial tubes secrete mucus, causing a chronic cough. Emphysema is an over-inflation of the alveoli, or air sacs in the lungs. This condition causes shortness of breath.

Asthma is a chronic respiratory disease characterized by inflammation of the airways, excess mucus production and airway hyper-responsiveness, and a condition in which airways narrow excessively or too easily respond to a stimulus. Asthma episodes or attacks cause narrowing of the airways, which make breathing difficult. Asthma attacks can have a significant impact on a patient's life, limiting participation in many activities. In severe cases, asthma attacks can be life threatening. Presently, there is no known cure for asthma.

Chronic sinusitis is an inflammation of the membrane lining of one or more paranasal sinuses. Chronic sinusitis lasts longer than three weeks and often continues for months. In cases of chronic sinusitis, there is usually tissue damage. According to the Center for Disease Control (CDC), thirty-seven million cases of chronic sinusitis are reported annually.

Radiation (e.g., radiotherapy) is used as one of mode of treatment for localized cancers. Localized cancer is the most commonly diagnosed cancer. The majority of patients are diagnosed in potentially curable early stages. Standard local treatment options include active surveillance, radical prostatectomy (RP) for prostate cancer, and, generally for all cancer treatments, radiotherapy (RT). Radiotherapy can be delivered via external beam (EBRT) or brachytherapy (BT). The side effects associated with each treatment can vary significantly. Localized cancers include prostate cancers, urethral cancers, ureteral cancers, esophageal cancers, biliary cancers, stomach cancers, small intestine cancers, duodenum cancers, jejunum cancers, ileum cancers, colon cancers, rectum cancers, large intestine cancers, and pulmonary cancers. The radiation treatment can create injury in adjacent health tissue, such as strictures. Radiation treatment-induced strictures can include urethral strictures, ureteral strictures, esophageal strictures, biliary tract strictures, stomach strictures, small intestine strictures, duodenum strictures, jejunum strictures, ileum strictures, colon strictures, rectum strictures, and large intestine strictures. Treatment of radiation-induced strictures can be complex and difficult. Due to the high survival rates, the number of prostate cancer survivors in the United States annually increased by 220,000 men up to almost 2.8 million in 2015, leaving a large number of men at risk for short- or long-term side effects of radiation therapy for prostate cancer treatment. The development of urethral strictures as a side effect of radiation therapy for prostate cancer treatment is particularly problematic.

An anastomosis is a connection or opening between two body structures that carry fluid. A surgical anastomosis is an anastomosis formed via a surgical technique to connect together two fluid-carrying body structures. An anastomotic stricture is a narrowing of an anastomosis. Anastomotic strictures are a common complication of surgical anastomoses and of various other surgical procedures. Anastomotic strictures are usually fibrotic and can be difficult to manage and treat. An anastomotic stricture can include a stricture in an anastomosis between two portions of the same body structure, or between two different body structures, wherein the body structure can be an esophagus, biliary tract, stomach, small intestine, duodenum, jejunum, ileum, colon, rectum, large intestine, colon, rectum, urethra, ureter, or bladder neck. An anastomotic stricture can be a colorectal stricture, a stricture after gastric bypass, an ileocolonic stricture, a gastrointestinal stricture, a J-pouch stricture, or a bladder neck stricture (e.g., stenosis). While balloon dilation has been shown to be a safe and effective nonsurgical method of managing anastomotic strictures, problems still remain, such as a need for repeated balloon dilations due to refractory or reoccurring anastomotic strictures.

Inflammatory bowel disease (IBD) includes Crohn's disease (CD) and ulcerative colitis (UC). Chrohn's disease- and ulcerative colitis-induced strictures are a common complication of inflammatory bowel disease and surgeries for the treatment thereof. Stricture rates for those suffering from inflammatory bowel disease range from 34% to 70% over time. Some of the strictures are refractory or reoccurring, which require repeated endoscopic dilation for treatment.

Eosinophilic esophagitis (EoE) is a chronic inflammatory disease. The symptoms of the disease include dysphagia and food impaction, and are often a consequence of esophageal strictures. Repeated endoscopic dilation of the esophageal fibrostenotic eosinophilic esophagitis strictures using bougie and balloon catheter is used for treatment of such strictures.

Barrett's disease, also called Barrett's esophagus, is a condition in which there is an abnormal (metaplastic) change in the mucosal cells lining the lower portion of the esophagus, from normal stratified squamous epithelium to simple columnar epithelium with interspersed goblet cells that are normally present only in the colon. This change is considered to be a premalignant condition because it is associated with a high incidence of further transition to esophageal adenocarcinoma, an often-deadly cancer.

Various minimally invasive methods used to treat various cancers, large colon polyps, and Barrett's esophagus are worldwide practice. The various minimally invasive methods are gaining favor over surgical procedures when the patients prefer to avoid a surgical operation. Several randomized controlled trials and meta-analyses have proven the clinical and oncological safety and effectiveness of the laparoscopic gastrectomy, robot-assisted gastrectomy, EMR (endoscopic mucosal resection) and ESD (endoscopic sub-mucosal dissection) in treatment of cancers and Barrett's esophagus of various stages. EMR (endoscopic mucosal resection) and ESD (endoscopic sub-mucosal dissection) are safe and effective for treatment of superficial cancers during the early stages, such as esophageal cancers, biliary cancers, stomach cancers, small intestine cancers, duodenum cancers, jejunum cancers, ileum cancers, colon cancers, rectum cancers, colorectal cancers, ileocolonic cancers, and gastrointestinal cancers. EMR and ESD are safe and effective for treatment of high-graded Barrett's esophagus. Laparoscopic gastrectomy, robot-assisted gastrectomy, EMR, and ESD are feasible procedures in terms of clinical and oncological safety; however, the recurrences of malignancy and refractory stricture were noted in some of patients. The local reoccurrence rate of cancers after minimally invasive treatments is in the range of 2-20%, depending on the type and stage of the cancer and on follow-up times. The occurrence rate of strictures or stenoses after minimally invasive procedures is about 26%-70%. Repeated endoscopic balloon dilations are needed to treat refractory or reoccurring strictures or stenoses.

SUMMARY OF THE INVENTION

In various embodiments, the present invention provides a balloon catheter. The balloon catheter can be used for treating, preventing, or reducing the recurrence of strictures and/or cancer in a non-vascular body lumen. The balloon catheter includes an elongated balloon. The balloon catheter includes a coating layer overlying an exterior surface of the balloon. The coating layer includes one or more water-soluble additives and an initial drug load of a therapeutic agent. In some embodiments, the balloon catheter also includes a length-control mechanism that stretches and elongates the balloon while the balloon is in a deflated state.

In various embodiments, the present invention provides a method of treating a target site in a non-vascular body lumen. The method can be a method of treating, preventing, or reducing the recurrence of a stricture and/or cancer, or for treating BPH, at a target site in a non-vascular body lumen. The method includes inserting a balloon catheter into a target site in the non-vascular body lumen. The balloon catheter includes an elongated balloon. The balloon catheter also includes a coating layer overlying an exterior surface of the balloon. The coating layer includes one or more water-soluble additives and an initial drug load of a therapeutic agent. The method includes inflating the balloon at the target site to contact the coating layer with walls of the body lumen at the target site until the balloon achieves an inflated balloon diameter for an inflation period. The method includes deflating the balloon after the inflation period. The method also includes withdrawing the balloon catheter from the body lumen.

In various embodiments, the present invention provides a method for treatment of a cancer treatment-induced non-vascular stricture. The method includes inserting a balloon catheter into a target site in a body lumen including the cancer treatment-induced non-vascular stricture, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the location of the cancer treatment-induced non-vascular stricture until the balloon achieves an inflated balloon diameter for an inflation period. The method includes deflating the balloon after the inflation period. The method includes withdrawing the balloon catheter from the body lumen. In some embodiments, the cancer treatment is radiation treatment. In some embodiments, the stricture is a urethral stricture, ureteral stricture, esophageal stricture, sinus stricture, stomach stricture, small intestine stricture, colon stricture, rectum stricture, large intestine stricture, bladder neck stricture, or a biliary tract stricture. In some embodiments, the cancer treatment is radiation treatment of the prostate, wherein the stricture is a bladder neck stricture. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for reducing the occurrence of or prevention of a cancer treatment-induced non-vascular stricture, or for reducing or preventing recurrence of cancer. The method includes inserting a balloon catheter into a target site in a body lumen, wherein the target site is at, proximate to, proximal to, or distal to a site of a performed cancer treatment, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the target site until the balloon achieves an inflated balloon diameter for an inflation period. The method includes deflating the balloon after the inflation period. The method includes withdrawing the balloon catheter from the body lumen. In some embodiments, the method further includes performing the cancer treatment of the body lumen at, proximate to, proximal to, or distal to the target site prior to the insertion of the balloon catheter into the target site. In some embodiments, a cancer treatment-induced non-vascular stricture is present at the target site, and the method further includes performing a stricturotomy at the target site prior to the insertion of the balloon catheter into the target site. In some embodiments, the stricturotomy includes needle knife electroincision, episiotomy, urethrotomy, direct vision internal urethrotomy (DVIU), endoscopic mucosal resection (EMR), or endoscopic sub-mucosal dissection (ESD). In some embodiments, the cancer treatment is radiation treatment. In some embodiments, wherein the stricture is a urethral stricture, ureteral stricture, esophageal stricture, sinus stricture, stomach stricture, small intestine stricture, colon stricture, rectum stricture, large intestine stricture, a bladder neck stricture, or a biliary tract stricture. In some embodiments, wherein the cancer treatment is radiation treatment of the prostate, wherein the stricture is a bladder neck stricture. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for treatment of a surgical anastomosis-induced non-vascular stricture. The method includes inserting a balloon catheter into a target site in a body lumen including the surgical anastomosis-induced non-vascular stricture, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the location of the surgical anastomosis-induced non-vascular stricture until the balloon achieves an inflated balloon diameter for an inflation period. The method includes deflating the balloon after the inflation period. The method includes withdrawing the balloon catheter from the body lumen. In some embodiments, the stricture is a fibrotic stricture. In some embodiments, the stricture is an esophageal stricture, stomach stricture, small intestine stricture, duodenum stricture, jejunum stricture, ileum stricture, colon stricture, rectum stricture, large intestine stricture, colorectal stricture, a stricture resulting from gastric bypass, ileocolonic stricture, gastrointestinal stricture, urethral stricture, ureteral stricture, J-pouch strictures, or a bladder neck stricture. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for reducing the occurrence of or prevention of a surgical anastomosis-induced non-vascular stricture. The method includes inserting a balloon catheter into a target site in a body lumen, wherein the target site is at a site of a performed surgical anastomosis, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the target site until the balloon achieves an inflated balloon diameter for an inflation period. The method includes deflating the balloon after the inflation period. The method includes withdrawing the balloon catheter from the body lumen. In some embodiments, the method further includes performing forming the surgical anastomosis at the target site prior to the insertion of the balloon catheter into the target site. In some embodiments, a surgical anastomosis-induced non-vascular stricture is present at the target site, and the method further includes performing a stricturotomy at the target site prior to the insertion of the balloon catheter into the target site. In some embodiments, the stricturotomy includes needle knife electroincision, episiotomy, urethrotomy, direct vision internal urethrotomy (DVIU), endoscopic mucosal resection (EMR), or endoscopic sub-mucosal dissection (ESD). In some embodiments, the stricture is a fibrotic stricture. In some embodiments, the stricture is an esophageal stricture, biliary stricture, stomach stricture, small intestine stricture, duodenum stricture, jejunum stricture, ileum stricture, colon stricture, rectum stricture, large intestine stricture, colorectal stricture, a stricture resulting from gastric bypass, ileocolonic stricture, gastrointestinal stricture, urethral stricture, ureteral stricture, J-pouch strictures, or a bladder neck stricture. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for treatment of an inflammatory disease-induced non-vascular stricture. The method includes inserting a balloon catheter into a target site in a body lumen including the inflammatory disease-induced non-vascular stricture, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the location of the inflammatory disease-induced non-vascular stricture until the balloon achieves an inflated balloon diameter for an inflation period. The method includes deflating the balloon after the inflation period. The method includes withdrawing the balloon catheter from the body lumen. In some embodiments, the inflammatory disease is Crohn's disease. In some embodiments, the inflammatory disease is ulcerative colitis. In some embodiments, the stricture is a small intestine stricture, duodenum stricture, jejunum stricture, ileum stricture, colon stricture, rectum stricture, large intestine stricture, colorectal stricture, ileocolonic stricture, or gastrointestinal stricture. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for reducing the occurrence of or prevention of an inflammatory disease treatment-induced non-vascular stricture. The method includes inserting a balloon catheter into a target site in a body lumen, wherein the target site is at a site of a performed inflammatory disease treatment, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the target site until the balloon achieves an inflated balloon diameter for an inflation period. The method includes deflating the balloon after the inflation period. The method includes withdrawing the balloon catheter from the body lumen. In some embodiments, the method further includes performing the inflammatory disease treatment at the target site prior to the insertion of the balloon catheter into the target site. In some embodiments, an inflammatory disease treatment-induced stricture is present at the target site, and the method further includes performing a stricturotomy at the target site prior to the insertion of the balloon catheter into the target site. In some embodiments, the strictrotomy includes needle knife electroincision, or endoscopic mucosal resection (EMR). In some embodiments, the inflammatory disease is Crohn's disease. In some embodiments, the inflammatory disease is ulcerative colitis. In some embodiments, the stricture is a small intestine stricture, duodenum stricture, jejunum stricture, ileum stricture, colon stricture, rectum stricture, large intestine stricture, colorectal stricture, ileocolonic stricture, or gastrointestinal stricture. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for treatment of a gastrectomy-induced non-vascular stricture. The method includes inserting a balloon catheter into a target site in a body lumen including the gastrectomy-induced non-vascular stricture, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the location of the gastrectomy-induced non-vascular stricture until the balloon achieves an inflated balloon diameter for an inflation period. The method includes deflating the balloon after the inflation period. The method includes withdrawing the balloon catheter from the body lumen. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for reducing the occurrence of or prevention of a gastrectomy-induced non-vascular stricture. The method includes inserting a balloon catheter into a target site in a body lumen, wherein the target site is at a site of a performed gastrectomy, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the target site until the balloon achieves an inflated balloon diameter for an inflation period. The method includes deflating the balloon after the inflation period. The method includes withdrawing the balloon catheter from the body lumen. In some embodiments, the method further includes performing the gastrectomy at the target site prior to the insertion of the balloon catheter into the target site. In some embodiments, a gastrectomy-induced non-vascular stricture is present at the target site, and the method further includes performing a stricturotomy at the target site prior to the insertion of the balloon catheter into the target site. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for treatment of a needle knife electroincision-, episiotomy-, urethrotomy-, direct vision internal urethrotomy (DVIU)-, endoscopic mucosal resection (EMR)-, or endoscopic sub-mucosal dissection (ESD)-induced non-vascular stricture. The method includes inserting a balloon catheter into a target site in a body lumen including the needle knife electroincision-, episiotomy-, urethrotomy-, direct vision internal urethrotomy (DVIU)-, endoscopic mucosal resection (EMR)-, or endoscopic sub-mucosal dissection (ESD)-induced non-vascular stricture, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the location of the needle knife electroincision-, urethrotomy-, direct vision internal urethrotomy (DVIU)-, EMR (endoscopic mucosal resection)-, or endoscopic sub-mucosal dissection (ESD)-induced non-vascular stricture until the balloon achieves an inflated balloon diameter for an inflation period. The method includes deflating the balloon after the inflation period. The method includes withdrawing the balloon catheter from the body lumen. In some embodiments, the electroincision, episiotomy, endoscopic mucosal resection (EMR), or endoscopic sub-mucosal dissection (ESD) is a treatment for esophageal cancer, biliary cancer, stomach cancer, small intestine cancer, duodenum cancer, jejunum cancer, ileum cancer, colon cancer, rectum cancer, colorectal cancer, ileocolonic cancer, or gastrointestinal cancers. In some embodiments, the electroincision, episiotomy, endoscopic mucosal resection (EMR), or endoscopic sub-mucosal dissection (ESD) is a treatment for removing polyps from the colon, wherein the stricture is a colon stricture. In some embodiments, the electroincision, episiotomy, endoscopic mucosal resection (EMR), or endoscopic sub-mucosal dissection (ESD) is a treatment for Barrett's esophagus and wherein the stricture is an esophageal stricture. In some embodiments, the stricture is an esophageal stricture, biliary stricture, small intestine stricture, duodenum stricture, jejunum stricture, ileum stricture, colon stricture, rectum stricture, colorectal stricture, ileocolonic stricture, or gastrointestinal stricture. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for reducing the occurrence of or prevention of a needle knife electroincision-, episiotomy-, urethrotomy-, direct vision internal urethrotomy (DVIU)-, endoscopic mucosal resection (EMR)-, or endoscopic sub-mucosal dissection (ESD)-induced non-vascular stricture. The method includes inserting a balloon catheter into a target site (e.g., a resected site) in a body lumen, wherein the target site is at a site of a performed needle knife electroincision, episiotomy, urethrotomy, DVIU, EMR, or ESD, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the target site until the balloon achieves an inflated balloon diameter for an inflation period. The method includes deflating the balloon after the inflation period. The method includes withdrawing the balloon catheter from the body lumen. In some embodiments, the method further includes performing the needle knife electroincision, episiotomy, urethrotomy, DVIU, EMR, or ESD at the target site prior to the insertion of the balloon catheter into the target site. In some embodiments, the target site includes a needle knife electroincision-, episiotomy-, urethrotomy-, direct vision internal urethrotomy (DVIU)-, endoscopic mucosal resection (EMR)-, or endoscopic sub-mucosal dissection (ESD)-induced non-vascular stricture, and the method further includes performing a stricturotomy at the target site prior to the insertion of the balloon catheter into the target site. In some embodiments, the electroincision, episiotomy, urethrotomy, direct vision internal urethrotomy (DVIU), endoscopic mucosal resection (EMR), or endoscopic sub-mucosal dissection (ESD) is a treatment for esophageal cancer, biliary cancer, stomach cancer, small intestine cancer, duodenum cancer, jejunum cancer, ileum cancer, colon cancer, rectum cancer, colorectal cancer, ileocolonic cancer, or gastrointestinal cancers. In some embodiments, the electroincision, episiotomy, urethrotomy, direct vision internal urethrotomy (DVIU), endoscopic mucosal resection (EMR), or endoscopic sub-mucosal dissection (ESD) is a treatment for Barrett's esophagus and wherein the resected site is an esophageal stricture. In some embodiments, the target site or resected site is an esophageal site, biliary site, small intestine site, duodenum site, jejunum site, ileum site, colon site, rectum site, colorectal site, ileocolonic site, or gastrointestinal site. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for treatment of a bladder neck stricture. The method includes inserting a balloon catheter into a target site in a body lumen including the bladder neck stricture, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the location of the bladder neck stricture until the balloon achieves an inflated balloon diameter for an inflation period. The method includes deflating the balloon after the inflation period. The method includes withdrawing the balloon catheter from the body lumen. In some embodiments, the bladder neck stricture is fibrotic. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for reducing the occurrence of or prevention of a prostate cancer treatment- or stricturotomy-induced bladder neck stricture. The method includes inserting a balloon catheter into a target site in a body lumen, wherein the target site is in a bladder neck and is at, proximate to, proximal to, or distal to a site of a prostate cancer treatment or stricturotomy, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the target site until the balloon achieves an inflated balloon diameter for an inflation period. The method includes deflating the balloon after the inflation period. The method includes withdrawing the balloon catheter from the body lumen. In some embodiments, the method further includes performing the prostate cancer treatment or stricturotomy prior to the insertion of the balloon catheter into the target site. In some embodiments, the stricturotomy includes needle knife electroincision, episiotomy, urethrotomy, direct vision internal urethrotomy (DVIU-, endoscopic mucosal resection (EMR), or endoscopic sub-mucosal dissection (ESD). In some embodiments, the target site includes a prostate cancer treatment- or stricturotomy-induced bladder neck stricture, and the method further includes performing a stricturotomy prior to the insertion of the balloon catheter into the target site. In some embodiments, the prostate cancer treatment includes radical prostatectomy (RP), radiotherapy, cryotherapy, or high intensity focused ultrasound (HIFU). In some embodiments, the bladder neck stricture is fibrotic. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for treatment of an esophageal fibrostenotic stricture of eosinophilic esophagitis. The method includes inserting a balloon catheter into a target site in a body lumen including the esophageal fibrostenotic stricture of eosinophilic esophagitis, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the location of the esophageal fibrostenotic stricture of eosinophilic esophagitis until the balloon achieves an inflated balloon diameter for an inflation period. The method includes deflating the balloon after the inflation period. The method includes withdrawing the balloon catheter from the body lumen. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for treatment of achalasia. The method includes inserting a balloon catheter into a target site in a body lumen including the lower esophageal sphincter, the balloon catheter including an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the location of the lower esophageal sphincter until the balloon achieves an inflated balloon diameter for an inflation period. The method includes deflating the balloon after the inflation period. The method includes withdrawing the balloon catheter from the body lumen. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for treatment of benign prostatic hyperplasia (BPH). The method includes inserting a balloon catheter into a target site in a body lumen that is the prostatic urethra. The balloon catheter includes an elongated balloon. The balloon catheter also includes a coating layer overlying an exterior surface of the balloon. The coating layer includes one or more water-soluble additives and an initial drug load of a therapeutic agent. The method includes inflating the balloon at the target site to contact the coating layer with walls of the body lumen at the location of the prostatic urethra until the balloon achieves an inflated balloon diameter for an inflation period. The method includes deflating the balloon after the inflation period. The method includes withdrawing the balloon catheter from the body lumen.

In various embodiments, the present invention provides a method for treatment of a urethral stricture that is a trauma-induced stricture, an idiopathic stricture, and/or an iatrogenic stricture. The method includes inserting a balloon catheter into a target site in a body lumen including the urethral stricture. The balloon catheter includes an elongated balloon. The balloon catheter also includes a coating layer overlying an exterior surface of the balloon. The coating layer includes one or more water-soluble additives and an initial drug load of a therapeutic agent. The method includes inflating the balloon at the target site to contact the coating layer with walls of the body lumen at the target site until the balloon achieves an inflated balloon diameter for an inflation period. The method includes deflating the balloon after the inflation period. The method also includes withdrawing the balloon catheter from the body lumen.

In various embodiments, the present invention provides a method of treating a target site in a non-vascular body lumen. The method includes inserting an uncoated balloon catheter into the non-vascular body lumen to the target site. The method includes inflating the uncoated balloon catheter at the target site to contact with walls of the body lumen at the target site until the balloon achieves an inflated balloon diameter for an inflation period. The method includes deflating the uncoated balloon after the inflation period. The method includes withdrawing the uncoated balloon catheter from the body lumen. The method includes flushing the target site with water or saline. The method includes inserting a balloon catheter into the target site. The balloon catheter includes an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the target site until the balloon achieves an inflated balloon diameter for an inflation period. The method includes deflating the balloon after the inflation period. The method includes withdrawing the balloon catheter from the body lumen. The method also includes using a scope in the body lumen including the target site to visualize the insertion of the drug-coated balloon catheter to the target site, the inflation of the drug-coated balloon at the target site, the deflation of the drug-coated balloon at the target site, or a combination thereof.

In various embodiments, the present invention provides method of treating a target site in a non-vascular body lumen. The method includes performing a needle knife electroincision-, episiotomy-, urethrotomy-, direct vision internal urethrotomy (DVIU)-, endoscopic mucosal resection (EMR)-, or endoscopic sub-mucosal dissection (ESD) on the target site. The method includes flushing the target site with water or saline. The method includes inserting a balloon catheter into the target site in the non-vascular body lumen. The balloon catheter includes an elongated balloon, and a coating layer overlying an exterior surface of the balloon, wherein the coating layer includes one or more water-soluble additives and an initial drug load of a therapeutic agent. The method includes inflating the balloon at the target site to contact the coating layer with walls of the body lumen at the target site until the balloon achieves an inflated balloon diameter for an inflation period. The method includes deflating the balloon after the inflation period. The method includes withdrawing the balloon catheter from the body lumen. The method also includes using a scope in the body lumen including the target site to visualize the insertion of the drug-coated balloon catheter to the target site, the inflation of the drug-coated balloon at the target site, the deflation of the drug-coated balloon at the target site, or a combination thereof.

Various embodiments of the present invention provide a method of treating benign prostatic hyperplasia (BPH). The method includes inserting a first sheath comprising a pre-dilation balloon catheter into the urethra, the pre-dilation balloon catheter comprising a pre-dilation balloon. The method includes removing the first sheath from the urethra while leaving the pre-dilation catheter in the urethra. The method includes inserting a cystoscope into the urethra. The method includes using the cystoscope to visualize placement of the pre-dilation balloon in the prostatic urethra. The method includes inflating the pre-dilation balloon to dilate the prostatic urethra with the pre-dilation balloon to form an initial commissurotomy of the prostatic urethra. The method includes deflating the pre-dilation balloon. The method includes using the cystoscope to verify that the pre-dilation balloon has created the initial commissurotomy. The method includes removing the cystoscope from the urethra. The method includes reinserting the first sheath into the urethra over the pre-dilation balloon catheter. The method includes pulling the pre-dilation balloon into the first sheath. The method includes removing the first sheath comprising the pre-dilation balloon catheter from the urethra. The method includes inserting a second sheath comprising a drug-coated balloon catheter into the urethra, the drug-coated balloon catheter comprising a drug-coated balloon, the drug-coated balloon comprising a coating layer overlying an exterior surface thereof, the coating layer comprising one or more water-soluble additives and an initial drug load of a therapeutic agent. The method includes removing the second sheath from the urethra while leaving the drug-coated balloon catheter in the urethra. The method includes inserting a cystoscope into the urethra. The method includes using the cystoscope to visualize placement of the drug-coated balloon in the prostatic urethra. The method includes inflating the drug-coated balloon to contact the coating layer with the prostatic urethra. The method includes removing the cystoscope from the urethra. The method includes maintaining the drug-coated balloon in an inflated state for at least 5 minutes. The method includes deflating the drug-coated balloon. The method includes reinserting the second sheath into the urethra over the drug-coated balloon catheter. The method includes pulling the drug-coated balloon into the second sheath. The method also includes removing the second sheath comprising the drug-coated balloon catheter from the urethra.

In various embodiments, the present invention provides a method of treating benign prostatic hyperplasia (BPH). The method includes inserting a first sheath into the urethra. In one embodiment the first sheath contains optics to allow visualization for proper placement during insertion. In another embodiment the first sheath has an obturator to facilitate insertion. The method includes inserting a pre-dilation balloon catheter comprising a pre-dilation balloon into the first sheath until the pre-dilatation balloon is in the prostatic urethra and then removing the first sheath. A guidewire may be used to facilitate sheath tracking. The method includes removing the first sheath. The method includes inserting a cystoscope into the urethra side-by-side with the pre-dilation balloon catheter. The method includes using the cystoscope to visualize placement of the pre-dilation balloon in the prostatic urethra. The method includes inflating the pre-dilation balloon to dilate the prostatic urethra with the pre-dilation balloon to form an initial commissurotomy of the prostatic urethra. The method includes deflating the pre-dilation balloon. The method includes using the cystoscope to verify that the pre-dilation balloon has created the initial commissurotomy. The method includes removing the cystoscope from the urethra. The method includes re-inserting the first sheath over the pre-dilation balloon and pulling the pre-dilation balloon into the first sheath. The method includes either removing the pre-dilation balloon from the first sheath while leaving the first sheath in place, wherein the first sheath is a second sheath; or removing the pre-dilation balloon and the first sheath from the urethra, and inserting the second sheath which contains a cystoscope or obturator into the urethra (e.g., wherein the second sheath is the same as or different than the first sheath). If a second sheath was used, the method includes removing the cystoscope or obturator after the second sheath is properly positioned. A guidewire may be used to facilitate sheath tracking. The method includes inserting a drug-coated balloon catheter into the second sheath, the drug-coated balloon catheter comprising a drug-coated balloon, the drug-coated balloon comprising a coating layer overlying an exterior surface thereof, the coating layer comprising one or more water-soluble additives and an initial drug load of a therapeutic agent. The method includes removing the second sheath from the urethra. The method includes inserting a cystoscope into the urethra side-by-side with the drug-coated balloon catheter. The method includes using the cystoscope to visualize placement of the drug-coated balloon in the prostatic urethra. The method includes inflating the drug-coated balloon to contact the coating layer with the prostatic urethra. The method includes removing the cystoscope from the urethra. The method includes maintaining the drug-coated balloon in an inflated state for at least 5 minutes. The method includes deflating the drug-coated balloon. The method includes inserting the second sheath over the drug-coated balloon and pulling the drug-coated balloon into the second sheath. The method includes removing the second sheath comprising the drug-coated balloon catheter from the urethra.

In various embodiments, the present invention provides a method for treating a radiation-induced stricture. The method includes optionally pre-dilating the radiation-induced stricture with a pre-dilation balloon with a smaller nominal diameter than a balloon catheter, or performing a stricturotomy on the radiation-induced stricture. The method includes optionally flushing the radiation-induced stricture with water, saline solution or a water solution including at least one water soluble additive. The method includes inserting the balloon catheter into a target site in the radiation stricture. The balloon catheter includes a balloon, and a coating layer overlying external surfaces of the balloon. The coating layer includes at least one water-soluble additive and a therapeutic agent with an initial drug load of from 1 to 6 micrograms of the therapeutic agent per square millimeter of the balloon. The therapeutic agent is chosen from paclitaxel, taxol, docetaxel, rapamycin, sirolimus, zotarolimus, tacrolimus, everolimus, mTOR inhibitors, or their analogues, and combinations thereof. The water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof. The ratio by weight of the therapeutic agent in the coating layer to the total weight of the one or more water-soluble additives in the coating layer is from about 0.05 to 20. The method includes inflating the balloon until the coating layer contacts walls of the radiation-induced stricture at the target site and the balloon achieves an inflated balloon diameter for an inflation period. The method includes deflating the balloon after the inflation period, wherein the inflation period is from 0.1 minutes to 10 minutes. The method includes withdrawing the balloon catheter from radiation-induced stricture. The method includes optionally using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The stretch ratio at the location of treatment is about 1.0 to about 40. The radiation-induced stricture includes a urethral stricture, ureteral stricture, esophageal stricture, sinus stricture, stomach stricture, small intestine stricture, colon stricture, rectum stricture, large intestine stricture, or a biliary tract stricture.

In various embodiments, the drug-coating on the balloon catheter can prevent or reduce the occurrence of strictures at the treatment site, can prevent or reduce the occurrence of cancer or malignancy at the treatment site, can treat BPH, or a combination thereof.

BRIEF DESCRIPTION OF THE FIGURES

The drawings illustrate generally, by way of example, but not by way of limitation, various embodiments of the present invention.

DETAILED DESCRIPTION OF THE INVENTION

Figure 1A:
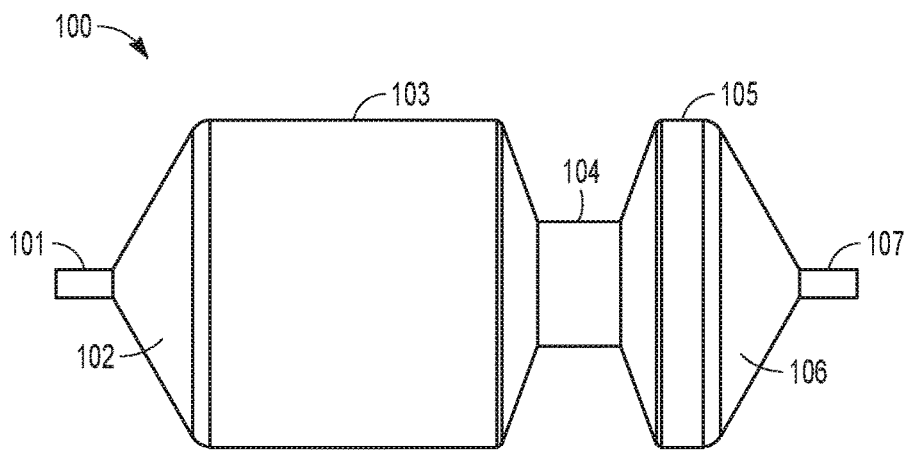
FIG. 1A illustrates a balloon catheter having one neck section, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

One aspect of various embodiments of the invention is to deliver a therapeutic agent such as paclitaxel, taxol, docetaxel, rapamycin, sirolimus, zotarolimus, tacrolimus, everolimus, mTOR inhibitors, or their analogues, to the wall of a body lumen to treat or prevent a narrowing or stricture. These drugs can be considered anti-inflammatory or antiproliferative drugs. The stricture can be in a vascular lumen (e.g., a vascular stenosis in a coronary artery or a peripheral artery) or the stricture can be in a nonvascular lumen. The drug can be a water-insoluble drug.

The antimicrobial properties of various fatty acids and monoglycerides of C8-C12 fatty acids have been investigated for many years. The studies have confirmed that both fatty acids and monoglycerides can inhibit the growth of numerous types of bacteria and viruses. The coating formulation of the present invention can include various fatty acids and monoglycerides of C8-C12 fatty acids, such as caprylic acid, monocaprilin, capric acid, monocaprin, lauric acid and monolaurin, as one of the additives for the treatment of various diseases.

Causes of nonvascular body lumen strictures, and related nonvascular diseases, such as benign prostatic hyperplasia (BPH), urethral strictures, ureteral strictures, prostate cancer, esophageal strictures, achalasia strictures, strictures in stents, biliary tract strictures, stomach strictures, small intestine strictures, duodenum strictures, jejunum strictures, ileum strictures, colon strictures, rectum strictures, large intestine strictures, colorectal strictures, strictures after gastric bypass, ileocolonic strictures, gastrointestinal strictures, J-pouch strictures, bladder neck strictures (stenosis), fibrostenotic eosinophilic esophagitis strictures, Crohn's disease (CD)- and ulcerative colitis (UC)-induced strictures, radiation-induced strictures, endoscopic resection (EMR and ESD)-induced stricture, surgery-related anastomotic strictures, achalasia strictures, gastrectomy-induced strictures, and asthma and chronic obstructive pulmonary disease (COPD), can include cancer, infections and inflammations by pathogens such as bacteria and viruses, radiotherapy, laparoscopic gastrectomy, robot-assisted gastrectomy, EMR (endoscopic mucosal resection), ESD (endoscopic sub-mucosal dissection), surgically-formed anastomosis, or an inflammatory disease. Various embodiments of the present invention provide delivery of coating formulations to the stricture that contain drugs and additives which have properties that kill and inhibit bacteria and viruses.

The present invention provides new methods for treatment of body lumen strictures to have a long term and persistent effect. The new methods open the lumen and prevent, reduce, or minimize re-narrowing and recurrent strictures. The methods involve delivering of therapeutic agents such as anti-inflammatory and antiproliferative drugs (e.g., paclitaxel, taxol, docetaxel, rapamycin, sirolimus, zotarolimus, tacrolimus, everolimus, mTOR inhibitors, or their analogues) and one or more water-soluble additives to a target tissue.

Embodiments of the present invention provide a medical device coating formulation including a drug for treatment of the strictures in nonvascular body lumens, and additives that enhance absorption of the drug into tissue of body lumens. The additives can have antibacterial and antiviral properties. The balloon catheter includes a coating layer overlying an exterior surface of the balloon, wherein the coating layer includes one or more water-soluble additives and an initial drug load of an antiproliferative therapeutic agent.

By coating the exterior surface of the balloon catheter, for example, with a layer including a therapeutic agent and additives, it is useful in solving problems associated with using the one or more therapeutic agents in a drug coating. For example, the additive can have a hydrophilic part and a drug affinity part. The drug affinity part can be a hydrophobic part and/or can have an affinity to the therapeutic agent by hydrogen bonding and/or van der Waals interactions. Surprisingly, additives according to embodiments of the present invention which include a hydrophilic part and a drug affinity part, in combination with an antiproliferative therapeutic agent, form an effective drug delivery coating on a medical device without the use of oils and lipids, thereby avoiding the lipolysis dependence and other disadvantages of conventional oil-based coating formulations. Moreover, the additives according to embodiments of the present invention facilitate rapid drug elution and superior permeation of drug into tissues at a disease site. Thus, coatings according to embodiments of the present invention provide an enhanced rate and/or extent of absorption of the antiproliferative therapeutic agent in nonvascular diseased tissues or nonvascular body lumens. In embodiments of the present invention, the coated device delivers antiproliferative therapeutic agent to nonvascular tissues during a very brief deployment time of less than 10 minutes, less than 2 minutes, and reduces re-narrowing and reoccurring of the strictures of a nonvascular body lumen.

Various embodiments of the present invention relate to a medical device for delivering a therapeutic agent to strictures of vascular or nonvascular body lumen, the device including a layer overlying an exterior surface of the medical device. The device includes one of a balloon catheter, a fixed wire balloon catheter, over-the-wire balloon catheter, rapid exchange balloon catheter, a perfusion balloon catheter, a spaced double balloon, a cutting balloon catheter, a scoring balloon catheter, or an infusion catheter (e.g., a distal perforated drug infusion tube, a perforated balloon, spaced double balloon, porous balloon, or a weeping balloon). The balloon catheter includes an elongated balloon having a narrowed diameter middle section. The balloon catheter includes at least one neck section on the balloon including a smaller diameter than the main diameter, the at least one neck section dividing the balloon into at least two main sections each having a diameter equal to the main diameter or different than the main diameter. In some embodiments, the balloon catheter includes a cylindrical balloon that does not have a neck section. Further, the nonvascular lumen or nonvascular stricture includes one of esophagus, airways, sinus, trachea, colon, biliary tract, stomach, small intestine, duodenum, jejunum, ileum, rectum, large intestine, urinary tract, prostate, urethra, ureter, and other nonvascular lumens. Vascular lumens include arteries, veins, or any lumens with blood. Nonvascular lumens include those lumens without blood. The balloon catheters shafts and balloon materials can be constructed of polyether-amide block copolymers, polyamides, nylons, polyethylene terephthalate, or a combination thereof. The balloon catheter shaft can include a rigid material such as stainless steel, polycarbonate, titanium, polyether ether ketone (PEEK), any other rigid biocompatible material, or a combination thereof.

In some embodiments, the additive is at least one of a surfactant and a chemical compound. A coating layer overlying the exterior of the medical device can include one or more water-soluble additives. A coating layer overlying the exterior of the medical device can include one or more water-soluble additives (e.g., a water-soluble first additive, a water-soluble second additive, and a water-soluble third additive).

The medical device can further include a dimethylsulfoxide solvent layer, wherein the dimethylsulfoxide solvent layer is overlying the exterior surface of the medical device.

The device can be capable of releasing the therapeutic agent and the additive and delivering therapeutic agent to the tissue in about 0.1 to 10 minutes. The concentration of the therapeutic agent in the layer can be from 1 to 20 $\mu g/mm^2$, measured when the balloon is inflated to nominal diameter. The concentration of the therapeutic agent in the layer can be from 2 to 10 $\mu g/mm^2$.

In some embodiments, the additives can enhance release of the therapeutic agent off the balloon. The additive can enhance penetration and absorption of the therapeutic agent in tissue. The additive can have a water and ethanol solubility of at least 1 mg/mL and the therapeutic agent can be water-insoluble.

The layer overlying the exterior surface of the medical device can include a therapeutic agent and at least two additives, wherein each of the additives includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein each additive is soluble in polar organic solvent and is soluble in water. In one aspect of this embodiment, the polar organic solvent is chosen from methanol, ethanol, isopropanol, acetone, dimethylformide, tetrahydrofuran, methylethyl ketone, dimethylsulfoxide, acetonitrile, ethyl acetate, and chloroform and mixtures of these polar organic solvents with water. In another aspect of this embodiment, the device further includes a top layer overlying the surface of the layer overlying the exterior surface of the medical device to reduce loss of drug during transit through a body to the target tissue.

In some embodiments, the additive reduces crystal size and number of particles of the therapeutic agent, and wherein the additive is water-soluble, and the therapeutic agent is not water-soluble. The additive can have a fatty chain of an acid, ester, ether, or alcohol, wherein the fatty chain can directly insert into lipid membrane structures of the tissue. The additive can penetrate into and rearrange lipid membrane structures of the tissue. The additive can have one or more functional groups which have affinity to the drug by hydrogen bonding and/or van der Waals interactions. In some embodiments, the additive can be at least one of a surfactant and a chemical compound, and wherein the chemical compound has a molecular weight of 50 to 750 g/mol (e.g., 50 g/mol or more, or less than, equal to, or greater than 75 g/mol, 100, 125, 150, 175, 200, 225, 250, 275, 300, 325, 350, 375, 400, 425, 450, 475, 500, 525, 550, 575, 600, 625, 650, 675, 700, 725 g/mol, or 750 g/mol or less. The chemical compound can have more than four hydroxyl groups. In some embodiments, the chemical compound having more than four hydroxyl groups has a melting point of 120° C. or less, and the chemical compound is an alcohol or an ester. In some embodiments, the therapeutic agent is not water soluble.

The medical device coating for delivering a drug to a nonvascular tissue or nonvascular stricture that can be prepared from a mixture. The coating can be prepared from a mixture including an organic phase containing drug particles dispersed therein and an aqueous phase containing a water-soluble additive. The water-soluble additive can be chosen from polyethylene glycol, polyvinyl alcohol, polyvinylpyrrolidinone, polypeptides, water-soluble surfactants, water-soluble vitamins, and proteins. The preparation of the mixture can include homogenization under high shear conditions and optionally under pressure.

The coating layer overlying an exterior surface of the medical device can consists essentially of the therapeutic agent and the additive. The coating layer overlying an exterior surface of the medical device can consists essentially of a therapeutic agent, a water-soluble first additive and a water-soluble second additive. The coating overlying an exterior surface of the medical device can consist essentially of a therapeutic agent, and one or more water-soluble additives (e.g., a water-soluble first additive, a water-soluble second additive, and a water-soluble third additive).

In some embodiments, a method for treating a stricture in a nonvascular body lumen includes inserting a balloon catheter including a coating layer into an body stricture, wherein the stricture is one of urethral strictures, benign prostatic hyperplasia (BPH) strictures, ureteral strictures, esophageal strictures, achalasia strictures, biliary strictures, stomach strictures, small intestine strictures, duodenum strictures, jejunum strictures, ileum strictures, colon strictures, rectum strictures, strictures in stents, large intestine strictures, sinus strictures, colorectal strictures, strictures after gastric bypass, ileocolonic strictures, gastrointestinal strictures, J-pouch strictures, bladder neck strictures (e.g., stenosis), fibrostenotic eosinophilic esophagitis strictures, Crohn's disease (CD)- and ulcerative colitis (UC)-induced strictures, radiation-induced strictures, endoscopic resection (EMR and ESD)-induced strictures, achalasia strictures, gastrectomy-induced strictures, and surgery-related anastomotic strictures, wherein the coating layer includes a drug and an additive, inflating the balloon catheter and releasing the drug to a wall of the stricture, deflating the balloon; and withdrawing the balloon catheter, wherein the residual drug can be about 1 to 70% of the total loading drug on the balloon catheter. In one aspect of this embodiment, the additive enhances absorption of the drug into tissue of the nonvascular body lumen.

Some drugs for use in various embodiments that are considered particularly suitable for the airway, sinus and other nasal lumens are corticosteroids such as, budesonide, flunisolide, triamcinolone, beclomethasone, fluticasone, mometasone, mometasone furoate, dexamethasone, hydrocortisone, methylprednisolone, prednisone, cortisone, betamethasone, triamcinolone acetonide, or the like.

Various embodiments relate to a method for treating a stricture in a nonvascular body lumen and can include flushing the lumen with water, saline solution, or water solutions of the additives described herein, inserting a balloon catheter including a coating layer into a body lumen, wherein the coating layer includes a drug and an additive, inflating the balloon catheter and releasing the drug to a wall of the body lumen, deflating the balloon, and withdrawing the balloon catheter. A method for treating a stricture in a nonvascular body lumen can include infusing water, saline solution, or a water solution including at least one of the additives described herein, inserting a balloon catheter including a coating layer into a stricture in a nonvascular body lumen, wherein the stricture in the nonvascular body lumen is one of, urethral strictures, ureteral strictures, esophageal strictures, achalasia strictures, strictures in stents, sinus strictures, stomach strictures, small intestine strictures, duodenum strictures, jejunum strictures, ileum strictures, rectum strictures, large intestine strictures, and biliary tract strictures, wherein the coating layer includes a drug and an additive, inflating the balloon catheter and releasing the drug to a wall of the stricture in a nonvascular body lumen, deflating the balloon, and withdrawing the balloon catheter. In one aspect of this embodiment, the additive enhances absorption of the drug into tissue of the nonvascular body lumens. In another aspect of this embodiment, the additive includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions. In another aspect of this embodiment, the drug is chosen from paclitaxel, docetaxel, taxol and analogues thereof and rapamycin, sirolimus, zotarolimus, everolimus, tacrolimus and analogues thereof. In another aspect of this embodiment, the additive is chosen from PEG-fatty acids and PEG-fatty acid mono and diesters, polyethylene glycol glycerol fatty acid esters, alcohol-oil transesterification products, polyglyceryl fatty acids, propylene glycol fatty acid esters, sterol and derivatives thereof, polyethylene glycol sorbitan fatty acid esters, polyethylene glycol alkyl ethers, sugars and derivatives thereof, polyethylene glycol alkyl phenols, polyoxyethylene-polyoxypropylene block copolymers, sorbitan fatty acid esters, fat-soluble vitamins and salts thereof, water-soluble vitamins and amphiphilic derivatives thereof, amino acid and salts thereof, oligopeptides, peptides and proteins, and organic acids and esters and anhydrides thereof. In yet another aspect of this embodiment, the drug can be released to the wall of the airway prior to, during, or after an asthma attack. In yet another aspect of this embodiment, the drug can be released to the wall of the esophagus. In yet another aspect of this embodiment, the drug can be released to the wall of the sinus. In yet another aspect of this embodiment, the drug can be released to the wall of the biliary tract. In yet another aspect of this embodiment, the drug can be released to the wall of the urinary tract, prostate, urethral, and ureteral lumens. In yet another aspect of this embodiment, the drug can be released to the wall of the stomach, small intestine, duodenum, jejunum, ileum, colon, rectum, or large intestine. In another embodiment of this embodiment, the drug can be released to the wall of the nonvascular stricture in the stent.

In various embodiments, the present invention provides a method for treating a body lumen including inserting a balloon catheter, such as any balloon catheter described herein, to a target site in a body lumen. The method includes inserting the balloon catheter of FIG. 1A, 1B, 1C, 2, 3, 5A-5D, or 7A-7C to a target site in the body lumen. The method can include inserting the balloon catheter and a scope to a target site in the body lumen side by side or with the balloon catheter in the lumen of the scope. The scope can be an endoscope, enteroscope, colonoscope, sigmoidoscope, rectoscope, anoscope, rhinoscope, bronchoscope, or a cystoscope. The scope can be used to ensure that the balloon catheter is properly positioned within the targeted lumen. The method can include, prior to, during, or after the insertion of the balloon to the target site, flushing the body lumen with water, saline solution, or a water solution including at least one water soluble additive. The method includes inflating the balloon until the coating layer contacts walls of the stricture in the body lumen at the target site and the balloon achieves an inflated balloon diameter for an inflation period. Feature (a), or (b), or (c), or (a) and (b), or (a) and (c), or (b) and (c), or (a) and (b) and (c), are present: (a) the ratio of the inflated balloon diameter to an untreated body lumen diameter at the target site is about 1.0 to about 40; or (b) the inflating includes inflating the balloon to a pressure equal to or greater than a nominal pressure of the balloon catheter, and the stretch ratio is about 1.0 to about 40; or (c) the inflating includes inflating to a pressure greater than the nominal pressure of the balloon catheter, and the nominal diameter of the balloon catheter is less than the inflated balloon diameter; or (d) a combination of (a), (b), and (c). The method includes deflating the balloon after the inflation period. The method also includes withdrawing the balloon catheter from the stricture in the body lumen.

In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In some embodiments, the balloon is inflated until the coating layer contacts walls of the stricture and the stricture is dilated, with simultaneous transfer of the drug to the stricture. In some embodiments, the balloon is inflated until the coating layer contacts walls of the stricture, the inflation dilates the stricture to increase its diameter, such that the contacting with the stricture can provide full circumferential transfer of the drug to the wall of the stricture. In some embodiments, the portion of the balloon that includes the drug (e.g., in embodiments including less than 100% of the surface area coated with the drug) can contact the stricture uniformly. In other embodiments, the contacting of various portions of the surface of the balloon with the stricture is non-uniform.

The inflated diameter of the balloon can be any suitable diameter that is achieved during or throughout the inflation period such that a desired ratio of the inflated balloon diameter to the untreated diameter of the body lumen at the target site is achieved. The inflated diameter of the balloon can correspond to the pressure used to inflate the balloon during the inflation period. The inflation pressure can be in the range of nominal inflation pressure to rated burst pressure. The nominal pressure is the pressure at the nominal diameter of the inflated balloon catheter. The nominal diameter is the diameter at the nominal pressure of the balloon catheter and is specified on the product labeling. In some embodiments, the inflated pressure can be the nominal pressure for the balloon, and the inflated diameter of the balloon can be about equal to the nominal diameter of the balloon, or can be less than the nominal diameter of the balloon due to constraint from the stricture. In some embodiments, the inflated pressure of the balloon during the inflation period can be above or below the nominal pressure and the inflated diameter of the balloon can be, correspondingly, above or below the nominal diameter of the balloon.

In various embodiments, the present invention provides a method for treating a body lumen. The method includes 1) backloading a balloon catheter into the scope (e.g., cystoscope). The method includes 2) inserting the scope-balloon catheter assembly into the body lumen. The method includes 3) inflating the balloon to the initial pressure (for example 0.5 atm, 1 atm or 1.5 atm) and maintaining the initial pressure until the pressure no longer drops, for 1-2 minutes. The method includes 4) inflating to the next higher pressure with an 0.5, 1, or 1.5 atm increase from the previous pressure and maintaining the higher pressure until the pressure no longer drops, for 1-2 minutes. The method includes 5) repeating the steps of 4) until the lumen tissue, such as prostatic tissue, yields. The method includes 6) keeping the balloon inflated for 1 minute to 7 days, or 1 minute to 1 day, or 1-10 minutes to release the drug into tissue and to prevent bleeding. The method includes 7) deflating the balloon catheter. The method includes 8) withdrawing the scope-balloon catheter assembly from the body lumen. In this embodiment, the scope can be used to ensure that the balloon catheter is properly positioned before and/or during the inflation.

In various embodiments, the present invention provides a method for treating a body lumen. The method includes 1) inserting a flexible scope and a balloon catheter in a sheath to the body lumen side by side. The method includes 2) removing the sheath from over the balloon and inflating to the initial pressure (for example 0.5 atm, 1 atm or 1.5 atm) and maintaining the initial pressure until the pressure no longer drops, for 1-2 minutes. The method includes 3) inflating to the next higher pressure with an 0.5, 1, or 1.5 atm increase from the previous pressure and maintaining the higher pressure until the pressure no longer drops, for 1-2 minutes. The method includes 4) repeating the steps of 3) until the tissue of body lumen yields. The method includes 5) keeping the balloon inflated for 1 minute to 7 days, 1 minute to 1 day, or 1-10 minutes to release the drug into tissue and to prevent bleeding. The method includes 6) deflating the balloon catheter. The method includes 7) pulling balloon catheter back inside of the sheath. The method includes 8) withdrawing the scope and the balloon catheter/sheath from the body lumen. In this embodiment, the scope can be used to ensure that the balloon is properly positioned before and/or during inflation.

In various embodiments, the present invention provides a method for treating a body lumen. The method includes 1) inserting a flexible scope to the body lumen. The method also includes 2) inserting a balloon catheter and the scope in the body lumen side by side. The method includes 3) inflating to the initial pressure (for example 0.5 atm, 1 atm or 1.5 atm) and maintaining the initial pressure until the pressure no longer drops, for 1-2 minutes. The method includes 4) inflating to the next higher pressure with 0.5, 1, or 1.5 atm increasing from the previous pressure and maintaining the higher pressure until the pressure no longer drops for 1-2 minutes. The method includes 5) repeating the steps of 4) until the tissue of body lumen yields. The method includes 6) keeping the balloon inflated for 1 minute to 7 days, 1 minute to 1 day, or 1-10 minutes to release the drug into tissue and to prevent bleeding. The method includes 7) deflating the balloon catheter. The method includes 8) withdrawing the scope and the balloon catheter assembly from the body lumen. In this embodiment, the scope can be used to ensure that the balloon catheter is properly positioned before and/or during inflation.

In various embodiments, the present invention provides a method for treating a body lumen. The method includes 1) inserting a flexible scope to the body lumen and placing a guidewire. The method also includes 2) inserting a balloon catheter over the guidewire and placing the scope in the body lumen side by side. The method includes 3) inflating to the initial pressure (for example 0.5 atm, 1 atm or 1.5 atm) and maintaining the initial pressure until the pressure no longer drops, for 1-2 minutes. The method includes 4) inflating to the next higher pressure with 0.5, 1, or 1.5 atm increasing from the previous pressure and maintaining the higher pressure until the pressure no longer drops for 1-2 minutes. The method includes 5) repeating the steps of 4) until the tissue of body lumen yields. The method includes 6) keeping the balloon inflated for 1 minute to 7 days, 1 minute to 1 day, or 1-10 minutes to release the drug into tissue and to prevent bleeding. The method includes 7) deflating the balloon catheter. The method includes 8) withdrawing the scope, the guidewire, and the balloon catheter assembly from the body lumen. In this embodiment, the scope can be used to ensure that the balloon catheter is properly positioned before and/or during inflation. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

In various embodiments, the present invention provides a method for treatment of benign prostate hyperplasia. The method includes 1) inserting a balloon catheter sheath assembly and the scope (e.g., cystoscope). The method includes 2) putting the scope and the proximal edge of the balloon side by side near the external sphincter. The method includes 3) removing the sheath from over the balloon and inflating to the initial pressure (for example 0.5 atm, 1 atm or 1.5 atm) and maintaining the initial pressure until the pressure no longer drops for 1-2 minutes. The method includes 4) inflating to the next higher pressure with an 0.5, 1, or 1.5 atm increase from the previous pressure and maintaining the higher pressure until the pressure no longer drops, for 1-2 minutes. The method includes 5) repeating the steps of 4) until the prostatic tissue yield and the commissurotomy is formed. The method includes 6) keeping the balloon inflated for 1 minute to 7 days, 1 minute to 1 day, or 1-10 minutes to release the drug into tissue and to prevent bleeding. The method includes 7) deflating the balloon catheter. The method includes 8) withdrawing the scope and balloon catheter assembly from the body lumen. Feature (a), or (b), or (c), or (a) and (b), or (a) and (c), or (b) and (c), or (a) and (b) and (c), are present: (a) the ratio of the inflated balloon diameter to an untreated body lumen diameter at the target site is about 1.0 to about 40; or (b) the inflating includes inflating the balloon to a pressure equal to or greater than a nominal pressure of the balloon catheter, and the stretch ratio at the target site is about 1.0 to about 40, or (c) the inflating includes inflating to a pressure greater than the nominal pressure of the balloon catheter, and the nominal diameter of the balloon catheter is less than the inflated balloon diameter; or (d) a combination of (a), (b), and (c).

Various embodiments of the present disclosure are directed to the treatment of strictures in body lumens by delivering of an effective amount of a therapeutic agent such as anti-inflammatory and antiproliferative drugs (e.g., rapamycin, sirolimus, zotarolimus, everolimus, tacrolimus, paclitaxel, taxol, docetaxel or their analogues) to a target tissue. The strictures in body lumens include vascular strictures, nonvascular strictures, urethral strictures, ureteral strictures, esophageal strictures, achalasia strictures, strictures in stents, sinus strictures, biliary tract strictures, stomach strictures, small intestine strictures, duodenum strictures, jejunum strictures, ileum strictures, colon strictures, rectum strictures, large intestine strictures. Embodiments of the present disclosure are directed to methods for treating at least one of stenosis of vascular and nonvascular lumens, benign prostatic hyperplasia (BPH), narrowing urethral, prostate cancer, asthma, and chronic obstructive pulmonary disease (COPD). The treatment is intended for a variety of animals, such as premature neonates to adult humans.

The drug on the coating of the balloon catheter can be released to the targeted body lumen. The multiple-sectioned continuous balloon with the neck section having a smaller diameter mechanically anchors the balloon in the body lumen, therefore it prevents slipping of the balloon in the body lumen. If the balloon slips or moves off the targeted diseased site, the target site can be missed, and the healthy lumen can be injured.

In various embodiments, the present invention has advantages, at least some of which are unexpected. For example, coating the exterior surface of a balloon catheter with a layer including a therapeutic agent and additives that have a hydrophilic part and a drug affinity part is useful for treating the disorders disclosed herein. The drug affinity part is a hydrophobic part and/or has an affinity to the therapeutic agent by hydrogen bonding and/or van der Waals interactions. Surprisingly, additives according to embodiments of the present invention, which include a hydrophilic part and a drug affinity part, in combination with a therapeutic agent, forms an effective drug delivery coating on a medical device. Moreover, the additives according to embodiments of the present invention can facilitate rapid drug elution and superior permeation of drug into tissues at a disease site. Thus, coatings according to embodiments of the present invention can provide an enhanced rate and/or extent of absorption of the therapeutic agent in diseased tissues or body lumens. In embodiments of the present invention, the coated device can deliver therapeutic agent to tissues during a very brief deployment time of less than 10 minutes (e.g., less than 2 minutes), and can reduce re-narrowing and reoccurring of the strictures of a body lumen, such as compared to other balloon catheters lacking such a neck section or configuration of neck sections.

In various embodiments, the balloon catheter of the present invention is compatible with flexible or rigid scopes that allow visualization of the treatment zone, allowing more accurate and more efficient placement than other balloon catheters. The scope can be an endoscope, enteroscope, colonoscope, sigmoidoscope, rectoscope, anoscope, rhinoscope, bronchoscope, or a cystoscope. In various embodiments, the balloon catheter of the present invention is self-seeking, in that the neck section of the balloon catheter directs the balloon catheter to a proper position during inflation (e.g., with the neck section of the balloon catheter, such as a distal-most neck section, in the bladder neck) even if the balloon catheter is slightly off-position at the time of initiation of inflation.

Balloon Catheter and Method of Using the Same.

In various embodiments, the present invention provides a balloon catheter for delivering a therapeutic agent to a target site of a body lumen. The balloon catheter can include an elongated balloon having multiple main, or body, sections and at least one neck section with a smaller diameter than that of the main sections. The balloon catheter can include an elongated balloon having a main diameter, such as multiple main sections having the main diameter or having an average diameter equal to the main diameter. The multiple-sectioned balloon with smaller a diameter neck section mechanically anchors the balloon in the body lumen; therefore, it can prevent slipping of the balloon in the body lumen. If the balloon slips away from the targeted diseased site it can be missed and the site of health lumen can be injured. The balloon catheter can include at least one neck section on the balloon including a smaller diameter than the main diameter. The balloon catheter can also include a coating layer overlying an exterior surface of the balloon. The coating layer can include one or more water-soluble additives and an initial drug load of a therapeutic agent (e.g., paclitaxel, taxol, docetaxel, their analogues, rapamycin, sirolimus, zotarolimus, everolimus, tacrolimus, their analogues, and combinations thereof). In a method of using the balloon catheter, Feature (a), or (b), or (c), or (a) and (b), or (a) and (c), or (b) and (c), or (a) and (b) and (c), are present: (a) the ratio of the inflated balloon diameter to an untreated body lumen diameter at the target site is about 1.0 to about 40; or (b) the inflating includes inflating the balloon to a pressure equal to or greater than a nominal pressure of the balloon catheter, and the stretch ratio at the target site is about 1.0 to about 40; or (c) the inflating includes inflating to a pressure greater than the nominal pressure of the balloon catheter, and the nominal diameter of the balloon catheter is less than the inflated balloon diameter; or (d) a combination of (a), (b), and (c).

The main diameter of the balloon can be the diameter of the main sections of the balloon when the balloon is inflated. In some embodiments, the inflated pressure used to determine the main diameter can be any pressure that eliminates any folded or creased areas of the balloon and achieves taughtness of the balloon. The inflated pressure used to determine the main diameter can be a pressure such that the inflated balloon has a shape and size that corresponds to the desired shape and size of the balloon during the intended treatment of the body lumen. The inflated pressure used to determine the main diameter can be the nominal pressure of the balloon, such that the nominal diameter of the balloon catheter is equal to the main diameter of the balloon.

In one embodiment, the drug-coated balloon includes two main sections at both ends with the same diameters, one neck section with a smaller diameter between the two main sections, and the two cones at proximal and distal balloon body. The drug-coated balloon can include three main sections with the same diameters, two neck sections with a smaller diameter, wherein three main sections and two neck sections are aligned alternatively and the neck sections are adjacent to the main sections with larger diameters, and the two cones at proximal and distal balloon body. The drug-coated balloon can include four main sections with a larger diameter, three neck sections with a smaller diameter, wherein the four main sections with a larger diameter and three neck sections are aligned alternatively and the neck sections are adjacent to the main sections with larger diameters, and the two cones at proximal and distal balloon body. The drug-coated balloon can include five main sections with a larger diameter, four neck sections with a smaller diameter, wherein the five main sections with a larger diameter and four neck sections are aligned alternatively and the neck sections are adjacent to the main sections with larger diameters, and the two cones at proximal and distal balloon body. The balloon catheter includes at least one neck section on the balloon including a smaller diameter than the balloon diameter of the main sections. The balloon catheter can include an elongated (e.g., cylindrical) balloon having multiple sections with various diameters. Feature (a), or (b), or (c), or (a) and (b), or (a) and (c), or (b) and (c), or (a) and (b) and (c), are present: (a) the ratio of the inflated balloon diameter to an untreated body lumen diameter at the target site is about 1.0 to about 40; or (b) the inflating includes inflating the balloon to a pressure equal to or greater than a nominal pressure of the balloon catheter, and the stretch ratio at the target site is about 1.0 to about 40; or (c) the inflating includes inflating to a pressure greater than the nominal pressure of the balloon catheter, and the nominal diameter of the balloon catheter is less than the inflated balloon diameter; or (d) a combination of (a), (b), and (c). The multiple sectioned balloon with smaller necks increases the friction between the balloon and the body lumen; therefore, it prevents the slipping of the balloon in the body lumen.

The drug-coated balloon catheter can be a medical device for the treatment of benign prostatic hyperplasia (BPH). The balloon catheter can dilate the prostatic urethra and can include a catheter shaft for insertion into the urethra and a compliant, semi-compliant, or non-compliant balloon for inflation in the prostatic urethra. The balloon can be coated with a therapeutic agent which is delivered to the prostate tissue and prostatic urethra upon balloon inflation. The balloon can be positioned within the prostate using any suitable method, such as via a separate location balloon in the bladder, a location balloon in the bulbous urethra, marker bands on or under the balloon visible with fluoroscopy, or the catheter shaft can be scope- (e.g., cystoscope-) compatible allowing placement via direct visualization, or the catheter can be side by side with the scope. For example, several possible catheter designs allow direct visualization of the balloon during positioning and inflation. One design is cystoscope-compatible, with the catheter being back-loaded through the working channel. Once through the cystoscope, a Touhy Borst adapter and 1-way stopcock can be attached to the catheter shaft to allow inflation of the balloon. Another design can include a multilumen catheter with a lumen in the center of the shaft that allows the optics of a rigid cystoscope to be inserted and positioned next to the proximal edge of the balloon.

In some embodiments, when treating the prostate, the balloon catheter should be sized so that the main body section(s) of the catheter are between the bladder neck sphincter (at the outlet of the bladder) and the external sphincter. In other embodiments, the main body section(s) of the catheter are above the external sphincter, placed through the prostate and one or more body sections go through the bladder neck sphincter and sit in the bladder. In these embodiments, preferably, a neck region of the balloon catheter is aligned with the bladder neck. As discussed herein, a scope equipped with visualization can be used to properly size and place the balloon catheter.

In some embodiments where the balloon catheter includes a soft tip, a Coude tip, or the like, the tip can used to aid in device insertion and tracking through the urethra. In other embodiments, the balloon catheter includes a lumen or channel designed to allow insertion and tracking to the target site or prostate through the urethra.

An achalasia stricture is a rare disorder that makes it difficult for food and liquid to pass from the esophagus to the stomach. In some embodiments, when treating an achalasia stricture, the balloon catheter as shown in FIG. 1A should be sized so that the proximal main body section(s) of the catheter are in the achalasia stricture and above the lower esophageal sphincter. In these embodiments, the neck region of the balloon catheter can be aligned with the lower esophageal sphincter neck. As discussed herein, a scope equipped with visualization can be used to properly size and place the balloon catheter. In embodiments where the balloon catheter includes a soft tip, the tip can be inserted into the sphincter (e.g., the lower esophageal sphincter) or the stomach to aid in placing the balloon catheter in the desired location.

The balloon catheter can alleviate the lower urinary tract symptoms (LUTS) due to BPH through the direct dilation of the prostatic tissue. Dilation of the prostate with the balloon with a ratio of the inflated balloon diameter to the untreated body lumen diameter at the target site of 1.0 to 40, or with a balloon having a stretch ratio at the target site of 1.0 to 40, can create a commissurotomy at the natural plane that separates the lateral sections in the transition zone of the prostate. Concurrently, drug can be released from the coating into the prostatic tissue, which can, for example, preventing enlargement of the prostate and re-narrowing of the newly formed opening.

In various embodiments, during inflation of the balloon in a body lumen (e.g., during performance of a method of the present invention), the nominal balloon diameter of the catheter (e.g., the diameter normally achieved at nominal pressure) can be such that the ratio of the nominal balloon diameter to the untreated diameter of the body lumen at the location of treatment is any suitable ratio, such as 1.0, 1.1, 1.2, 1.3, or 1.4 to 40 (e.g., 1, or greater than, less than, or equal to 1.1, 1.2, 1.3, 1.4, 1.5, 1.6, 1.7, 1.8, 1.9, 2, 2.2, 2.4, 2.6, 2.8, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 or less, or any value therebetween), or a combination thereof. In some embodiments, the inflated diameter of the balloon at the target site during inflation to the nominal pressure is equal to the nominal diameter; however, during actual use, some strictures can prevent achievement of the nominal diameter, or can constrain the inflated balloon to form "dog-bone" shape. The nominal balloon diameter at predetermined pressure (e.g., 2 atm, 3 atm, 6 atm, or 9 atm) can be different for different diameters of balloons for various diseases. For example, nominal diameters of urethral stricture balloons can be 6 mm, 8 mm, 10 mm, 12 mm, and 14 mm with balloon lengths of 20 mm, 25 mm, 30 mm, 35 mm, 40 mm, 45 mm, and 50 mm for 6 mm, 8 mm, 10 mm, 12 mm, and 14 mm balloon catheters at 4 atom, 5 atm, 6 atm, 8 atm, or 12 atm inflation. The nominal diameters of the BPH stricture balloons can be 25 mm, 30 mm, 35 mm, 40 mm, and 45 mm with balloon lengths of 20 mm, 25 mm, 30 mm, 35 mm, 40 mm, 45 mm, 50 mm, 55 mm, and 60 mm balloon catheters at nominal pressure of 2 atm, 3 atm, 4 atm, 6 atm, or 9 atm inflation. Table 1 illustrates examples of nominal balloon sizes, nominal pressures, and ratios of minimal balloon diameter to untreated lumen diameter for used to treat strictures of various diseases. Nominal pressure is the pressure required to bring the balloon to its labeled nominal diameter in an unconstrained pressure ramp test. Nominal diameter is the desired diameter that the product is labeled with. All physicians purchase balloons and select balloons for use according to the nominal diameter. The rated burst pressure is the maximum pressure that the balloon can be inflated to and have a very high confidence that it will not burst, a labeling requirement for balloon catheters that is calculated from a statistical analysis of the pressures observed when the balloons burst in an unconstrained pressure ramp test.

TABLE 1

Examples of nominal balloon sizes, nominal pressures, and ratios of minimal balloon diameter to untreated lumen diameter for used to treat strictures of various diseases, assuming an untreated target site diameter of 3 mm.

| Disease | Nominal balloon diameter × length (mm) | Nominal pressure (atm) | Rated burst pressure (atm) | Ratio of nominal balloon diameter/ untreated lumen diameter |
|---|---|---|---|---|
| BPH | 20-50 × 20-80, such as 30-40 × 30-50 | 1.5 minimum, such as 2 or more | 2 minimum, such as 4 or more | 6.7-16.7 |
| Urethral stricture | 6-14 × 20-180, such as 6-14 × 30-50 | 3 minimum, such as 8 or more | 8 minimum, such as 10-12 | 2-4.7 |
| Esophageal stricture | 6-20 × 30-80 | 3 minimum | 9 minimum | 2-6.7 |
| Achalasia (stricture of lower esophagus) | 30-40 × 80-100 | 1.5 minimum | 9 minimum | 10-16.7 |
| Gastrointestinal strictures | 6-20 × 40-60 | 3 minimum | 9 minimum | 2-6.7 |
| Biliary strictures | 4-10 × 20-40 | 3 minimum | 9 minimum | 1.3-3.3 |

In various embodiments, the balloon catheter can be sufficient such that at a predetermined pressure (e.g., the nominal pressure) the balloon can have any suitable ratio of inflated balloon catheter diameter to an untreated diameter of the body lumen at the location of treatment; for example, at a pressure of about 1 atm (304 kPa) to about 30 atm (3040 kPa) (e.g., about 1 atm or less, or less than, equal to, or more than about 4 atm, 5, 6, 7, 8, 9, 10, 11, 12, 13, 14, 15, 16, 17, 18, 19, 20, 22, 24, 26, 28, or about 30 atm or more).

The stretch ratio is defined herein, unless otherwise indicated, as the ratio of the nominal diameter of the balloon to the untreated diameter of the body lumen in the area being treated by the balloon catheter. The untreated diameter of the body lumen at the target site is the diameter prior to dilation with the drug-coated balloon, and also prior to any pre-dilation methods performed during the same procedure (e.g., performed on the same day), such as before use of a pre-dilation balloon or cutting techniques such as DVIU or hot knife. The nominal diameter of the balloon for determining the stretch ratio is the diameter the balloon achieves in an unrestricted environment at the nominal pressure. The untreated lumen diameter is the average diameter of the target site (e.g., of the lumen at the target site, or of the stricture, stenosis, or lesion). For the urinary tract, for example, for a stricture in the urethra, the untreated body lumen diameter will be the average diameter of the stricture location in the urethra prior to dilation with the drug-coated balloon (and prior to any pre-dilation or cutting such as DVIU). For a stricture in the urethra or prostatic urethra, the untreated body lumen diameter at the target site can be the untreated body lumen diameter at the target site during urination (e.g., the urination diameter), especially in cases where the untreated body lumen diameter at the target site without urination is zero or close to zero. For BPH and the prostatic urethra, the untreated body lumen diameter will be the average diameter of the prostatic urethra at the location of treatment. The inflated balloon diameter can be the actual diameter of the balloon following inflation, which in some embodiments can equal to, less than, or greater than the nominal diameter of the balloon. In various embodiments, the stretch ratio of the balloon catheter of the present invention makes it more effective for treating non-vascular lumens than other catheters. During performance of a method of the present invention, the stretch ratio can be selected to be any suitable ratio that achieves the desired ratio of actual inflated balloon diameter to untreated lumen diameter at the range of pressures used during the method. In various embodiments, the stretch ratio of the balloon can be about 1.0 to about 40, or about 4 to about 40, or less than, equal to, or greater than about 1.1, 1.2, 1.3, 1.31, 1.4, 1.5, 1.6, 1.7, 1.8, 1.9, 2, 2.5, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or about 40 or more; such a stretch ratio can result in a desired ratio of inflated balloon diameter to untreated lumen diameter at the pressures used during the inflation period that can be the same, similar to, or different than the stretch ratio, such as about 1.0 to about 40, or about 4 to about 40, or less than, equal to, or greater than about 1.1, 1.2, 1.3, 1.31, 1.4, 1.5, 1.6, 1.7, 1.8, 1.9, 2, 2.5, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or about 40 or more.

In various embodiments, the method includes measuring the body lumen stricture to be treated. The distal and proximal healthy tissue diameter and the length of the stricture can be assessed to select the drug-coated balloon to be used. The physician will select a balloon based on the untreated diameter of the body lumen stricture and achieving a stretch ratio of 1.0 to 40, or 4 to 40. The physician can then inflate the balloon to at least the nominal pressure, and in some cases, can inflate the balloon past the nominal pressure, up to the rated burst pressure of the balloon. The range of pressure used during the inflation period can be called the working pressure range of the drug-coated balloon. In some cases, the method can include exceeding the rated burst pressure of the balloon. Because the nominal diameter of the balloon is determined without any constrictions, the inflated diameter of the balloon during treatment while in the stricture will be about the same or less or greater than the nominal diameter. At, above, or below burst pressure, the inflated diameter of the balloon can be less than the nominal diameter, equal to the nominal diameter, or can exceed the nominal diameter. For example, a body lumen stricture can be measured to have an untreated diameter of 10 mm. The physician can choose a 14 mm nominal diameter drug-coated balloon that has a nominal pressure of 6 atm and a rated burst pressure of 10 atm. The stretch ratio is 1.4. The physician would inflate the balloon to at least 6 atm and in some cases inflate to 8 atm or 10 atm and in some cases inflate to over 10 atm to achieve the desired inflated balloon diameter during treatment.

In various embodiments, the balloon catheter has one or more neck sections separating one or more main sections, and the at least one neck section of the balloon catheter of the present invention, or the configuration of the one or more neck sections, allows the balloon catheter to stay in place during treatment more consistently and effectively to dilate the stricture and deliver the drug, as compared to other balloon catheters lacking such a neck section or configuration of neck sections.

In various embodiments, the balloon catheter can be assembled with a sheath. The catheter assembly and scope (e.g., cystoscope) are inserted transurethrally into the prostatic urethra and they are positioned side by side near the external sphincter. Using the live video feed from the scope, the external sphincter can be located. The balloon can be positioned adjacent to the external sphincter and within the prostatic urethra. The balloon dilation, drug release, and balloon deflation can be visualized by the scope.

In various embodiments, the balloon catheter can be assembled with a cystoscope by backloading the shaft through the working channel and attaching a Tuohy Borst and one-way stopcock at the proximal end. The cystoscope-catheter assembly is inserted transurethrally into the prostatic urethra. Using the live video feed from the cystoscope, the external sphincter can be located. The balloon can be positioned adjacent to the external sphincter and within the prostatic urethra.

In some embodiments, when treating the prostate, it is preferable to place the proximal balloon waist in the external sphincter so that the external sphincter is not dilated. It is also preferable to size the balloon so that when the balloon waist is in the external sphincter, a balloon neck (e.g., a distal-most balloon neck) is aligned with the bladder neck. This arrangement provides holding forces so that the balloon will not slip during expansion. If a balloon neck cannot be aligned with the bladder neck, it can be preferable to inflate the balloon slowly so that the prostate can yield as the balloon is inflated.

Once properly positioned the balloon is inflated, such as using an inflation device with a pressure gauge. The balloon can be inflated slowly, allowing the prostatic tissue to yield and reducing the propensity for the balloon to slip proximally into the bladder and slip backward distally. Although a single- or multi-necked shape of the balloon can prevent balloon movement by aligning the distal-most neck with the bladder neck, in some abnormal situations such as with an enlarged median lobe (e.g., about 10-15% of cases) the neck of the balloon may not stay aligned to the neck of the bladder during inflation and additional techniques can be useful to further prevent balloon migration. In some examples, inflating at a rate of about 0.5 to 1 atm/min can prevent balloon movement. As the tissue yields, the balloon pressure correspondingly drops, allowing for additional fluid to be instilled within the balloon without increasing the pressure. When the pressure is stable for about 1-2 minutes the pressure can be increased in 0.5 or 1 atm increments and maintained in a similar method. The pressure can be continually increased, following this method of increasing pressure, allowing pressure to stabilize after pressure drops, and continuing to increase pressure, until a commissurotomy or a split is achieved. Alternatively, a very slow inflation can prevent balloon migration to achieve a commissurotomy or a prostate split. Once a commissurotomy or a prostatic urethra and prostate split is observed and confirmed with the video feed from the scope, mechanical decompression can be achieved. The balloon can remain inflated for a period of about 1 minute to 7 days, 1 minute to 1 day, or 1-10 minutes to allow the drug in the coating to transfer into the tissue. Once the treatment is completed, the balloon can be deflated and the catheter and scope can be removed from the body lumen of the patient.

In some embodiments, when treating the prostate, it can be desirable to pre-dilate the stricture. In this embodiment, the pre-dilation catheter can be shorter and/or of less diameter than the drug-coated balloon treatment catheter and can be free of the drug coating. In this scenario, the pre-dilation catheter is positioned with the proximal waist of the balloon in the external sphincter and a neck region aligned with the bladder neck. The balloon is slowly inflated as described herein to aid in yielding the prostate while protecting against balloon slippage. Once inflated, the pre-dilation balloon is deflated and removed and the drug-coated treatment balloon is inserted. The treatment balloon's proximal waist is aligned with the external sphincter. If the prostate was properly pre-dilated, it is not as necessary to align a balloon neck with the bladder neck as the balloon will not be as prone to slipping as it would be in a non-pre-dilated body lumen. In some embodiments, other strictures as described herein can be predilated with a non-drug-coated balloon catheter prior to treatment with the drug-coated balloon.

The drug-coated balloon catheter can include an elongated balloon body with multiple main sections, two cones at distal and proximal ends of the balloon body, an inflation lumen, and a wire lumen, wherein the balloon body includes at least two main sections with a larger diameter and at least one neck section with a smaller diameter, wherein the main section with a larger diameter and neck section are aligned alternatively and adjacently. The elongated balloon can have a generally cylindrical shape, with the exception of any neck section on the balloon, any tapered sections (e.g., cones) between the neck section and the main sections having the main diameter, and any tapered or shaped sections at the longitudinal ends of the balloon. The elongated balloon can have any suitable profile taken perpendicular to a longitudinal direction of the balloon, such as circular (e.g., cylindrical balloon), oval, curvilinear, asymmetric, or polygonal (e.g., pentagonal, hexagonal, heptagonal, octagonal, and the like), or a combination thereof. The stated diameter of a non-cylindrical balloon can be the largest size perpendicular to the longitudinal direction, or the average size perpendicular to the longitudinal direction.

The balloon can be formed from any suitable material, such as a non-compliant or semi-compliant biocompatible material. In some embodiments, the balloon can be made by blow-forming to accomplish a desired geometry. In some embodiments, the balloon can include materials that do not interact with the drug coating, or materials such as nylon (e.g., any suitable nylon, such as nylon 6,6 or nylon 12), polyether block amide (PEBA), polyethylene terephthalate (PET), polyvinylchloride (PVC), polyester, polyurethane, derivatives thereof, or combinations thereof.

The balloon can have any suitable size. The balloon can be designed to fit within the prostatic urethra with the distal section of the balloon being positioned in the bladder. Main diameters and nominal balloon diameters can range from about 5 mm to about 50 mm, 25 mm up to 45 mm, at least 10 mm, at least 15 mm, at least 20 mm, at least 30 mm, such as about 5 mm or less, or less than, equal to, or greater than about 6 mm, 7, 8, 9, 10, 11, 12, 13, 14, 15, 16, 17, 18, 19, 20, 21, 22, 23, 24, 25, 26, 27, 28, 29, 30, 32, 34, 36, 38, 40, 41, 42, 43, 44, 45, 46, 47, 48, 49, or about 50 mm or more; main section diameters can independently range from any of these ranges or specific sizes. The balloon can have a length of about 20 mm to about 160 mm, 40 mm to about 80 mm, or about 20 mm or less, or less than, equal to, or greater than about 22 mm, 24, 26, 28, 30, 32, 34, 36, 38, 40, 42, 44, 46, 48, 50, 52, 54, 56, 58, 60, 62, 64, 66, 68, 70, 72, 74, 76, 78 mm, or about 80 mm or more. Balloon length and diameter can be selected based on the unique prostate anatomy of the patient.

The balloon can include at least one neck section. The neck section is a section of the balloon having a smaller diameter than the main nominal diameter of the balloon. The neck section diameter can be about 2 mm to about 35 mm, about 5 mm to about 35 mm, 10 mm to about 35 mm, or about 2 mm or less, or less than, equal to, or greater than about 3 mm, 4, 5, 6, 8, 9, 10, 12, 14, 16, 18, 20, 22, 24, 26, 28, 30, 32, 34 mm, or about 35 mm or more. The at least one neck section can have a diameter that is independently about 5% to about 99% of the main diameter, such as about 20% to about 99%, or about 5% or less, or less than, equal to, or greater than about 10%, 15, 20, 25, 30, 35, 40, 45, 50, 55, 60, 65, 70, 75, 80, 85, 90, 95, 96, 97, 98, or about 99% or more. In some embodiments, the neck section diameter is from 35% to 75% of the diameter of the main section of the balloon. In some embodiments where the balloon main section has a nominal diameter of 30 to 40 mm, the neck section would have a diameter of 12 to 20 mm. In some embodiments, if the neck diameter is too similar to the diameter of the main section, its ability to prevent balloon slippage can be lessened. In some embodiments, a balloon neck can be directly attached to the catheter shaft, which can create separation between adjacent lobes. In some embodiments, separation between adjacent balloon lobes can be achieved by individually attaching the two adjacent balloons to the catheter in close proximity, such as with a distance separating the two balloons of 0 mm, or less than, equal to, or greater than 1 mm, 2, 3, 4, 5, 6, 7, 8, 9, or about 10 mm or more.

The neck section can be a rigid or semi-rigid neck section, such that the diameter of the neck section (e.g., the portion of the neck section having the neck section diameter) remains substantially static during inflation of the balloon. The neck section can include a substantially nonelastic (e.g., non-compliant, or minimally non-compliant) portion of the balloon, a reinforced portion of the balloon, or a combination thereof. The neck section can include an inelastic material circulated around a circumference of the neck section, such as a suture or monofilament or multifilaments of such material, such as nylon, polyamide, aromatic polyamides, ultra-high molecular weight polyethylene (UHMWPE), polyesters, aromatic polyesters, polyethylene terephthalate (PET) or a combination thereof.

In some embodiments, the balloon neck section can be semi-compliant and expand at different rates than the main balloon body. The neck section compliance can be more, less or equal to the compliance of the balloon body. Table 2 illustrates example measurements of a balloon that has neck section that expands more than the balloon body. The expansion rate of the neck diameter can be higher than the expansion rate of the diameter of the main body section in the tested pressure range of 1-5 atm. The expansion rate of the neck diameter can be in the range of 1.1 to 10 times that of the diameter of the main body section (main diameter) in the tested pressure range of 1-5 atm, such as in the range of 2 to 6 times the main diameter. The expansion rate of the neck diameter is 12.38% per atm. The expansion rate of the body diameter is 2.4% per atm. The difference of the expansion rates is 9.98% per atm. Table 3 illustrates example measurements of a balloon that has a neck section that expands less than the balloon body when inflated from 2 atmospheres to 4 atmospheres. The expansion rate of the neck diameter can be less than the expansion rate of the diameter of the main body section in the tested pressure range of 2-4 atm.

TABLE 2

Example measurements of a balloon that has neck section that expands more than the balloon body.

| Balloon Pressure [atm] | Neck Diameter [mm] | Body Diameter [mm] | Body Compliance | Neck Compliance |
|---|---|---|---|---|
| 1 | 21.5 | 39.0 | 2.3% (1-2 atm) | 12.2% (1-2 atm) |
| 2 | 24.0 | 40.0 | 2.4% (2-3 atm) | 15.7% (2-3 atm) |
| 3 | 27.5 | 40.5 | 2.6% (3-4 atm) | 13.4% (3-4 atm) |

TABLE 2-continued

Example measurements of a balloon that has neck
section that expands more than the balloon body.

| Balloon Pressure [atm] | Neck Diameter [mm] | Body Diameter [mm] | Body Compliance | Neck Compliance |
|---|---|---|---|---|
| 4 | 31.5 | 41.5 | 2.3% (4-5 atm) | 8.2% (4-5 atm) |
| 5 | 34.0 | 42.5 | — | — |

TABLE 3

Example measurements of a balloon that has a neck
section that expands less than the balloon body.

| Balloon Pressure [atm] | Neck Diameter [mm] | Body Diameter [mm] | Body Compliance | Neck Compliance |
|---|---|---|---|---|
| 2 | 15.28 | 34.06 | 8.7% (2-4 atm) | 0.4% (2-4 atm) |
| 4 | 15.34 | 37.02 | — | — |

The neck section can create a wedge of tissue between the larger diameter sections of the balloon that can hold the balloon in place. The larger sections of the balloon cannot overcome the tissue barriers created at the neck section, thus the balloon with the neck section is preventing, reducing, or minimizing balloon migration during inflation. Balloon neck sections can be placed at various locations along the balloon, can number more or less than two (e.g., 1, 2, 3, 4, or more), and can vary in diameter. Neck section placement can be designed to facilitate the greatest increase in traction while still maintaining treatment efficacy.

The neck section can include a central narrow portion having the smallest diameter of the neck section, and an adjacent portion that can have a varying diameter and that occurs between the central narrow portion and portions of the balloon having the main diameter. When the diameter of a neck section is referred to herein, it refers to the diameter of the central narrow portion which has the smallest diameter, and not to the tapered sections, unless otherwise indicated. The tapered sections of the balloon can be rigid, flexible (e.g., elastic), or a combination thereof. The neck section, as measured including the central narrow portion and the tapered portions (e.g., cones) adjacent thereto, can have any suitable length, such as about 1% to about 50% of the balloon length, or about 1% or less, or less than, equal to, or greater than about 2%, 4, 6, 8, 10, 12, 14, 16, 18, 20, 22, 24, 26, 28, 30, 32, 34, 36, 38, 40, 42, 44, 46, 48%, or about 50% or more, or about 0.5 mm to about 40 mm, or about 0.5 mm or less, or less than, equal to, or greater than about 1 mm, 2, 3, 4, 5, 6, 7, 8, 9, 10, 12, 14, 16, 18, 20, 22, 24, 26, 28, 30, 32, 34, 36, 38, or about 40 mm.

In some embodiments, the balloon can include one neck section and is free of other neck sections, such that the balloon includes two main sections separated by one neck section. The one neck section can have any suitable position on the balloon, such as approximately centered with respect to the balloon length, or off-center with respect to the balloon length. The one neck section can be off-center with respect to the length of the balloon and can be at a distal end of the balloon. An embodiment of the balloon including one neck section that is off-center with respect to the length of the balloon is illustrated in FIG. 1A.

Figure 1B:
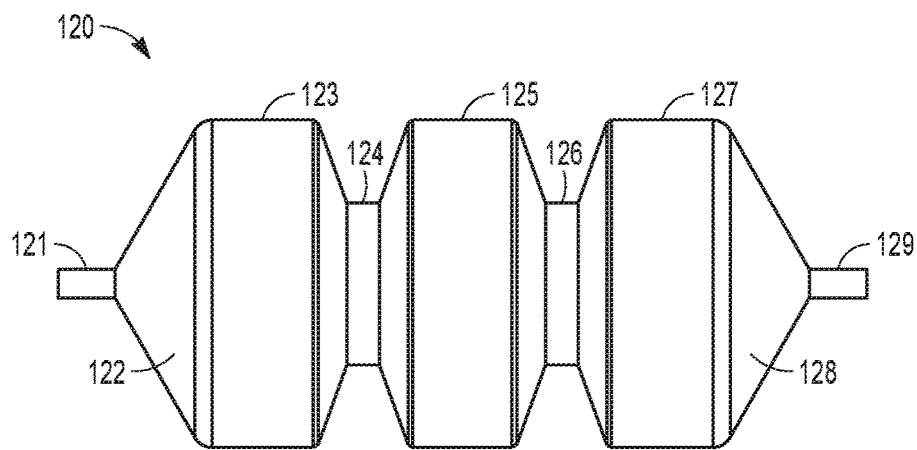
FIG. 1B illustrates a balloon catheter having two neck sections, in accordance with various embodiments.

In some embodiments, the balloon can include two neck sections and is free of other neck sections, such that the balloon includes three lobes separated by two neck sections. The two neck sections can have about the same diameter, or one of the neck sections can have a smaller diameter than the other neck sections. The two neck sections can be symmetrically or asymmetrically located with respect to the center of the balloon length. The three main sections can have approximately equal length or can have different lengths. FIG. 1B illustrates an embodiment of a balloon catheter having two neck sections with three main sections, wherein the neck sections are symmetrically located about the center of the length of the balloon, and wherein the three main sections of the balloon have about the same length. During use, the distal neck section (e.g., the neck section on the distal end of the balloon catheter which is inserted into the body first) can anchor and locate the balloon at the bladder neck, while the proximal neck section can be positioned in the prostatic urethra. In some embodiments, the distal main section of the balloon catheter can be free of the therapeutic agent.

Figure 1C:
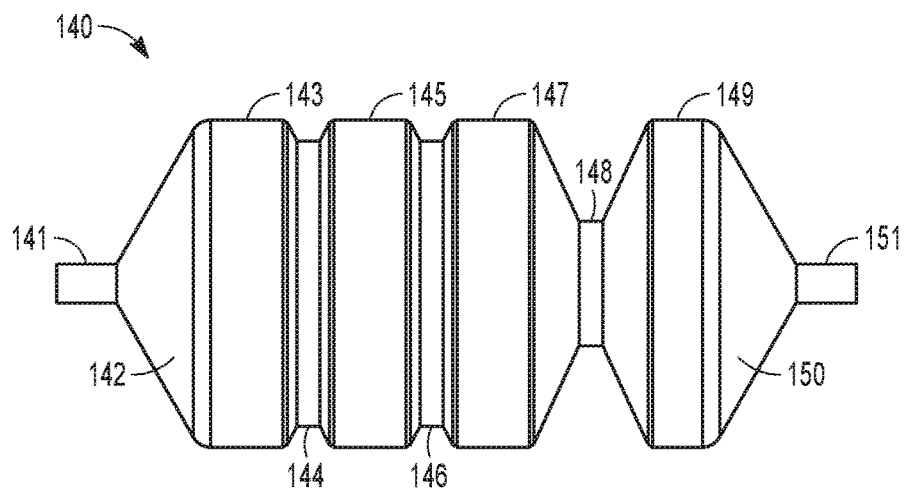
FIG. 1C illustrates a balloon catheter having three neck sections, in accordance with various embodiments.

In some embodiments, the balloon can include three necks and is free of other neck sections, such that the balloon includes four sections separated by the three necks. The three neck sections can be positioned in any suitable way along the length of the balloon. The four main sections formed by the three neck sections can have equal or different lengths. The three neck sections can have equal diameters, or different diameters. In some embodiments two of the neck sections have an equal diameter that is smaller than the diameter of the other neck section. FIG. 1C illustrates an embodiment of a balloon catheter having three neck sections with four main sections each having an approximately equal length, wherein two of the neck sections have an equal diameter that is smaller than the diameter of the other neck section.

The balloon catheter can be a fixed wire balloon catheter. The outer shaft can be bonded to the proximal balloon neck, the distal end of the tapered wire can be bonded with distal neck of balloon, and the proximal ends of the wire and outer shaft can be bonded with the hub (e.g., a valve, connector, or adapter) at the proximal end of the balloon catheter. The balloon catheter can be a moveable wire catheter. The outer shaft is bonded to proximal balloon neck, the distal end of the tapered wire is bonded with distal neck of balloon, the proximal end of the wire is free to move relative to the hub at the proximal end of the balloon catheter. The balloon catheter can be an over-the wire balloon catheter. The balloon catheter can be a rapid exchanged balloon catheter. The balloon catheter can include a catheter shaft on a longitudinal end of the balloon (e.g., on the proximal end of the balloon, inserted into the body after insertion of the distal end), the catheter shaft including an interior lumen for delivery of air, liquid, or a combination thereof, to the balloon interior. The catheter shaft can include a thermoplastic material that is thermally attached (e.g., attached via heating or melting) to the balloon, such as a high durometer material, such as a material similar or identical to the balloon material, such as polyurethane, polyamides, nylon (e.g., nylon 6,6, or nylon 12), polyether block amide (PEBA), or a combination thereof. In some embodiments, the catheter shaft can be a scope (e.g., cystoscope). A high durometer material can help to prevent, reduce, or minimize crushing, and can allow pushability and flexibility. The catheter shaft outer diameter can be sized to allow passage through the working channel of a standard cystoscope or be sufficiently small in diameter to fit side-by-side with a cystoscope in the body lumen. A fluidic connection between the inner lumen and the inside of the balloon can be included, such as holes in the catheter shaft underneath the balloon attachment point to allow inflation of the balloon by instilling media through the inner lumen.

In some embodiments, the balloon can be inflated through a single inflation channel or lumen that communicates to the proximal catheter and inflates all main sections and neck sections of the balloon simultaneously. In some embodiments, the balloon can be inflated through separate channels or lumens that communicate to different sections of the balloon, such as one lumen for the proximal main section of the balloon, a second lumen for the neck section, and a third lumen for the distal main section of the balloon. Any suitable combination of inflation lumens or channels and communication locations within the balloon can be used create the appropriate one or more pressures for carrying out the method.

Figure 5A:
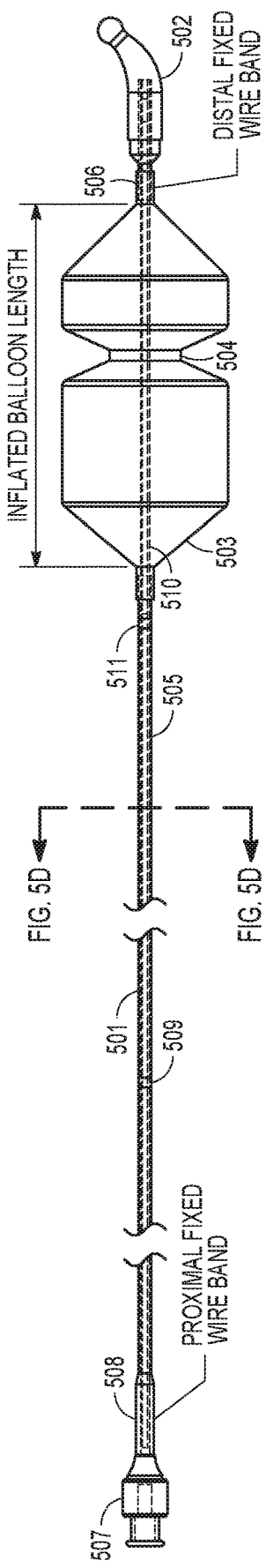
FIGS. 5A-5D illustrate a balloon catheter that includes an elongated rigid member, in accordance with various embodiments.
Figure 5B:
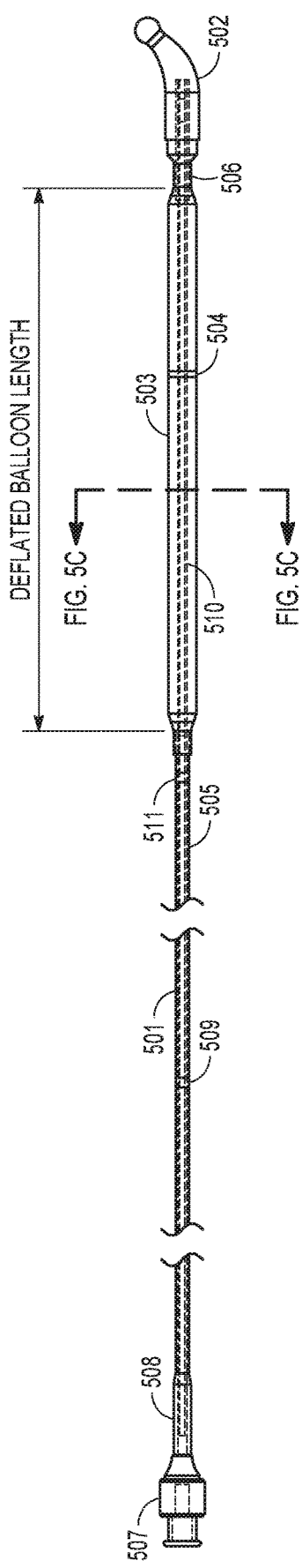
Figure 5C:
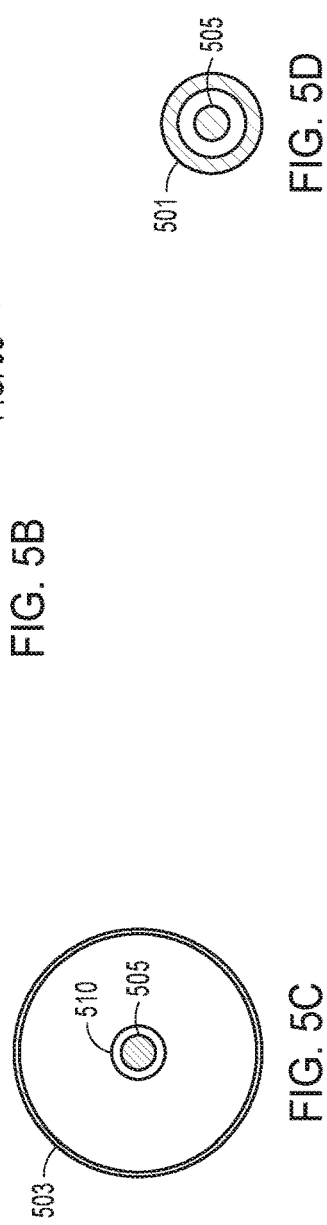
Figure 5D:

In some embodiments, the catheter shaft can include an elongated rigid component, such as a rod, mandrel, or wire, aligned longitudinally with the catheter shaft. FIGS. 5A-5D illustrate a balloon catheter that includes an elongated rigid component, core wire 505. FIG. 5A illustrates the embodiment with the balloon inflated and FIG. 5B illustrates the balloon in the non-expanded state. At the proximal end of the shaft, core wire 505 is attached to catheter shaft 501 under strain relief 508. Core wire 505 extends distally in catheter shaft 501. In some embodiments, catheter shaft is made from 72D PEBA polymer. The shaft 501 is made from a material that exhibits an amount of elasticity when under tension. Under balloon 503, core wire 505 is covered by a hypotube 510. Hypotube 510 provides lateral strength to core wire 505 so that it does not buckle when the balloon 503 is inflated. Near the distal end of the catheter, hypotube 510 and core wire 505 are bonded to tip 502. Tip extrusion 506 connects tip 502 to hypotube 510 and core wire 505. The space between shaft 501 and core wire 505 is the inflation lumen for balloon 503, with the interior of balloon 503 being in fluid communication with Luer hub 507. While this embodiment can be used with any suitable balloons of the invention, FIGS. 5A and 5B show balloon 503 with one neck, with polyethylene fiber 504 used to reinforce the neck. FIG. 5C illustrates a cutaway view of the deflated balloon in FIG. 5A, illustrating balloon 504, hypotube 510, and core wire 505. FIG. 5D illustrates a cutaway view in FIG. 5B, showing shaft 501 and core wire 505.

The elongated rigid component can have a cross-sectional profile that is cylindrical, tapered, rectangular, hexagonal, or another shape and can be made from metal or a non-metallic material that is relatively non-compressible. The elongated component can run from the proximal side of the balloon to the distal side of the balloon, or from a location proximal to the proximal side of the balloon to the distal side of the balloon. The elongated component can float freely within a central lumen of the catheter shaft, can be positioned in a dedicated lumen in a multilumen catheter shaft, or can run longitudinally on the outside of the main catheter shaft. The elongated component can be anchored at a single point, at two points, or at more than two points along the catheter shaft. The elongated component can be anchored by thermally fusing it directly to the catheter shaft, adhesively or chemically bonding it to the catheter shaft, swaging or crimping to one or more portions of the catheter, overmolding, or via any other suitable method. The elongated component can be reinforced along its entire length or along certain sections such as under the balloon to prevent buckling; for example, the elongated metallic component can be a reinforced wire. The reinforcement can be constructed using any rigid material such as stainless steel, Nitinol (i.e., nickel titanium alloy), steel, tungsten, iridium, superalloys (e.g., containing elements such as nickel (Ni), chromium (Cr), aluminum (Al), titanium (Ti), tungsten (W), nioium (Nb), tantalum (Ta), or cobalt (Co)), PEEK, or combinations thereof, and can have any suitable cross-sectional shape. In some embodiments, the reinforcement is a tube that is cylindrical, rectangular, hexagonal, or having any suitable outer profile. The elongated component can be disposed inside of the reinforcement tube, such as shown in FIG. 5C, or along the outside of the reinforcement tube.

Figure 6:
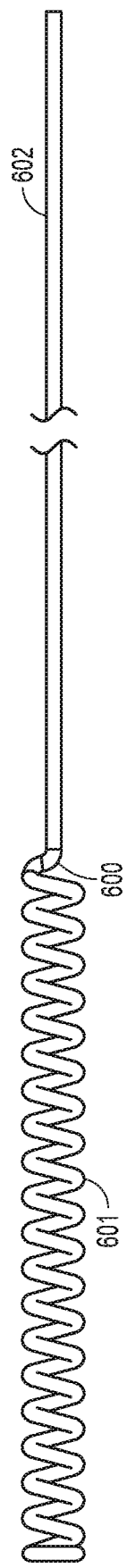
FIG. 6 illustrates an elongated rigid member that is a spring, in accordance with various embodiments.

As shown in FIGS. 5A and 5B, the catheter can include a balloon length-control mechanism which stretches and elongates the balloon when it is in a deflated state, giving the balloon a smaller cross-sectional deflated profile for tracking through the body lumen and for removal after treatment. When the balloon is inflated, the length-control mechanism can allow the balloon to shorten in overall length and inflate to the predetermined inflated diameter and length for the balloon (e.g., as created during the molding or forming process). In one embodiment the force generated from balloon inflation could be transferred from the distal end of the balloon, such as via a balloon bond to the elongated metallic component or via a connection between the catheter tip and the elongated metallic component, back through the catheter shaft by the elongated rigid metallic component to the catheter shaft proximal to the balloon, such as via a connection between the elongated metallic component and the catheter shaft at the proximal end of the balloon or proximal to the proximal end of the balloon. This transfer of force to the catheter shaft would allow the catheter shaft material to act as a spring while working in the elastic region of the catheter shaft material's stress-strain curve. Energy can be stored in the catheter shaft material during balloon inflation, when the catheter shaft is elongated under tension due to balloon inflation, and can be released by the catheter shaft to press on elongated metallic component during deflation to elongate the balloon. In some embodiments, a spring oriented longitudinally along the catheter shaft can be used to store and release force for the balloon length-control mechanism. FIG. 6 illustrates an embodiment of the spring, 600, which can be used as an alternative to core wire 505 shown in FIGS. 5A-5D. Referring to FIG. 6, spring 600 has a spring section 601 and wire section 602. In some embodiments, spring section 601 can be located at the proximal end of the catheter shaft. The spring can be located within a lumen in the catheter shaft, outside the lumen but within the catheter shaft, or outside the catheter shaft. The spring can be within the balloon, or can be located separately from the balloon, such as proximally to the proximal end of the balloon, or a combination thereof. As compared to the length of the inflated balloon, the elongated length of the deflated balloon can be about 0.1 mm longer to about 100 mm longer, or less than, equal to, or greater than about 0.1 mm longer, 0.2, 0.4, 0.6, 0.8, 1, 1.5, 1, 2.5, 3, 4, 5, 6, 8, 10, 12, 15, 20, 25, 30, 40, 50, 60, 70, 80, 90, or about 100 mm longer or more. The catheter shaft can include various materials to achieve the desired amount of force to elongate the balloon, such as polyamides, nylon (e.g., nylon 6,6, or nylon 12), a polyether block amide (PEBA) (e.g., 35D PEBA, 55D PEBA, or 72D PEBA), polyurethanes, silicones, rubbers, another thermoplastic polymer, or a combination thereof. The catheter shaft can be uniform in composition, or can include a combination of materials that are distributed along one or more portions of the catheter shaft to create the desired elongation force. Different materials can yield different elastic strain and different force applied to the elongated rigid metallic component for balloon elongation. The catheter shaft can be an extruded catheter shaft.

The catheter shaft, the balloon, or a combination thereof, can include single or multiple markings along its length to aid in positioning and alignment with certain anatomical structures. The markings can have any suitable orientation, such as circumferential, or longitudinally along the catheter shaft or balloon. Marks on the catheter shaft or balloon can be used to aid in positioning the balloon in the treatment area, indicate that the balloon is fully recovered in the sheath, or locate the device within a patient's anatomy. Markings on the catheter shaft can be visualized using an endoscope, cystoscope, or with the unaided eye, or markings can include radiologically distinguishable components such as radiopaque materials. Markings can be created by thermally bonding polymer to the surface of the catheter shaft having a distinguishable color, via pad print, via laser marking, or via any other method. FIGS. 5A and 5B illustrate an embodiment of balloon recapture mark 509 and positioning mark 511. Balloon recapture mark 509 can be used when the balloon catheter includes a sheath that covers the balloon. Mark 509 can be located just proximal of the proximal end of the sheath when the sheath is covering the balloon. After the user advances the catheter to the desired location, removes the sheath, and inflates the balloon, the user may want to later advance the sheath so that the balloon is covered for removal. In this case, after deflating, the user will distally advance the sheath until the recapture mark 509 is visible. Positioning mark 511 can be used to aid the user in positioning the catheter within a body lumen. For example, when a single neck balloon, as shown in FIGS. 5A and 5B, is used for a BPH treatment, the positioning mark which can be located just proximal of the proximal end of the balloon, can be placed just proximal of the external sphincter. In various embodiments, the user can see mark 511 through the scope and when the mark is just proximal of the external sphincter, the user can be confident that the balloon is properly positioned.

In various embodiments, the catheter shaft can have a separate lumen which creates a pathway for urine to flow from the bladder through the catheter shaft and out through the external portion of the device. This embodiment can allow the drug-coated balloon catheter to remain in place for a period of time, such as 0.1 to about 7 days, while preventing bleeding while the tissue healed into the new configuration. The drug-coated balloon not only can be used for dilation and drug delivery but also can be used as a Foley or urine drainage catheter.

The catheter shaft at an end that remains outside the body (e.g., proximal end) can include a hub (e.g., a valve, connector, or adapter) that provides a connection to the interior lumen of the catheter shaft. During inflation, the hub (e.g., when closed, or always), can prevent backflow of fluid or air from the balloon. The hub can include any suitable valve, such as a Tuohy Borst adapter. The Tuohy Borst adapter is a compression sealing device that can be placed over the catheter shaft and tightened to provide a liquid/air-tight connection to the inner lumen of the catheter shaft. A one-way stopcock can allow control over fluid flow into the balloon and can connect via a standard Luer to an inflation device.

The proximal side of the catheter shaft can include a hub or any other attachment manifold to connect and infuse a liquid, air, or other gas through the catheter to inflate the balloon, allow passage of a guidewire, allow urine to drain, or to make any other suitable connection to the catheter shaft. The connections to the hub or attachment manifold can be made via any suitable one or more connections, such as a single female or male Luer hub, or a Luer manifold with multiple channels. The hub or manifold can be constructed with any appropriate biocompatible material such as polycarbonate, acrylonitrile butadiene styrene, nylon, PEBAX®, silicone, any other polymeric material capable of being molded, or a combination thereof. The hub can be attached to the catheter in any suitable way, such as using adhesive (e.g., cyanoacrylate adhesive, silicone adhesive, epoxy, any other adhesive suitable for the substrates, or a combination thereof) or using chemical bonding. The hub or manifold can be over-molded to the catheter shaft to directly fuse it to the catheter shaft. The catheter shaft can include a strain-relief component at the junction between the catheter shaft and the hub or manifold. The strain-relief component can help to prevent kinking. The strain-relief component can include a polyolefin, PET, FEP, another heat-shrinkable material, or a combination thereof. The strain-relief component can be a heat shrink. The strain-relief component can be a flexible molded material that interfaces with the hub (e.g., the strain-relief component can be attached to the hub).

The balloon catheter can include a catheter tip at a longitudinal end of the balloon, at the distal end which is inserted into the body first. The catheter tip can facilitate passage of the balloon through the urethra. The tip can be an atraumatic tip that helps prevent damage to the urethra during insertion therein. The tip can be a Coude atraumatic tip. The atraumatic Coude tip is designed to facilitate passage of the catheter through the bends in the male urethra while preventing damage to the urethral walls during tracking. It can be a low durometer biocompatible material overmolded onto the catheter shaft or adhesively bonded onto the shaft. For example, the Coude tip can be formed from a PEBAX® or liquid silicone rubber.

In some embodiments, the catheter can include an insertion sheath that covers the balloon during insertion (e.g., the coated and folded/pleated balloon) and can be removed completely from the body during treatment. The sheath can be designed to couple with an obturator or dilator to facilitate reinsertion of the sheath into the body lumen. The sheath can include one material, or more than one material. The sheath can have a laminated construction where several different layers of materials are combined to create the sheath or can be constructed using simple extrusion or co-extrusion. In one embodiment the sheath includes an inner layer that includes a fluoropolymer such as PTFE or FEP, a middle reinforcing layer that includes a braided or coiled wire filament such as stainless steel, Nitinol, PEEK, or other material, and an outer layer including a polymer such as PEBAX®, nylon, polyurethane, or another thermoplastic material. The durometer of the outer sheath material and the pitch of the braid or coil reinforcement can be uniform or can vary along the length of the sheath. The obturator can be an extruded tube or can be molded into a specific geometry and can include a wide range of materials such as LDPE, HDPE, PE, PEBA, nylons, silicones, polyurethanes or other biocompatible materials. The distal tip (inserted into the body) of the obturator can include a taper, radius, or some combination that facilities passage through a body lumen. The sheath and obturator can have over-molded, swaged, crimped, or adhesively-bonded hub connections which allow them to interface together. Alternately, the obturator can be flared at the proximal side to create a grasping feature and create an interference connection with the sheath. After treatment, the obturator and sheath can be inserted through the body lumen to the proximal side of the balloon. Once in position, the obturator can be separated from the sheath, and the sheath can be replaced over the deflated balloon to facilitate removal of the balloon catheter.

Figure 2:
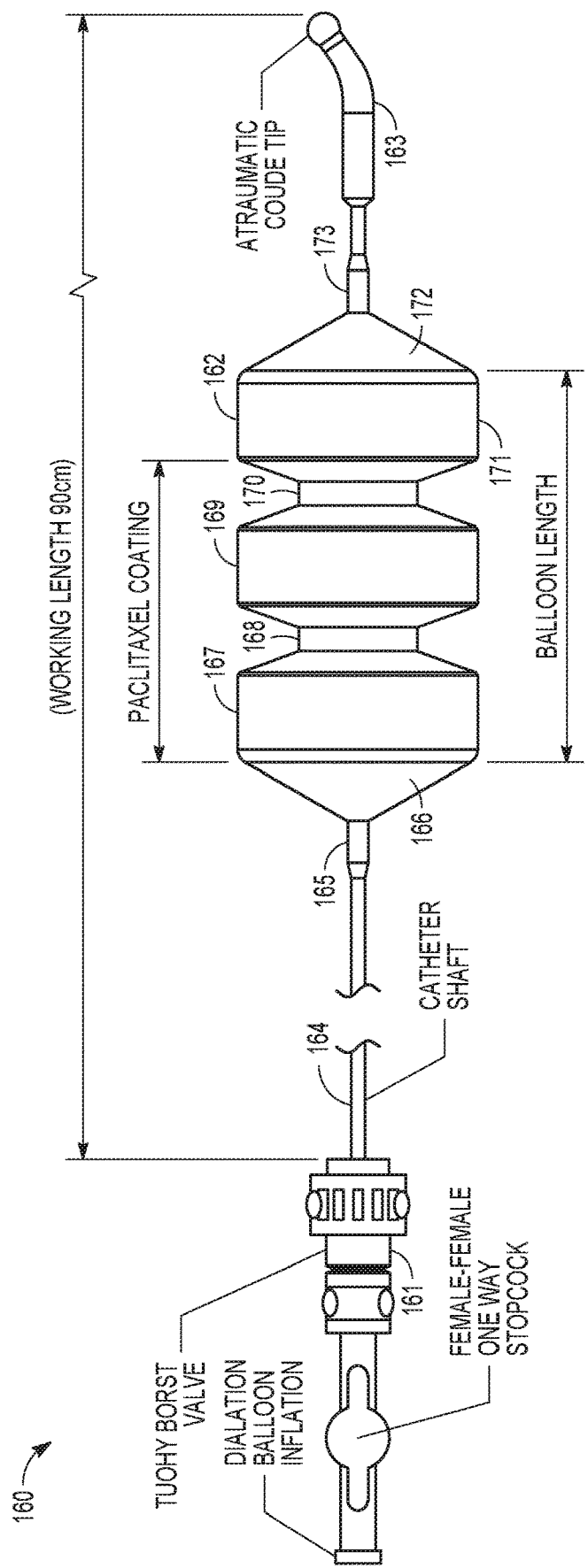
FIG. 2 illustrates a two-necked drug-coated balloon catheter including a catheter shaft, catheter tip, and Tuohy Borst adapter, in accordance with various embodiments (the balloon catheter includes a fixed wire, over-the-wire, and rapid exchanged balloon catheters details not shown in FIG. 2), in accordance with various embodiments.

FIG. 2 illustrates an embodiment of the balloon catheter including a catheter shaft, catheter tip, and Tuohy Borst adapter/stopcock assembly. All materials can be biocompatible. The balloon is coated with a paclitaxel solution but can be coated with any multitude of other drugs or biologics that could facilitate improvement of BPH symptoms. Only the proximal two main sections of the balloon are coated with drug, since during use the distal section is in the bladder.

The balloon catheter can include an inflation device including a pressure gauge or pressure sensor, the inflation device fluidly connected to a catheter shaft connected to the balloon catheter.

The balloons shown in FIGS. 1A, 1B, 1C, and 2 are blow molded in a mold that includes the main sections and the neck sections. A tube of balloon material is inserted into a mold with the desired shape. The balloon material tube can be prestretched. The balloon mold has a shape that corresponds to the balloons shown in FIG. 1A, 1B, 1C, or 2. This will include a proximal cone, at least one main body section, at least one neck section, at least one more main body section, and the distal cone. The balloon material can be any of polyesters, polyamides, nylon 12, nylon 11, polyamide 12, block copolymers of polyether and polyamide, PEBAX®, polyurethanes, and block copolymers of polyether and polyester. The tube and mold are heated to a temperature above the glass transition temperature of the tube of balloon material and pressurized with gas, air, fluid, or the like resulting in the material of the tube taking the shape of the mold. The formed balloon is then cooled, trimmed, and is then ready to be attached to the catheter.

In an embodiment, the balloon is inflated at a low pressure and a neck section reinforcement is attached to the one or more neck regions. The neck section reinforcement is used to control the expansion of the neck section during balloon expansion. The neck section can be a substantially nonelastic portion of the balloon, a reinforced portion of the balloon, or a combination thereof. The neck section can include an inelastic material circulated around a circumference of the neck section, such as a suture or monofilament or multifilaments of such material, such as steel, stainless steel, nitinol, tungsten, aluminum, copper, silver, gold, platinum, iridium, superalloys contain elements, including nickel (Ni) chromium (Cr), aluminum (Al), titanium (Ti), molybdenum (Mo), tungsten (W), niobium (Nb), tantalum (Ta) and cobalt (Co), nylon, polyamide, aromatic polyamides, ultra-high molecular weight polyethylene (UHMWPE), polyesters, aromatic polyesters, polyethylene terephthalate (PET) or a combination thereof. In some embodiments, the polymer material is in strand or filament form and is wrapped numerous times around the neck section and then held in place by using a continuous bead of glue or adhesive, two or more spots of glue or adhesive, thermally welded, adhesively bonded after plasma treatment, or adhesively bonded to an adherent layer. The adherent layer, which is a separate layer applied to the balloon before the fiber attachment process, can improve the adherence of the fiber adhesive or glue to the exterior surface of one or more balloon necks.

The main sections of the balloon can be formed with identical or similar diameters. In some embodiments, the diameters of the various main sections can differ from each other by as much as 30%, when measured at nominal balloon diameter. In FIGS. 1A, 1B, 1C, and 2, the main sections of the balloon are shown with equal diameters, that is the diameter of each main section is constant. In practice, at higher pressures, the diameter of the main sections will become slightly bowed out, in that the diameter of the mid part of the main sections can have a slightly larger diameter than the edges of the main sections near the balloon cone and/or near the neck sections.

Figure 3:
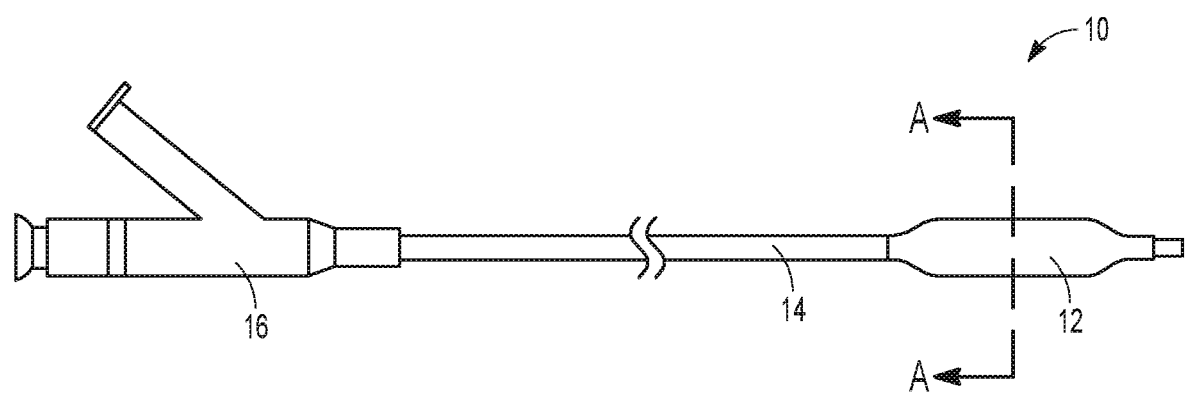
FIG. 3 is a perspective view of an embodiment of a balloon catheter according to the present invention (the balloon catheter includes a fixed wire, over-the-wire, and rapid exchanged balloon catheters details not shown in FIG. 3), in accordance with various embodiments.

For embodiments where the balloon has neck and main sections, as shown in FIGS. 1A, 1B, 1C, and 2, and where the balloon doesn't have any neck sections, as shown in FIG. 3, after the balloon catheter is assembled, the balloon can be coated with the at least one water-soluble additive and drug as discussed herein. In some embodiments where the balloon has multiple main sections, the distal main section may not be coated. The balloon can be coated according to the process discussed herein. If a sheath is used, it can be put over the balloon after the balloon is coated. The catheter is then packaged, sterilized, and labeled as is known in the art.

Embodiments of the present invention relate to balloon catheters having a rapid drug-releasing coating and methods for preparing such coated devices. The therapeutic agent according to embodiments of the present invention does not require a delayed or long-term release and instead, for example, the therapeutic agent and the additive are released in a very short time period to provide a therapeutic effect upon contact with tissue. An object of embodiments of the present invention is to facilitate rapid and efficient uptake of drug by target tissue during transitory device deployment at a target site.

The drug coating can cover any suitable proportion of the exterior surface of the balloon (e.g., proportion of the surface of the balloon that obtains the main diameter during inflation to the nominal pressure, excluding necks and end-cones), such as about 1% to about 100%, or about 50% to about 100%, to about 80% to about 100%, or about 10% or less, or less than, equal to, or greater than 20%, 30, 40, 50, 60, 70, 75, 80, 85, 90, 95, 96, 97, 98, 99, or about 100% or more.

The drug coating can include a water-soluble additive, such as chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof. The water-soluble additive can include a first water soluble additive that is a surfactant such as a PEG sorbitan monolaurate, a PEG sorbitan monooleate, or a combination thereof. The water-soluble additive can include a second water-soluble additive that is a chemical compound with one or more moieties that are hydroxyl, amine, carbonyl, carboxyl, or ester, such as sorbitol, sorbitan, xylitol, gluconolactone, or a combination thereof. The drug coating can include both the first water-soluble additive and the second water-soluble additive. In some embodiments, the distal end of the balloon can be free of the therapeutic agent.

In various embodiments, the present invention provides a method for treating a body lumen. The body lumen can be a vascular body lumen or a nonvascular body lumen. The method can include inserting the balloon catheter (e.g., any embodiment of the balloon catheter described herein) to a target site in the body lumen. The method can include inflating the balloon until (e.g., at least until) the coating layer contacts walls of the stricture in the body lumen at the target site and the balloon achieves an inflated balloon diameter for an inflation period. Feature (a), or (b), or (c), or (a) and (b), or (a) and (c), or (b) and (c), or (a) and (b) and (c), are present: (a) the ratio of the inflated balloon diameter to an untreated body lumen diameter at the target site is about 1.0 to about 40; or (b) the inflating includes inflating the balloon to a pressure equal to or greater than a nominal pressure of the balloon catheter, and the stretch ratio at the target site is about 1.0 to about 40; or (c) the inflating includes inflating to a pressure greater than the nominal pressure of the balloon catheter, and the nominal diameter of the balloon catheter is less than the inflated balloon diameter; or (d) a combination of (a), (b), and (c). The method can include deflating the balloon after the inflation period. The method can include withdrawing the balloon catheter from the stricture in the body lumen.

Various embodiments provide a method of treating a benign prostatic hyperplasia (BPH) stricture, a urethral stricture, a ureteral stricture, prostate cancer, an esophageal stricture, a biliary tract stricture, stomach strictures, small intestine strictures, duodenum strictures, jejunum strictures, ileum strictures, colon strictures, rectum strictures, large intestine strictures, colorectal strictures, strictures after gastric bypass, ileocolonic strictures, gastrointestinal strictures, J-pouch strictures, bladder neck strictures (e.g., stenosis), fibrostenotic eosinophilic esophagitis strictures, Crohn's disease (CD)- and ulcerative colitis (UC)-induced strictures, radiation-induced strictures, endoscopic resection (EMR and ESD) induced stricture, surgery-related anastomotic strictures, achalasia strictures, gastrectomy-induced strictures, asthma, or chronic obstructive pulmonary disease (COPD). The method is a method of treating a stricture in the body lumen, such as a urethral stricture, a benign prostatic hyperplasia (BPH) stricture, a ureteral stricture, an esophageal stricture, a sinus stricture, stomach strictures, small intestine strictures, duodenum strictures, jejunum strictures, ileum strictures, colon strictures, rectum strictures, large intestine strictures, and biliary tract strictures. The stricture in the body lumen can be a benign prostatic hyperplasia (BPH) stricture, a urethral structure, or an esophageal stricture. The method can be a method of treating benign prostatic hyperplasia, prostate cancer, or a combination thereof, wherein the body lumen is a prostate.

The method can include, prior to, during, or after the insertion of the balloon to the target site, flushing the body lumen with water, saline solution, or a water solution including at least one water soluble additive.

The body lumen can be a prostate, wherein inserting the balloon catheter includes positioning the balloon catheter in the prostate using a scope (e.g., flexible or rigid, such as a cystoscope). The balloon catheter can include a scope, and the method can include using video feed from the scope to locate the target site. The method can include using video feed from the scope to position the balloon catheter at the target site.

The body lumen can be a prostate, the balloon can have multiple main sections divided by one or more necks, and inserting the balloon catheter can include positioning one of the balloon catheter main sections in the prostate and positioning a second main section of the balloon catheter in the bladder.

The inserting can include positioning the at least one neck section of the balloon in a bladder neck. The at least one neck section of the balloon catheter can be a distal neck section, and the inserting can include positioning the distal neck section in the bladder neck. The balloon catheter can include a proximal neck section, and the inserting can include positioning the proximal neck section in the prostatic urethra.

The inflation period can be any suitable inflation period, such as about 0.1 minutes to about 10 minutes, about 0.5 minutes to about 2 minutes, or about 0.1 minutes or less, or about 0.2 minutes, 0.3, 0.4, 0.5, 0.6, 0.7, 0.8, 0.9, 1, 1.1, 1.2, 1.3, 1.4, 1.5, 1.6, 1.8, 2, 2.2, 2.4, 2.6, 2.8, 3, 3.5, 4, 4.5, 5, 6, 7, 8, 9, or about 10 minutes or more.

The inflating can include increasing pressure within the balloon at any suitable rate (e.g., which can exclude periods wherein pressure drops due to tissue yielding and pressure can be maintained during these times), such as about 0.1 atm/minute to about 10 atm/minute, or about 0.5 to about 1.5 atm/minute, or about 0.1 atm/minute or less, or less than, equal to, or greater than about 0.2 atm/minute, 0.3, 0.4, 0.5, 0.6, 0.7, 0.8, 0.9, 1, 1.1, 1.2, 1.3, 1.4, 1.5, 1.6, 1.8, 2, 2.2, 2.4, 2.6, 2.8, 3, 3.5, 4, 4.5, 5, 6, 7, 8, 9, or about 10 atm/minute or more.

The inflating can include observing the pressure within the balloon, such as via a pressure gauge. During yielding of the stricture, which can result in a decrease in pressure, the inflating can include allowing pressure within the balloon to stabilize and maintaining the stabilized pressure in the balloon for a stabilization period during tissue yielding, then resuming increasing pressure in the balloon until a desired inflation diameter is achieved. The stabilization period can be any suitable period, such as about 0.1 minutes to about 10 minutes, about 0.5 minutes to about 2 minutes, or about 0.1 minutes or less, or about 0.2 minutes, 0.3, 0.4, 0.5, 0.6, 0.7, 0.8, 0.9, 1, 1.1, 1.2, 1.3, 1.4, 1.5, 1.6, 1.8, 2, 2.2, 2.4, 2.6, 2.8, 3, 3.5, 4, 4.5, 5, 6, 7, 8, 9, or about 10 minutes or more.

As shown in FIG. 3, in one embodiment, the medical device is a balloon catheter. The balloon catheter can be any suitable catheter for the desired use, including conventional balloon catheters known to one of ordinary skill in the art. For example, balloon catheter 10 can include an expandable, inflatable balloon 12 at a distal end of the catheter 10, a handle assembly 16 at a proximal end of the catheter 10, and an elongate flexible member 14 extending between the proximal and distal ends. Handle assembly 16 can connect to and/or receive one or more suitable medical devices, such as a source of inflation media (e.g., air, saline, or contrast media). Flexible member 14 can be a tube made of suitable biocompatible material and having one or more lumens therein. At least one of the lumens is configured to receive inflation media and pass such media to balloon 12 for its expansion. The balloon catheter can be a rapid exchange or over-the-wire catheter and made of any suitable biocompatible material. The material of balloon 12 can include one or more of polyesters, polyamides, nylon 12, nylon 11, polyamide 12, block copolymers of polyether and polyamide, PEBAX®, polyurethanes, and block copolymers of polyether and polyester.

Figure 4A:
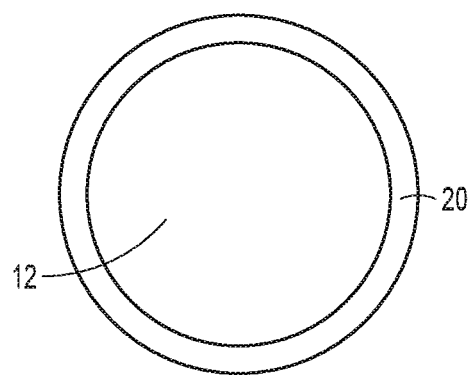
FIGS. 4A-4C are cross-sectional views of different embodiments of the distal portion of the balloon catheter of FIG. 3, taken along line A-A, showing exemplary coating layers, in accordance with various embodiments.
Figure 4B:
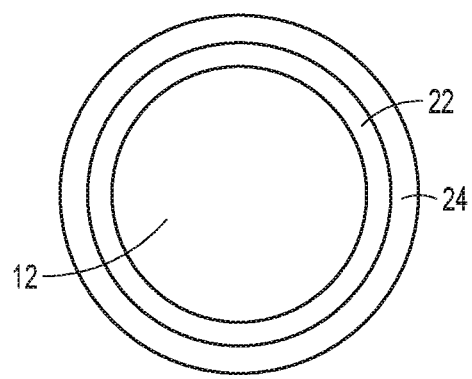
Figure 4C:
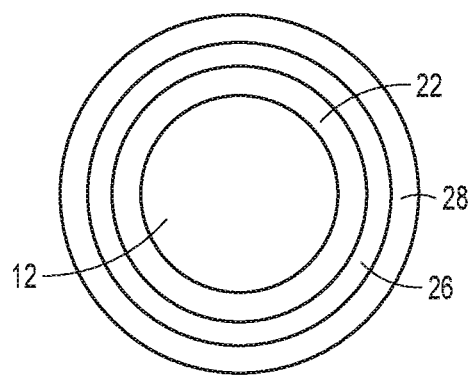

In one embodiment, the present invention provides a balloon catheter for delivering a therapeutic agent to a tissue, such as a vascular tissue or a nonvascular tissue. The device includes a layer applied to an exterior surface of the balloon catheter. The layer includes a therapeutic agent and one or more additives. The additive can be any suitable additive. The layer can include one additive, or the layer can include more than one additive, such as a water-soluble first additive and a water-soluble second additive. For example, as shown in the embodiment depicted in FIG. 4A, the balloon 12 is coated with a layer 20 that includes a therapeutic agent and an additive. In some embodiments, the layer consists essentially of a therapeutic agent and an additive, e.g., the layer includes only the therapeutic agent and the additive, without any other materially significant components. In some embodiments, the device can optionally include an adherent layer. For example, as shown in the embodiment depicted in FIG. 4B, the balloon 12 is coated with an adherent layer 22. A layer 24 that includes a therapeutic agent and an additive is overlying the adherent layer. The adherent layer, which is a separate layer underlying the drug coating layer, improves the adherence of the drug coating layer to the exterior surface of the medical device and protects coating integrity. For example, if drug and additive differ in their adherence to the medical device, the adherent layer can prevent differential loss of components and maintain drug-to-additive ratio in the coating during transit to a target site for therapeutic intervention. Furthermore, the adherent layer can function to facilitate rapid release of coating layer components off the device surface upon contact with tissues at the target site. In other embodiments, the device can include a top layer. For example, as shown in the embodiment depicted in FIG. 4C, the balloon 12 is coated with an adherent layer 22, a layer 26 that includes a therapeutic agent and an additive overlying the adherent layer, and a top layer 28. The top layer can reduce loss of the drug layer before it is brought into contact with target tissues, for example during transit of the balloon 12 to the site of therapeutic intervention or during the first moments of inflation of balloon 12 before coating layer 20 is pressed into direct contact with target tissue.

Embodiments of the present invention are directed to the treatment of strictures in body lumens by delivering of an effective amount of therapeutic agents, such as anti-inflammatory and antiproliferative drugs (e.g., paclitaxel, taxol, docetaxel, rapamycin, sirolimus, zotarolimus, tacrolimus, everolimus, mTOR inhibitors, or their analogues, or a combination thereof). The strictures in a body lumen include vascular stenosis, urethral strictures, ureteral strictures, esophageal strictures, achalasia strictures, strictures in stents, sinus strictures, stomach strictures, small intestine strictures, duodenum strictures, jejunum strictures, ileum strictures, colon strictures, rectum strictures, large intestine strictures, and biliary tract strictures. Embodiments of the present invention are directed to methods for treating at least one of vascular stenosis, benign prostatic hyperplasia (BPH), urethral issues, prostate cancer, colorectal strictures, strictures after gastric bypass, ileocolonic strictures, gastrointestinal strictures, J-pouch strictures, bladder neck strictures (e.g., stenosis), fibrostenotic eosinophilic esophagitis strictures, Crohn's disease (CD)- and ulcerative colitis (UC)-induced strictures, radiation-induced strictures, endoscopic resection (EMR and ESD)-induced strictures, surgery-related anastomotic strictures, achalasia strictures, gastrectomy-induced strictures, asthma, and chronic obstructive pulmonary disease (COPD). According to embodiments, the method involves delivering of therapeutic agents such as anti-inflammatory and antiproliferative drugs (e.g., rapamycin, paclitaxel, or their analogues) via coated medical devices, such as balloon catheters. The therapeutic agent can be coated on the medical device alone or with one or more additives.

In one embodiment, the present invention relates to a method for treating a stricture in a body lumen including inserting a balloon catheter including a coating layer into the stricture, wherein the stricture is one of urethral strictures, ureteral strictures, esophageal strictures, sinus strictures, achalasia strictures, strictures in stents, stomach strictures, small intestine strictures, duodenum strictures, jejunum strictures, ileum strictures, colon strictures, rectum strictures, large intestine strictures, colorectal strictures, strictures after gastric bypass, ileocolonic strictures, gastrointestinal strictures, J-pouch strictures, bladder neck strictures (e.g., stenosis), fibrostenotic eosinophilic esophagitis strictures, Crohn's disease (CD)- and ulcerative colitis (UC)-induced strictures, radiation-induced strictures, endoscopic resection (EMR and ESD)-induced strictures, surgery-related anastomotic strictures, achalasia strictures, gastrectomy-induced strictures, and biliary tract strictures, wherein the coating layer includes a drug and an additive, inflating the balloon catheter and releasing the drug to a wall of the stricture, deflating the balloon; and withdrawing the balloon catheter, wherein the residual drug can be about 1 to 70% of the total loading drug on the balloon catheter, wherein the drug in the wall of body lumen can be about 0.1 to 25% of the total loading drug on the balloon catheter. In one aspect of this embodiment, the additive enhances absorption of the drug into tissue of the stricture in the body lumen.

In one embodiment, the present invention relates to a method for treating a stricture of the body lumen including inserting a balloon catheter including a coating layer into a body lumen, wherein the body lumen is one of esophagus, airways, sinus, trachea, colon, biliary tract, stomach, small intestine, duodenum, jejunum, ileum, rectum, large intestine, urinary tract, prostate, urethra, ureter, and other lumens, wherein the coating layer includes a drug and an additive, inflating the balloon catheter and releasing the drug to a wall of the body lumen, deflating the balloon; and withdrawing the balloon catheter, wherein the residual drug can be about 1 to 70% of the total loading drug on the balloon catheter, wherein the drug in the wall of body lumen can be about 0.1 to 25% of the total loading drug on the balloon catheter. In one aspect of this embodiment, the additive enhances absorption of the drug into tissue of the body lumens. In another aspect of this embodiment, the additive includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions.

In one embodiment, the present invention relates to a balloon catheter for delivering a therapeutic agent to a target site of a body lumen stricture, the balloon catheter including a coating layer overlying an exterior surface of a balloon, wherein the coating layer includes an initial drug load of a therapeutic agent, and one or more water-soluble additive; the therapeutic agent is chosen from paclitaxel, docetaxel, taxol, their analogues, rapamycin, sirolimus, zotarolimus, everolimus, tacrolimus, and their analogues, and combinations thereof; the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof.

In one embodiment of the balloon catheter, the one or more water-soluble additives promote a rapid release of the therapeutic agent from the balloon, and whereby the rapid release includes a residual drug amount of the therapeutic agent remaining on the balloon after the balloon is inflated at the target site of the body lumen for an inflation period of from about 0.1 minutes to 10 minutes and subsequently removed from the body lumen.

In one embodiment of the balloon catheter, the ratio by weight of the therapeutic (e.g., hydrophobic) agent in the coating layer to the total weight of the one or more additives in the coating layer can be about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more. In one embodiment of the balloon catheter, the ratio by weight of the therapeutic agent in the coating layer to the total weight of the one or more water-soluble additives (e.g., a first and second water soluble additive in the coating layer, or to the total weight of a first, second, and third water soluble additive) in the coating layer, is from about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more.

In one embodiment, the present invention relates to a method for treating a stricture in a body lumen, the method including flushing the body lumen with water, saline solution, or a water solution including at least one water soluble additive; inserting a balloon catheter into a target site in the stricture in the body lumen, the balloon catheter including a balloon and a coating layer overlying external surfaces of the balloon. The coating layer includes at least one water-soluble additive, and an initial drug load of a therapeutic agent; the therapeutic agent is chosen from paclitaxel, docetaxel, taxol, their analogues, rapamycin, sirolimus, zotarolimus, everolimus, tacrolimus, their analogues, and combinations thereof; the water-soluble additive is chosen from N-acetylglucosamine, N-octyl-D-gluconamide, N-Nonanoyl-N-methylglycamine, N-octanoyl-N-methyl glutamine C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-Lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl) urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; inflating the balloon until the coating layer contacts walls of the stricture in the body lumen at the target site and the balloon achieves an inflated balloon diameter for an inflation period; deflating the balloon after the inflation period, wherein the inflation period is from 0.1 minutes to 10 minutes; and withdrawing the balloon catheter from the stricture in the body lumen. The inflated balloon catheter diameter can be such that the ratio of the inflated balloon diameter to an untreated diameter of the treated body lumen can be about 1.0 to about 40, or about 4 to about 40; the stretch ratio at the location of treatment can be about 1.0 to about 40, or about 4 to about 40. Optionally the inflating can include inflating to a pressure equal to or greater than the nominal pressure of the balloon catheter.

The balloon can have thereon a residual drug amount after the withdrawing. Any suitable residual drug amount can remain after the withdrawing, such as greater than, equal to, or less than about 90 wt %, 88, 86, 84, 82, 80, 78, 76, 74, 72, 70, 68, 66, 64, 62, 60, 58, 56, 54, 52, 50, 48, 46, 44, 42, 40, 38, 36, 34, 32, 30, 28, 26, 24, 22, 20, 18, 16, 14, 12, 10, 8, 6, 4, 3, 2, 1 wt %, or about 0 wt %.

In one embodiment, the present invention relates to a method for treating at least one of a benign prostatic hyperplasia and prostate cancer, the method including flushing the prostate with water, saline solution, or a water solution including at least one water soluble additive; inserting a balloon catheter into a target site in the prostate, the balloon catheter including a balloon and a coating layer overlying external surfaces of the balloon. The coating layer can include one or more water-soluble additives, and an initial drug load of a therapeutic agent; inflating the balloon until the coating layer contacts walls of the benign prostatic hyperplasia or prostate cancer at the target site and the balloon achieves an inflated balloon diameter for an inflation period; deflating the balloon after the inflation period, wherein the inflation period is from 0.1 minutes to 10 minutes; and withdrawing the balloon catheter from the prostate. The ratio of the inflated balloon diameter to an untreated diameter of the body lumen can be about 1.0 to about 40, or about 4 to about 40; the stretch ratio at the location of treatment can be about 1.0 to about 40, or about 4 to about 40. Optionally the inflating can include inflating to a pressure equal to or greater than the nominal pressure of the balloon catheter.

In one embodiment, the present invention relates to a method for treating a urethral stricture, the method including flushing the urethral stricture with water, saline solution, or a water solution including at least one water soluble additive; inserting a balloon catheter into a target site in the urethral stricture, the balloon catheter including a balloon and a coating layer overlying external surfaces of the balloon, wherein the coating layer includes at least one water-soluble additive, and an initial drug load of a therapeutic agent; and the ratio by weight of the therapeutic agent in the coating layer to the total weight of the one or more water-soluble additives in the coating layer is from about 0.05 to 20; inflating the balloon until the coating layer contacts walls of the urethral stricture at the target site and the balloon achieves an inflated balloon diameter for an inflation period; deflating the balloon after the inflation period, wherein the inflation period is from 0.1 minutes to 10 minutes; and withdrawing the balloon catheter from the urethral stricture. The ratio of the inflated balloon diameter to an untreated diameter of the urethra in the location of the stricture can be about 1.0 to about 40, or about 4 to about 40; the stretch ratio at the location of treatment can be about 1.0 to about 40, or about 4 to about 40. After dilation, the diameter of the urethral stricture can be 6.7 mm or more, such as about 6.7 mm to about 50 mm, or about 6.7 mm to about 20 mm, or less than, equal to, or greater than about 6.7, 6.8, 6.9, 7.0, 7.2, 7.4, 7.6, 7.8, 8, 8.5, 9, 9.5, 10, 11, 12, 13, 14, 15, 16, 17, 18, 19, 20, 25, 30, 35, 40, 45 mm, or about 50 mm or more. Optionally the inflating can include inflating to a pressure equal to or greater than the nominal pressure of the balloon catheter.

In one embodiment, the present invention relates to a method for treating an esophageal stricture such as an achalasia stricture, the method including optionally flushing the esophageal stricture prior to, during, or after insertion of the balloon catheter with water, saline solution or a water solution including at least one water soluble additive; inserting a balloon catheter into a target site in the esophageal stricture, the balloon catheter including a balloon and a coating layer overlying external surfaces of the balloon, wherein the coating layer includes at least one water-soluble second additive, and a therapeutic agent with an initial drug load of from 1 to 6 micrograms of the therapeutic agent per square millimeter of the balloon at its nominal diameter; and the ratio by weight of the therapeutic agent in the coating layer to the total weight of the one or more water-soluble additives in the coating layer is from about 0.05 to 20; inflating the balloon until the coating layer contacts walls of the esophageal stricture at the target site and the balloon achieves an inflated balloon diameter for an inflation period; deflating the balloon after the inflation period, wherein the inflation period is from 0.1 minutes to 10 minutes; and withdrawing the balloon catheter from the esophageal stricture. The ratio of the balloon diameter to an untreated diameter of the esophagus at the location of the stricture can be about 1.0 to about 40, or about 4 to about 40; the stretch ratio at the location of treatment can be about 1.0 to about 40, or about 4 to about 40. In some embodiments, the balloon catheter properties are equal or similar to those given in Table 4, having a growth rate that slows at higher pressures. Compliance is the percent change in balloon diameter from nominal diameter to rated burst pressure (RBP) diameter, calculated as: Diameter @ RBP−Diameter @ nominal pressure)/Diameter @ nominal pressure)*100%. Optionally the inflating can include inflating to a pressure equal to or greater than the nominal pressure of the balloon catheter.

TABLE 4

Examples of properties of balloon catheters for treating esophageal and gastrointestinal strictures.

| Nominal diameter (mm) | Rated burst pressure diameter (mm) | Nominal pressure (atm) | Rated burst pressure (atm) | Compliance (%) |
|---|---|---|---|---|
| 4 | 6 | 3 | 12 | 50 |
| 6 | 8 | 3 | 10 | 30 |
| 8 | 10 | 3 | 9 | 25 |
| 10 | 12 | 3 | 8 | 20 |
| 12 | 15 | 3 | 8 | 17 |
| 15 | 18 | 3 | 1 | 20 |
| 18 | 20 | 3 | 6 | 11 |
| 20 | 23 | 3 | 6 | 15 |
| 23 | 25 | 3 | 6 | 9 |
| 30 | 34 | 2 | 4 | 13 |
| 35 | 40 | 2 | 4 | 14 |
| 40 | 45 | 2 | 4 | 12 |

In one embodiment, the present invention relates to a method for treating an esophageal stricture such as an achalasia stricture, the method including flushing the esophageal stricture with water, saline solution or a water solution including at least one water soluble additive optionally prior to, during, after insertion of balloon catheter; inserting a balloon catheter into a target site in the esophageal stricture, the balloon catheter including a balloon and a coating layer overlying external surfaces of the balloon, wherein the coating layer includes at least one water-soluble second additive, and a therapeutic agent with an initial drug load of from 1 to 6 micrograms of the therapeutic agent per square millimeter of the balloon at its nominal diameter; and the ratio by weight of the therapeutic agent in the coating layer to the total weight of the one or more water-soluble additives in the coating layer is from about 0.05 to 20; inflating the balloon until the coating layer contacts walls of the esophageal stricture at the target site and the balloon achieves an inflated balloon diameter for an inflation period; deflating the balloon after the inflation period, wherein the inflation period is from 0.1 minutes to 10 minutes; and withdrawing the balloon catheter from the esophageal stricture. The ratio of the inflated balloon diameter to an untreated diameter of the esophagus at the location of the stricture can be about 1.0 to about 40, or about 4 to about 40; the stretch ratio at the location of treatment can be about 1.0 to about 40, or about 4 to about 40. Optionally the inflating can include inflating to a pressure equal to or greater than the nominal pressure of the balloon catheter. In some embodiments, the balloon catheter properties are equal or similar to those given in Table 5, a single balloon catheter having the ability to achieve a wide range of balloon diameters at relatively high working pressures compared to conventional compliant balloons. Balloons in Table 5 have a unique feature that there are three increasing balloon diameters at three increasing inflation pressure stages. Then nominal inflation diameter is the diameter at stage I. The diameter increases about 0.5-4 mm, preferably 0.75-3 mm, most preferably 0.9-2 mm for every stage of pressure increase. For example, a balloon that has diameter of 15 mm at Pressure I (3 atm) has a diameter of 16.5 mm at pressure II (4.5 atm) and has a diameter of 18 mm at pressure III (7 atm).

TABLE 5

Examples of properties of balloon catheters for treating esophageal and gastrointestinal strictures.

| Three inflation pressure stages (atm) | Diameter at pressure stage I (mm) [Nominal Diameter] | Diameter at pressure stage II (mm) | Diameter at pressure stage III (mm) |
|---|---|---|---|
| 3, 6, 10 | 4 | 5 | 6 |
| 3, 6, 10 | 6 | 7 | 8 |
| 3, 5.5, 9 | 8 | 9 | 10 |
| 3, 5, 8 | 10 | 11 | 12 |
| 3, 4.5, 8 | 12 | 13.5 | 15 |
| 3, 4.5, 7 | 15 | 16.5 | 18 |
| 3, 4.5, 6 | 18 | 19 | 20 |
| 3, 4.5, 5.5 | 20 | 21.5 | 23 |
| 3, 4, 5 | 23 | 24 | 25 |
| 2, 3.5, 4.5 | 30 | 32.5 | 35 |
| 2, 3, 4 | 35 | 37.5 | 40 |
| 2, 3, 4 | 40 | 42.5 | 45 |

In one embodiment, the present invention relates to a method for treating a gastrointestinal stricture, the gastrointestinal strictures including stomach strictures, small intestine strictures, duodenum strictures, jejunum strictures, ileum strictures, colon strictures, rectum strictures, large intestine strictures, or biliary tract strictures, the method including flushing the gastrointestinal stricture with water, saline solution or a water solution including at least one water soluble additive; inserting a balloon catheter into a target site in the gastrointestinal stricture, the balloon catheter including a balloon and a coating layer overlying external surfaces of the balloon, wherein the coating layer includes at least one water-soluble second additive, and a therapeutic agent with an initial drug load of from 1 to 6 micrograms of the therapeutic agent per square millimeter of the balloon at its nominal diameter; and the ratio by weight of the therapeutic agent in the coating layer to the total weight of the one or more water-soluble additives in the coating layer is from about 0.05 to 20; inflating the balloon until the coating layer contacts walls of the esophageal stricture at the target site and the balloon achieves an inflated balloon diameter for an inflation period; deflating the balloon after the inflation period, wherein the inflation period is from 0.1 minutes to 10 minutes; and withdrawing the balloon catheter from the esophageal stricture. The inflated balloon catheter diameter can be such that the ratio of the balloon diameter to an untreated diameter of the esophagus at the location of the stricture can be about 1.0 to about 40, or about 4 to about 40; the stretch ratio at the location of treatment can be about 1.0 to about 40, or about 4 to about 40. Optionally the inflating can include inflating to a pressure equal to or greater than the nominal pressure of the balloon catheter. In some embodiments, the balloon catheter has properties are that are equal or similar to those given in Tables 4 and 5, having a growth rate that slows at higher pressures and a single balloon catheter having the ability to achieve a wide range of balloon diameters at high working pressures.

In various embodiments, the drug-coated balloon catheters used to treat the esophageal strictures, achalasia stricture, gastrointestinal strictures, the gastrointestinal strictures include stomach strictures, small intestine strictures, duodenum strictures, jejunum strictures, ileum strictures, colon strictures, rectum strictures, large intestine strictures, colorectal strictures, strictures after gastric bypass, ileocolonic strictures, gastrointestinal strictures, J-pouch strictures, bladder neck strictures (e.g., stenosis), fibrostenotic eosinophilic esophagitis strictures, Crohn's disease (CD)- and ulcerative colitis (UC)-induced strictures, radiation-induced strictures, endoscopic resection (EMR and ESD)-induced strictures, surgery-related anastomotic strictures, achalasia strictures, gastrectomy-induced strictures, and biliary tract strictures, have a catheter design that is fixed wire, wire-guided, over-the-wire catheter, or rapid exchange design catheters.

In one embodiment, the present invention relates to a method for treating a sinus stricture, the method including: flushing the sinus stricture with water, saline solution, or a water solution including at least one water soluble additives; inserting a balloon catheter into a target site in the sinus stricture, the balloon catheter including a balloon and a coating layer overlying external surfaces of the balloon, wherein the coating layer includes at least one water-soluble additive, and a therapeutic agent with an initial drug load of from 1 to 6 micrograms of the therapeutic agent per square millimeter of the balloon at its nominal diameter; the therapeutic agent is chosen from budesonide, flunisolide, triamcinolone, beclomethasone, fluticasone, mometasone, mometasone furoate, dexamethasone, hydrocortisone, methylprednisolone, prednisone, cortisone, betamethasone, triamcinolone acetonide, paclitaxel, taxol, docetaxel, rapamycin, sirolimus, zotarolimus, tacrolimus, everolimus, mTOR inhibitors, an analogue thereof, and combinations thereof; the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; and the ratio by weight of the therapeutic agent in the coating layer to the total weight of the one or more water-soluble additives in the coating layer is from about 0.05 to 20; inflating the balloon until the coating layer contacts walls of the sinus stricture at the target site and the balloon achieves an inflated balloon diameter for an inflation period; deflating the balloon after the inflation period, wherein the inflation period is from 0.1 minutes to 10 minutes; and withdrawing the balloon catheter from the sinus stricture.

In some embodiments, it can be desirable to pre-dilate the target region of the body lumen, such as the prostatic urethra or any other target site, prior to using the drug-coated balloon. In some embodiments, the pre-dilation balloon is selected to be slightly shorter and/or have a slightly smaller nominal diameter than the treatment balloon. If the pre-dilation balloon is shorter than the treatment balloon, it will be more likely that the entire pre-dilated zone or region gets treated by the treatment balloon. In some embodiments, the pre-dilation balloon can be sized substantially identically to the treatment balloon such that the nominal diameter and length of the pre-dilation balloon substantially match those of the treatment balloon. In some embodiments, it can be desirable to treat the target region of the body lumen directly without pre-dilation. In some embodiments, the method includes using a scope that visualizes inserting to and placing of the pre-dilation balloon catheter at the target site, the inflating and deflating processes, balloon diameter increasing during the inflating, balloon diameter reduction the during deflating, yielding of the target site, or any combination thereof.

Embodiments of the present invention relate to balloon catheters having a rapid drug-releasing coating and methods for preparing such coated devices. The therapeutic agent according to embodiments of the present invention does not require a delayed or long-term release and instead, for example, the therapeutic agent and the additive are released in a very short time period to provide a therapeutic effect upon contact with tissue. An object of embodiments of the present invention is to facilitate rapid and efficient uptake of drug by target tissue during transitory device deployment at a target site.

In various embodiments, the balloon catheter can have 1 or multiple (e.g., 2) neck sections along the body of the balloon. Neck sections have smaller nominal diameters than the nominal balloon body diameter (e.g., 1.5 to 2.5× smaller) and can be any suitable length, such as about 10-20 mm long. Neck sections can divide the balloon symmetrically or can result in certain balloon body sections being longer than others. Nominal balloon diameters can range from 6-45 mm with working lengths of 20 to 160 mm.

In FIG. 1A, in one embodiment, a balloon with one neck section is shown. Balloon 100 has waist 101, cone 102, first body section 103, neck 104, second body section 105, cone 106, and waist 107. When assembled into a balloon catheter, as is known in the art, waists 101 and 107 will be attached or bonded or the like to the catheter shaft (not shown). During inflation, waists 101 and 107 do not inflate as they are attached to the catheter shaft. Sections 102, 103, 104, 105, and 106 can all be inflated simultaneously through a single inflation point in communication with the catheter shaft and external Luer hub. In FIG. 1B, in one embodiment, a balloon with two neck sections is shown. Balloon 120 has waist 121, cone 122, first body section 123, first neck 124, second body section 125, second neck 126, third body section 127, cone 128, and waist 129. When assembled into a balloon catheter, as is known in the art, waists 121 and 129 will be attached or bonded or the like to the catheter shaft. During inflation, waists 121 and 129 do not inflate as they are attached to the catheter shaft. Sections 122, 123, 124, 125, 126, 127, and 128 can all be inflated simultaneously through a single inflation point in communication with the catheter shaft and external Luer hub. While neck sections 124 and 126 are shown as being the same diameter at the present state of inflation, they can be the same or different diameters with the same or different compliance. In FIG. 1C, in one embodiment, a balloon with three neck sections is shown. Balloon 140, has waist 141, cone 142, first body section 143, first neck 144, second body section 145, second neck 146, third body section 147, third neck 148, fourth body section 149, cone 150, and waist 151. When assembled into a balloon catheter, as is known in the art, waists 141 and 151 will be attached or bonded or the like to the catheter shaft. During inflation, waists 141 and 151 do not inflate as they are attached to the catheter shaft. Sections 142, 143, 144, 145, 146, 147, 148, 149, and 150 can all be inflated simultaneously through a single inflation point in communication with the catheter shaft and external Luer hub. While neck sections 144, 146, and 148 are shown with different diameters at the present state of inflation, they can be the same or different diameters with the same of different compliance.

As shown in FIG. 2, in one embodiment, the medical device is a balloon catheter, a fixed wire balloon catheter, a moveable wire catheter, an over-the-wire balloon catheter, a rapid exchanged balloon catheter, including conventional balloon catheters known to one of ordinary skill in the art. For example, balloon catheter 160 can include an expandable, inflatable balloon 162 at a distal end of the catheter 160, a handle assembly 161 at a proximal end of the catheter 160, an elongate flexible member 164 extending between the proximal and distal ends, and an atraumatic Coude tip 163 at the distal end. Handle assembly 161 can connect to and/or receive one or more suitable medical devices, such as a source of inflation media (e.g., air, water, saline, or contrast media). Flexible member 164 can be a tube made of suitable biocompatible material and having one or more lumens therein. At least one of the lumens is configured to receive inflation media and pass such media to balloon 162 for its expansion. The balloon catheter can be a fixed wire or a rapid exchange or over-the-wire catheter and made of any suitable biocompatible material. The material of balloon 162 can include one or more of polyesters, polyamides, nylon 12, nylon 11, polyamide 12, block copolymers of polyether and polyamide, PEBAX®, polyurethanes, and block copolymers of polyether and polyester. In FIG. 2, in one embodiment, a balloon with two neck sections is shown. Balloon 162 has waist 165, cone 166, first body section 167, first neck 168, second body section 169, second neck 170, third body section 171, cone 172, and waist 173. When assembled into a balloon catheter, as is known in the art, waists 165 and 173 will be attached or bonded or the like to the catheter shaft. During inflation, waists 165 and 173 do not inflate as they are attached to the catheter shaft. Sections 166, 167, 168, 169, 170, 171, and 172 can all be inflated simultaneously through a single inflation point in communication with the catheter shaft and external Luer hub. While neck sections 168 and 170 are shown as being the same diameter at the present state of inflation, they can be the same or different diameters with the same or different compliance.

As shown in FIG. 3, in one embodiment, the medical device is a balloon catheter. The balloon catheter can be any suitable catheter for the desired use, including a fixed wire balloon catheter, a moveable wire catheter, an over-the-wire balloon catheter, a rapid exchanged balloon catheter, including conventional balloon catheters known to one of ordinary skill in the art. For example, balloon catheter 10 can include an expandable, inflatable balloon 12 at a distal end of the catheter 10, a handle assembly 16 at a proximal end of the catheter 10, and an elongate flexible member 14 extending between the proximal and distal ends. Handle assembly 16 can connect to and/or receive one or more suitable medical devices, such as a source of inflation media (e.g., air, saline, or contrast media). Flexible member 14 can be a tube made of suitable biocompatible material and having one or more lumens therein. At least one of the lumens is configured to receive inflation media and pass such media to balloon 12 for its expansion. The balloon catheter 10 can be a rapid exchange or over-the-wire catheter and made of any suitable biocompatible material. The material of balloon 12 can include one or more of polyesters, polyamides, nylon 12, nylon 11, polyamide 12, block copolymers of polyether and polyamide, PEBAX®, polyurethanes, and block copolymers of polyether and polyester.

Figure 7A:
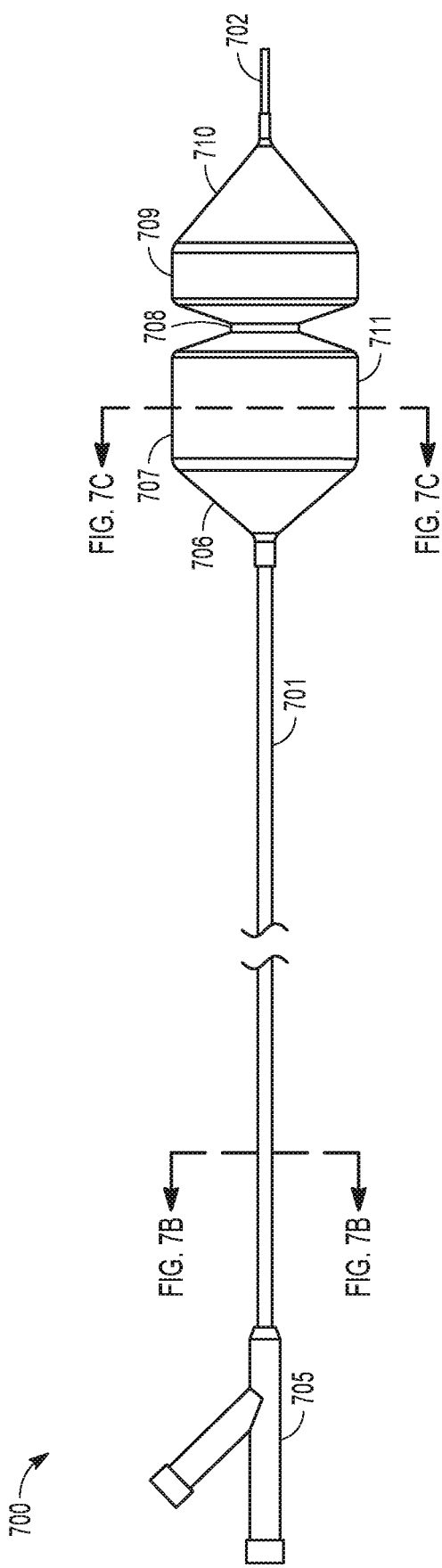
FIGS. 7A-7C illustrate an over-the-wire catheter with a balloon having one neck section, in accordance with various embodiments.
Figure 7C:
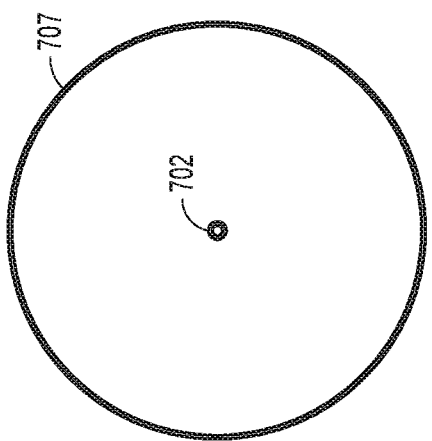
Figure 7B:
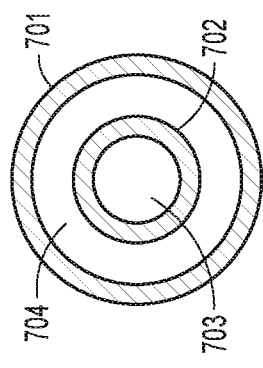

As shown in FIG. 7A-7C, in one embodiment, the medical device is an over-the-wire balloon catheter or rapid exchange balloon catheter. FIG. 7A shows a side profile. FIG. 7B illustrates a cutaway view of the shaft in FIG. 7A. FIG. 7C illustrates a cutaway view of the balloon from FIG. 7A. Balloon catheter 700 can include an expandable, inflatable balloon at a distal end of the catheter 700. The balloon 711 can have proximal cone section 706, first main body section 707, neck section 708, second main body section 709, and distal cone section 710. Balloon catheter 700 can have a handle or Luer assembly 705 which communicates through channel 704 to inflate the balloon 711 and allows guidewire placement through channel 703. Handle assembly 705 can connect to and/or receive one or more suitable medical devices, such as a source of inflation media (e.g., air, water, saline, or contrast media). Flexible member 701 and 702 can be tubes made of suitable biocompatible material and having one or more lumens therein. Outer flexible member or extrusion 701 is positioned over the top of flexible member or extrusion 702 and terminates at the proximal balloon bond. Inner flexible member or extrusion 702 runs the entire length of the balloon catheter 700, under the balloon 711 and terminates in a flexible radiused tip at the distal end of the catheter. The material of balloon 711 can include one or more of polyesters, polyamides, nylon 12, nylon 11, polyamide 12, block copolymers of polyether and polyamide, PEBAX®, polyurethanes, block copolymers of polyether and polyester, or combinations thereof.

In one embodiment, the present invention provides a medical device for delivering a therapeutic agent to a diseased tissue or stricture, such as a vascular tissue or a nonvascular tissue. The device includes a layer applied to an exterior surface of the balloon catheter. The layer includes a therapeutic agent and one or more additives. The additive can be any suitable additive. The layer can include one additive, or the layer can include more than one additive, such as a water-soluble first additive and a water-soluble second additive. For example, as shown in the embodiment depicted in FIG. 4A, the balloon 12 is coated with a layer 20 that includes a therapeutic agent and an additive. In some embodiments, the layer consists essentially of a therapeutic agent and an additive, e.g., the layer includes only the therapeutic agent and the additive, without any other materially significant components. In some embodiments, the device can optionally include an adherent layer. For example, as shown in the embodiment depicted in FIG. 4B, the balloon 12 is coated with an adherent layer 22. A layer 24 that includes a therapeutic agent and an additive is overlying the adherent layer. The adherent layer, which is a separate layer underlying the drug coating layer, improves the adherence of the drug coating layer to the exterior surface of the medical device and protects coating integrity. For example, if drug and additive differ in their adherence to the medical device, the adherent layer can prevent differential loss of components and maintain drug-to-additive ratio in the coating during transit to a target site for therapeutic intervention. Furthermore, the adherent layer can function to facilitate rapid release of coating layer components off the device surface upon contact with tissues at the target site. In other embodiments, the device can include a top layer. The top layer can reduce loss of the drug layer before it is brought into contact with target tissues, for example during transit of the balloon 12 to the site of therapeutic intervention or during the first moments of inflation of balloon 12 before coating layer 20 is pressed into direct contact with target tissue.

Embodiments of the present invention are directed to the treatment of strictures in nonvascular body lumens by delivering of an effective amount of a therapeutic agent such as anti-inflammatory and antiproliferative drugs (e.g., rapamycin, sirolimus, zotarolimus, everolimus, tacrolimus, paclitaxel, taxol, docetaxel or their analogues). The strictures in a nonvascular body lumen include urethral strictures, ureteral strictures, esophageal strictures, sinus strictures, achalasia strictures, strictures in stents, stomach strictures, small intestine strictures, duodenum strictures, jejunum strictures, ileum strictures, colon strictures, rectum strictures, large intestine strictures, colorectal strictures, strictures after gastric bypass, ileocolonic strictures, gastrointestinal strictures, J-pouch strictures, bladder neck strictures (e.g., stenosis), fibrostenotic eosinophilic esophagitis strictures, Crohn's disease (CD)- and ulcerative colitis (UC)-induced strictures, radiation-induced strictures, endoscopic resection (EMR and ESD)-induced strictures, surgery-related anastomotic strictures, achalasia strictures, gastrectomy-induced strictures, and biliary tract strictures. Embodiments of the present invention are directed to methods for treating at least one of benign prostatic hyperplasia (BPH), prostate cancer, asthma, and chronic obstructive pulmonary disease (COPD). According to various embodiments, the method involves delivering of a therapeutic agent such as anti-inflammatory and antiproliferative drugs (e.g., rapamycin, sirolimus, zotarolimus, everolimus, tacrolimus, paclitaxel, taxol, docetaxel, or their analogues) via coated balloon catheters. The anti-inflammatory and antiproliferative drugs can be coated on the medical device alone or with one or more additives.

A method for treating a stricture in a nonvascular body lumen includes inserting a balloon catheter including a coating layer into a body lumen, wherein the coating layer includes a drug and an additive, inflating the balloon catheter and releasing the drug to a wall of the nonvascular body lumen, deflating the balloon; and withdrawing the balloon catheter, wherein the residual drug can be about 1 to 70% of the total loading drug on the balloon catheter, wherein the drug in the wall of body lumen can be about 0.1 to 25% of the total loading drug on the balloon catheter. The method can include, prior to, during, or after the insertion of the balloon to the target site, flushing the body lumen with water, saline solution, or a water solution including at least one water soluble additive. In one aspect of this embodiment, the additive enhances absorption of the drug into tissue of the nonvascular body lumens. In another aspect of this embodiment, the additive includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions.

A balloon catheter for delivering a therapeutic agent to a target site of a nonvascular body lumen can include a coating layer overlying an exterior surface of a balloon, wherein the coating layer includes an initial drug load of a therapeutic agent, and one or more water-soluble additive; the therapeutic agent is chosen from paclitaxel, taxol, docetaxel, their analogues, rapamycin, sirolimus, zotarolimus, everolimus, and their analogues, and combinations thereof; the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof.

The nonvascular body lumen can be one of esophagus, airways, sinus, trachea, colon, biliary tract, stomach, small intestine, duodenum, jejunum, ileum, rectum, large intestine, urinary tract, prostate, urethra, ureter, and other nonvascular lumens.

In some embodiments, the one or more water-soluble additives can promote a rapid release of the therapeutic agent from the balloon, and whereby the rapid release includes a residual drug amount of the therapeutic agent remaining on the balloon after the balloon is inflated at the target site of the nonvascular body lumen for an inflation period of from about 0.1 minutes to 10 minutes and subsequently removed from the nonvascular lumen.

The ratio by weight of the therapeutic agent in the coating layer to the total weight of the one or more additives in the coating layer can be about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more. The ratio by weight of the therapeutic agent in the coating layer to the total weight of the one or more water-soluble additives (e.g., a first and second water soluble additive in the coating layer, or to the total weight of a first, second, and third water soluble additive) in the coating layer, can be from about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more.

The initial drug load can be from 1 microgram to 20 micrograms of the therapeutic agent per square millimeter of the balloon (i.e., per external surface area of the nominal diameter of the balloon), or about 2 to about 6 micrograms, or about 1 microgram or less, or less than, equal to, or greater than about 2, 3, 4, 5, 6, 7, 8, 9, 10, 12, 14, 16, 18, or about 20 micrograms or more. The residual drug amount can be 70% or less of the initial drug load.

A method for treating a stricture in a nonvascular body lumen includes flushing the nonvascular body lumen with water, saline solution, or a water solution including at least one water soluble additive; inserting a balloon catheter into a target site in the stricture in the nonvascular body lumen, the balloon catheter including a balloon and a coating layer overlying external surfaces of the balloon. The coating layer includes a at least one water-soluble additive, and an initial drug load of a therapeutic agent; the therapeutic agent is chosen from paclitaxel, taxol, docetaxel, their analogues, rapamycin, sirolimus, zotarolimus, everolimus, and their analogues, and combinations thereof; the water-soluble additive is chosen from N-acetylglucosamine, N-octyl-D-gluconamide, N-Nonanoyl-N-methylglycamine, N-octanoyl-N-methyl glutamine C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-Lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl) urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; inflating the balloon until the coating layer contacts walls of the stricture in the nonvascular body lumen at the target site and the balloon achieves an inflated balloon diameter for an inflation period; deflating the balloon after the inflation period, wherein the inflation period is from 0.1 minutes to 10 minutes; and withdrawing the balloon catheter from the stricture in the nonvascular body lumen. In some embodiments, the balloon diameter is 10 mm at the nominal inflation pressure of 6 atm. The ratio of the inflated balloon diameter to an untreated diameter of the target site of the body lumen can be about 1.0 to about 40, or about 4 to about 40; the stretch ratio at the location of treatment can be about 1.0 to about 40, or about 4 to about 40. Optionally the inflating can include inflating to a pressure equal to or greater than the nominal pressure of the balloon catheter.

The balloon can have thereon a residual drug amount after the withdrawing. Any suitable residual drug amount can remain after the withdrawing, such as greater than, equal to, or less than about 70 wt %, 65, 60, 55, 50, 45, 40, 35, 30, 25, 20, 15, 10, 5 wt %, or about 0 wt %.

The ratio by weight of the therapeutic agent in the coating layer to the total weight of the one or more additives in the coating layer can be about 0.05 to about 20, about 0.1 to about 10, about 0.1 to about 5, about 0.5 to about 8, about 0.5 to about 3, about 2 to about 6, or about 0.05 or less, or less than, equal to, or greater than about 1, 2, 3, 4, 5, 6, 7, 8, 9, 10, 11, 12, 13, 14, 15, 16, 17, 18, 19, or about 20 or more.

In various embodiments, the coating layer can include one or more water-soluble additives, and an initial drug load of a therapeutic agent; the therapeutic agent is chosen from paclitaxel, taxol, docetaxel, rapamycin, sirolimus, zotarolimus, tacrolimus, everolimus, mTOR inhibitors, analogues thereof, and combinations thereof; the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof.

In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

A method for treating at least one of a benign prostatic hyperplasia and prostate cancer can include optionally flushing the prostate with water, saline solution, or a water solution including at least one water soluble additive; inserting a balloon catheter into a target site in the prostate, the balloon catheter including a balloon and a coating layer overlying external surfaces of the balloon; and positioning the balloon body in the prostate and above the external urethral sphincter such that the balloon neck is in the bladder neck upon balloon inflation. The method can include inflating the balloon until the coating layer contacts walls of the benign prostatic hyperplasia or prostate cancer at the target site, the enlarged prostate splits and creates a commissurotomy, and the balloon achieves an inflated balloon diameter for an inflation period; deflating the balloon after the inflation period, wherein the inflation period is from 0.1 minutes to 10 minutes; and withdrawing the balloon catheter from the prostate. The ratio of inflated balloon diameter to untreated body lumen diameter at the target site can be about 1.0 to about 40, or about 4 to about 40; the stretch ratio at the location of treatment can be about 1.0 to about 40, or about 4 to about 40. Optionally the inflating can include inflating to a pressure equal to or greater than the nominal pressure of the balloon catheter. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

A method for treating an achalasia stricture includes optionally flushing the achalasia stricture with water, saline solution, or a water solution including at least one water soluble additive; inserting a balloon catheter into a target site in the esophagus, the balloon catheter including a balloon and a coating layer overlying external surfaces of the balloon; positioning the balloon body in the esophagus and above the esophageal sphincter, such that the balloon neck is in the lower esophageal sphincter upon balloon inflation, and the distal segment of the balloon is in the upper end of the stomach. The method can include inflating the balloon until the coating layer contacts walls of the achalasia stricture at the target site, and the balloon achieves an inflated balloon diameter for an inflation period; deflating the balloon after the inflation period, wherein the inflation period is from 0.1 minutes to 10 minutes; and withdrawing the balloon catheter from the esophagus. The ratio of inflated balloon diameter to untreated body lumen diameter at the target site can be about 1.0 to about 40, or about 4 to about 40; the stretch ratio at the location of treatment can be about 1.0 to about 40, or about 4 to about 40. In some instances, the achalasia stricture can be pre-dilated with a balloon without a coating layer which can be of smaller nominal diameter than the treatment balloon. Optionally, the inflating can include inflating to a pressure equal to or greater than the nominal pressure of the balloon catheter. The balloon catheter can include one or more necks, as shown in FIGS. 1A-1C and FIG. 2. In various embodiments, the neck of the balloon can be positioned in the lower esophageal sphincter, with the one or more balloon lobes distal to the neck within the stomach, and with the one or more balloon lobes proximal to the neck within the esophagus.

A method for treating a urethral stricture includes flushing the urethral stricture with water, saline solution, or a water solution including at least one water soluble additive; inserting a balloon catheter into a target site in the urethral stricture, the balloon catheter including a balloon and a coating layer overlying external surfaces of the balloon, wherein the coating layer includes at least one water-soluble additive, and an initial drug load of a therapeutic agent; and the ratio by weight of the therapeutic agent in the coating layer to the total weight of the one or more water-soluble additives in the coating layer is from about 0.05 to 20; inflating the balloon until the coating layer contacts walls of the urethral stricture at the target site and the balloon achieves an inflated balloon diameter for an inflation period; deflating the balloon after the inflation period, wherein the inflation period is from 0.1 minutes to 10 minutes; and withdrawing the balloon catheter from the urethral stricture. The ratio of inflated balloon diameter to an untreated diameter of the body lumen at the site of the urethral stricture can be about 1.0 to about 40, or about 4 to about 40; the stretch ratio at the location of treatment can be about 1.0 to about 40, or about 4 to about 40. After dilation, the diameter of the urethral stricture can be 6.7 mm or more, such as about 6.7 mm to about 50 mm, or about 6.7 mm to about 20 mm, or less than, equal to, or greater than about 6.7, 6.8, 6.9, 7.0, 7.2, 7.4, 7.6, 7.8, 8, 8.5, 9, 9.5, 10, 11, 12, 13, 14, 15, 16, 17, 18, 19, 20, 25, 30, 35, 40, 45 mm, or about 50 mm or more. Optionally the inflating can include inflating to a pressure equal to or greater than the nominal pressure of the balloon catheter.

In one embodiment, the balloon has thereon a residual drug amount of less than 70% of the initial drug load after the withdrawing.

A method for treating an esophageal stricture includes optionally flushing the esophageal stricture with water, saline solution or a water solution including at least one water soluble additive; inserting a balloon catheter into a target site in the esophageal stricture, the balloon catheter including a balloon and a coating layer overlying external surfaces of the balloon, wherein the coating layer includes at least one water-soluble second additive, and a therapeutic agent with an initial drug load of from 1 to 6 micrograms of the therapeutic agent per square millimeter of the balloon;

the therapeutic agent is chosen from paclitaxel, taxol, docetaxel, rapamycin, sirolimus, zotarolimus, tacrolimus, everolimus, mTOR inhibitors, or their analogues, and combinations thereof; the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; and the ratio by weight of the therapeutic agent in the coating layer to the total weight of the one or more water-soluble additives in the coating layer is from about 0.05 to 20; inflating the balloon until the coating layer contacts walls of the esophageal stricture at the target site and the balloon achieves an inflated balloon diameter for an inflation period; deflating the balloon after the inflation period, wherein the inflation period is from 0.1 minutes to 10 minutes; and withdrawing the balloon catheter from the esophageal stricture. The ratio of the inflated balloon diameter to the untreated diameter of the esophagus at the location of the stricture can be about 1.0 to about 40, or about 4 to about 40; the stretch ratio at the location of treatment can be about 1.0 to about 40, or about 4 to about 40. In some instances where there is a severe stricture, it may not be possible to inflate the balloon to the untreated lumen diameter and the balloon can achieve an expansion ratio of 0.7, 0.8, 0.9, or more. Optionally the inflating can include inflating to a pressure equal to or greater than the nominal pressure of the balloon catheter.

Eosinophilic esophagitis (EoE) is a chronic inflammatory disease. The symptoms of the disease include dysphagia and food impaction and are often a consequence of esophageal strictures or narrowing. Repeated endoscopic dilation of the esophageal fibrostenotic eosinophilic esophagitis strictures using bougie and balloon catheter is needed for treatment of the esophageal strictures of EoE.

A method for treating an esophageal stricture of eosinophilic esophagitis includes optionally flushing the esophageal stricture with water, saline solution or a water solution including at least one water soluble additive; inserting a balloon catheter into a target site in the esophageal stricture, the balloon catheter including a balloon and a coating layer overlying external surfaces of the balloon, wherein the coating layer includes at least one water-soluble additive, and a therapeutic agent with an initial drug load of from 1 to 6 micrograms of the therapeutic agent per square millimeter of the balloon; the therapeutic agent is chosen from paclitaxel, taxol, docetaxel, rapamycin, sirolimus, zotarolimus, tacrolimus, everolimus, mTOR inhibitors, or their analogues, and combinations thereof; the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; and the ratio by weight of the therapeutic agent in the coating layer to the total weight of the one or more water-soluble additives in the coating layer is from about 0.05 to 20; inflating the balloon until the coating layer contacts walls of the esophageal stricture at the target site and the balloon achieves an inflated balloon diameter for an inflation period; deflating the balloon after the inflation period, wherein the inflation period is from 0.1 minutes to 10 minutes; and withdrawing the balloon catheter from the esophageal stricture of the eosinophilic esophagitis. The ratio of the inflated balloon diameter to the untreated diameter of the esophagus at the location of the stricture can be about 1.0 to about 40, or about 4 to about 40; the stretch ratio at the location of treatment can be about 1.0 to about 40, or about 4 to about 40. In some instances where there is a severe stricture, it may not be possible to inflate the balloon to the untreated lumen diameter and the balloon can achieve an expansion ratio of 0.7, 0.8, 0.9, or more. In some instances, the esophageal stricture can be pre-dilated with a balloon without a coating layer which can be of smaller nominal diameter than the treatment balloon. Optionally the inflating can include inflating to a pressure equal to or greater than the nominal pressure of the balloon catheter.

Inflammatory bowel disease (IBD) includes Crohn's disease (CD) and ulcerative colitis (UC). CD and UC induced strictures are a common complication of Inflammatory bowel disease (IBD) and its related surgeries. The stricture rate can range from 34% to 70% over time. Some of the strictures are refractory or reoccurring. Using prior art techniques, repeated endoscopic dilation is needed for treatment of refractory or reoccurring strictures.

A method for treating an inflammatory bowel stricture of Crohn's disease (CD) and ulcerative colitis (UC) includes optionally flushing the inflammatory bowel stricture with water, saline solution or a water solution including at least one water soluble additive; inserting a balloon catheter into a target site in the treating an inflammatory bowel stricture, the balloon catheter including a balloon and a coating layer overlying external surfaces of the balloon, wherein the coating layer includes at least one water-soluble additive, and a therapeutic agent with an initial drug load of from 1 to 6 micrograms of the therapeutic agent per square millimeter of the balloon; the therapeutic agent is chosen from paclitaxel, taxol, docetaxel, rapamycin, sirolimus, zotarolimus, tacrolimus, everolimus, mTOR inhibitors, or their analogues, and combinations thereof; the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; and the ratio by weight of the therapeutic agent in the coating layer to the total weight of the one or more water-soluble additives in the coating layer is from about 0.05 to 20; inflating the balloon until the coating layer contacts walls of the inflammatory bowel stricture at the target site and the balloon achieves an inflated balloon diameter for an inflation period; deflating the balloon after the inflation period, wherein the inflation period is from 0.1 minutes to 10 minutes; and withdrawing the balloon catheter from the inflammatory bowel stricture. The ratio of the inflated balloon diameter to the untreated diameter of the inflammatory bowel at the location of the stricture can be about 1.0 to about 40, or about 4 to about 40; the stretch ratio at the location of treatment can be about 1.0 to about 40, or about 4 to about 40. In some instances where there is a severe stricture, it may not be possible to inflate the balloon to the untreated lumen diameter and the balloon can achieve an expansion ratio of 0.7, 0.8, 0.9, or more. In some instances, the stricture can be pre-dilated with a balloon without a coating layer which can be of smaller nominal diameter than the treatment balloon. Optionally the inflating can include inflating to a pressure equal to or greater than the nominal pressure of the balloon catheter. The inflammatory bowel strictures of Crohn's disease (CD) and ulcerative colitis (UC) include small intestine strictures, duodenum strictures, jejunum strictures, ileum strictures, colon strictures, rectum strictures, large intestine strictures, colorectal strictures, strictures after gastric bypass, ileocolonic strictures, gastrointestinal strictures, and J-pouch stricture. While balloon dilation has been shown to be a safe and effective nonsurgical method of treating an inflammatory bowel stricture of Crohn's disease (CD) and ulcerative colitis (UC), problems remain. The strictures can be refractory or reoccurring strictures, and using prior art techniques, repeated balloon dilations are needed. In another embodiment, the method for treating an inflammatory bowel stricture of Crohn's disease (CD) and ulcerative colitis (UC) include performing a stricturotomy prior to drug-coated balloon dilation. The stricturotomy can include endoscopic mucosal resection, endoscopic submucosal dissection, needle knife electroincision, and electrocauterization. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

A method for treating a radiation induced stricture includes optionally flushing the radiation induced stricture with water, saline solution or a water solution including at least one water soluble additive; inserting a balloon catheter into a target site in the radiation stricture, the balloon catheter including a balloon and a coating layer overlying external surfaces of the balloon, wherein the coating layer includes at least one water-soluble additive, and a therapeutic agent with an initial drug load of from 1 to 6 micrograms of the therapeutic agent per square millimeter of the balloon; the therapeutic agent is chosen from paclitaxel, taxol, docetaxel, rapamycin, sirolimus, zotarolimus, tacrolimus, everolimus, mTOR inhibitors, or their analogues, and combinations thereof; the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; and the ratio by weight of the therapeutic agent in the coating layer to the total weight of the one or more water-soluble additives in the coating layer is from about 0.05 to 20; inflating the balloon until the coating layer contacts walls of the radiation induced stricture at the target site and the balloon achieves an inflated balloon diameter for an inflation period; deflating the balloon after the inflation period, wherein the inflation period is from 0.1 minutes to 10 minutes; and withdrawing the balloon catheter from radiation induced stricture. The ratio of the inflated balloon diameter to the untreated diameter of the radiation body lumen at the location of the stricture can be about 1.0 to about 40, or about 4 to about 40; the stretch ratio at the location of treatment can be about 1.0 to about 40, or about 4 to about 40. In some instances, the radiation induced stricture can be pre-dilated with a balloon without a coating layer which can be of smaller nominal diameter than the treatment balloon. Optionally the inflating can include inflating to a pressure equal to or greater than the nominal pressure of the balloon catheter. The radiation induced stricture includes any stricture induced by radiation injury due to treatment of cancers. The radiation stricture can include urethral strictures, ureteral strictures, esophageal strictures, sinus strictures, stomach strictures, small intestine strictures, colon strictures, rectum strictures, large intestine strictures, and biliary tract strictures. In another embodiment, the method for treating a radiation stricture includes performing a stricturotomy prior to drug-coated balloon dilation. The stricturotomy can include urethrotomy, endoscopic mucosal resection, endoscopic submucosal dissection, needle knife electroincision, direct vision internal urethrotomy (DVIU), and electrocauterization. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

A method for treating a surgical anastomotic stricture includes optionally flushing the surgical anastomotic stricture with water, saline solution or a water solution including at least one water soluble additive; inserting a balloon catheter into a target site in the surgical anastomotic stricture, the balloon catheter including a balloon and a coating layer overlying external surfaces of the balloon, wherein the coating layer includes at least one water-soluble additive, and a therapeutic agent with an initial drug load of from 1 to 6 micrograms of the therapeutic agent per square millimeter of the balloon; the therapeutic agent is chosen from paclitaxel, taxol, docetaxel, rapamycin, sirolimus, zotarolimus, tacrolimus, everolimus, mTOR inhibitors, or their analogues, and combinations thereof; the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; and the ratio by weight of the therapeutic agent in the coating layer to the total weight of the one or more water-soluble additives in the coating layer is from about 0.05 to 20; inflating the balloon until the coating layer contacts walls of the surgical anastomotic stricture at the target site and the balloon achieves an inflated balloon diameter for an inflation period; deflating the balloon after the inflation period, wherein the inflation period is from 0.1 minutes to 10 minutes; and withdrawing the balloon catheter from the surgical anastomotic stricture. The ratio of the inflated balloon diameter to the untreated diameter of the body lumen at the location of the stricture can be about 1.0 to about 40, or about 4 to about 40; the stretch ratio at the location of treatment can be about 1.0 to about 40, or about 4 to about 40. In some instances where there is a severe stricture, it may not be possible to inflate the balloon to the untreated lumen diameter and the balloon can achieve an expansion ratio of 0.7, 0.8, 0.9, or more. In some instances, the anastomatic stricture can be pre-dilated with a balloon without a coating layer which can be of smaller nominal diameter than the treatment balloon. Optionally the inflating can include inflating to a pressure equal to or greater than the nominal pressure of the balloon catheter. The surgical anastomotic stricture includes any stricture of the surgical connection between two body strictures that carry fluid. The surgical anastomosis is a surgical technique used to make a new connection between two body strictures that carry fluid. Anastomotic strictures are common complication of various surgery procedures. These strictures are mostly fibrotic and is difficult to manage. The anastomotic strictures include esophageal strictures, biliary strictures, stomach strictures, small intestine strictures, duodenum strictures, jejunum strictures, ileum strictures, colon strictures, rectum strictures, large intestine strictures, colorectal strictures, strictures after gastric bypass, ileocolonic strictures, gastrointestinal strictures, urethral strictures, ureteral strictures, J-pouch strictures, and bladder neck strictures (stenosis). Balloon dilation has been shown to be a safe and effective nonsurgical method of managing surgical anastomotic strictures. The anastomotic strictures can be refractory or reoccurring strictures, which require repeated balloon dilations using prior art techniques. In another embodiment, the method for treating a surgical anastomotic stricture includes performing a stricturotomy prior to drug-coated balloon dilation. The stricturotomy can include urethrotomy, endoscopic mucosal resection, endoscopic submucosal dissection, needle knife electroincision, direct vision internal urethrotomy (DVIU), and electrocauterization. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

Bladder neck stricture (stenosis or contracture) is recognized complication of many treatments for prostate cancer. Recalcitrant bladder neck strictures are relatively rare overall; however, they are associated with significant morbidity, often requiring multiple interventions with associated complications and impact upon quality of life. These bladder neck stricture diseases are often complications following treatment for prostate cancer, including radical prostatectomy (RP), radiotherapy, cryotherapy and high intensity focused ultrasound (HIFU), and can form following prostate treatments, or can form due to other conditions.

A method for treating a bladder neck stricture (stenosis or contracture) includes optionally flushing the bladder neck stricture with water, saline solution or a water solution including at least one water soluble additive; inserting a balloon catheter into a target site in the bladder neck stricture, the balloon catheter including a balloon and a coating layer overlying external surfaces of the balloon, wherein the coating layer includes at least one water-soluble additive, and a therapeutic agent with an initial drug load of from 1 to 6 micrograms of the therapeutic agent per square millimeter of the balloon; the therapeutic agent is chosen from paclitaxel, taxol, docetaxel, rapamycin, sirolimus, zotarolimus, tacrolimus, everolimus, mTOR inhibitors, or their analogues, and combinations thereof; the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; and the ratio by weight of the therapeutic agent in the coating layer to the total weight of the one or more water-soluble additives in the coating layer is from about 0.05 to 20; inflating the balloon until the coating layer contacts walls of the bladder neck stricture at the target site and the balloon achieves an inflated balloon diameter for an inflation period; deflating the balloon after the inflation period, wherein the inflation period is from 0.1 minutes to 10 minutes; and withdrawing the balloon catheter from the bladder neck stricture. The ratio of the inflated balloon diameter to the untreated diameter of the bladder neck at the location of the stricture can be about 1.0 to about 40, or about 4 to about 40; the stretch ratio at the location of treatment can be about 1.0 to about 40, or about 4 to about 40. In some instances where there is a severe stricture, it may not be possible to inflate the balloon to the untreated lumen diameter and the balloon can achieve an expansion ratio of 0.7, 0.8, 0.9, or more. In some instances, the stricture can be pre-dilated with a balloon without a coating layer which can be of smaller nominal diameter than the treatment balloon. Optionally the inflating can include inflating to a pressure equal to or greater than the nominal pressure of the balloon catheter. The bladder neck stricture includes any stricture of the surgical connection between the bladder and the prostate or urethral lumen. Bladder neck strictures are common complication of various surgery procedures including radical prostatectomy (RP), radiotherapy, cryotherapy and high intensity focused ultrasound (HIFU). These strictures are mostly fibrotic and is difficult to manage. Bladder neck strictures can be refractory or reoccurring strictures, which, using prior art techniques, require repeated balloon dilations. In another embodiment, the method for treating a bladder neck stricture includes performing a stricturotomy prior to drug-coated balloon dilation. The stricturotomy can include urethrotomy, endoscopic mucosal resection, endoscopic submucosal dissection, needle knife electroincision, direct vision internal urethrotomy (DVIU), and electrocauterization.

EMR (endoscopic mucosal resection) and ESD (endoscopic sub-mucosal dissection) in treatment of cancers and Barrett's esophagus of various stages. Needle knife, EMR (endoscopic mucosal resection) and ESD (endoscopic sub-mucosal dissection) are used in the treatment of superficial cancers at early stages. The cancers include esophageal cancers, biliary cancers, stomach cancers, small intestine cancers, duodenum cancers, jejunum cancers, ileum cancers, colon cancers, rectum cancers, colorectal cancers, ileocolonic cancers, and gastrointestinal cancers. EMR (endoscopic mucosal resection) and ESD (endoscopic sub-mucosal dissection) are used in the treatment of high graded Barrett's esophagus. EMR and ESD are feasible procedures in terms of clinical efficacy and safety; however, the recurrences of malignancy and refractory stricture were noted in some of patients. The local reoccurring rate of cancers after the treatment is in the range of 2-20% depending on the kind and stages of cancers and following up times. The reoccurring rate of stricture or stenosis is about 26%-70%. Repeated endoscopic balloon dilations are needed to treat the refractory or reoccurring strictures or stenosis using prior art techniques. In various embodiments, the present invention reduced the recurrence of malignancy or cancers using dilation of drug-coated balloon following the EMR (endoscopic mucosal resection) and ESD (endoscopic sub-mucosal dissection). In various embodiments, the present invention reduces the need for repeated balloon dilations of the stricture using dilation of drug-coated balloon following the EMR (endoscopic mucosal resection) or ESD (endoscopic sub-mucosal dissection).

A method is provided for reducing the recurrences of the strictures and cancers following the surgical procedures of needle knife, EMR (endoscopic mucosal resection) and ESD (endoscopic sub-mucosal dissection). The method includes performing the endoscopic resection of a cancerous area of the body lumen using the needle knife, EMR (endoscopic mucosal resection) and ESD (endoscopic sub-mucosal dissection); optionally flushing the resected body lumen with water, saline solution or a water solution including at least one water soluble additive; inserting a balloon catheter into a target site in the resected body lumen, the balloon catheter including a balloon and a coating layer overlying external surfaces of the balloon, wherein the coating layer includes at least one water-soluble second additive, and a therapeutic agent with an initial drug load of from 1 to 6 micrograms of the therapeutic agent per square millimeter of the balloon; the therapeutic agent is chosen from paclitaxel, taxol, docetaxel, rapamycin, sirolimus, zotarolimus, tacrolimus, everolimus, mTOR inhibitors, or their analogues, and combinations thereof; the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; and the ratio by weight of the therapeutic agent in the coating layer to the total weight of the one or more water-soluble additives in the coating layer is from about 0.05 to 20; inflating the balloon until the coating layer contacts walls of the resected body lumen at the target site and the balloon achieves an inflated balloon diameter for an inflation period; deflating the balloon after the inflation period, wherein the inflation period is from 0.1 minutes to 10 minutes; and withdrawing the balloon catheter from the resected body lumen. The ratio of the inflated balloon diameter to the untreated diameter of the body lumen can be about 1.0 to about 40, or about 4 to about 40; the stretch ratio at the location of treatment can be about 1.0 to about 40, or about 4 to about 40. In some instances, the stricture can be pre-dilated with a balloon without a coating layer which can be of smaller nominal diameter than the treatment balloon. Optionally the inflating can include inflating to a pressure equal to or greater than the nominal pressure of the balloon catheter. The length of drug-coated balloon is longer than the length of resected body lumen, therefore the resected area is covered fully with drug formulation after the balloon dilation. The length of drug-coated balloon is 1 to 2 mm longer than the length of resected body lumen. Sometimes two drug-coated balloons can be used overlappingly to cover the longer length of the lesion. The cancers can include esophageal cancers, biliary cancers, stomach cancers, small intestine cancers, duodenum cancers, jejunum cancers, ileum cancers, colon cancers, rectum cancers, colorectal cancers, ileocolonic cancers, and gastrointestinal cancers, especially those early stages of the cancers. The recurrences of the cancers and the strictures can increase with increase of the resected area and depth of the body lumen. In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

A method for reducing the recurrences of the strictures, colon polyps, or Barrett's esophagus following the surgical procedures of needle knife, EMR (endoscopic mucosal resection) and ESD (endoscopic sub-mucosal dissection) includes first performing the endoscopic resection of colon polyps or Barrett's area of the body lumen using the needle knife, EMR (endoscopic mucosal resection), or ESD (endoscopic sub-mucosal dissection); optionally flushing the resected body lumen with water, saline solution or a water solution including at least one water soluble additive; inserting a balloon catheter into a target site in the resected body lumen, the balloon catheter including a balloon and a coating layer overlying external surfaces of the balloon, wherein the coating layer includes at least one water-soluble second additive, and a therapeutic agent with an initial drug load of from 1 to 6 micrograms of the therapeutic agent per square millimeter of the balloon; the therapeutic agent is chosen from paclitaxel, taxol, docetaxel, rapamycin, sirolimus, zotarolimus, tacrolimus, everolimus, mTOR inhibitors, or their analogues, and combinations thereof; the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; and the ratio by weight of the therapeutic agent in the coating layer to the total weight of the one or more water-soluble additives in the coating layer is from about 0.05 to 20; inflating the balloon until the coating layer contacts walls of the resected body lumen at the target site and the balloon achieves an inflated balloon diameter for an inflation period; deflating the balloon after the inflation period, wherein the inflation period is from 0.1 minutes to 10 minutes; and withdrawing the balloon catheter from the resected body lumen. The ratio of the inflated balloon diameter to the untreated diameter of the body lumen can be about 1.0 to about 40, or about 4 to about 40; the stretch ratio at the location of treatment can be about 1.0 to about 40, or about 4 to about 40. In some instances where there is a severe stricture, it may not be possible to inflate the balloon to the untreated lumen diameter and the balloon can achieve an expansion ratio of 0.7, 0.8, 0.9, or more. In some instances, the stricture can be pre-dilated with a balloon without a coating layer which can be of smaller nominal diameter than the treatment balloon. Optionally the inflating can include inflating to a pressure equal to or greater than the nominal pressure of the balloon catheter. The length of drug-coated balloon is longer than the length of resected body lumen, therefore the resected area is covered fully with drug formulation after the balloon dilation. The length of drug-coated balloon is 1 to 2 mm longer than the length of resected body lumen. The recurrences of the polyps or Barrett's esophagus and the strictures increase with increase of the resected area and depth of the body lumen.

A method for treating a sinus stricture includes flushing the sinus stricture with water, saline solution, or a water solution including at least one water soluble additives; inserting a balloon catheter into a target site in the sinus stricture, the balloon catheter including a balloon and a coating layer overlying external surfaces of the balloon, wherein the coating layer includes at least one water-soluble additive, and a therapeutic agent with an initial drug load of from 1 to 6 micrograms of the therapeutic agent per square millimeter of the balloon; the therapeutic agent is chosen from budesonide, flunisolide, triamcinolone, beclomethasone, fluticasone, mometasone, mometasone furoate, dexamethasone, hydrocortisone, methylprednisolone, prednisone, cortisone, betamethasone, triamcinolone acetonide, paclitaxel, taxol, docetaxel, rapamycin, sirolimus, zotarolimus, tacrolimus, everolimus, mTOR inhibitors, analogues thereof, and combinations thereof; the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof; and the ratio by weight of the therapeutic agent in the coating layer to the total weight of the one or more water-soluble additives in the coating layer is from about 0.05 to 20; inflating the balloon until the coating layer contacts walls of the sinus stricture at the target site and the balloon achieves an inflated balloon diameter for an inflation period; deflating the balloon after the inflation period, wherein the inflation period is from 0.1 minutes to 10 minutes; and withdrawing the balloon catheter from the sinus stricture.

In some embodiments, the method includes using a scope that visualizes inserting to and placing of the drug coating balloon catheter at the target site, the inflating and deflating processes, balloon diameter increasing during the inflating, balloon diameter reduction the during deflating, yielding of the target site, released drug on the wall of the target site after the balloon deflation, or any combination thereof. The method can include flushing the target site with water or saline solution through the scope before inserting the balloon catheter into the stricture or target site.

Additive

In various embodiments, the additive can have two parts. One part is hydrophilic and the other part is a drug affinity part. The drug affinity part is a hydrophobic part and/or has an affinity to the therapeutic agent by hydrogen bonding and/or van der Waals interactions. The drug affinity part of the additive can bind the lipophilic drug, such as paclitaxel, taxol, docetaxel, rapamycin, sirolimus, zotarolimus, tacrolimus, everolimus, mTOR inhibitors, or their analogues, and combinations thereof. The hydrophilic portion accelerates diffusion and increases permeation of the drug into tissue. It can facilitate rapid movement of drug off the medical device during deployment at the target site by preventing hydrophobic drug molecules from clumping to each other and to the device, increasing drug solubility in interstitial spaces, and/or accelerating drug lumen through polar head groups to the lipid bilayer of cell membranes of target tissues. The additives of embodiments of the present invention have two parts that function together to facilitate rapid release of drug off the device surface and uptake by target tissue during deployment (by accelerating drug contact with tissues for which drug has high affinity) while preventing the premature release of drug from the device surface prior to device deployment at the target site.

In embodiments of the present invention, the therapeutic agent is rapidly released after the medical device is brought into contact with tissue and is readily absorbed. For example, certain embodiments of devices of the present invention include drug-coated balloon catheters that deliver a therapeutic agent such as a lipophilic antiproliferative pharmaceutical (such as paclitaxel or rapamycin) to non-vascular tissue through brief, direct pressure contact at high drug concentration during balloon nonvascular body balloon dilation. The lipophilic drug, for example, is retained in target tissue at the delivery site, where it inhibits hyperplasia and restenosis yet allows epithelization. In these embodiments, coating formulations of the present invention not only facilitate rapid release of drug from the balloon surface and transfer of drug into target tissues during deployment, but also prevent drug from diffusing away from the device during transit through tortuous anatomy prior to reaching the target site and from dislodging off the device during the initial phase of balloon inflation, before the drug coating is pressed into direct contact with the surface of the body lumen.

The additive according to certain embodiments has a drug affinity part and a hydrophilic part. The drug affinity part is a hydrophobic part and/or has an affinity to the therapeutic agent by hydrogen bonding and/or van der Waals interactions. The drug affinity part can include aliphatic and aromatic organic hydrocarbon compounds, such as benzene, toluene, and alkanes, among others. These parts are not water soluble. They can bind both hydrophobic drug, with which they share structural similarities, and lipids of cell membranes. The drug affinity part can include functional groups that can form hydrogen bonds with drug and with itself. The hydrophilic part can include hydroxyl groups, amine groups, amide groups, carbonyl groups, carboxylic acid and anhydrides, ethyl oxide, ethyl glycol, polyethylene glycol, ascorbic acid, amino acid, amino alcohol, glucose, sucrose, sorbitan, glycerol, polyalcohol, phosphates, sulfates, organic salts and their substituted molecules, among others. One or more hydroxyl, carboxyl, acid, amide or amine groups, for example, can be advantageous since they easily displace water molecules that are hydrogen-bound to polar head groups and surface proteins of cell membranes and can function to remove this barrier between hydrophobic drug and cell membrane lipid. These parts can dissolve in water and polar solvents. The additive of embodiments of the present invention has components to both bind drug and facilitate its rapid movement off the medical device during deployment and into target tissues.

The additives in embodiments of the present invention can be surfactants and chemical compounds with one or more hydroxyl, amino, carbonyl, carboxyl, acid, amide, or ester moieties. The surfactants include ionic, nonionic, aliphatic, and aromatic surfactants. The chemical compounds with one or more hydroxyl, amino, carbonyl, carboxyl, acid, amide, or ester moieties are chosen from amino alcohols, hydroxyl carboxylic acid and anhydrides, ethyl oxide, ethyl glycols, amino acids, peptides, proteins, sugars, glucose, sucrose, sorbitan, glycerol, polyalcohol, phosphates, sulfates, organic acids, esters, salts, vitamins, and their substituted molecules.

As is well-known in the art, the terms "hydrophilic" and "hydrophobic" are relative terms. To function as an additive in exemplary embodiments of the present invention, the compound includes polar or charged hydrophilic moieties as well as non-polar hydrophobic (lipophilic) moieties.

An empirical parameter commonly used in medicinal chemistry to characterize the relative hydrophilicity and hydrophobicity of pharmaceutical compounds is the partition coefficient, P, the ratio of concentrations of unionized compound in the two phases of a mixture of two immiscible solvents, usually octanol and water, such that P=([solute] octanol/[solute]water). Compounds with higher log Ps are more hydrophobic, while compounds with lower log Ps are more hydrophilic. Lipinski's rule suggests that pharmaceutical compounds having log P<5 can be more membrane permeable. For purposes of certain embodiments of the present invention, for example, the additive has log P less than log P of the drug to be formulated (as an example, log P of paclitaxel is 7.4). A greater log P difference between the drug and the additive can facilitate phase separation of drug. For example, if log P of the additive is much lower than log P of the drug, the additive can accelerate the release of drug in an aqueous environment from the surface of a device to which drug might otherwise tightly adhere, thereby accelerating drug delivery to tissue during brief deployment at the site of intervention. In certain embodiments of the present invention, log P of the additive is negative. In other embodiments, log P of the additive is less than log P of the drug. While a compound's octanol-water partition coefficient P or log P is useful as a measurement of relative hydrophilicity and hydrophobicity, it is merely a rough guide that can be useful in defining suitable additives for use in embodiments of the present invention.

Suitable additives that can be used in embodiments of the present invention include, without limitation, organic and inorganic pharmaceutical recipients, natural products and derivatives thereof (such as sugars, vitamins, amino acids, peptides, proteins, and fatty acids), low molecular weight oligomers, surfactants (anionic, cationic, non-ionic, and ionic), and mixtures thereof. The additives described herein as useful in the present invention is provided for exemplary purposes only and is not intended to be comprehensive. Many other additives can be useful for purposes of the present invention.

Surfactants

The surfactant can be any surfactant suitable for use in pharmaceutical compositions. Such surfactants can be anionic, cationic, zwitterionic or non-ionic. Mixtures of surfactants are also within the scope of various embodiments of the invention, as are combinations of surfactant and other additives. Surfactants often have one or more long aliphatic chains such as fatty acids that can insert directly into lipid bilayers of cell membranes to form part of the lipid structure, while other components of the surfactants loosen the lipid structure and enhance drug penetration and absorption. The contrast agent iopromide does not have these properties.

An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10. In certain embodiments of the present invention, a higher HLB value is utilized, since increased hydrophilicity can facilitate release of hydrophobic drug from the surface of the device. In one embodiment, the HLB of the surfactant additive is higher than 10. The additive HLB can be higher than 14. Alternatively, surfactants having lower HLB can be utilized to prevent drug loss prior to device deployment at the target site, for example in a top coat over a drug layer that has a very hydrophilic additive.

The HLB value of a surfactant is merely a rough guide generally used to enable formulation of industrial, pharmaceutical and cosmetic emulsions, for example. For many important surfactants, including several polyethoxylated surfactants, it has been reported that HLB values can differ by as much as about 8 HLB units, depending upon the empirical method chosen to determine the HLB value (Schott, J. Pharm. Sciences, 79(1), 87-88 (1990)). Keeping these inherent difficulties in mind, and using HLB values as a guide, surfactants can be identified that have suitable hydrophilicity or hydrophobicity for use in embodiments of the present invention, as described herein.

PEG-Fatty Acids and PEG-Fatty Acid Mono and Diesters.

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful in embodiments of the present invention. Examples of hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. The HLB values are in the range of 4-20.

Polyethylene glycol fatty acid diesters are also suitable for use as surfactants in the compositions of embodiments of the present invention. Hydrophilic surfactants include PEG-20 dilaurate, PEG-20 dioleate, PEG-20 distearate, PEG-32 dilaurate and PEG-32 dioleate. The HLB values are in the range of 5-15.

In general, mixtures of surfactants are also useful in embodiments of the present invention, including mixtures of two or more commercial surfactants as well as mixtures of surfactants with another additive or additives. Several PEG-fatty acid esters are marketed commercially as mixtures or mono- and di-esters.

Polyethylene Glycol Glycerol Fatty Acid Esters.

Hydrophilic surfactants can include PEG-20 glyceryl laurate, PEG-30 glyceryl laurate, PEG-40 glyceryl laurate, PEG-20 glyceryl oleate, and PEG-30 glyceryl oleate.

Alcohol-Oil Transesterification Products.

Many surfactants of different degrees of hydrophobicity or hydrophilicity can be prepared by reaction of alcohols or polyalcohol with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Alcohols include glycerol, propylene glycol, ethylene glycol, polyethylene glycol, sorbitol, and pentaerythritol. Among these alcohol-oil transesterified surfactants, hydrophilic surfactants are PEG-35 castor oil (Incrocas-35), PEG-40 hydrogenated castor oil (Cremophor RH 40), PEG-25 trioleate (TAGA™ TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). For example, hydrophobic surfactants in this class include PEG-5 hydrogenated castor oil, PEG-7 hydrogenated castor oil, PEG-9 hydrogenated castor oil, PEG-6 corn oil (Labrafil™ M 2125 CS), PEG-6 almond oil (Labrafil™ M 1966 CS), PEG-6 apricot kernel oil (Labrafil™ M 1944 CS), PEG-6 olive oil (Labrafil™ M 1980 CS), PEG-6 peanut oil (Labrafil™ M 1969 CS), PEG-6 hydrogenated palm kernel oil (Labrafil™ M 2130 BS), PEG-6 palm kernel oil (Labrafil™ M 2130 CS), PEG-6 triolein (Labrafil™ M 2735 CS), PEG-8 corn oil (Labrafil™ WL 2609 BS), PEG-20 corn glycerides (Crovol M40), and PEG-20 almond glycerides (Crovol A40).

Polyglyceryl Fatty Acids.

Polyglycerol esters of fatty acids are also suitable surfactants for use in embodiments of the present invention. Among the polyglyceryl fatty acid esters, hydrophobic surfactants include polyglyceryl oleate (Plurol Oleique), polyglyceryl-2 dioleate (Nikkol DGDO), polyglyceryl-10 trioleate, polyglyceryl stearate, polyglyceryl laurate, polyglyceryl myristate, polyglyceryl palmitate, and polyglyceryl linoleate. Hydrophilic surfactants include polyglyceryl-10 laurate (Nikkol Decaglyn 1-L), polyglyceryl-10 oleate (Nikkol Decaglyn 1-0), and polyglyceryl-10 mono, dioleate (Caprol™ PEG 860), polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate. Polyglyceryl polyricinoleates (Polymuls) are also surfactants.

Propylene Glycol Fatty Acid Esters.

Esters of propylene glycol and fatty acids are suitable surfactants for use in embodiments of the present invention. In this surfactant class, hydrophobic surfactants include propylene glycol monolaurate (Lauroglycol FCC), propylene glycol ricinoleate (Propymuls), propylene glycol monooleate (Myverol P-06), propylene glycol dicaprylate/dicaprate (Captex™ 200), and propylene glycol dioctanoate (Captex™ 800).

Sterol and Sterol Derivatives.

Sterols and derivatives of sterols are suitable surfactants for use in embodiments of the present invention. Derivatives include the polyethylene glycol derivatives. A surfactant in this class is PEG-24 cholesterol ether (Solulan C-24).

Polyethylene Glycol Sorbitan Fatty Acid Esters.

A variety of PEG-sorbitan fatty acid esters are available and are suitable for use as surfactants in embodiments of the present invention. Among the PEG-sorbitan fatty acid esters, surfactants include PEG-20 sorbitan monolaurate (Tween-20), PEG-20 sorbitan monopalmitate (Tween-40), PEG-20 sorbitan monostearate (Tween-60). PEG-20 sorbitan monooleate (Tween-80). In some embodiments, laurate esters are utilized because they have a short lipid chain compared with oleate esters, increasing drug absorption.

Polyethylene Glycol Alkyl Ethers.

Ethers of polyethylene glycol and alkyl alcohols are suitable surfactants for use in embodiments of the present invention. Ethers include PEG-3 oleyl ether (Volpo 3) and PEG-4 lauryl ether (Brij 30).

Sugar and its Derivatives.

Sugar derivatives are suitable surfactants for use in embodiments of the present invention. Surfactants in this class include sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, and octyl-β-D-thioglucopyranoside.

Polyethylene Glycol Alkyl Phenols.

Several PEG-alkyl phenol surfactants are available, such as PEG-10-100 nonyl phenol and PEG-15-100 octyl phenol ether, Tyloxapol, octoxynol, octoxynol-9, nonoxynol, and are suitable for use in embodiments of the present invention.

Polyoxyethylene-Polyoxypropylene (POE-POP) Block Copolymers.

The POE-POP block copolymers are a unique class of polymeric surfactants. The unique structure of the surfactants, with hydrophilic POE and hydrophobic POP moieties in well-defined ratios and positions, provides a wide variety of surfactants suitable for use in embodiments of the present invention. These surfactants are available under various trade names, including Synperonic PE series (ICI); Pluronic™ series (BASF), Emkalyx, Lutrol (BASF), Supronic, Monolan, Pluracare, and Plurodac. The generic term for these polymers is "poloxamer" (CAS 9003-11-6). These polymers have the formula: $HO(C_2H_4O)_a(C_3H_6O)(C_2H_4O)_aH$ where "a" and "b" denote the number of polyoxyethylene and polyoxypropylene units, respectively.

Hydrophilic surfactants of this class include Poloxamers 108, 188, 217, 238, 288, 338, and 407. Hydrophobic surfactants in this class include Poloxamers 124, 182, 183, 212, 331, and 335.

Sorbitan Fatty Acid Esters.

Sorbitan esters of fatty acids are suitable surfactants for use in embodiments of the present invention. Among these esters, hydrophobic surfactants include sorbitan monolaurate (Arlacel 20), sorbitan monopalmitate (Span-40), and sorbitan monooleate (Span-80), sorbitan monostearate.

The sorbitan monopalmitate, an amphiphilic derivative of Vitamin C (which has Vitamin C activity), can serve two important functions in solubilization systems. First, it possesses effective polar groups that can modulate the microenvironment. These polar groups are the same groups that make vitamin C itself (ascorbic acid) one of the most water-soluble organic solid compounds available: ascorbic acid is soluble to about 30 wt/wt % in water (very close to the solubility of sodium chloride, for example). Second, when the pH increases so as to convert a fraction of the ascorbyl palmitate to a more soluble salt, such as sodium ascorbyl palmitate.

Ionic Surfactants.

Ionic surfactants, including cationic, anionic and zwitterionic surfactants, are suitable hydrophilic surfactants for use in embodiments of the present invention. Ionic surfactants include quaternary ammonium salts, fatty acid salts and bile salts. Specifically, ionic surfactants include benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, dialkylester of sodium sulfonsuccinic acid, sodium dioctyl sulfosuccinate, sodium cholate, and sodium taurocholate. They can be dissolved in both organic solvents (such as ethanol, acetone, and toluene) and water. This is especially useful for medical device coatings because it simplifies the preparation and coating process and has good adhesive properties. Water insoluble drugs are commonly dissolved in organic solvents.

Some of the surfactants described herein are very stable under heating. They survive an ethylene oxide sterilization process. They do not react with drugs such as paclitaxel or rapamycin under the sterilization process. The hydroxyl, ester, amide groups are utilized because they are unlikely to react with drug, while amine and acid groups often do react with paclitaxel or rapamycin during sterilization. Furthermore, surfactant additives improve the integrity and quality of the coating layer, so that particles do not fall off during handling. When the surfactants described herein are formulated with paclitaxel, experimentally it protects drug from premature release during the device delivery process while facilitating rapid release and elution of paclitaxel during a very brief deployment time of 0.2 to 10 minutes at the target site. Drug absorption by tissues at the target site is unexpectedly high experimentally.

Chemical Compounds with One or More Hydroxyl, Amino, Carbonyl, Carboxyl, Acid, Amide, or Ester Moieties.

The chemical compounds with one or more hydroxyl, amino, carbonyl, carboxyl, acid, amide, or ester moieties include creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, N-acetylglucosamine, N-octyl-D-gluconamide, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-Lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate (e.g., Labrasol@), PEG caprate, PEG caproate, glyceryl monocaprylate, glyceryl monocaprate, glyceryl monocaproate, monolaurin, monocaprin, monocaprylin, monomyristin, monopalmitolein, and monoolein.

The chemical compounds with one or more hydroxyl, amino, carbonyl, carboxyl, acid, amide, or ester moieties include amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohols and organic acids, and their substituted molecules. Hydrophilic chemical compounds with one or more hydroxyl, amino, carbonyl, carboxyl, acid, amide, or ester moieties having a molecular weight less than 5,000-10,000 are utilized in certain embodiments. In other embodiments, molecular weight of the additive with one or more hydroxyl, amino, carbonyl, carboxyl, acid, amide, or ester moieties is less than 1000-5,000, or less than 750-1,000, or less than 750. In these embodiments, the molecular weight of the additive is to be less than that of the drug to be delivered. Further, the molecular weight of the additive is to be higher than 80 since molecules with molecular weight less than 80 very easily evaporate and do not stay in the coating of a medical device. Small molecules can diffuse quickly. They can release themselves easily from the delivery balloon, accelerating release of drug, and they can diffuse away from drug when the drug binds tissue of the body lumens.

In certain embodiments, additives with more than four hydroxyl groups are utilized, for example in the case of a high molecular weight additive. Large molecules diffuse slowly. If the molecular weight of the additive or the chemical compound is high, for example if the molecular weight is above 800, above 1000, above 1200, above 1500, or above 2000; large molecules can elute off the surface of the medical device too slowly to release drug under 2 minutes. If these large molecules contain more than four hydroxyl groups they have increased hydrophilic properties, which is necessary for relatively large molecules to release drug quickly. The increased hydrophilicity helps elute the coating off the balloon, accelerates release of drug, and improves or facilitates drug movement through water barrier and polar head groups of lipid bilayers to penetrate tissues.

In one embodiment, the hydroxyl group is utilized as the hydrophilic moiety because it is unlikely to react with water insoluble drug, such as paclitaxel or rapamycin. In some embodiments, the chemical compound having more than four hydroxyl groups has a melting point of 120° C. or less. In some embodiments, the chemical compound having more than four hydroxyl groups has three adjacent hydroxyl groups that in stereo configuration are all on one side of the molecule. For example, sorbitol and xylitol have three adjacent hydroxyl groups that in stereo configuration are all on one side of the molecule, while galactitol does not. The difference impacts the physical properties of the isomers such as the melting temperature. The stereo configuration of the three adjacent hydroxyl groups can enhance drug binding. This will lead to improved compatibility of the water insoluble drug and hydrophilic additive, and improved tissue uptake and absorption of drug.

Some of the chemical compounds with one or more hydroxyl, amine, carbonyl, carboxyl, or ester moieties described herein are very stable under heating. They survive an ethylene oxide sterilization process and do not react with the water insoluble drug paclitaxel or rapamycin during sterilization. L-ascorbic acid and its salt and diethanolamine, on the other hand, do not necessarily survive such a sterilization process, and they react with paclitaxel. A different sterilization method is therefore utilized for L-ascorbic acid and diethanolamine. For example, hydroxyl, ester, and amide groups are utilized because they are unlikely to react with therapeutic agents such as paclitaxel or rapamycin. Sometimes, amine and acid groups do react with paclitaxel, for example, experimentally, benzoic acid, gentisic acid, diethanolamine, and ascorbic acid were not stable under ethylene oxide sterilization, heating, and aging process and reacted with paclitaxel. When the chemical compounds described herein are formulated with paclitaxel, a top coat layer can be advantageous to prevent premature drug loss during the device delivery process before deployment at the target site, since hydrophilic small molecules sometimes release drug too easily. The chemical compounds herein rapidly elute drug off the balloon during deployment at the target site. Surprisingly, even though some drug is lost during transit of the device to the target site when the coating contains these additives, experimentally drug absorption by tissue is unexpectedly high after only 0.2-10 minutes of deployment, for example, with the additive hydroxyl lactones such as ribonic acid lactone and gluconolactone.

Fat-Soluble Vitamins and Salts Thereof.

Vitamins A, D, E and K in many of their various forms and provitamin forms are considered as fat-soluble vitamins and in addition to these several other vitamins and vitamin sources or close relatives are also fat-soluble and have polar groups, and relatively high octanol-water partition coefficients. Clearly, the general class of such compounds has a history of safe use and high benefit to risk ratio, making them useful as additives in embodiments of the present invention.

The following examples of fat-soluble vitamin derivatives and/or sources are also useful as additives: alpha-tocopherol, beta-tocopherol, gamma-tocopherol, delta-tocopherol, tocopherol acetate, ergosterol, 1-alpha-hydroxycholecalciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K-S(II). Folic acid is also of this type, and although it is water-soluble at physiological pH, it can be formulated in the free acid form. Other derivatives of fat-soluble vitamins useful in embodiments of the present invention can easily be obtained via well-known chemical reactions with hydrophilic molecules.

Water-Soluble Vitamins and their Amphiphilic Derivatives.

Vitamins B, C, U, pantothenic acid, folic acid, and some of the menadione-related vitamins/provitamins in many of their various forms are considered water-soluble vitamins. These can also be conjugated or complexed with hydrophobic moieties or multivalent ions into amphiphilic forms having relatively high octanol-water partition coefficients and polar groups. Again, such compounds can be of low toxicity and high benefit to risk ratio, making them useful as additives in embodiments of the present invention. Salts of these can also be useful as additives in the present invention. Examples of water-soluble vitamins and derivatives include, without limitation, acetiamine, benfotiamine, pantothenic acid, cetotiamine, cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U. Also, as mentioned above, folic acid is, over a wide pH range including physiological pH, water-soluble, as a salt.

Compounds in which an amino or other basic group is present can easily be modified by simple acid-base reaction with a hydrophobic group-containing acid such as a fatty acid (especially lauric, oleic, myristic, palmitic, stearic, or 2-ethylhexanoic acid), low-solubility amino acid, benzoic acid, salicylic acid, or an acidic fat-soluble vitamin (such as riboflavin). Other compounds might be obtained by reacting such an acid with another group on the vitamin such as a hydroxyl group to form a linkage such as an ester linkage, etc. Derivatives of a water-soluble vitamin containing an acidic group can be generated in reactions with a hydrophobic group-containing reactant such as stearylamine or riboflavine, for example, to create a compound that is useful in embodiments of the present invention. The linkage of a palmitate chain to vitamin C yields ascorbyl palmitate.

Amino Acids and their Salts.

Alanine, arginine, asparagines, aspartic acid, cysteine, cystine, glutamic acid, glutamine, glycine, histidine, proline, isoleucine, leucine, lysine, methionine, phenylalanine, serine, threonine, tryptophan, tyrosine, valine, and derivatives thereof are other useful additives in embodiments of the invention.

Certain amino acids, in their zwitterionic form and/or in a salt form with a monovalent or multivalent ion, have polar groups, relatively high octanol-water partition coefficients, and are useful in embodiments of the present invention. In the context of the present disclosure we take "low-solubility amino acid" to mean an amino acid which has solubility in unbuffered water of less than about 4% (40 mg/mL). These include cystine, tyrosine, tryptophan, leucine, isoleucine, phenylalanine, asparagine, aspartic acid, glutamic acid, and methionine.

Amino acid dimers, sugar-conjugates, and other derivatives are also useful. Through simple reactions well-known in the art hydrophilic molecules can be joined to hydrophobic amino acids, or hydrophobic molecules to hydrophilic amino acids, to make additional additives useful in embodiments of the present invention.

Catecholamines, such as dopamine, levodopa, carbidopa, and DOPA, are also useful as additives.

Oligopeptides, Peptides and Proteins.

Oligopeptides and peptides are useful as additives, since hydrophobic and hydrophilic amino acids can be easily coupled and various sequences of amino acids can be tested to maximally facilitate permeation of tissue by drug.

Proteins are also useful as additives in embodiments of the present invention. Serum albumin, for example, is a useful additive since it is water-soluble and contains significant hydrophobic parts to bind drug: paclitaxel is 89% to 98% protein-bound after human intravenous infusion, and rapamycin is 92% protein bound, primarily (97%) to albumin. Furthermore, paclitaxel solubility in PBS increases over 20-fold with the addition of BSA. Albumin is naturally present at high concentrations in serum and is thus very safe for human use.

Other useful proteins include, without limitation, other albumins, immunoglobulins, caseins, hemoglobins, lysozymes, immunoglobins, a-2-macroglobulin, fibronectins, vitronectins, firbinogens, lipases, and the like.

Organic Acids and their Esters and Anhydrides.

Examples include acetic acid and anhydride, benzoic acid and anhydride, diethylenetriaminepentaacetic acid dianhydride, ethylenediaminetetraacetic dianhydride, maleic acid and anhydride, succinic acid and anhydride, diglycolic anhydride, glutaric anhydride, ascorbic acid, citric acid, tartaric acid, lactic acid, oxalic acid aspartic acid, nicotinic acid, 2-pyrrolidone-5-carboxylic acid, and 2-pyrrolidone.

These esters and anhydrides are soluble in organic solvents such as ethanol, acetone, methylethylketone, ethylacetate. The water insoluble drugs can be dissolved in organic solvent with these esters and anhydrides, then coated easily on to the medical device, then hydrolyzed under high pH conditions. The hydrolyzed anhydrides or esters are acids or alcohols, which are water soluble and can effectively carry the drugs off the device into the walls of the body lumen.

Other Chemical Compounds with One or More Hydroxyl, Amine, Carbonyl, Carboxyl, or Ester Moieties.

The additives according to embodiments include amino alcohols, alcohols, amines, acids, amides, and hydroxyl acids in both cyclo and linear aliphatic and aromatic groups. Examples are L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sinapic acid, vanillic acid, vanillic acid diethylamide, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described herein, polyglycidol, glycerol, multiglycerols (e.g., chemical compounds with multiple hydroxyl, amino, carbonyl, carboxyl, or ester moieties), galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, and derivatives and combinations thereof.

Combinations of additives can also be useful for purposes of the present invention. One embodiment includes the combination or mixture of two additives, for example, a first additive including a surfactant and a second additive including a chemical compound with one or more hydroxyl, amine, carbonyl, carboxyl, or ester moieties.

The combination or mixture of the surfactant and the small water-soluble molecule (the chemical compounds with one or more hydroxyl, amine, carbonyl, carboxyl, or ester moieties) has advantages. Formulations including mixtures of the two additives with water-insoluble drug are in certain cases superior to mixtures including either additive alone. The hydrophobic drugs bind extremely water-soluble small molecules more poorly than they do surfactants. They are often phase separated from the small water-soluble molecules, which can lead to suboptimal coating uniformity and integrity. The water-insoluble drug has Log P higher than both that of the surfactant and that of small water-soluble molecules. However, Log P of the surfactant is typically higher than Log P of the chemical compounds with one or more hydroxyl, amine, carbonyl, carboxyl, or ester moieties. The surfactant has a relatively high Log P (usually above 0) and the water-soluble molecules have low Log P (e.g., below 0). Some surfactants, when used as additives in embodiments of the present invention, adhere so strongly to the water-insoluble drug and the surface of the medical device that drug is not able to rapidly release from the surface of the medical device at the target site. On the other hand, some of the water-soluble small molecules (with one or more hydroxyl, amine, carbonyl, carboxyl, or ester moieties) adhere so poorly to the medical device that they release drug before it reaches the target site, for example, into serum during the transit of a coated balloon catheter to the site targeted for intervention. Surprisingly, by adjusting the ratio of the concentrations of the small hydrophilic molecule and the surfactant in the formulation, the inventor has found that the coating stability during transit and rapid drug release when inflated and pressed against tissues of the lumen wall at the target site of therapeutic intervention in certain cases is superior to a formulation including either additive alone. Furthermore, the presence of the surfactant improves the miscibility and compatibility of the water-insoluble drug and the highly water-soluble molecules. The surfactant also improves coating uniformity and integrity by its good adhesion to the drug and the small molecules. The long chain hydrophobic part of the surfactant binds the drug while the hydrophilic part of the surfactant binds the water-soluble small molecules.

The surfactants in the mixture or the combination include all of the surfactants described herein for use in embodiments of the invention. The surfactant in the mixture can be chosen from PEG sorbitan fatty esters; PEG omega-3 fatty esters, ethers, and alcohols; glycerol fatty esters, sorbitan fatty esters, PEG glyceryl fatty esters, PEG fatty esters and alcohols, sugar fatty esters, PEG sugar esters, Tween 20, Tween 40, Tween 60, p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG laurayl ether, Tween 20, Tween 40, Tween 60, Tween 80, octoxynol, octoxynol-9, monoxynol, tyloxapol, sucrose monopalmitate, sucrose monolaurate, decanoyl-N-methylglucamide, n-decyl-β-D-glucopyranoside, n-decyl-p-D-maltopyranoside, n-dodecyl-β-D-glucopyranoside, n-dodecyl-o-D-maltoside, heptanoyl-N-methylglucamide, n-heptyl-o-D-glucopyranoside, n-heptyl-o-D-thioglucoside, n-hexyl-O-D-glucopyranoside, nonanoyl-N-methylglucamide, n-nonyl-o-D-glucopyranoside, octanoyl-N-methylglucamide, n-octyl-R-D-glucopyranoside, octyl-O-D-thioglucopyranoside and their derivatives.

Embodiments of the chemical compound with one or more hydroxyl, amine, carbonyl, carboxyl, or ester moieties in the mixture or the combination can include any of the chemical compounds with one or more hydroxyl, amine, carbonyl, carboxyl, or ester moieties described herein for use in embodiments of the invention. In various embodiments, the chemical compound with one or more hydroxyl, amine, carbonyl, carboxyl, or ester moieties in the mixture has at least one hydroxyl group. In certain embodiments, additives with more than four hydroxyl groups are utilized, for example in the case of a high molecular weight additive. In some embodiments, the chemical compound having more than four hydroxyl groups has a melting point of 120° C. or less. Large molecules diffuse slowly. If the molecular weight of the additive or the chemical compound is high, for example if the molecular weight is above 800, above 1000, above 1200, above 1500, or above 2000; large molecules can elute off the surface of the medical device too slowly to release drug under 2 minutes. If these large molecules contain more than four hydroxyl groups they have increased hydrophilic properties, which is necessary for relatively large molecules to release drug quickly. The increased hydrophilicity helps elute the coating off the balloon, accelerates release of drug, and improves or facilitates drug movement through water barrier and polar head groups of lipid bilayers to penetrate tissues. In one embodiment, the hydroxyl group is utilized as the hydrophilic moiety because it is unlikely to react with water insoluble drug, such as paclitaxel or rapamycin.

The chemical compound with one or more hydroxyl, amine, carbonyl, carboxyl, or ester moieties in the mixture is chosen from L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sinapic acid, vanillic acid, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described herein, polyglycidol, glycerol, multiglycerols, galactitol, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, di(ethylene glycol), tri(ethylene glycol), tetra(ethylene glycol), penta(ethylene glycol), poly (ethylene glycol) oligomers, di(propylene glycol), tri(propylene glycol), tetra(propylene glycol), and penta(propylene glycol), poly(propylene glycol) oligomers, a block copolymer of polyethylene glycol and polypropylene glycol, and derivatives and combinations thereof.

Mixtures or combinations of a surfactant and a water-soluble small molecule confer the advantages of both additives. The water insoluble drug often has a poor compatibility with highly water-soluble chemical compounds, and the surfactant improves compatibility. The surfactant also improves the coating quality, uniformity, and integrity, and particles do not fall off the balloon during handling. The surfactant reduces drug loss during transit to a target site. The water-soluble chemical compound improves the release of drug off the balloon and absorption of the drug in the tissue. Experimentally, the combination was surprisingly effective at preventing drug release during transit and achieving high drug levels in tissue after very brief 0.2 to 2 minute deployment. Furthermore, in animal studies it effectively reduced stenosis and late lumen loss.

Some of the mixtures or combinations of surfactants and water-soluble small molecules are very stable under heating. They survived an ethylene oxide sterilization process and do not react with the water insoluble drug or drugs during sterilization (e.g., paclitaxel, taxol, docetaxel, rapamycin, sirolimus, zotarolimus, tacrolimus, everolimus, mTOR inhibitors, or their analogues, and combinations thereof). In one embodiment, the hydroxyl, ester, amide groups are utilized because they are unlikely to react with therapeutic agents such as paclitaxel or rapamycin. Sometimes amine and acid groups do react with paclitaxel and are not stable under ethylene oxide sterilization, heating, and aging. When the mixtures or combinations described herein are formulated with paclitaxel, a top coat layer can be advantageous in order to protect the drug layer and from premature drug loss during the device.

Examples of additives include p-isononylphenoxy-polyglycidol, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, octoxynol, octoxynol-9, monoxynol, tyloxapol, sucrose monopalmitate, sucrose monolaurate, decanoyl-N-methylglucamide, n-decyl-p-D-glucopyranoside, n-decyl-o-D-maltopyranoside, n-dodecyl-p-D-glucopyranoside, n-dodecyl-p-D-maltoside, heptanoyl-N-methylglucamide, n-heptyl-p-D-glucopyranoside, n-heptyl-o-D-thioglucoside, n-hexyl-o-D-glucopyranoside, nonanoyl-N-methylglucamide, n-nonyl-o-D-glucopyranoside, octanoyl-N-methylglucamide, n-octyl-o-D-glucopyranoside, octyl-p-D-thioglucopyranoside; cystine, tyrosine, tryptophan, leucine, isoleucine, phenylalanine, asparagine, aspartic acid, glutamic acid, and methionine (amino acids), cetotiamine, cyclothiamine, dexpanthenol, niacinamide, nicotinic acid and its salt, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium doceсylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl) urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, di(ethylene glycol), tri(ethylene glycol), tetra(ethylene glycol), penta(ethylene glycol), poly (ethylene glycol) oligomers, di(propylene glycol), tri(propylene glycol), tetra(propylene glycol), and penta(propylene glycol), poly(propylene glycol) oligomers, a block copolymer of polyethylene glycol and polypropylene glycol, and derivatives and combinations thereof. (chemical compounds with one or more hydroxyl, amino, carbonyl, carboxyl, or ester moieties). Some of these additives are both water-soluble and soluble in organic solvents. They have good adhesive properties and adhere to the surface of polyamide medical devices, such as balloon catheters. They can therefore be used in the adherent layer, top layer, and/or in the drug layer of embodiments of the present invention. The aromatic and aliphatic groups increase the solubility of water insoluble drugs in the coating solution, and the polar groups of alcohols and acids accelerate drug permeation of tissue.

Other additives according to embodiments of the invention include hydroxyl ketone, hydroxyl lactone, hydroxyl acid, hydroxyl ester, and hydroxyl amide. Examples are gluconolactone, D-glucoheptono-1,4-lactone, glucooctanoic lactone, gulonic acid lactone, mannoic lactone, erythronic acid lactone, ribonic acid lactone, glucuronic acid, gluconic acid, gentisic acid, lactobionic acid, lactic acid, acetaminophen, vanillic acid, sinapic acid, hydroxybenzoic acid, methyl paraben, propyl paraben, and derivatives thereof.

From a structural point of view, these additives share structural similarities and are compatible with water insoluble drugs (such as paclitaxel and rapamycin). They often contain double bonds such as $C=C$, $C=N$, $C=O$ in aromatic or aliphatic structures. These additives also contain amine, alcohol, ester, amide, anhydride, carboxylic acid, and/or hydroxyl groups. They can form hydrogen bonds and/or van der Waals interactions with drug. They are also useful in the top layer in the coating. Compounds containing one or more hydroxyl, carboxyl, or amine groups, for example, are especially useful as additives since they facilitate drug release from the device surface and easily displace water next to the polar head groups and surface proteins of cell membranes and can thereby remove this barrier to hydrophobic drug permeability. They accelerate movement of a hydrophobic drug off the balloon to the lipid layer of cell membranes and tissues for which it has very high affinity. They can also carry or accelerate the movement of drug off the balloon into more aqueous environments such as the interstitial space, for example, of nonvascular tissues that have been injured by balloon angioplasty or stent expansion. Additives such as polyglyceryl fatty esters, ascorbic ester of fatty acids, sugar esters, alcohols and ethers of fatty acids have fatty chains that can integrate into the lipid structure of target tissue membranes, carrying drug to lipid structures. Some of the amino acids, vitamins and organic acids have aromatic C=N groups as well as amino, hydroxyl, and carboxylic components to their structure. They have structural parts that can bind or complex with hydrophobic drug, such as paclitaxel or rapamycin, and they also have structural parts that facilitate tissue penetration by removing barriers between hydrophobic drug and lipid structure of cell membranes.

For example, isononylphenylpolyglycidol (Olin-10 G and Surfactant-10G), PEG glyceryl monooleate, sorbitan monolaurate (Arlacel 20), sorbitan monopalmitate (Span-40), sorbitan monooleate (Span-80), sorbitan monostearate, polyglyceryl-10 oleate, polyglyceryl-10 laurate, polyglyceryl-10 palmitate, and polyglyceryl-10 stearate all have more than four hydroxyl groups in their hydrophilic part. These hydroxyl groups have very good affinity for walls of the body lumen and can displace hydrogen-bound water molecules. At the same time, they have long chains of fatty acid, alcohol, ether, and ester that can both complex with hydrophobic drug and integrate into the lipid structure of the cell membranes to form the part of the lipid structure. This deformation or loosening of the lipid membrane of target cells can further accelerate permeation of hydrophobic drug into tissue.

For another example, L-ascorbic acid, thiamine, maleic acids, niacinamide, and 2-pyrrolidone-5-carboxylic acid all have a very high water and ethanol solubility and a low molecular weight and small size. They also have structural components including aromatic C=N, amino, hydroxyl, and carboxylic groups. These structures have very good compatibility with paclitaxel and rapamycin and can increase the solubility of these water-insoluble drugs in water and enhance their absorption into tissues. However, they often have poor adhesion to the surface of medical devices. They are therefore used in combination with other additives in the drug layer and top layer where they are useful to enhance drug absorption. Vitamin D2 and D3 are especially useful because they themselves have anti-restenotic effects and reduce thrombosis, especially when used in combination with paclitaxel.

In embodiments of the present invention, the additive is soluble in aqueous solvents and is soluble in organic solvents. Extremely hydrophobic compounds that lack sufficient hydrophilic parts and are insoluble in aqueous solvent, such as the dye Sudan Red, are not useful as additives in these embodiments. Sudan red is also genotoxic.

In one embodiment, the concentration density of the at least one therapeutic agent applied to the surface of the medical device is from about 1 to 20 µg/mm$^2$, or from about 2 to 6 µg/mm$^2$, or about 0.5 microgram/mm$^2$ or less, or less than, equal to, or greater than about 1, 2, 3, 4, 5, 6, 7, 8, 9, 10, 12, 14, 16, 18, or about 20 micrograms/mm$^2$ or more. If the medical device is a balloon, these measurements are calculated at nominal diameter. In one embodiment, the concentration of the at least one additive applied to the surface of the medical device is from about 0.5 to 20 µg/mm$^2$, or from about 2 to 6 µg/mm$^2$, or about 0.5 microgram/mm$^2$ or less, or less than, equal to, or greater than about 1, 2, 3, 4, 5, 6, 7, 8, 9, 10, 12, 14, 16, 18, or about 20 micrograms/mm$^2$ or more. The ratio of additives to drug by weight in the coating layer in embodiments of the present invention can be about 20 to 0.05, about 10 to 0.1, or about 5 to 0.15.

The relative amount of the therapeutic agent and the additive in the coating layer, can vary depending on applicable circumstances. The optimal amount of the additive can depend upon, for example, the particular therapeutic agent and additive selected, the critical micelle concentration of the surface modifier if it forms micelles, the hydrophilic-lipophilic-balance (HLB) of a surfactant or an additive's octonol-water partition coefficient (P), the melting point of the additive, the water solubility of the additive and/or therapeutic agent, the surface tension of water solutions of the surface modifier, and the like.

Other considerations will further inform the choice of specific proportions of different additives. These considerations can include the degree of bioacceptability of the additives and the desired dosage of therapeutic agent to be provided.

Therapeutic Agent.

The therapeutic agent which can be used in embodiments of the present invention, can be any drugs or biologically active materials. The therapeutic agent can be a hydrophobic therapeutic agent, an antiproliferative therapeutic agent, an anti-inflammatory agent, or a combination thereof. The drugs can be of various physical states, e.g., molecular distribution, crystal forms or cluster forms. Examples of drugs that are especially useful in embodiments of the present invention are lipophilic substantially water insoluble drugs, such as paclitaxel, rapamycin, daunorubicin, doxorubicin, lapachone, vitamin D2 and D3 and analogues and derivatives thereof. These drugs are especially suitable for use in a coating on a balloon catheter used to treat tissue of the vasculature. Therapeutic agents, such as antiproliferative drugs, such as paclitaxel, taxol, docetaxel, rapamycin, sirolimus, zotarolimus, tacrolimus, everolimus, mTOR inhibitors (i.e., a class of drugs that inhibit the mechanistic target of rapamycin), or their analogues, can be delivered to the wall of a body lumen to treat the narrowing or stricture.

Other drugs that can be useful in embodiments of the present invention include, without limitation, glucocorticoids (e.g., dexamethasone, betamethasone), hirudin, angiopeptin, aspirin, growth factors, antisense agents, anti-cancer agents, antiproliferative agents, oligonucleotides, and, more generally, anti-platelet agents, anti-coagulant agents, anti-mitotic agents, antioxidants, anti-metabolite agents, anti-chemotactic, anti-inflammatory agents, and combinations thereof.

Some drugs that can be useful in various embodiments, such as particularly for the airway, sinus, and other nasal lumens but also for urethral applications are corticosteroids such as, budesonide, flunisolide, triamcinolone, beclomethasone, fluticasone, mometasone, mometasone furoate, dexamethasone, hydrocortisone, methylprednisolone, prednisone, cortisone, betamethasone, triamcinolone acetonide, or the like. Some other suitable drugs are terbutaline, albuterol, ipratropium, pirbuterol, epinephrine, salmeterol, levalbuterol, formoterol, or the like; the drug can be a bronchodilator or a vasoconstrictor.

Also useful in embodiments of the present invention are polynucleotides, antisense, RNAi, or siRNA, for example, that inhibit inflammation and/or smooth muscle cell or fibroblast proliferation.

Anti-platelet agents can include drugs such as aspirin and dipyridamole. Aspirin is classified as an analgesic, antipyretic, anti-inflammatory and anti-platelet drug. Dipyridamole is a drug similar to aspirin in that it has anti-platelet characteristics. Dipyridamole is also classified as a coronary vasodilator. Anti-coagulant agents for use in embodiments of the present invention can include drugs such as heparin, protamine, hirudin and tick anticoagulant protein. Antioxidant agents can include probucol. Antiproliferative agents can include drugs such as amlodipine and doxazosin. Antimitotic agents and anti-metabolite agents that can be used in embodiments of the present invention include drugs such as methotrexate, azathioprine, vincristine, vinblastine, 5-fluorouracil, adriamycin, and mutamycin. Antibiotic agents for use in embodiments of the present invention include penicillin, cefoxitin, oxacillin, tobramycin, and gentamicin. Suitable antioxidants for use in embodiments of the present invention include probucol. Additionally, genes or nucleic acids, or portions thereof can be used as the therapeutic agent in embodiments of the present invention. Furthermore, collagen-synthesis inhibitors, such as tranilast, can be used as a therapeutic agent in embodiments of the present invention.

Photosensitizing agents for photodynamic or radiation therapy, including various porphyrin compounds such as porfimer, for example, are also useful as drugs in embodiments of the present invention.

Drugs for use in embodiments of the present invention also include everolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, ifosfamide, trofosfamide, chlorambucil, bendamustine, dacarbazine, busulfan, procarbazine, treosulfan, temozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, betulinic acid, camptothecin, lapachol, beta.-lapachone, podophyllotoxin, betulin, podophyllic acid 2-ethylhydrazide, molgramostim (rhuGM-CSF), peginterferon a-2b, lenograstim (r-HuG-CSF), filgrastim, macrogol, dacarbazine, basiliximab, daclizumab, selectin (cytokine antagonist), CETP inhibitor, cadherines, cytokinin inhibitors, COX-2 inhibitor, NFkB, angiopeptin, ciprofloxacin, camptothecin, fluoroblastin, monoclonal antibodies, which inhibit the muscle cell proliferation, bFGF antagonists, probucol, prostaglandins, 1,11-dimethoxycanthin-6-one, 1-hydroxy-11-methoxycanthin-6-one, scopoletin, colchicine, NO donors such as pentaerythritol tetranitrate and syndnoeimines, S-nitrosoderivatives, tamoxifen, staurosporine, beta.-estradiol, a-estradiol, estriol, estrone, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors (tyrphostines), cyclosporine A, 6-a-hydroxy-paclitaxel, baccatin, taxotere and other macrocyclic oligomers of carbon suboxide (MCS) and derivatives thereof, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, 3-sitosterin, ademetionine, myrtecaine, polidocanol, non ivamide, levomenthol, benzocaine, aescin, ellipticine, D-24851 (Calbiochem), colcemid, cytochalasin A-E, indanocine, nocodazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics such as cefadroxil, cefazolin, cefaclor, cefotaxim, tobramycin, gentamycin, penicillins such as dicloxacillin, oxacillin, sulfonamides, metronidazol, antithrombotics such as argatroban, aspirin, abciximab, synthetic antithrombin, bivalirudin, coumadin, enoxaparin, desulphated and N-reacetylated heparin, tissue plasminogen activator, GpIIb/IIIa platelet membrane receptor, factor Xa inhibitor antibody, heparin, hirudin, r-hirudin, PPACK, protamin, prourokinase, streptokinase, warfarin, urokinase, vasodilators such as dipyramidole, trapidil, nitroprussides, PDGF antagonists such as triazolopyrimidine and seramin, ACE inhibitors such as captopril, cilazapril, lisinopril, enalapril, losartan, thiol protease inhibitors, prostacyclin, vapiprost, interferon α, β- and γ, histamine antagonists, serotonin blockers, apoptosis inhibitors, apoptosis regulators such as p65 NF-kB or BcI-xL antisense oligonucleotides, halofuginone, nifedipine, tranilast, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainamide, retinoic acid, quinidine, disopyramide, flecamide, propafenone, sotalol, amidorone, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudine, antimycotics such as clotrimazole, flucytosine, griseofulvin, ketoconazole, miconazole, nystatin, terbinafine, antiprozoal agents such as chloroquine, mefloquine, quinine, moreover natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-a-senecioyloxychaparrin, taxamairin A and B, regenilol, triptolide, moreover cymarin, apocymarin, aristolochic acid, anopterin, hydroxyanopterin, anemonin, protoanemonin, berberine, cheliburin chloride, cictoxin, sinococuline, bombrestatin A and B, cudraisoflavonei A, curcumin, dihydronitidine, nitidine chloride, 12-beta-hydroxypregnadien-3,20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, bisparthenolidine, oxoushinsunine, aristolactam-AII, bisparthenolidine, periplocoside A, ghalakinoside, ursolic acid, deoxypsorospermin, psychorubin, ricin A, sanguinarine, manwu wheat acid, methylsorbifolin, sphatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, and vismione A and B.

A combination of drugs can also be used in embodiments of the present invention. Some of the combinations have additive effects because they have a different mechanism, such as paclitaxel and rapamycin, paclitaxel and active vitamin D, paclitaxel and lapachone, rapamycin and active vitamin D, rapamycin and lapachone. Because of the additive effects, the dose of the drug can be reduced as well. These combinations can reduce complications from using a high dose of the drug.

Solvents.

Solvents for preparing of the coating layer can include, as examples, one or combination of the following: (a) water, (b) alkanes such as hexane, octane, cyclohexane, and heptane, (c) aromatic solvents such as benzene, toluene, and xylene, (d) alcohols such as ethanol, propanol, and isopropanol, diethylamide, ethylene glycol monoethyl ether, Trascutol, and benzyl alcohol (e) ethers such as dioxane, dimethyl ether and tetrahydrofuran, (f) esters/acetates such as ethyl acetate and isobutyl acetate, (g) ketones such as acetone, acetonitrile, diethyl ketone, and methyl ethyl ketone, and (h) mixture of water and organic solvents such as water/ethanol, water/acetone, water/methanol, water/tetrahydrofuran. A solvent in the top coating layer can be, for example, methanol, ethanol, and acetone.

Organic solvents, such as short-chained alcohol, dioxane, tetrahydrofuran, dimethylformamide, acetonitrile, dimethylsulfoxide, etc., are particularly useful solvents in embodiments of the present invention because these organic solvents generally disrupt colloidal aggregates and co-solubilize all the components in the coating solution.

The therapeutic agent and additive or additives can be dispersed in, solubilized, or otherwise mixed in the solvent. The weight percent of drug and additives in the solvent can be in the range of 0.1-80% by weight, or 2-20% by weight.

Various embodiments provide a method for preparing a balloon catheter. First, a coating solution or suspension including at least one solvent, at least one therapeutic agent, and at least one additive is prepared. In at least one embodiment, the coating solution or suspension includes only these three components. The content of the therapeutic agent in the coating solution can be from 0.5-50% by weight based on the total weight of the solution. The content of the additive in the coating solution can be from about 0.1 wt % to about 45 wt %, about 0.2 wt % to about 40 wt % by weight, about 0.3 to about 15 wt %, or about 0.1 wt % or less, or less than, equal to, or greater than about 0.2 wt %, 0.3, 0.4, 0.5, 0.6, 0.8, 1, 2, 3, 4, 5, 6, 7, 8, 9, 10, 12, 14, 16, 18, 20, 22, 24, 26, 28, 30, 35, 40, or about 45 wt % or more, based on the total weight of the solution. The amount of solvent used depends on the coating process and viscosity. It will affect the uniformity of the drug-additive coating but will be evaporated.

In other embodiments, two or more solvents, two or more therapeutic agents, and/or two or more additives can be used in the coating solution.

In other embodiments, a therapeutic agent, an additive and a polymeric material can be used in the coating solution for the balloon catheter. In the coating, the therapeutic agent is not encapsulated in polymer particles.

Various techniques can be used for applying a coating solution to a medical device such as casting, fixed volume liquid dispensing, metering (e.g., dispense a fixed amount of coating solution based on volume onto the balloon), spinning, spraying, dipping (immersing), ink jet printing, electrostatic techniques, and combinations of these processes. During the application of the coating solution, the balloon can be at least partially inflated. The metering can be performed in any suitable way, such as by pumping liquid coating solution from a reservoir to a nozzle that is proximate the surface of the balloon (e.g., the surface of an at least partially inflated balloon). The nozzle can dispense the liquid therefrom, which can be immediately transferred to the exterior of the balloon due to its proximity to the nozzle (e.g., the nozzle can be so close to the balloon that the liquid emerging from the nozzle can contact and be transferred to the exterior of the balloon before forming a drop of liquid that leaves the nozzle). The nozzle can dispense the liquid to the exterior of the balloon such that substantially none of the liquid is lost. The balloon can be rotated around its longitudinal axis during the dispensing of the liquid from the nozzle. The nozzle can move during the dispensing, such as along the exterior of the balloon parallel to the longitudinal axis of the balloon. In some embodiments, the balloon can be rotated around its longitudinal axis during the dispensing, and the nozzle can move parallel to the longitudinal axis of the balloon, such that substantially all of the balloon surface is coated with the coating solution (e.g., similar to the movement of a woodworker's chisel on a cylindrical piece of spinning wood in a lathe).

Choosing an application technique principally depends on the viscosity and surface tension of the solution. In some embodiments of the present invention, metering can be utilized because it makes it easier to control the uniformity of the thickness of the coating layer as well as the concentration of the therapeutic agent applied to the medical device.

In one embodiment of the present invention, the balloon is inflated or partially inflated, the coating solution is applied to the inflated balloon by metering it on while the balloon is inflated and rotating along its longitudinal axis. The balloon is then allowed to dry before being deflated, folded, and sheathed.

The description of an embodiment of an application device, fixture, and metering technique is an example. Any suitable metering or other technique can be used for coating the balloon catheter.

After the medical device is coated with the coating solution, the coated balloon is subjected to a drying in which the solvent in the coating solution is evaporated. This produces a coating matrix on the balloon containing the therapeutic agent. One example of a drying technique is placing a coated balloon into an oven at approximately 20° C. or higher for approximately 24 hours. Any other suitable method of drying the coating solution can be used. The time, temperature, and relative humidity can vary with particular additives and therapeutic agents.

An embodiment of the present invention relates to a method of treating a benign prostatic hyperplasia. The method includes inserting a medical device including a coating into a prostatic urethra. The coating layer includes a therapeutic agent and an additive. In this embodiment, the medical device can be configured as having at least an expandable portion. Some examples of such devices include balloon catheters, fixed wire balloon catheter, over-the-wire balloon catheter, rapid exchange catheter, perfusion balloon catheters, an infusion catheter (e.g., distal perforated drug infusion catheters, a perforated balloon, spaced double balloon, porous balloon, and weeping balloon, cutting balloon catheters), spaced double balloons, cutting balloon catheter, scoring balloon catheters, self-expanded and balloon expanded-stents, guide catheters, guide wires, embolic protection devices, and various imaging devices.

As mentioned herein, one example of a medical device that is particularly useful in the present invention is a coated balloon catheter. A balloon catheter typically has a long, narrow, hollow tube tabbed with a miniature, deflated balloon. In embodiments of the present invention, the balloon is coated with a drug solution. Then, the balloon is maneuvered through the stricture in the nonvascular body lumen to the site of a blockage, occlusion, or other tissue requiring a therapeutic agent. Once in the proper position, the balloon is inflated and contacts the walls of the stricture in the nonvascular body lumen and/or a blockage or occlusion. It is an object of embodiments of the present invention to rapidly deliver drug to and facilitate absorption by target tissue. In various embodiments, it can be advantageous to efficiently deliver drug to tissue in as brief a period as possible while the device is deployed at the target site. The therapeutic agent can be released into such tissue, for example the lumen walls, in about 0.1 to 30 minutes, for example, or about 0.1 to 10 minutes, or about 0.2 to 2 minutes, or about 0.1 to 1 minutes, of balloon inflation time pressing the drug coating into contact with diseased nonvascular tissue.

Given that a therapeutically effective amount of the drug can be delivered by embodiments of the present invention into, for example, the prostate, in some cases the need for a stent can be eliminated, obviating the complications of fracture and dripping associated therewith.

The balloon catheter can be used to treat nonvascular tissue/disease alone or in combination with other methods and medical devices for treating the non-vasculature, for example, direct vision internal urethrotomy (DVIU) for strictures and transurethral resection of the prostate (TURP) for BPH. DVIU is a procedure used to open a urethral stricture. Specifically, DVIU is a procedure in which relaxing incisions are made in a stricture to create urethral luminal gain. DVIU can be accomplished using cold knife (urethrotome) or a hot knife (electrode). The cutter is inserted into the body and advanced through the urethra to the area of narrowing. After the relaxing incisions have been made, balloon dilation using the coated balloon of embodiments of the present invention can be performed. In addition, stenting can be performed thereafter, or simultaneous with expansion of the coated balloon as described herein. In another embodiment, balloon dilation using the coated balloon of embodiments of the present invention can be performed inside a placed stent. For TURP the medical device typically used is a hot knife (electrode) or a laser. In either case the device is inserted into the body and advanced through the urethra to the prostatic urethra. After the prostatic tissue has been excised, balloon dilation using the coated balloon of embodiments of the present invention can be performed. In addition, stenting can be performed thereafter, or simultaneous with expansion of the coated balloon as described herein. In another embodiment a self-expanding stent coated with the therapeutic agents and additives of the present invention can be delivered and placed inside the body lumen strictures including esophageal strictures, achalasia strictures, biliary strictures, stomach strictures, small intestine strictures, duodenum strictures, jejunum strictures, ileum strictures, colon strictures, rectum strictures, and large intestine strictures.

Preparation.

Various embodiments of the present invention provide a method of forming a balloon. The method can include placing a tube including balloon material or extruding the balloon material into a mold having any suitable shape, such as a balloon mold having a shape including a proximal cone, at least one main body section, at least one neck section having a diameter less than the at least one main body section, another at least one main body section, and a distal cone. The method can include heating the balloon material to a temperature above the glass transition temperature thereof, pressurizing the interior of the balloon material tube, and stretching the balloon material to reduce the balloon thickness. The method can also include expanding the balloon material tube into contact with the interior of the mold.

Various embodiments of the present invention provide a method of forming a balloon and then shrinking it to get a large diameter range. The method includes placing a tube including balloon material into a balloon mold wherein the balloon mold has a shape including a proximal cone, at least one main body section, and a distal cone. The method includes pressurizing the interior of the balloon material tube. The method includes expanding the balloon material tube into contact with the interior of the mold at pressures of 200-400 psi and temperatures of 100-200° C. The formed balloon is then shrunk by annealing the balloon at a temperature lower than the forming process with low inflation pressure for a specified amount of time, preferably 1-30 psi at 70-90° C., for 3-30 seconds. Once the balloon is shrunk it can be attached to a catheter shaft and coated with drug. Any of the manufacturing techniques, methods of treating body lumens, or balloons described in the following patents, which are hereby incorporated by reference as if they were reproduced herein in their entirety, can be used in embodiments of the present invention: U.S. Pat. Nos. 7,163,522 and 7,108,826.

The medical device and the coating layers of embodiments of the present invention can be made according to various methods. For example, the coating solution can be prepared by dispersing, dissolving, diffusing, or otherwise mixing all the ingredients, such as a therapeutic agent, an additive, and a solvent, simultaneously together. Also, the coating solution can be prepared by sequentially adding each component based on solubility or any other parameters. For example, the coating solution can be prepared by first adding the therapeutic agent to the solvent and then adding the additive. Alternatively, the additive can be added to the solvent first and then the therapeutic agent can be later added. If the solvent used does not sufficiently dissolve the drug, it is useful to first add the additive to the solvent, then the drug, since the additive will increase drug solubility in the solvent.

International Prostate Symptom Score (IPSS) and $Q_{max}$.

$Q_{max}$ is a measure of the maximum urine flow rate obtained during a urodynamic test. It is the maximum volumetric flow rate of urine during urination. It is a measure of the quantity of urine voided in a specified period of time (per second or per minute). It can be measured with uroflowmetry. $Q_{max}$ indicates the maximum flow rate during a voiding cycle. $Q_{max}$ is used as an indicator for the diagnosis of enlarged prostate or other urinary tract occlusion or urethral stricture A lower $Q_{max}$ can indicate obstruction caused by an enlarged prostate or that the urethral stricture has partially occluded the urethra.

By using this invention, for example, the balloon shown in FIG. 3, a patient with urethral strictures can experience an increase in $Q_{max}$. The typical $Q_{max}$ for a person with a urethral stricture is in the range of 0 to 10 mL/s. Following treatment (measurements usually taken between 14 and 30 days following treatment) with the balloon of this invention, the $Q_{max}$ would be expected to increase to 9 to 52 mL/s, or a minimum of 15 mUs or, in some embodiments, to a minimum of 20 mUs or, in some embodiments, to less than, equal to, or greater than about 8 mUs, 9, 10, 11, 12, 13, 14, 15, 16, 17, 18, 19, 20, 22, 24, 26, 28, 30, 35, 40, 45, or about 50 mL/s or more. This treatment has been shown to have a long-term effect on $Q_{max}$. In some embodiments, after 6 months, $Q_{max}$ can still be at or above 15 mL/s, 20 mL/s, or in the range of 6 to 50 mUs, or less than, equal to, or greater than about 8 mUs, 9, 10, 11, 12, 13, 14, 15, 16, 17, 18, 19, 20, 22, 24, 26, 28, 30, 35, 40, 45, or about 50 mL/s or more. After 12 months, in various embodiments, Q, can still be above 15 mL/s, 20 mL/s, or in the range of 6 to 50 mL/s, 9 to 32 mUs, or less than, equal to, or greater than about 8 mL/s, 9, 10, 11, 12, 13, 14, 15, 16, 17, 18, 19, 20, 22, 24, 26, 28, 30, 35, 40, 45, or about 50 mL/s or more.

By using this invention, for example, the balloon shown in FIG. 1A, 1B, 1C, 2, 5A-5D, or 7A-7C, a patient with benign prostate hyperplasia can experience an increase in $Q_{max}$. The typical $Q_{max}$ for a person with a BPH is in the range of 0 to 12 mUs. Following treatment with the balloon of this invention, in various embodiments, the $Q_{max}$ can increase to a minimum of 16 mL/s, to a range of 4 to 58 mL/s, or less than, equal to, or greater than about 8 mL/s, 9, 10, 11, 12, 13, 14, 15, 16, 17, 18, 19, 20, 22, 24, 26, 28, 30, 35, 40, 45, 50, 55, or about 60 mUs or more. The treatment has been shown to have a long-term effect on $Q_{max}$. After 6 months, $Q_{max}$ can be above a minimum of 16 mL/s or, in some embodiments, in the range of 16 to 32 mL/s, or less than, equal to, or greater than about 8 mUs, 9, 10, 11, 12, 13, 14, 15, 16, 17, 18, 19, 20, 22, 24, 26, 28, 30, 35, 40, 45, or about 50 mUs or more. After 12 months, $Q_{max}$ can be above a minimum of 16 mUs or, in some embodiments, in the range of 16 to 30 mL/s, or less than, equal to, or greater than about 8 mL/s, 9, 10, 11, 12, 13, 14, 15, 16, 17, 18, 19, 20, 22, 24, 26, 28, 30, 35, 40, 45, or about 50 mUs or more. These effects distinguish the current invention from prior art devices and methods.

The International Prostate Symptom Score (IPSS) is a validated patient-reported outcome measures (PROM) scoring system. Urologists accept it worldwide and it is used to screen for and diagnose benign prostatic hyperplasia (BPH) and other lower urinary tract symptoms (LUTS) and diseases such as urethral strictures. The IPSS score allows a urologist to monitor symptoms and guide decisions about how to manage the disease. The IPSS is based on the answers to eight questions, seven regarding disease symptoms and one question related to the patient's quality of life. For the symptom questions, the patient is asked to choose the rating that best represents their condition. The scale ranges from 0 to 5, with 5 representing the most symptomatic disease. The seven symptom scores are summed to give an overall maximum possible score of 35. The answer to the quality of life question is scored on a scale of 0 to 6. According to these scoring systems, the scores can be categorized as follows: symptoms are mild if the score is 7 or less; symptoms are moderate if the score is 8 to 19; and symptoms are severe if the score is 20 to 35.

By using this invention, for example the balloon shown in FIG. 3, a patient with urethral strictures can experience a decrease in IPSS. The typical IPSS for a person with a urethral stricture is in the range of 15 to 35. Following treatment with the balloon of this invention, the IPSS would be expected to be at a maximum of 14 or, in some embodiments be in the range of 0 to 13, 4 to 13, 0 to 11, or 0, or less than, equal to, or greater than about 1, 2, 3, 4, 5, 6, 7, 8, 9, 10, 11, 12, 13, or about 14. This treatment has been shown to have a long-term effect on IPSS. After 6 months, IPSS is still below a maximum of 14 and in some embodiments in the range of 0 to 13, 1 to 13, 0 to 11, or 0, or less than, equal to, or greater than about 1, 2, 3, 4, 5, 6, 7, 8, 9, 10, 11, 12, 13, or about 14. After 12 months, IPSS is still below a maximum of 14, or can be 0 to 7, or 0, or less than, equal to, or greater than about 1, 2, 3, 4, 5, 6, 7, 8, 9, 10, 11, 12, 13, or about 14. These effects distinguish the current invention from prior art devices and methods.

By using this invention, for example the balloon catheter shown in FIG. 1A, 1B, 1C, or 2, a patient with benign prostate hyperplasia can experience a decrease in IPSS. The typical IPSS for a person with bothersome symptomatic BPH is in the range of 15 to 35. Following treatment with the balloon of this invention, the IPSS can be at a maximum of 14 or, in some embodiments, in the range of 4 to 13, or 0, or less than, equal to, or greater than about 1, 2, 3, 4, 5, 6, 7, 8, 9, 10, 11, 12, 13, or about 14. This treatment can have a long-term effect on IPSS. After 6 months, IPSS can still be at a maximum of 14 and in some embodiments in the range of 1 to 13, or 0, or less than, equal to, or greater than about 1, 2, 3, 4, 5, 6, 7, 8, 9, 10, 11, 12, 13, or about 14. After 12 months, IPSS can still be under a maximum of 14 or in some embodiments in the range of 1 to 14, or 0, or less than, equal to, or greater than about 1, 2, 3, 4, 5, 6, 7, 8, 9, 10, 11, 12, 13, or about 14. These effects distinguish the current invention from prior art devices and methods.

To obtain the desired increase in $Q_{max}$ or the decrease in IPSS, in one embodiment, a balloon coated with a therapeutic agent such as an antiproliferative or anti-inflammatory drug and one or more water-soluble additives, as described herein, is positioned within the area of a urethral stricture or within the prostate. For strictures, the balloon is then inflated to a diameter that is 1.0 to 40 times larger than the diameter of the untreated target location in the urethra, such as about 1.2 to 3 times larger. For BPH treatment, the balloon is inflated to a diameter that can be about 1.0 to 40 times larger than the untreated prostatic urethra, or about 1.2 to 10 times larger. That is, the ratio of the inflated balloon diameter to the untreated diameter of the body lumen at the location of treatment for a urethral stricture can be from 1.2 to 3 and for BPH treatment can be 1.2 to 10; the stretch ratio can be the same or different. The balloon can be left inflated for 0.1 to 10 minutes to allow the drug to be delivered to the urethra. In some embodiments, a scope such as a cystoscope can be used to aid in the placement of the balloon. In some embodiments, the balloon catheter shaft can be within the lumen of the scope and in other embodiments it can be placed side by side with the scope. In some embodiments, the stricture or prostate can be pre-dilated with a non-drug-coated balloon prior to treatment by the drug-coated balloon. In some embodiments, the pre-dilation balloon will be slightly shorter than the treatment balloon, such as to ensure that the entire area of the urethra or prostate that is pre-dilated is later treated with the drug-coated balloon. In some embodiments, the lumen and/or the drug-coated balloon is flushed or soaked in water, saline, urine, or a water solution including at least one water soluble additive prior to drug-coated balloon insertion. The drug-coated balloon can be covered with a sheath to provide protection to the coating during delivery to the treatment site. The sheath can be removed from the balloon prior to inflating the balloon.
Treatment of BPH.

Various embodiments of the present invention provide a method of treating benign prostatic hyperplasia (BPH). The method can include inserting a first sheath including a pre-dilation balloon catheter into the urethra, the pre-dilation balloon catheter including a pre-dilation balloon. The method can include removing the first sheath from the urethra while leaving the pre-dilation catheter in the urethra. The method can include inserting a cystoscope into the urethra. The method can include using the cystoscope to visualize placement of the pre-dilation balloon in the prostatic urethra. The method can include inflating the pre-dilation balloon to dilate the prostatic urethra with the pre-dilation balloon to form an initial commissurotomy of the prostatic urethra. The method can include deflating the pre-dilation balloon. The method can include using the cystoscope to verify that the pre-dilation balloon has created the initial commissurotomy. The method can include removing the cystoscope from the urethra. The method can include reinserting the first sheath into the urethra over the pre-dilation balloon catheter. The method can include pulling the pre-dilation balloon into the first sheath. The method can include removing the first sheath including the pre-dilation balloon catheter from the urethra. The method can include inserting a second sheath including a drug-coated balloon catheter into the urethra, the drug-coated balloon catheter including a drug-coated balloon, the drug-coated balloon including a coating layer overlying an exterior surface thereof, the coating layer including one or more water-soluble additives and an initial drug load of a therapeutic agent. The method can include removing the second sheath from the urethra while leaving the drug-coated balloon catheter in the urethra. The method can include inserting a cystoscope into the urethra. The method can include using the cystoscope to visualize placement of the drug-coated balloon in the prostatic urethra. The method can include inflating the drug-coated balloon to contact the coating layer with the prostatic urethra. The method can include removing the cystoscope from the urethra. The method can include maintaining the drug-coated balloon in an inflated state for at least 5 minutes. The method can include deflating the drug-coated balloon. The method can include reinserting the second sheath into the urethra over the drug-coated balloon catheter. The method can include pulling the drug-coated balloon into the second sheath. The method also can include removing the second sheath including the drug-coated balloon catheter from the urethra.

The method of treating BPH can include inserting the first sheath, which can be a cysto-urethroscope, resectoscope, or other appropriately sized sheath, transurethrally into the bladder. The method can include removing optics or obturator from inside of sheath, leaving the sheath behind. A guidewire may be used to facilitate sheath tracking. If the pre-dilation balloon is covered by an insertion sheath, the method can include removing the insertion sheath. The method can include inserting the pre-dilation balloon into the sheath until the device is at least partially in the bladder. In some embodiments, the pre-dilation balloon will be of a smaller diameter than the drug coated balloon. The method can include removing the sheath from the body leaving the pre-dilation balloon catheter device behind and in the bladder/urethra. The method can include inserting a cystoscope side-by-side with the catheter shaft. The scope can have a constant flush to keep the urethra partially expanded. The method can include visualizing the placement of the pre-dilation balloon. The method can include inflating the pre-dilation balloon. The method can include using the scope to visualize whether or not the pre-dilation balloon has created an initial commissurotomy. The method can include removing the scope from the urethra. The method can include inserting the first sheath (e.g., cysto-urethroscope sheath, resectoscope sheath, or other appropriately sized sheath) over the pre-dilation balloon catheter until the distal end of the sheath hits the proximal end of the balloon. The method can include pulling the balloon into the sheath and removing both the sheath and the balloon catheter. In some embodiments, the balloon may be withdrawn, and the sheath will be left in the urethra. The method can include placing the scope or obturator into a second sheath (e.g., cysto-urethroscope, resectoscope, or other appropriately sized sheath, the same as or different than the first sheath) and inserting into the urethra until the distal end of the sheath is located in the bladder. A guidewire may be used to facilitate sheath tracking. The method can include removing the optics or obturator from the sheath. The method can include inserting the drug-coated balloon catheter into the sheath until the drug-coated balloon is at least partially in the bladder. The method can include removing the sheath. The method can include inserting the cystoscope side-by-side with the catheter shaft. The method can include visualizing the placement of the drug-coated balloon. The method can include inflating the drug coated balloon. Once the drug coated balloon is inflated, the method can include removing the scope. The method can include keeping the drug-coated balloon inflated for at least 5 minutes. The method can include deflating the drug-coated balloon and sliding the sheath over the catheter shaft until the proximal end of the drug-coated balloon is located. The method can include pulling the drug coated balloon into the sheath and removing the sheath/drug coated balloon from the urethra.

Treatment of BPH.

In various embodiments, the present invention provides a method of treating benign prostatic hyperplasia (BPH). The method can include inserting a first sheath into the urethra. The method can include inserting a pre-dilation balloon catheter including a pre-dilation balloon into the first sheath. The method can include removing the first sheath. The method can include inserting a cystoscope into the urethra side-by-side with the pre-dilation balloon catheter. The method can include using the cystoscope to visualize placement of the pre-dilation balloon in the prostatic urethra. The method can include inflating the pre-dilation balloon to dilate the prostatic urethra with the pre-dilation balloon to form an initial commissurotomy of the prostatic urethra. The method can include deflating the pre-dilation balloon. The method can include using the cystoscope to verify that the pre-dilation balloon has created the initial commissurotomy. The method can include removing the cystoscope from the urethra. The method can include inserting the first sheath over the pre-dilation balloon in the urethra. The method can include pulling the pre-dilation balloon into the first sheath.

The method can include either removing the pre-dilation balloon from the first sheath while leaving the first sheath in place, wherein the first sheath is a second sheath; or removing the pre-dilation balloon and the first sheath from the urethra, and inserting the second sheath into the urethra (e.g., wherein the second sheath is the same as or different than the first sheath). The method can include inserting a drug-coated balloon catheter into the second sheath, the drug-coated balloon catheter including a drug-coated balloon, the drug-coated balloon including a coating layer overlying an exterior surface thereof, the coating layer including one or more water-soluble additives and an initial drug load of a therapeutic agent. The method can include removing the second sheath from the urethra. The method can include inserting a cystoscope into the urethra side-by-side with the drug-coated balloon catheter. The method can include using the cystoscope to visualize placement of the drug-coated balloon in the prostatic urethra. The method can include inflating the drug-coated balloon to contact the coating layer with the prostatic urethra. The method can include removing the cystoscope from the urethra. The method can include maintaining the drug-coated balloon in an inflated state for at least 5 minutes. The method can include deflating the drug-coated balloon. The method can include inserting the second sheath over the drug-coated balloon in the urethra. The method can include pulling the drug-coated balloon into the second sheath. The method can include removing the second sheath including the drug-coated balloon catheter from the urethra.

Although various embodiments are specifically illustrated and described herein, it will be appreciated that modifications and variations of the present invention are covered by the above teachings and are within the purview of the appended claims without departing from the spirit and intended scope of the invention.

Other than the operating examples, or where otherwise indicated, all numbers expressing quantities of components in a layer, reaction conditions, and so forth used in the specification and claims are to be understood as being modified in all instances by the term "about." Accordingly, unless otherwise indicated to the contrary, the numerical parameters set forth in this specification and attached claims are approximations that can vary depending upon the desired properties sought to be obtained by the present disclosure.

EXAMPLES

Various embodiments of the present invention can be better understood by reference to the following Examples which are offered by way of illustration. The present invention is not limited to the Examples given herein.

Throughout the Examples, unless otherwise indicated, the stretch ratio was calculated as the ratio of the nominal diameter of the balloon to the untreated diameter of the body lumen at the location of treatment. The untreated diameter of the body lumen at the location of treatment is the normal diameter for the body lumen at the location of treatment and can be calculated as the average of the diameters of healthy tissue adjacent to the stricture, stenosis, or lesion, that is proximal and distal of the stricture or stenosis or lesion of the lumen. The inflated balloon diameter was about equal to the nominal balloon diameter for the pressure used during the inflation period and was within 10% of the nominal balloon diameter.

Part I. Preclinical and Bench Testing

Example I-1. Preparation of Coating Solutions

Formulation 1: 50-150 mg (0.06-0.18 mmole) paclitaxel, 25-300 mg PEG8 caprylic/capric glycerides, and 2-6 ml ethanol were mixed.

Formulation 2: 50-150 mg (0.06-0.18 mmole) paclitaxel, 25-300 mg PEG8 caprylic/capric glycerides, 25-300 mg uracil and 2-6 ml ethanol were mixed.

Formulation 3: 50-150 mg (0.06-0.18 mmole) paclitaxel, 25-300 mg PEG8 caprylic/capric glycerides, 25-300 mg uridine and 2-6 ml ethanol were mixed.

Formulation 4: 50-150 mg (0.06-0.18 mmole) paclitaxel, 25-300 mg PEG8 caprylic/capric glycerides, 25-300 mg sucralose and 2-6 ml ethanol were mixed.

Formulation 4a: 50-150 mg (0.06-0.18 mmole) paclitaxel, 25-300 mg PEG8 caprylic/capric glycerides, 25-300 mg sucralose and 2-6 ml ethanol were mixed, with a mass ratio of paclitaxel:PEG8 caprylic/capric glycerides:sucralose of 1:1:1.

Formulation 4b: 50-150 mg (0.06-0.18 mmole) paclitaxel, 25-300 mg PEG8 caprylic/capric glycerides, 25-300 mg sucralose and 2-6 ml ethanol were mixed, with a mass ratio of paclitaxel:PEG8 caprylic/capric glycerides:sucralose of 1:1:2.

Formulation 5: 50-150 mg (0.06-0.18 mmole) paclitaxel, 25-300 mg PEG8 caprylic/capric glycerides, 25-300 mg creatinine and 2-6 ml ethanol were mixed.

Formulation 6: 50-150 mg (0.06-0.18 mmole) paclitaxel, 25-300 mg PEG6 caprylic/capric glycerides, 25-300 mg uracil and 2-6 ml ethanol were mixed.

Formulation 7: 50-150 mg (0.06-0.18 mmole) paclitaxel, 25-300 mg C6-ceramide and 2-6 ml ethanol were mixed.

Formulation 8: 50-150 mg (0.06-0.18 mmole) paclitaxel, 25-300 mg monolaurin, 25-300 mg sucralose and 2-6 ml ethanol were mixed.

Formulation 9: 50-150 mg (0.06-0.18 mmole) paclitaxel, 25-300 mg sucralose and 2-6 ml ethanol were mixed.

Formulation 10: 50-150 mg (0.06-0.18 mmole) paclitaxel, 25-300 mg PEG8 mono caprylate/caprate and 1-6 ml ethanol were mixed.

Formulation 11: 50-150 mg (0.06-0.18 mmole) paclitaxel, 25-300 mg PEG8 mono caprylate/caprate, 25-300 mg sucralose and 1-6 ml ethanol were mixed.

Formulation 12: 50-150 mg (0.06-0.18 mmole) paclitaxel, 25-300 mg thymidine, and 1-6 ml (96/4 v/v) THF/water were mixed.

Formulation 13: 50-150 mg (0.06-0.18 mmole) paclitaxel, 25-300 mg uridine, and 1-6 ml (96/4 v/v) THF/water were mixed.

Formulation 14: 50-150 mg (0.06-0.18 mmole) paclitaxel, 25-300 mg caffeine, and 1-6 ml (96/4 v/v) THF/water were mixed.

Formulation 15: 50-150 mg (0.06-0.18 mmole) paclitaxel, 25-300 mg 18Crown6, and 1-6 ml ethanol were mixed.

Formulation 16: 50-150 mg (0.06-0.18 mmole) paclitaxel, 25-300 mg 18Crown6, and 1-6 ml ethanol were mixed.

Formulation 17: 50-150 mg (0.06-0.18 mmole) paclitaxel, 10-100 mg 18Crown6, 10-100 mg pentaerythritol ethoxylate (15/4) and 1-6 ml ethanol were mixed.

Formulation 18: 50-150 mg (0.06-0.18 mmole) paclitaxel, 25-300 mg pentaerythritol ethoxylate (15/4), and 1-6 ml ethanol were mixed.

Formulation 19: 50-150 mg (0.06-0.18 mmole) paclitaxel, 25-300 mg trimethylpropane ethoxylate (Mw~1014)), and 1-6 ml ethanol were mixed.

Formulation 20: 50-150 mg (0.06-0.18 mmole) paclitaxel, 25-300 mg pentaerythritol ethoxylate (3/4), and 1-6 ml ethanol were mixed.

Formulation 21: 50-150 mg (0.06-0.18 mmole) paclitaxel, 25-300 mg 15Crown5, and 1-6 ml ethanol were mixed.

Formulation 22: 25-100 mg (0.03-0.12 mmole) paclitaxel, 25-300 mg thymidine, and 1-6 ml (90/10 v/v) THF/water were mixed.

Formulation 23: 50-150 mg (0.06-0.18 mmole) paclitaxel, 5-75 mg pentaerythritol ethoxylate (15/4), 10-200 mg pentaerythritol ethoxylate (3/4), and 1-6 ml ethanol were mixed.

Formulation 24: 50-150 mg (0.06-0.18 mmole) paclitaxel, 25-300 mg trimethylpropane ethoxylate (Mw~170)), and 1-6 ml ethanol were mixed.

Example I-2. Preclinical Study 1 & 2: Prostate, Urethra and Ureter

Twenty-one balloon catheters (twelve 4 mm in diameter and 40 mm in length, six 8 mm in diameter and 40 mm in length, three 20 mm in diameter and 50 mm in length) were inflated to 1 to 2 atmospheres pressure and wiped with an ethanol wipe to clean the balloon surface. Next the balloons were coated using various formulations (1-6) from Example I-1 with sufficient coating solution to achieve 2-4 microgram paclitaxel per square mm of balloon surface. The balloons were then dried, folded, sheathed, packaged in a Tyvek pouch and ethylene oxide sterilized in preparation for animal testing.

For this study male dogs were used. Baseline urethrograms were taken to measure the inner diameter of the urethra treatment sites before drug-coated balloon treatment. Drug-coated balloon catheters were used with nonoverlapping treatments in the pelvic, bulbar, and distal urethra just proximal of the os penis. The os penis urethra was not treated. The treatment site diameters were approximately 3.5-4.5 mm. The balloon catheters were chosen such that the stretch ratio for the prostatic urethra balloons was approximately 4-10. For the anterior urethra, balloon catheters were chosen such that the stretch ratio was approximately 1.8-2.3. Prior to inserting the catheter approximately 5 mL of saline was used to flush the urethra. The 18-20 mm nominal diameter balloons were inflated in the prostatic urethra and the 8 mm nominal diameter balloons were inflated in the anterior urethra. The 18 to 20 mm nominal diameter balloons were inflated to 4 atmospheres at the treatment sites for 10 min to release drug and additive, then deflated and withdrawn from the dogs. The 8 mm nominal diameter balloons were inflated to 12 atmospheres at the treatment sites for 10 min to release drug and additive, then deflated and withdrawn from the dogs. The stretch ratio for the inflated 20 mm nominal diameter balloons was 4.4 to 6.3. The stretch ratio for the inflated 8 mm nominal diameter balloons was 2.0 to 2.5. The amount of drug in the treated urethra tissues of the sacrificed animal was measured after 4 hrs and 1 day and the residual drug remaining on the balloon after use was analyzed.

Drug-coated balloon catheters were inserted into the left ureter and urethra of a female pig. The 4 mm nominal diameter balloons were inflated to 14 atmospheres in the ureters and the 8 mm balloons were inflated to 12 atmospheres in the urethra. The balloons were inflated at the treatment sites for 10 min to release drug and additive, then deflated and withdrawn from the pigs. The stretch ratio for the 4 mm nominal diameter balloons was 2 to 2.5. The stretch ratio for the 8 mm nominal diameter balloons was 2.0 to 2.5. The drug concentration in the urethra and ureter tissues of the sacrificed animal was measured after 4 hrs. The residual drug remaining on the balloon after use was analyzed.

The dog tissue drug concentration from the prostatic urethra sample using Formulation 4a was 0.4 µg/g at 4 hours. The dog tissue drug concentration from the prostate sample using Formulation 4a was 0.367 µg/g at 4 hours. The dog tissue drug concentration from the pelvic urethra samples using Formulation 4b was 11.7 µg/g at 4 hours. The dog tissue drug concentration from the bulbar urethra samples using Formulation 4a was 25.2 µg/g at 4 hours. The dog tissue drug concentration from the prostatic urethra sample using Formulation 4a was 0.586 µg/g at 1 day. The dog tissue drug concentration from the prostate sample using Formulation 4a was 0.429 µg/g at 1 day. The dog tissue drug concentration from the pelvic urethra samples using Formulation 4b was 26.6 µg/g at day 1. The dog tissue drug concentration from the distal urethra samples using Formulation 4a was 2.04 µg/g at day 1. The residual balloon content as a percent of the original drug loading using Formulation 4a ranged from 45-87%.

The residual balloon content as a percent of the original drug loading from the samples using formulation 4b ranged from 83-85%.

At 4 hours the proximal (Formulation 4b) left ureter pig tissue drug concentration from the samples was 17.3 µg/g. At 4 hours the female pig urethra (Formulation 4a) drug concentration was 66.9 µg/g. The residual balloon content as a percent of the original drug loading ranged from 6-58%. The average residual balloon content for Formulation 4a was 52.8%. The average residual balloon content for Formulation 4b was 64.7%.

Example I-3. Preclinical Study 3: Urethra and Prostate

Twenty-three balloon catheters (twelve 8 mm in diameter and 40 mm in length, six 10 mm in diameter and 40 mm in length, four 12 mm in diameter and 30 mm in length, and three 10 mm in diameter and 30 mm in length) were inflated to 50% of their nominal inflation pressure and wiped with an ethanol wipe to clean the balloon surface. Next the balloons were coated using various formulations (1-6) in Example I-1 with sufficient coating solution to achieve 2 microgram paclitaxel per square mm of balloon surface. The balloons were then dried, folded, sheathed, packaged in a Tyvek pouch and ethylene oxide sterilized in preparation for animal testing.

For this study male dogs were used. Baseline retrograde urethrograms were taken to measure the inner diameter of the urethra treatment sites before drug-coated balloon treatment. Drug-coated balloon catheters were used with nonoverlapping treatments in the prostatic, pelvic, bulbar, and distal urethra just proximal of the os penis. The os penis urethra was not treated. The treatment site diameters were approximately 2.1-8.5 mm. The balloon catheters were chosen such that the stretch ratio for the prostatic urethra balloons was planned to be approximately 1.7-3.4. For the anterior urethra, balloon catheters were chosen such that the stretch ratio was approximately 1.8-2.3. Prior to inserting the catheter approximately 5 mL of saline was used to flush the urethra. The 12 mm nominal diameter balloons were inflated in the prostatic urethra and the 8 and 10 mm nominal diameter balloons were inflated in the anterior urethra. The 12 mm nominal diameter balloons were inflated to 9 atmospheres at the treatment sites for 10 min to release drug and additive, then deflated and withdrawn from the dogs. The 8 mm nominal diameter balloons were inflated to 10 atmospheres at the treatment sites for 10 min to release drug and additive, then deflated and withdrawn from the dogs. The stretch ratio for the 12 mm nominal diameter balloons was 2.0 to 3.0. The stretch ratio for the 8 and 10 mm nominal diameter balloons was 1.3 to 3.0. The amount of drug in the treated urethra tissues of the sacrificed animal was measured after 1 and 7 days and the residual drug remaining on the balloon after use was analyzed.

The dog tissue drug concentration from the samples ranged from 4-176 μg/g at 1 day and 0.003-23 μg/g at 7 days. The residual balloon content as a percent of the original drug loading from the samples ranged from 5-98%.

Example I-4. Preclinical Study 4: Prostate and Urethra

One hundred eight balloon catheters (forty-two 8 mm in diameter and 20 mm in length, twenty-seven 10 mm in diameter and 40 mm in length, twenty-five 12 mm in diameter and 40 mm in length, five 8 mm in diameter and 55 mm in length, nine 12 mm in diameter and 55 mm in length) were inflated to 50% of their nominal inflation pressure and wiped with an ethanol wipe to clean the balloon surface. Next the balloons were split into two groups; one group was coated using Formulation 1 and Formulation 4 from Example I-1 with sufficient coating solution to achieve 2 microgram paclitaxel per square mm of balloon surface, and the other group was coated using the same formulations from Example 1-1 with sufficient coating solution to achieve 4 microgram paclitaxel per square mm of balloon surface. The balloons were then dried, folded, sheathed, packaged in a Tyvek pouch and ethylene oxide sterilized in preparation for animal testing.

For this study male dogs were used. Baseline retrograde urethrograms were taken to measure the inner diameter of the urethra treatment sites before drug-coated balloon treatment. Drug-coated balloon catheters were used with non-overlapping treatments in the prostatic, pelvic, bulbar, and distal urethra just proximal of the os penis. The os penis urethra was not treated. The treatment site diameters were approximately 2.6-7.7 mm. The balloon catheters were chosen such that the stretch ratio for the prostatic urethra balloons was planned to be approximately 2-4. For the anterior urethra, balloon catheters were chosen such that the stretch ratio was approximately 1.8-2.3. Prior to inserting the catheter approximately 5 mL of saline was used to flush the urethra. Balloons having a nominal diameter of 8 and 12 mm were inflated in the prostatic urethra and 8 mm nominal diameter balloons were inflated in the anterior urethra. The prostatic urethra balloons were inflated to 6-9 atmospheres at the treatment sites for 10 min to release drug and additive, then deflated and withdrawn from the dogs. The 8 mm nominal diameter balloons were inflated to 10 atmospheres at the treatment sites for 10 min to release drug and additive, then deflated and withdrawn from the dogs. The stretch ratio for the prostatic urethra balloons was 2.0 to 5, 10, 15, or 20. The stretch ratio for the anterior urethra balloons was 1.1, 1.2, 1.3, 1.4, or 1.5 to 1.75, 2.0, 2.25, 2.50, 2.75, 3.0. The urethra diameter and the amount of drug in the treated urethra tissues of the sacrificed animal was measured after 1, 7 and 28 days and the residual drug remaining on the balloon after use was analyzed. At 28 days samples were taken for histological evaluation to compare drug-coated balloon tissue to plain old balloon and untreated tissue.

The dog tissue average drug concentration from the samples was 582 μg/g at 1 day, 0.347 μg/g at day 7, and 4 μg/g at day 28. The dog tissue average drug concentration from the 2 μg/g and 4 μg/g dose density Formulation 1 samples was 20.34 μg/g and 0.73 μg/g, respectively, at day 28. The dog tissue average drug concentration from the 2 μg/g and 4 μg/g dose density Formulation 4 samples was 0.01 μg/g and 1.20 μg/g, respectively, at day 28. The residual balloon content as a percent of the original drug loading from the samples ranged from 0-60%. The average residual balloon content as a percent of the original drug loading from the 2 μg/g and 4 μg/g dose density Formulation 1 samples was 11.5% and 2.4%, respectively. The average residual balloon content as a percent of the original drug loading from the 2 μg/g and 4 μg/g dose density Formulation 4 samples was 12.2% and 19.9%, respectively. The mean urethral gain at 28 days, treatment site urethra diameter at 28 days minus the urethral diameter at time of treatment, ranged from 1.6 mm to a lumen loss of 4.4 mm. Examination of the histology samples showed no discernable difference between the drug-coated balloon treatments, plain balloon treatments, and untreated tissue.

Example I-5. Preclinical Study 5: Urethra and Ureter

Forty balloon catheters (twenty 6 mm in diameter and 20 mm in length, twenty 8 mm in diameter and 20 mm in length) were inflated to 50% of their nominal inflation pressure and wiped with an ethanol wipe to clean the balloon surface. Next the balloons were split into two groups; one group was coated using various formulations (1-6) in Example I-1 with sufficient coating solution to achieve 3.5 microgram paclitaxel per square mm of balloon surface the other group was coated using various formulations (1-6) in Example I-1 with sufficient coating solution to achieve 10 microgram paclitaxel per square mm of balloon surface. The balloons were then dried, folded, sheathed, packaged in a Tyvek pouch and ethylene oxide sterilized in preparation for animal testing.

For this study female pigs were used to allow for easier access to the ureters. Before drug-coated balloon treatments baseline uretergrams and urethrograms were taken to measure the inner diameters of the ureter and urethra treatment sites before treatment. The treatment site diameters for the urethra were approximately 4.0-6.0 mm. For the urethra, balloon catheters were chosen such that the stretch ratio was approximately 1.8-2.3. The treatment site diameters for the ureters were approximately 2.0-4.0 mm. For the ureters, balloon catheters were chosen such that the stretch ratio was about 1.2-1.7 or up to 2.0. Drug-coated balloon catheters were used for nonoverlapping treatments. A controlled experiment was conducted to investigate two procedure parameters; balloon to urethra stretch, inflation time, and one product design feature; the drug dose density. Similarly, balloon stretch ration, inflation time, and dose density were evaluated for the ureter treatments. The amount of drug in the treated tissues of the sacrificed animal was measured after 1 day and the residual drug remaining on the balloon after use was analyzed.

The average tissue drug concentration at the urethra treatment site was 4.5 μg/g at 1 day. The average tissue drug concentration at the ureter treatment sites was 20.5 μg/g at 1 day. There was no difference in tissue drug concentration between the 3.5 μg and 10.0 μg dose density for both ureters and urethra treatments. Tissue drug concentration increased proportionally with the tissue stretch ratio independent of dose density. The residual balloon content for the ureter and urethra treatments ranged from 1-52% of the original drug loading.

Example I-6. Preclinical Study 6: Urethra

Eighty-seven balloon catheters (thirty-seven 12 mm in diameter and 20 mm in length, fifty 8 mm in diameter and 20 mm in length) were inflated to 50% of their nominal inflation pressure and wiped with an ethanol wipe to clean the balloon surface. Next the balloons were split into two groups; one group was coated using various formulations (1-6) in Example I-1 with sufficient coating solution to achieve 3.5 microgram paclitaxel per square mm of balloon surface the other group was coated using various formulations (1-6) in Example I-1 with sufficient coating solution to achieve 10 microgram paclitaxel per square mm of balloon surface. The balloons were then dried, folded, sheathed, packaged in a Tyvek pouch and ethylene oxide sterilized in preparation for animal testing.

For this study castrated male pigs were used. Before drug-coated balloon treatments baseline urethrograms were taken to measure the inner diameter of the urethra treatment sites before treatment. Drug-coated balloon catheters were used with nonoverlapping treatments. Prior to inflation 5-10 mL of saline was used to flush the urethra. A controlled experiment was conducted to investigate the effect of double inflation and drug dose density on the amount of drug in the treated urethra tissues. The tissue drug content was measured after 1 day and 28 days and the residual drug remaining on the balloon after use was analyzed. Histology samples were taken at 28 days to compare the two different drug dose density catheter groups The pig urethral tissue average drug concentration from the samples was 83 ng/g at 1 day and 2.5 ng/g at 28 days. The residual balloon content as a percent of the original drug loading from the samples ranged from 19-73%.

Example 1-7. Preclinical Study 7: Prostate and Urethra

Fifty-seven balloon catheters (forty-three 8 mm in diameter and 20 mm in length, fourteen 20 mm in diameter and 60 mm in length) were inflated to 50% of their nominal inflation pressure and wiped with an ethanol wipe to clean the balloon surface. The balloons were coated using various formulations (1-6) in Example 1-1 with sufficient coating solution to achieve 3.5 microgram paclitaxel per square mm of balloon surface. The balloons were then dried, folded, sheathed, packaged in a Tyvek pouch and ethylene oxide sterilized in preparation for animal testing.

For this study male dogs were used. These treatments were conducted under direct visualization using a 2.4 mm outer diameter endoscope. The endoscope utilized constant saline irrigation to flush visual obstructions away from the field of view, thus the treatment zones were constantly being flushed at all times. The first step in the treatment was to use cutting balloons (balloon catheters that have blades running longitudinally along the length of the balloon) in the prostatic urethra, middle urethra, and distal urethra. Next, uncoated balloons were used to dilate the treatment locations where the cutting balloons were used. Then baseline urethrograms were taken to measure the inner diameter of the urethra treatment sites before drug-coated balloon treatment. Finally, drug-coated balloon catheters and uncoated balloon catheters (as controls) were used. The 20 mm nominal diameter balloons were used in the prostatic urethra and the 8 mm nominal diameter balloons were used in the anterior urethra. The prostatic urethra balloons were inflated to 4-5 atmospheres at the treatment sites for 2 min to release drug and additive, then deflated and withdrawn from the dogs. The 8 mm nominal diameter balloons were inflated to 10 atmospheres at the treatment sites for 2 min to release drug and additive, then deflated and withdrawn from the dogs. The stretch ratio for the prostatic urethra balloons was 2.9 to 9.7. The stretch ratio for the anterior urethra balloons was 1.5 to 2.8. The tissue drug content was measured after 3 day, 7 days, and 28 days and the residual drug remaining on the balloon after use was analyzed. Histology samples were taken at 3 and 28 days to compare direct drug-coated balloon treatment to cutting balloon pretreatment followed by drug-coated balloon treatment.

The dog urethral tissue average drug concentration from the samples was 100 µg/g at day 3 and 62 µg/g at day 7 and 33 µg/g at day 28. The residual balloon content as a percent of the original drug loading from the samples ranged from 2-50%.

Example I-8. Preclinical Study 8: Urethra

Thirty-nine balloon catheters (8 mm in diameter and 30 mm in length) were inflated to 3 atmospheres and wiped with an ethanol wipe to clean the balloon surface. The balloons were coated using Formulations 18, 19, and 23 from Example I-1 with sufficient coating solution to achieve 2.5 microgram paclitaxel per square mm of balloon surface. The balloons were then dried, folded, sheathed, packaged in a Tyvek pouch and ethylene oxide sterilized in preparation for animal testing.

For this study male dogs were used. Baseline urethrograms were taken to measure the inner diameter of the urethra treatment sites before drug-coated balloon treatment. The treatment site diameters were approximately 3.5-4.5 mm. The balloon catheters were chosen such that the stretch ratio for the anterior urethra balloons was approximately 1.8-2.3. Drug-coated balloon catheters were used with nonoverlapping treatments in the pelvic, bulbar, and distal urethra just proximal of the os penis. The os penis urethra was not treated. Prior to inserting the catheter approximately 5 mL of saline was used to flush the urethra. The 8 mm nominal diameter balloons were inflated to 12 atmospheres at the treatment sites for 2 min to release drug and additive, then deflated and withdrawn from the dogs. The stretch ratio for the anterior urethra balloons was approximately 2.0-2.5. The tissue drug content was measured after 1 day and the residual drug remaining on the balloon after use was analyzed.

The dog tissue drug concentration from the pelvic urethra samples was 0.305, 1.17, 17.3, 33.4 µg/g at day 1. The dog tissue drug concentration from the bulbar urethra samples was 0.28, 4.31, 44.5, 57.8 µg/g at day 1. The dog tissue drug concentration from the distal urethra samples was 7.37, 38.9, 238, 268 µg/g at day 1. The average drug concentration from Formulations 18, 19, and 23 was 6.5, 33.6, and 137.7 µg/g, respectively, at day 1. The residual balloon content as a percent of the original drug loading from the samples ranged from 20.4-81.7%. The average residual balloon content as a percentage of the original drug loading from Formulations 18, 19, and 23 was 57.7%, 68.7%, and 51.9%, respectively.

Example I-9. Bench-Top Drug Release Testing Sample

Forty-nine balloon catheters (thirty-one 8 mm in diameter and 30 mm in length, six 10 mm in diameter and 20 mm in length, thirteen 12 mm in diameter and 20 mm in length) were inflated to 3 atmospheres and wiped with an ethanol wipe to clean the balloon surface. The balloons were coated using various formulations (1-34) in Example I-1 with sufficient coating solution to achieve either 2.5 or 3.5 microgram paclitaxel per square mm of balloon surface. The balloons were then dried, folded, sheathed, packaged in a Tyvek pouch and ethylene oxide sterilized in preparation for bench testing.

A bench top drug release apparatus was developed that consisted of a 10 inch long by 2 inch diameter cylindrical vessel placed inside a temperature controlled water bath. The cylindrical vessel was filled with 0.9% saline and maintained at 37° C. for the testing. An 8 French (i.e., wherein 3 French is 1 mm) by 13 cm long introducer sheath penetrated the top of the cylindrical vessel and was used as a conduit to pass balloon catheter samples into the cylindrical vessel. The samples were individually passed into the cylindrical vessel where they soaked for 1 minute prior to being inflated to 10 atmospheres for 1 minute and then withdrawn. The remaining drug on the balloon was analyzed to determine how much drug was released. The amount of drug released during this testing ranged from 37% to 97%.

Part II. Bench and Preclinical Testing: Prostatic Urethra with Multi-Lobed Balloon Example II-1. Bench Testing with Pig Urethras The purpose of this study was to evaluate if a necked balloon design could prevent movement during inflation in an anatomical model.

Intact male porcine bladders and urethras were obtained from a local research facility. Balloon catheters were constructed with 20 mm diameter×80 mm length 7233 PEBAX® balloons. Two balloon neck sections were created in the balloon using an UHMWPE suture. The suture was tied to the balloon at the desired location to prevent balloon expansion, thereby creating necks. Necks were positioned symmetrically along the length of the balloon splitting the 80 mm length into three about 20 mm body sections. Neck sections were sized to 10 mm lengths and were about 8 mm in diameter. Neck section lengths are measured from one larger body section to the adjacent larger body section. Balloons were attached to 10 Fr catheter shafts and were pleated/folded and placed in a sheath to facilitate insertion.

Intact pig urethra and bladders were placed in a 37° C. water bath to simulate body temperature. Balloon catheters were inserted through the urethra and positioned with the distal edge of the middle balloon lobe located at the bladder neck, such that the proximal neck was positioned in the prostatic urethra. Balloons were inflated until visual evidence of a urethral split or to the maximum rated burst pressure (RBP) of 6 atm. Balloons were deflated immediately after the urethral split was confirmed. Inflation speed was varied across samples using 0.5 atm/min, 1.0 atm/min, and 2.0 atm/min. Total inflation time was between 3 and 10 minutes depending on the inflation speed.

Necked balloons for this study were able to prevent balloon movement during inflation. The stretch ratio of the inflated balloon diameter to the untreated prostatic urethral diameter was between about 3.0-3.5. Additionally, this study indicated that inflation rate played a role in balloon movement. By inflating the balloon slower, and allowing the tissue to stress relax and yield, migration of the balloon into the bladder was further minimized. Rates of 0.5 atm/min and 1.0 atm/min had less balloon movement during inflation.

Example II-2. BPH Preclinical Study 1

Balloon catheters were constructed with 22 mm diameter×32 mm length balloons with a single neck. Balloons were made of 7233 Pebax. The single neck was located in the center of the balloon and was 17 mm diameter×12 mm in length. The two resulting body sections, at the distal and proximal sides, were 22 mm diameter×10 mm length. Balloons were attached to 10 Fr catheter shafts and were pleated/folded and placed in a balloon protector sheath.

This experiment was performed on mongrel canines. Balloon catheters were inserted transurethrally with the use of a guidewire. Balloons were positioned in the prostatic urethra using fluoroscopy with the balloon neck section in the dog bladder neck. Balloons were inflated at a rate of 1 atm/min until a commissurotomy was observed with fluoroscopy, typically 3-4 atm pressure. Total inflation time was between 3 to 5 minutes. Balloon movement was monitored with fluoroscopy during inflation. After a commissurotomy was achieved balloons were immediately deflated and removed. Transurethral cystoscopy was performed to visually confirm prostatic commissurotomy.

Splitting of the prostatic commissure was achieved on both animals with minimal balloon movement during inflation. The stretch ratio of the inflated balloon diameter to the canine prostatic urethra diameter was between about 4.0-4.5.

Example II-3. BPH Preclinical Study 2

Balloon catheters were constructed with 40 mm diameter×70 mm length balloons. The balloon material was nylon 12. Two balloon necks were created in the balloon using UHMWPE suture. The suture was tied to the balloon at the desired location to prevent balloon expansion and create the neck feature. Necks were positioned symmetrically along the length of the balloon splitting the 70 mm body length into three body sections. From the proximal end of the balloon the following sections were created: the proximal balloon body section was 40 mm diameter×20 mm length, the first neck section was 15 mm diameter×5 mm length, the middle balloon body section was 40 mm diameter×20 mm length, the second neck section was 15 mm diameter×5 mm length, and the distal balloon body section was 40 mm diameter×20 mm length. Balloons were attached to 12 Fr catheter shafts, pleated, and folded with balloon protector sheaths.

This experiment was performed on cadaveric human males. The perineum was dissected to access the bulbous urethra. The urethra was opened with a single vertical incision to allow catheter access. Catheters were inserted and digitally/visually positioned in the prostatic urethra. The proximal bond of the balloon was placed proximal to the external sphincter, such that one of the balloon necks was in the bladder neck. Balloons were inflated at a rate of 1 atm/min allowing the tissue to slowly yield and minimize balloon movement. Balloons were inflated to 4-5 atm, then immediately deflated and removed. Total inflation time was about 4-5 minutes. Prostatic commissures were inspected for split digitally and using a cystoscope.

No proximal migration of the balloons into the bladder was observed during inflation. All balloons were successfully inflated to between 4 and 5 atm within the prostatic urethra. All three cadavers evaluated had an anterior prostatic commissurotomy and significant luminal gain resulting from the dilatation of the balloon. The stretch ratio of the inflated balloon diameter to the human prostatic urethra diameter was between about 2.5-3.5. Results indicate that a smaller neck balloon will prevent balloon movement during inflation as the lobes of the balloon should be larger than the neck when the initial inflation is stopped by the tissue resistance. If the lobes are not of a larger diameter than the neck region when the balloon hits the tissue resistance, the balloon will act like a constant diameter cylindrical balloon.

Example II-4. BPH Preclinical Study 3

Balloon catheters (eight total) were constructed with 22 mm diameter×32 mm length balloons with a single neck. The balloon material was 7233 Pebax. The single neck was located in the center of the balloon and was 17 mm in diameter and 12 mm in length, creating 2 body sections of 22 mm diameter×10 mm length. Four balloons were drug coated using Formula 23 with 3.5 µg paclitaxel per square mm of balloon surface. Four balloons were left uncoated. Balloons were placed on 10 Fr catheter shafts. All balloons were folded, placed in a balloon protector sheath, packaged in Tyvek pouches, and sterilized.

Mongrel canines were used for this experiment as their prostate anatomy closely matches that of humans. Baseline retrograde urethrograms were completed, and the initial prostatic urethral diameter was measured. Balloon catheters were inserted transurethrally with the use of a guidewire. Balloons were positioned in the prostatic urethra using fluoroscopy with the balloon neck section in the dog bladder neck. Balloons were inflated at a rate of 1.0 atm/min to about 3.5-5.0 atm until a commissurotomy was observed with fluoroscopy. Balloon movement was monitored with fluoroscopy during inflation. Balloons were deflated and remove, and the commissurotomy was verified with a cystoscope. Paclitaxel drug-coated balloons were inserted over the guidewire and positioned in the prostatic urethra with fluoroscopy. Balloons were inflated to 4-5 atm and left in place for 5 min to allow drug transfer to the tissue. The remaining drug on the balloon was analyzed to determine how much drug was released. Animals were sacrificed at 1 hr, 7 days, and 28 days. Dog tissues were harvested at termination and analyzed for paclitaxel content. Retrograde urethrograms were completed prior to termination to determine luminal gain.

Split of the prostatic commissure was achieved in all three animals. The stretch ratio of the inflated balloon diameter to the dog prostatic urethra diameter was between about 4.0-4.5. prostatic urethral luminal gain was between 3.1 and 4.0. The amount of drug released during this testing ranged from 78% to 85%. The dog prostatic urethra drug concentration was 218 µg/g at 1 hour, 0.737 µg/g at day 7, and 0.375 µg/g at day 28. The dog prostate tissue drug concentration was 19.8 µg/g at 1 hour, 2.38 µg/g at day 7, and 0.081 µg/g at day 28.

Example II-5. BPH Preclinical Study 4

The device used had a double-lobe design with a single reinforced balloon neck and was made out of Nylon 12. The diameter of the prostate dilating lobe was 22 mm and the length was 20 mm. The balloon neck was 17 mm in diameter and was reinforced with UHMWPE fiber. The catheter had an over-the-wire design so it could be tracked on a guidewire to the canine prostate. The drug-coated balloons used for treatments in the maximum dose arm each had 9.8 mg of paclitaxel while the standard dose drug-coated balloons had a dose of 6.8 mg paclitaxel coating. The maximum dose arm included two overlapping treatments with the 9.8 mg paclitaxel coated balloons for a total drug delivery of 19.6 mg. The drug-coated balloons were coated such that the coating covered half the proximal cone, the entire treatment lobe, the neck section, and the body section of the distal bladder balloon. The uncoated control balloons had no drug coating.

This study was completed on mongrel canines. Balloon catheters were inserted transurethrally with the use of a guidewire. Balloons were positioned in the prostatic urethra using fluoroscopy with the balloon neck section in the dog bladder neck. The study had three arms: a max dose arm, a standard dose arm, and a control arm. The max dose arm contained 10 treated animals, the standard dose arm contained 18 animals, and the control arm had 4 animals. Animals in the max dose and standard dose arm were either acute (1 hr) or survived to 7, 28, or 70 days and the control arm animals were survived to either 7 or 28 days. The max dose and standard dose arm had tissue pharmacokinetics (PK) to analyze the paclitaxel drug content in the prostate, prostatic urethra, bladder, bladder neck, urethra at the external sphincter, vas deferens, ureters, testes & epididymis, and kidneys. The max dose and standard dose arm also evaluated PK drug content in the plasma and completed a histological evaluation of the prostate. The control arm was only evaluated for prostate histology. Additionally, the urethra lumen diameter was measured at baseline and at termination using retrograde urethrogram to determine any change in caliber.

Increase of urethral luminal diameter as a result of commissurotomy was approximately 50% and did not change between 7 days and 70 days. The baseline treatment site diameters were approximately 3.5-4.5 mm. The stretch ratio for the prostatic urethra was about 4.5 to 6.5. The average prostatic urethra paclitaxel concentration for the standard dose arm was 28.04 µg/g at 1 hour, 4.60 µg/g at 7 days, and 0.058 µg/g at 28 days, and 0.004 µg/g at 70 days. The average prostatic urethra paclitaxel concentration for the maximum dose arm was 0.66 µg/g at 28 days, and 0.082 µg/g at 70 days. The maximum dose arm prostatic urethra tissue had 11 times higher drug concentration than the standard dose at 28 days and 23 times higher drug concentration at 70 days. The average prostate paclitaxel concentration for the standard dose arm was 0.811 µg/g at 1 hour, 0.576 µg/g at 7 days, and 0.020 µg/g at 28 days, and 0.0003 µg/g at 70 days. The average prostate paclitaxel concentration for the maximum dose arm was 0.087 µg/g at 28 days, and 0.007 µg/g at 70 days. The maximum dose arm prostate tissue had 4.5 times higher drug concentration than the standard dose at 28 days and 23 times higher drug concentration at 70 days.

The adjacent tissue with the highest paclitaxel concentration was the membranous urethra with an average concentration of 1.29 µg/g immediately after treatment (1 hour acute) while the epididymis had the lowest average drug concentration, 0.0017 µg/g, immediately after treatment. Most nonurethral close proximity tissue sample concentrations were at or below the limit of quantification (BLOQ) at 28 days and beyond. The plasma paclitaxel concentration was measured at 1, 3, 7, 12 hours, 1, 3, 7, 14, and 28 days. All standard dose plasma paclitaxel concentrations were BLOQ at all time-points indicating negligible to no systemic exposure to paclitaxel in the standard dose animals. All maximum dose paclitaxel plasma concentrations at 12 hour and later were BLOQ. Histology results indicated that the maximum dose animals had ongoing healing at 28 days indicating a slower healing process relative to the standard dose and control animals.

The animals remained healthy for the duration of the study and all survived to their scheduled termination dates. No significant clinical abnormalities were observed in any animals in any of the studies. In all test animals, the urethra remained patent and animals were able to void normally. There were no abnormalities or complications from the maximum dose treatment arm using 19.6 mg of paclitaxel.

Part III. Human Clinical Testing Urethral Strictures

Uroflowmetry ($Q_{max}$ measurement). Uroflowmetry is performed by urinating into a special urinal, toilet, or disposable device that has a measuring device built into it. The parameter, $Q_{max}$, is the maximum flow rate measured during a uroflowmetery test. This method was used prior to treatment (baseline) and at follow-up visits of 14 days, 1, 3, 6, 12 months, and 2 years to demonstrate the longevity of the treatment.

Post-void residual (PVR) is a measurement of the volume of urine left in the bladder after voiding. It is measured using ultrasound prior to treatment (baseline) and at follow-up visits of 14 days, 1, 3, 6, 12 months, and 2 years, to demonstrate the longevity of the treatment.

International Prostate Symptom Score (IPSS). The IPSS is based on the answers to eight questions-seven regarding disease symptoms and one question related to the patient's quality of life: 1) Incomplete Emptying; How often have you had the sensation of not emptying your bladder? 2) Frequency; How often have you had to urinate less than every two hours? 3) Intermittency; How often have you found you stopped and started again several times when you urinated? 4) Urgency; How often have you found it difficult to postpone urination? 5) Weak Stream; How often have you had a weak urinary stream? 6) Straining; How often have you had to strain to start urination? 7) Nocturia; How many times did you typically get up at night to urinate? 8) Quality of Life Due to Urinary Symptoms; If you were to spend the rest of your life with your urinary condition just the way it is now, how would you feel about that? Although the IPSS was developed for BPH it can be applied to other bladder outlet obstructive diseases such as stricture to determine if obstructive symptoms are improved after a medical treatment. For the symptom questions, the patient is asked to choose the rating that best represents their condition. The scale ranges from 0 to 5, with 5 representing the most symptomatic disease. The seven symptom scores are summed to give an overall maximum possible score of 35. The answer to the quality of life question is scored on a scale of 0 to 6. According to these scoring systems, the scores can be categorized as follows: symptoms are mild if the score is 7 or less; symptoms are moderate if the score is 8 to 19; and symptoms are severe if the score is 20 to 35. This questionnaire was given prior to treatment (baseline) and at follow-up visits of 14 days, 1, 3, 6, 12 months, and 2 years to demonstrate the longevity of the treatment.

Example III-1. Testing of Drug-Coated Balloons in Urethral Strictures of Human Subjects Drug-coated balloon catheters with a dose density of 3.5 µg of paclitaxel per millimeter squared of balloon surface area were used to treat human subjects that had stricture disease in a clinical study. The drug-coated balloon catheters had nominal diameters of 6, 8, 10, 12, and 14 mm and lengths of 30 and 50 mm at nominal pressure of 6 atm. The paclitaxel (PTX) dosing per balloon size can be seen in Table 6.

TABLE 6

Paclitaxel (PTX) dosing per balloon size.

| Diameter (mm) | 30 mm Length | 50 mm Length |
| --- | --- | --- |
| 6 | 1979 µg PTX | 3299 µg PTX |
| 8 | 2639 µg PTX | 4398 µg PTX |
| 10 | 3299 µg PTX | 5498 µg PTX |
| 12 | 3958 µg PTX | 6597 µg PTX |
| 14 | 4618 µg PTX | 7697 µg PTX |

The drug-coated balloon catheters had a dual lumen shaft design with a single inflatable balloon. One lumen was sized to accommodate a 0.038" guide wire lumen. The other lumen was the inflation port lumen and allows the balloon to be inflated with mixture of saline and contrast fluid. The drug-coated balloon catheter had a manifold with two Luer-style connections, one connection was compatible with an inflation syringe, the other allowed the guidewire to protrude out of the manifold so the balloon catheter could freely slide onto the guidewire. The 6 and 8 mm drug-coated balloon catheters had a rated burst pressure of 12 atmospheres. The 10, 12, and 14 mm drug-coated balloon catheters had a rated burst pressure of 10 atmospheres. The balloon was made of polyamide.

Treatments were performed for 53 patients for bulbar urethral strictures. Of these patients, 5 were retreated due to stricture recurrence, bring the total number of treatments to 58. All patients were male as the study excluded female patients. Subjects enrolled in the study had a minimum of 1 and a maximum of 3 prior interventions for urethral stricture. The age range was 50.7±15.47 years. The etiologies of urethral stricture across the patient population were 50.9% traumatic, 45.3% iatrogenic, and 3.8% idiopathic. Of 53 patients, 7 had a suprapubic catheter at baseline. The stricture length on average was 0.9 cm and the average stricture diameter was 2.47 mm.

The clinical treatment strategy involved pre-dilation of the stricture with direct vision internal urethrotomy (DVIU), an uncoated non-compliant balloon, or a combination of both. An uncoated balloon was used to pre-dilate 32 patients, 16 patients were pre-dilated with both an uncoated balloon and DVIU, and 10 patients were pre-dilated with DVIU only. Following pre-dilation all subjects were treated with the paclitaxel drug-coated balloons. 26 patients were treated with the 8×30 mm balloons. 27 patients were treated with the 10×30 mm balloons.

Clinical subjects were evaluated at 14, 30, 90, 180, 365 days, and 2 years after the index procedure. Evaluations included analysis of stricture free rate, uroflowmetry including $Q_{max}$, and PVR. Additionally, pharmacokinetic analysis was completed for the paclitaxel content in the blood, urine, semen, and residual drug on the drug-coated balloons.

On average patient IPSS improved from a baseline average of 25.2, to 5.2 at 14 days, 4.3 at 30 days, 6.1 at 90 days, 4.6 at 180 days, 4.5 at 365 days, and 6.9 at 2 years. Average patient $Q_{max}$ at baseline was 5.0 mL/sec and improved to 22.2 mL/sec at 14 days, 22.8 mL/sec at 30 days, 21.4 mL/sec at 90 days, 19.8 mL/sec at 180 days, 20.1 mL/sec at 365 days, and 17.5 mL/sec at 2 years. Average patient PVR was 141.4 mL at baseline and improved to 35.7 mL at 14 days, 36.1 mL at 30 days, 38.8 mL at 90 days, 30.1 mL at 180 days, 24.6 mL at 365 days, and 45.5 mL at 2 years. Stricture free rate was 75.5% (37/49) at day 180 and 74.5% (37/47) at 365 days.

Human plasma paclitaxel concentration on average was 0.1 ng/mL immediately post treatment and was below the level of quantification for all other later time points, 1 hour, 3 hours, 5 hours, 10 hours, 24 hours, and 5 days. Human urine paclitaxel concentration on average was 184 ng/mL immediately post procedure, 2.6 ng/mL at 5 days, 0.3 ng/mL at 14 days, and 0.1 ng/mL at 30 days. Human semen paclitaxel concentration on average was 2.5 ng/mL at 14 days and 1.0 ng/mL at 30 days.

Residual drug content on the balloons used to treat human subject was on average 2.7% of the original dose with a range of 0.1% to 28.0%.

Example III-2. Human Clinical Subject a from Example III-1 Treated with an Uncoated Pre-Dilation Balloon Followed by an 8 mm Nominal Diameter Drug-Coated Balloon Catheter Subject A had a 0.6 cm length by 0.6 mm diameter stricture in his anterior urethra. Specifically, the bulbar portion of the anterior urethra. This was determined by conducting a retrograde urethrogram. The human clinical subject had a baseline $Q_{max}$ of 6.6 mL/second, a baseline PVR of 298 mL, and a baseline IPSS score of 25. First a cystoscope was inserted into the urethra. Then a guidewire was inserted into the working channel of the cystoscope. Next a pre-dilation balloon that had a nominal diameter of 7 mm and a length of 20 mm was inserted into the urethra over the guidewire and positioned so the balloon crossed the stricture. The pre-dilation balloon was inflated to 14 atmospheres with a syringe that had a pressure gauge on it. The syringe contained a mixture of saline and contrast media. A fluoroscopic image was acquired to ensure the balloon had a uniform expansion. Once this was confirmed the balloon was deflated and withdrawn from the urethra. Next a drug-coated balloon that had a nominal diameter of 8 mm and a length of 30 mm was inserted into the urethra over the guidewire. The drug-coated balloon was positioned such that the balloon body completely covered the pre-dilated stricture area. The drug-coated balloon was held in position for at least 1 minute prior to inflating to hydrate the coating. Then the drug-coated balloon was inflated with a mixture of saline and contrast media using the syringe that had a pressure gauge on it. The balloon was inflated to 11 atmospheres, achieved an inflated diameter of 8.5 mm, and was held at the inflation pressure for 5 minutes. Then the balloon was deflated and withdrawn from the human subject. The stretch ratio for the 8 mm nominal diameter drug-coated balloon was 13.3 to 14.7. The diameter of the dilated stricture was 7 mm after dilation. The residual drug remaining on the balloon after use was analyzed. The residual amount of paclitaxel left on the balloon was 28.2 µg (1.1 percent of the initial drug load). The human clinical subject had follow-up visits at 14, 30, 90, 180, 365 days, and 2 years to measure maximum urine flow rate, PVR, and IPSS score. Additionally, the urethral caliber of the human clinical subject was assessed at 6 and 12 months to determine if the urethra was greater than 16 French (5.3 mm) by visualizing and passing a flexible cystoscope past the previously treated area. The human clinical subject had a maximum urine flow rate improvement from 6.6 ml/second to 35.1, 38.8, 29.0, 26.6, 33.9, and 22.9 mL/second at follow-up visits of 14, 30, 90, 180, 365 days, and 2 years respectively. The human clinical subject had PVR improvement from 298 mL to 10, 106, 31, 58, 70, and 24 mL at follow-up visits of 14, 30, 90, 180, 365 days, and 2 years respectively. The human clinical subject had an IPSS improvement from 25 to 1, 1, 1, 1, 1, and 2 at follow-up visits of 14, 30, 90, 180, 365 days, and 2 years respectively. The human clinical subject had a urethra caliber greater than 16 French (5.3 mm) at 6 and 12 months.

Example III-3. Human Clinical Subject B from Example III-1 Treated with an Uncoated Pre-Dilation Balloon Followed by a 10 mm Nominal Diameter Drug-Coated Balloon Catheter Subject B had a 1.8 cm length by 2.0 mm diameter stricture in his anterior urethra. Specifically, the bulbar portion of the anterior urethra. This was determined by conducting a retrograde urethragram. The human clinical subject had a baseline $Q_{max}$ of 8 mL/second, PVR of 45 mL, and a baseline IPSS score of 30. First a cystoscope was inserted into the urethra. Then a guidewire was inserted into the working channel of the cystoscope. Next a pre-dilation balloon that had a nominal diameter of 10 mm and a length of 20 mm was inserted into the urethra over the guidewire and positioned so the balloon crossed the stricture. The pre-dilation balloon was inflated to 20 atmospheres with a syringe that had a pressure gauge on it. The syringe contained a mixture of saline and contrast media. A fluoroscopic image was acquired to ensure the balloon had a uniform expansion. Once this was confirmed the balloon was deflated and withdrawn from the urethra. Next a drug-coated balloon that had a nominal diameter of 10 mm and a length of 30 mm was inserted into the urethra over the guidewire. The drug-coated balloon was positioned such that the balloon body completely covered the pre-dilated stricture area. The drug-coated balloon was held in position for at least 1 minute prior to inflating to hydrate the coating. Then the drug-coated balloon was inflated with a mixture of saline and contrast media using the syringe that had a pressure gauge on it. The balloon was inflated to 10 atmospheres for 5 minutes. Then the balloon was deflated and withdrawn from the human subject. The stretch ratio for the 10 mm nominal diameter drug-coated balloon was 5.0 to 5.5. The diameter of the dilated stricture was 10 mm after dilation. The residual drug remaining on the balloon after use was analyzed. The residual amount of paclitaxel left on the balloon was 49.1 µg (1.5 percent of the initial drug load). The human clinical subject had follow-up visits at 14, 30, 90, 180, 365 days, and 2 years to measure maximum urine flow rate, PVR, and IPSS score. Additionally, the urethral caliber of the human clinical subject was assessed at 6 and 12 months to determine if the urethra was greater than 16 French (5.3 mm) by visualizing and passing a flexible cystoscope past the previously treated area. The human clinical subject had a maximum urine flow rate improvement from 8 mL/second to 25, 29, 36, 34, 34, and 23 mL/second at follow-up visits of 14, 30, 90, 180, 365 days, and 2 years respectively. The human clinical subject had PVR improvement from 45 mL to 30, 28, 35, 26, 3, and 10 mL at follow-up visits of 14, 30, 90, 180, 365 days, and 2 years respectively. The human clinical subject had an IPSS improvement from 30 to 4, 3, 5, 2, 3, and 3 at follow-up visits of 14, 30, 90, 180, 365 days, and 2 years respectively. The human clinical subject had a urethra caliber greater than 16 French (5.3 mm) at 6 and 12 months.

Example III-4. Human Clinical Subject C from Example III-1 Treated with Direct Visual Internal Urethrotomy (DVIU) Followed by a 10 mm Nominal Diameter Drug-Coated Balloon Catheter Subject C had a 0.6 cm length by 4.0 mm diameter stricture in his anterior urethra. Specifically, the bulbar portion of the anterior urethra. This was determined by conducting a retrograde urethragram. The human clinical subject had a baseline $Q_{max}$ of 5 mL/second, PVR of 360 mL, and an IPSS score of 24. First a resectoscope was inserted into the urethra. Then a guidewire was inserted into the working channel of the resectoscope. Next the resectoscope was used to cut the urethra at the 12 o'clock position to open the structured urethra to greater than 20 French (6.7 mm). The length of the cut was the length of the stricture. Next a drug-coated balloon that had a nominal diameter of 10 mm and a length of 30 mm was inserted into the urethra over the guidewire. The drug-coated balloon was positioned such that the balloon body completely covered the cut stricture area. The drug-coated balloon was held in position for at least 1 minute prior to inflating to hydrate the coating. Then the drug-coated balloon was inflated with a mixture of saline and contrast media using the syringe that had a pressure gauge on it. The balloon was inflated to 10 atmospheres for 5 minutes. Then the balloon was deflated and withdrawn from the human subject. The stretch ratio for the 10 mm nominal diameter drug-coated balloon was 2.5 to 2.75. The diameter of the dilated stricture was 9.5 mm after dilation. The residual drug remaining on the balloon after use was analyzed. The residual amount of paclitaxel left on the balloon was 28.6 µg (0.9 percent of the initial drug load). The human clinical subject had follow-up visits at 14, 30, 90, 180, 365 days, and 2 years to measure maximum urine flow rate, PVR, and IPSS score. Additionally, the urethral caliber of the human clinical subject was assessed at 6 and 12 months to determine if the urethra was greater than 16 French (5.3 mm) by visualizing and passing a flexible cystoscope past the previously treated area. The human clinical subject had a maximum urine flow rate improvement from 5 mL/second to 50, 43, 37, 27, 19, and 19 mL/second at follow-up visits of 14, 30, 90, 180, 365 days, and 2 years respectively. The human clinical subject had PVR improvement from 360 mL to 21, 32, 28, 30, 1 and 111 mL at follow-up visits of 14, 30, 90, 180, 365 days, and 2 years respectively. The human clinical subject had an IPSS improvement from 24 to 9, 9, 1, 15, 11, and 4 at follow-up visits of 14, 30, 90, 180, 365 days, and 2 years respectively. The human clinical subject had a urethra caliber greater than 16 French (5.3 mm) at 6 and 12 months.

Example III-5. Human Clinical Subject D from Example III-1 Treated Directly with a 10 mm Diameter Drug-Coated Balloon Catheter Subject D had a 1.7 cm length by 2.5 mm diameter stricture in his anterior urethra. Specifically, the bulbar portion of the anterior urethra. This was determined by conducting a retrograde urethragram. The human clinical subject had a baseline $Q_{max}$ of 3.0 mL/second and a baseline IPSS score of 27. First a cystoscope was inserted into the urethra. Then a guidewire was inserted into the working channel of the cystoscope. Next a drug-coated balloon that had a nominal diameter of 10 mm and a length of 30 mm was inserted into the urethra over the guidewire. The drug-coated balloon was positioned such that the balloon body centered on the stricture. The drug-coated balloon was held in position for at least 1 minute prior to inflating to hydrate the coating. Then the drug-coated balloon was inflated with a mixture of saline and contrast media using the syringe that had a pressure gauge on it. The balloon was inflated to 10 atmospheres for 5 minutes. Then the balloon was deflated and withdrawn from the human subject. The stretch ratio for the 10 mm nominal diameter drug-coated balloon was 4.0 to 4.4. The diameter of the dilated stricture was 8 mm after dilation. The residual drug remaining on the balloon after use was analyzed. The residual amount of paclitaxel left on the balloon was 99 µg (3 percent of the initial drug load). The human clinical subject had follow-up visits at 14, 30, 90, 180, and 365 days to measure maximum urine flow rate and IPSS score. Additionally, the urethral caliber of the human clinical subject was assessed at 6 months to determine if the urethra was greater than 16 French (5.3 mm) by visualizing and passing a flexible cystoscope past the previously treated area. The human clinical subject had a maximum urine flow rate of 40.0, 37.0, 36.0, and 31.0 mL/second at follow-up visits of 14, 90, 180, and 365 days respectively. The human clinical subject had an IPSS of 4, 2, 3, and 2 at follow-up visits of 30, 90, 180, and 365 days respectively. The human clinical subject had a urethra caliber greater than 16 French (5.3 mm) at 6 months.

Example III-6. Human Clinical Subject E from Example III-1 Treated with an Uncoated Pre-Dilation Balloon Followed by an 8 mm Nominal Diameter Drug-Coated Balloon Catheter Subject A had a 0.6 cm length by 1.0 mm diameter stricture in his anterior urethra. Specifically, the bulbar portion of the anterior urethra. This was determined by conducting a retrograde urethragram. The human clinical subject had a baseline $Q_{max}$ of 2 mL/second, a baseline PVR of 172 mL, and a baseline IPSS score of 32. First a cystoscope was inserted into the urethra. Then a guidewire was inserted into the working channel of the cystoscope. Next a pre-dilation balloon that had a nominal diameter of 7 mm and a length of 20 mm was inserted into the urethra over the guidewire and positioned so the balloon crossed the stricture. The pre-dilation balloon was inflated to 14 atmospheres with a syringe that had a pressure gauge on it. The syringe contained a mixture of saline and contrast media. A fluoroscopic image was acquired to ensure the balloon had a uniform expansion. Once this was confirmed the balloon was deflated and withdrawn from the urethra. Next a drug-coated balloon that had a nominal diameter of 8 mm and a length of 30 mm was inserted into the urethra over the guidewire. The drug-coated balloon was positioned such that the balloon body completely covered the pre-dilated stricture area. The drug-coated balloon was held in position for at least 1 minute prior to inflating to hydrate the coating. Then the drug-coated balloon was inflated with a mixture of saline and contrast media using the syringe that had a pressure gauge on it. The balloon was inflated to 11 atmospheres, achieved an inflated diameter of 8.7 mm, and was held at the inflation pressure for 5 minutes. Then the balloon was deflated and withdrawn from the human subject. The stretch ratio for the 8 mm nominal diameter drug-coated balloon was 8.0 to 8.8. The diameter of the dilated stricture was 8 mm after dilation. The residual drug remaining on the balloon after use was analyzed. The residual amount of paclitaxel left on the balloon was 46.3 µg (17.5 percent of the initial drug load). The human clinical subject had follow-up visits at 14, 30, 90, 180, 365 days, and 2 years to measure maximum urine flow rate, PVR, and IPSS score. Additionally, the urethral caliber of the human clinical subject was assessed at 6 and 12 months to determine if the urethra was greater than 16 French (5.3 mm) by visualizing and passing a flexible cystoscope past the previously treated area. The human clinical subject had a maximum urine flow rate improvement from 2 ml/second to 16, 21, 16, 18, 16, and 13 mL/second at follow-up visits of 14, 30, 90, 180, 365 days, and 2 years respectively. The human clinical subject had PVR improvement from 172 mL to 17, 15, 60, 10, 10, and 20 mL at follow-up visits of 14, 30, 90, 180, 365 days, and 2 years respectively. The human clinical subject had an IPSS improvement from 32 to 12, 7, 11, 11, 12, and 12 at follow-up visits of 14, 30, 90, 180, 365 days, and 2 years respectively. The human clinical subject had a urethra caliber greater than 16 French (5.3 mm) at 6 and 12 months.

Part IV. Human Clinical Testing Benign Prostatic Hyperplasia

Uroflowmetry ($Q_{max}$ measurement), post-void residual (PVR), and international Prostate Symptom Score (IPSS) are as defined in Part III.

Example IV-1. BPH Human Clinical Testing: Single Lumen & Reinforced Fixed Wire Drug-Coated Balloon Catheter Drug-coated balloon catheters with a dose density of 2.4 μg of paclitaxel per millimeter squared were used to treat human subjects that had benign prostatic hyperplasia disease in a clinical study. The balloons had a single neck positioned approximately 10 mm from the distal cone of the balloon. The neck length was 2 mm for all the balloons. The proximal lobe or treatment lobe had a range of different diameters and length, while the distal lobe or bladder lobe was always the same 10 mm length and matched the diameter of the treatment lobe. The drug-coated balloon catheters had nominal diameters of 30, 35, 40, and 45 mm and dilation lengths of 30, 35, 40, 45, and 50 mm at a nominal inflation pressure of 2 atm. For balloon diameters of 30 mm the neck diameter was 12 mm, for balloon diameters of 35 mm the neck diameter was 15 mm, for balloon diameters of 40 mm the neck diameter was 20 mm, and for balloon diameters of 45 mm the neck diameter was 23 mm. All balloons sizes had a rated burst pressure of 4 atm. The balloons were coated with paclitaxel from halfway up the proximal cone, over the entire treatment lobe, over the entire neck section, and the body portion of the bladder lobe. The paclitaxel (PTX) dosing per balloon size can be seen in Table 7.

TABLE 7

Paclitaxel (PTX) dosing per balloon size.

| Diameter (mm) | 30 mm Length | 35 mm Length | 40 mm Length | 45 mm Length | 50 mm Length |
|---|---|---|---|---|---|
| 30 | 9586 μg PTX | 11433 μg PTX | 12567 μg PTX | 13661 μg PTX | 15256 μg PTX |
| 35 | 12403 μg PTX | 13915 μg PTX | 15238 μg PTX | 16561 μg PTX | 18073 μg PTX |
| 40 | 15220 μg PTX | 16543 μg PTX | 18055 μg PTX | 19567 μg PTX | 20890 μg PTX |
| 45 | 18037 μg PTX | 19455 μg PTX | 20872 μg PTX | 22290 μg PTX | 23707 μg PTX |

Two catheter designs were used in this study. The balloon shape, material, and dimensions were identical across the two catheter platforms. The difference between the two balloon catheters was the catheter shaft design. The first design was a single lumen design without a Luer hub and was designed to be back loaded into a cystoscope. The second design was a reinforce fixed wire catheter shaft with a Luer hub attached and was designed to be positioned side-by-side with a cystoscope.

Single lumen design: The drug-coated balloon catheters had a single lumen nylon 12 shaft design with holes punched under the balloon to allow inflation of the drug-coated balloon. The catheter shaft did not have a Luer and was designed to connect to a Tuohy Borst valve and Luer compatible stopcock after passing through the working channel of a cystoscope. The balloon neck was reinforced with ultra-high molecular weight polyethylene (UHMWPE) fibers that were fixed in place to minimize diameter growth during inflation. The balloon neck anchors into the bladder neck during balloon inflation and prevents migration of the proximal balloon lobe into the bladder. The proximal lobe of the balloon (treatment lobe) is located in the prostatic urethra and sized to fit the prostate. The distal balloon lobe is used for positioning and provides dilation of the bladder neck and any intra prostatic protrusion present during balloon inflation. The balloon is made of a high durometer polyether block amide (74D PEBA). At the distal end of the catheter a silicone Coude tip is attached that allows the catheter to be tracked in the prostatic urethra. The Coude tip is specially curved to conform to the male urethra anatomy and is atraumatic to prevent damage during insertion. The balloon portion of the catheter was pleat and folded down to a caliber of 19 French and a sheath was place over the balloon. The delivery sheath had three functions. One was to cover and protect the balloon. Two was to form a smooth cylindrical catheter body that allows the balloon catheter to be tracked through the urethra and positioned into the prostatic urethra. The last was to recapture the balloon after the treatment to facilitate removal of the device. Balloon catheters with a diameter of 30 or 35 mm had a 21 Fr sheath while balloon catheters with a diameter of 40 or 45 mm had a 24 Fr sheath. The sheath was constructed with an inner layer of etched PTFE liner, a middle layer of a flat coiled wire, and an outer layer of polyether block amine (35D PEBA). The sheath and Coude tip were sized identically and have mating features to make a single smooth insertion surface.

Reinforce fixed wire design: The drug-coated balloon catheters had a catheter shaft that consisted of a single lumen extrusion of high durometer polyether block amide (72D PEBA). Within the extrusion lumen a cylindrical 304 stainless steel mandrel ran the length of the catheter and under the balloon. The mandrel is thermally bonded into the distal tip and the proximal end of the catheter near the Luer hub. The mandrel is reinforced under the balloon section with a 304 stainless steel tube to prevent buckling. The catheter shaft extrusion is terminated under the proximal balloon bond allowing inflation of the drug-coated balloon. At the proximal end of the catheter shaft a female Luer hub is adhesively bonded to the catheter shaft extrusion to allow connection to an inflation device. The balloon neck is reinforced with ultra-high molecular weight polyethylene (UHMWPE) fibers that were fixed in place to minimize diameter growth during inflation. The balloon neck anchors into the bladder neck during balloon inflation and prevents migration of the proximal balloon lobe into the bladder. The proximal lobe of the balloon (treatment lobe) is located in the prostatic urethra and sized to fit the prostate. The distal balloon lobe is used for positioning and provides dilation of the bladder neck and any intra prostatic protrusion present during balloon inflation. The balloon was made of a high durometer polyether block amide (74D PEBA). At the distal end of the catheter a silicone Coude tip is attached that allows the catheter to be tracked in the prostatic urethra. The Coude tip is specially curved to conform to the male urethra anatomy and is atraumatic to prevent damage during insertion. The balloon portion of the catheter was pleat and folded down to a caliber of 19 French and a sheath was place over the balloon. The delivery sheath had three functions. One was to cover and protect the balloon. Two was to form a smooth cylindrical catheter body that allows the balloon catheter to be tracked through the urethra and positioned into the prostatic urethra. The last was to recapture the balloon after the treatment to facilitate removal of the device. Balloon catheters with a diameter of 30 and 35 mm had a 21 Fr sheath while balloon catheters with a diameter of 40 and 45 mm had a 24 Fr sheath. The sheath was constructed with an inner layer of etched PTFE liner, a middle layer of a flat coiled wire, and an outer layer of polyether block amine (72D PEBA). The sheath and Coude tip were sized identically and have mating features to make a single smooth insertion surface. This design also included a preloaded obturator place over the top of the catheter shaft. The obturator was made of LDPE, had a radiused distal tip, and had a flared proximal end to interface with the sheath. The combined sheath and obturator were used to track through the urethra and recapture the balloon after the treatment.

In total 80 patients were treated for benign prostatic hyperplasia. All patients were male as the study excluded female patients. Subjects enrolled in the study had a minimum IPSS score of 13, a $Q_{max}$ ranging from 5 to 15 mL, prostate volumes between 20 and 80 grams, and prostatic urethral lengths between 35 and 55 mm. The average age was 65.8±7.82 years.

The clinical treatment strategy involved pre-dilation of the prostate to create a commissurotomy between the lateral lobes. The pre-dilation balloon was an uncoated balloon catheter identical in size or smaller than the selected drug-coated balloon. The pre-dilation balloons were designed identically to the drug-coated balloons. 49 patients were treated with the single lumen catheter shaft design and 31 patients were treated with the reinforced fixed wire catheter shaft design. 18 patients were treated with a 30×35 mm drug-coated balloon, 32 patients were treated with a 35×35 mm drug-coated balloon, 8 patients were treated with a 35×45 mm drug-coated balloon, and 22 patients were treated with a 40×45 mm drug-coated balloon.

Clinical subjects were evaluated at 14, 30, 90, 180, and 365 days after the index procedure. Evaluations included analysis IPSS, uroflowmetry including $Q_{max}$, and PVR. Additionally, pharmacokinetic analysis was completed for the paclitaxel content in the blood, urine, semen, and residual drug on the drug-coated balloons.

On average patient IPSS improved from a baseline average of 22.3, to 10.7 at 14 days, 9.0 at 30 days, 8.1 at 90 days, 8.0 at 180 days, and 8.3 at 365 days. Average patient $Q_{max}$ at baseline was 10.9 mL/sec and improved to 18.5 mL/sec at 14 days, 20.1 mL/sec at 30 days, 20.4 mL/sec at 90 days, 20.1 mL/sec at 180 days, and 18.3 mL/sec at 365 days. Average patient PVR was 64.0 mL at baseline and improved to 41.4 mL at 14 days, 28.4 mL at 30 days, 33.9 mL at 90 days, 29.7 mL at 180 days, and 31.7 mL at 365 days.

Human plasma paclitaxel concentration on average was 0.2 ng/mL immediately post treatment, 0.2 ng/mL at 1 hour, 0.1 ng/mL at 3 hours, 0.1 ng/mL at 5 hours, 0.07 ng/mL at 10 hours, 0.03 ng/mL at 24 hours, and 0.02 ng/mL at 4 days. Human urine paclitaxel concentration on average was 598 ng/mL immediately post procedure, 202 ng/mL at 4 days, 5.2 ng/mL at 14 days, and 5.1 ng/mL at 30 days. Human semen paclitaxel concentration on average was 5.3 ng/mL at 14 days, 3.2 ng/mL at 30 days, and 0.12 ng/mL at 6 months.

Residual drug content on the balloons used to treat human subject was on average 23.0% of the original dose with a range of 7.7% to 47.1%.

Example IV-2. BPH Human Clinical Subject a from Example IV-1: 35 mm by 35 mm Single Lumen Drug-Coated Balloon Catheter Human subject A had a 22.9 g prostate with a prostate width of 45.2 mm, a height of 25.2 mm, and a length of 38.5 mm. This was determined by conducting trans rectal ultrasound (TRUS). The human clinical subject had a baseline $Q_{max}$ of 9 mL/second, a baseline IPSS score of 25, and a baseline PVR of 116 mL. First a cystoscope was inserted into the urethra to survey for urethra stricture, view and assess prostatic obstruction due to BPH, and to also gather fluoroscopy images of anatomical landmarks such as the bladder neck and the external sphincter. Then the cystoscope was removed, and the pre-dilation balloon was inserted into the urethra and tracked so the balloon was in the prostatic urethra. The Tuohy Borst valve was connected to the catheter shaft. Next the delivery sheath was removed to expose the balloon and the cystoscope was inserted side by side with the catheter shaft. Next the position of the balloon was slightly adjusted such that the proximal bond of the balloon was adjacent to the external sphincter. The proximal bond of the balloon is the small constant diameter part of the balloon that is bonded to the shaft. By properly measuring the prostatic urethra and choosing a properly dimensioned balloon catheter, by placing the proximal bond of the balloon proximally adjacent to the external sphincter, the distal neck with naturally be located at the bladder neck. The balloon was inflated until a commissurotomy was created between the lateral lobes at about 2 atm. The commissurotomy was visually confirmed with the video image from the cystoscope. After a commissurotomy was achieved the balloon was deflated, the sheath was reinserted through the urethra, the balloon was recaptured in the sheath, and the pre-dilation balloon was removed. The drug-coated balloon was then inserted into the urethra and tracked to the prostatic urethra and the delivery sheath was removed. The Tuohy Borst valve was connected to the catheter shaft. The balloon was positioned as described above with a cystoscope. The balloon was held uninflated for at least 1 minute prior to inflating to hydrate the drug coating. Then the drug-coated balloon was inflated with a mixture of saline and contrast media using the syringe with pressure gauge. The balloon was inflated to the rated burst pressure of 4 atmospheres and held at that pressure for 5 minutes. Then the balloon was deflated, the delivery sheath was re-inserted into the urethra, and the balloon was recaptured and removed from the subject. The stretch ratio for the 35 mm nominal diameter drug-coated balloon was 7.0 to 7.6. The residual drug remaining on the balloon after use was analyzed. The residual amount of paclitaxel left on the balloon was 2304 µg (16.6 percent of the initial drug load). The human clinical subject had follow-up visits at 14, 30, 90, 180, and 365 days to measure maximum urine flow rate, IPSS score, and PVR. The human clinical subject had a maximum urine flow rate improvement from 9 mL/second to 7, 18, 20, 18, and 19 mL/second at follow-up visits of 14, 30, 90, 180 and 365 days respectively. The human clinical subject had PVR improvement from 116 mL to 76, 23, 22, 15, and 38 mL at follow-up visits of 14, 30, 90, 180 and 365 days respectively.

The human clinical subject had an IPSS improvement from 25 to 12, 8, 5, 0, and 0 at follow-up visits of 14, 30, 90, 180 and 365 days respectively.

Example IV-3. BPH Human Clinical Subject B from Example IV-1: 35 mm by 45 mm Single Lumen Drug-Coated Balloon Catheter Human subject B had a 39 g prostate with a prostate width of 51 mm, a height of 31 mm, and a length of 48 mm. This was determined by conducting trans rectal ultrasound (TRUS). The human clinical subject had a baseline $Q_{max}$ of 15 mL/second, a baseline IPSS score of 27, and a baseline PVR of 34 mL. First a cystoscope was inserted into the urethra to survey for urethra stricture, view and assess prostatic obstruction due to BPH, and to also gather fluoroscopy images of anatomical landmarks such as the bladder neck and the external sphincter. Then the cystoscope was removed, and the pre-dilation balloon was inserted into the urethra and tracked so the balloon was in the prostatic urethra. The Tuohy Borst valve was connected to the catheter shaft. Next the delivery sheath was removed to expose the balloon and the cystoscope was inserted side by side with the catheter shaft. Next the position of the balloon was slightly adjusted such that the proximal bond of the balloon was adjacent to the external sphincter. The balloon was inflated until a commissurotomy was created between the lateral lobes at about 2 atm. The commissurotomy was visually confirmed with the video image from the cystoscope. After a commissurotomy was achieved the balloon was deflated, the sheath was reinserted through the urethra, the balloon was recaptured in the sheath, and the pre-dilation balloon was removed. The drug-coated balloon was then inserted into the urethra and tracked to the prostatic urethra and the delivery sheath was removed. The Tuohy Borst valve was connected to the catheter shaft. The balloon was position as described above with a cystoscope. The balloon was held uninflated for at least 1 minute prior to inflating to hydrate the drug coating. Then the drug-coated balloon was inflated with a mixture of saline and contrast media using the syringe with pressure gauge. The balloon was inflated to the rated burst pressure of 4 atmospheres and held at that pressure for 5 minutes. Then the balloon was deflated, the delivery sheath was re-inserted into the urethra, and the balloon was recaptured and removed from the subject. The stretch ratio for the 35 mm nominal diameter drug-coated balloon was 7.0 to 7.6. The residual drug remaining on the balloon after use was analyzed. The residual amount of paclitaxel left on the balloon was 2682 µg (16.2 percent of the initial drug load). The human clinical subject had follow-up visits at 14, 30, 90, 180, and 365 days to measure maximum urine flow rate, IPSS score, and PVR. The human clinical subject had a maximum urine flow rate improvement from 15 mL/second to 20, 19, 22, 14, and 20 mL/second at follow-up visits of 14, 30, 90, 180 and 365 days respectively. The human clinical subject had PVR improvement from 34 mL to 0, 12, 98, 2, and 0 mL at follow-up visits of 14, 30, 90, 180 and 365 days respectively. The human clinical subject had an IPSS improvement from 27 to 13, 9, 4, 5, and 1 at follow-up visits of 14, 30, 90, 180 and 365 days respectively.

Example IV-4. BPH Human Clinical Subject C from Example IV-1: 40 mm by 45 mm Single Lumen Drug-Coated Balloon Catheter Human subject C had a 78.4 g prostate with a prostate width of 64 mm, a height of 48 mm, and a length of 48 mm. This was determined by conducting trans rectal ultrasound (TRUS). The human clinical subject had a baseline $Q_{max}$ of 12 mL/second, a baseline IPSS score of 29, and a baseline PVR of 122 mL. First a cystoscope was inserted into the urethra to survey for urethra stricture, view and assess prostatic obstruction due to BPH, and to also gather fluoroscopy images of anatomical landmarks such as the bladder neck and the external sphincter. Then the cystoscope was removed, and the pre-dilation balloon was inserted into the urethra and tracked so the balloon was in the prostatic urethra. The Tuohy Borst valve was connected to the catheter shaft. Next the delivery sheath was removed to expose the balloon and the cystoscope was inserted side by side with the catheter shaft. Next the position of the balloon was slightly adjusted such that the proximal bond of the balloon was adjacent to the external sphincter. The balloon was inflated until a commissurotomy was created between the lateral lobes at about 3 atm. The commissurotomy was visually confirmed with the video image from the cystoscope. After a commissurotomy was achieved the balloon was deflated, the sheath was reinserted through the urethra, the balloon was recaptured in the sheath, and the pre-dilation balloon was removed. The drug-coated balloon was then inserted into the urethra and tracked to the prostatic urethra and the delivery sheath was removed. The Tuohy Borst valve was connected to the catheter shaft. The balloon was position as described above with a cystoscope. The balloon was held uninflated for at least 1 minute prior to inflating to hydrate the drug coating. Then the drug-coated balloon was inflated with a mixture of saline and contrast media using the syringe with pressure gauge. The balloon was inflated to the rated burst pressure of 4 atmospheres and held at that pressure for 5 minutes. Then the balloon was deflated, the delivery sheath was re-inserted into the urethra, and the balloon was recaptured and removed from the subject. The stretch ratio for the 40 mm nominal diameter drug-coated balloon was 8.0 to 9.0. The residual drug remaining on the balloon after use was analyzed. The residual amount of paclitaxel left on the balloon was 6767 µg (34.6 percent of the initial drug load). The human clinical subject had follow-up visits at 14, 30, 90, 180, and 365 days to measure maximum urine flow rate, IPSS score, and PVR. The human clinical subject had a maximum urine flow rate improvement from 12 mL/second to 21, 23, 31, 43, and 30 mL/second at follow-up visits of 14, 30, 90, 180 and 365 days respectively. The human clinical subject had PVR improvement from 122 mL to 0, 0, 0, 0, and 0 mL at follow-up visits of 14, 30, 90, 180 and 365 days respectively. The human clinical subject had an IPSS improvement from 29 to 12, 10, 13, 9, and 5 at follow-up visits of 14, 30, 90, 180 and 365 days respectively.

Example IV-5. BPH Human Clinical Subject D from Example IV-1: 30 mm by 35 mm Reinforced Fixed Wire Drug-Coated Balloon Catheter Human subject D had a 26.7 g prostate with a prostate width of 50 mm, a height of 29 mm, and a length of 39 mm. This was determined by conducting trans rectal ultrasound (TRUS). The human clinical subject had a baseline $Q_{max}$ of 14 mL/second, a baseline IPSS score of 21, and a baseline PVR of 80 mL. First a cystoscope was inserted into the urethra to survey for urethra stricture, view and assess prostatic obstruction due to BPH. This procedure was completed without the use of fluoroscopy. The cystoscope was removed, and the pre-dilation balloon was inserted into the urethra and tracked so the balloon was in the prostatic urethra. An inflation device with pressure monitoring capability was connected to the Luer hub at the proximal end of the device. Next the delivery sheath was removed to expose the balloon and the cystoscope was inserted side by side with the catheter shaft. Next the position of the balloon was slightly adjusted such that the proximal bond of the balloon was adjacent to the external sphincter. The balloon was inflated until a commissurotomy was created between the lateral lobes at about 2 atm. The commissurotomy was visually confirmed with the video image from the cystoscope. After a commissurotomy was achieved the balloon was deflated, the sheath was reinserted through the urethra, the balloon was recaptured in the sheath, and the pre-dilation balloon was removed. The drug-coated balloon was then inserted into the urethra and tracked to the prostatic urethra and the delivery sheath was removed. An inflation device with pressure monitoring capability was connected to the Luer hub at the proximal end of the device. The balloon was position as described above with a cystoscope. The balloon was held uninflated for at least 1 minute prior to inflating to hydrate the drug coating. Then the drug-coated balloon was inflated with a saline using the syringe with pressure gauge. The balloon was inflated to the rated burst pressure of 4 atmospheres and held at that pressure for 5 minutes. Then the balloon was deflated, the delivery sheath was re-inserted into the urethra, and the balloon was recaptured and removed from the subject. The stretch ratio for the 30 mm nominal diameter drug-coated balloon was 6.0 to 6.6. The residual drug remaining on the balloon after use was analyzed. The residual amount of paclitaxel left on the balloon was 1281 μg (11.2 percent of the initial drug load). The human clinical subject had follow-up visits at 14, 30, 90, 180, and 365 days to measure maximum urine flow rate, IPSS score, and PVR. The human clinical subject had a maximum urine flow rate improvement from 14 mL/second to 30, 23, 27, 18, and 31 mL/second at follow-up visits of 14, 30, 90, 180 and 365 days respectively. The human clinical subject had PVR improvement from 80 mL to 15, 18, 11, 23, and 9 mL at follow-up visits of 14, 30, 90, 180 and 365 days respectively. The human clinical subject had an IPSS improvement from 21 to 6, 4, 7, 6, and 4 at follow-up visits of 14, 30, 90, 180 and 365 days respectively.

Example IV-6. BPH Human Clinical Subject E from Example IV-1: 35 mm by 35 mm Reinforced Fixed Wire Drug-Coated Balloon Catheter Human subject E had a 30 g prostate with a prostate width of 48 mm, a height of 28 mm, and a length of 41 mm. This was determined by conducting trans rectal ultrasound (TRUS). The human clinical subject had a baseline $Q_{max}$ of 10 mL/second, a baseline IPSS score of 35, and a baseline PVR of 100 mL. First a cystoscope was inserted into the urethra to survey for urethra stricture, view and assess prostatic obstruction due to BPH. This procedure was completed without the use of fluoroscopy. The cystoscope was removed, and the pre-dilation balloon was inserted into the urethra and tracked so the balloon was in the prostatic urethra. An inflation device with pressure monitoring capability was connected to the Luer hub at the proximal end of the device. Next the delivery sheath was removed to expose the balloon and the cystoscope was inserted side by side with the catheter shaft. Next the position of the balloon was slightly adjusted such that the proximal bond of the balloon was adjacent to the external sphincter. The balloon was inflated until a commissurotomy was created between the lateral lobes at about 2 atm. The commissurotomy was visually confirmed with the video image from the cystoscope. After a commissurotomy was achieved the balloon was deflated, the sheath was reinserted through the urethra, the balloon was recaptured in the sheath, and the pre-dilation balloon was removed. The drug-coated balloon was then inserted into the urethra and tracked to the prostatic urethra and the delivery sheath was removed. An inflation device with pressure monitoring capability was connected to the Luer hub at the proximal end of the device. The balloon was position as described above with a cystoscope. The balloon was held uninflated for at least 1 minute prior to inflating to hydrate the drug coating. Then the drug-coated balloon was inflated with a mixture of saline and contrast media using the syringe with pressure gauge. The balloon was inflated to the rated burst pressure of 4 atmospheres and held at that pressure for 5 minutes. Then the balloon was deflated, the delivery sheath was re-inserted into the urethra, and the balloon was recaptured and removed from the subject. The stretch ratio for the 35 mm nominal diameter drug-coated balloon was 7.0 to 7.6. The residual drug remaining on the balloon after use was analyzed. The residual amount of paclitaxel left on the balloon was 2982 μg (21.4 percent of the initial drug load). The human clinical subject had follow-up visits at 14, 30, 90, 180, and 365 days to measure maximum urine flow rate, IPSS score, and PVR. The human clinical subject had a maximum urine flow rate improvement from 10 mL/second to 9, 11, 12, 16, and 17 mL/second at follow-up visits of 14, 30, 90, 180 and 365 days respectively. The human clinical subject had PVR improvement from 100 mL to 10, 5, 20, 10, and 10 mL at follow-up visits of 14, 30, 90, 180 and 365 days respectively. The human clinical subject had an IPSS improvement from 35 to 22, 21, 6, 2, and 4 at follow-up visits of 14, 30, 90, 180 and 365 days respectively.

Example IV-7. BPH Human Clinical Subject E from Example IV-1: 35 mm by 35 mm Reinforced Fixed Wire Drug-Coated Balloon Catheter Human subject E had a 43.2 g prostate with a prostate width of 52 mm, a height of 39 mm, and a length of 41 mm. This was determined by conducting trans rectal ultrasound (TRUS). The human clinical subject had a baseline $Q_{max}$ of 12 mL/second, a baseline IPSS score of 29, and a baseline PVR of 85 mL. First a cystoscope was inserted into the urethra to survey for urethra stricture, view and assess prostatic obstruction due to BPH. The cystoscope was removed, and the pre-dilation balloon was inserted into the urethra and tracked so the balloon was in the prostatic urethra. An inflation device with pressure monitor capability was connected to the Luer hub at the proximal end of the device. Next the delivery sheath was removed to expose the balloon and the cystoscope was inserted side by side with the catheter shaft. Next the position of the balloon was slightly adjusted such that the proximal bond of the balloon was adjacent to the external sphincter. The balloon was inflated until a commissurotomy was created between the lateral lobes at about 3 atm. The commissurotomy was visually confirmed with the video image from the cystoscope. After a commissurotomy was achieved the balloon was deflated, the sheath was reinserted through the urethra, the balloon was recaptured in the sheath, and the pre-dilation balloon was removed. The drug-coated balloon was then inserted into the urethra and tracked to the prostatic urethra and the delivery sheath was removed. An inflation device with pressure monitor capability was connected to the Luer hub at the proximal end of the device. The balloon was position as described above with a cystoscope. The balloon was held uninflated for at least 1 minute prior to inflating to hydrate the drug coating. Then the drug-coated balloon was inflated with saline using the syringe with pressure gauge. The balloon was inflated to the rated burst pressure of 4 atmospheres and held at that pressure for 5 minutes. Then the balloon was deflated, the delivery sheath was re-inserted into the urethra, and the balloon was recaptured and removed from the subject. The stretch ratio for the 35 mm nominal diameter drug-coated balloon was 7.0 to 7.6. The residual drug remaining on the balloon after use was analyzed. The residual amount of paclitaxel left on the balloon was 3569 µg (25.6 percent of the initial drug load). The human clinical subject had follow-up visits at 14, 30, 90, 180, and 365 days to measure maximum urine flow rate, IPSS score, and PVR. The human clinical subject had a maximum urine flow rate improvement from 12 mL/second to 14, 20, 19, 16, and 14 mL/second at follow-up visits of 14, 30, 90, 180 and 365 days respectively. The human clinical subject had PVR improvement from 85 mL to 35, 96, 29, 29, and 35 mL at follow-up visits of 14, 30, 90, 180 and 365 days respectively. The human clinical subject had an PSS improvement from 29 to 10, 7, 7, 8, and 9 at follow-up visits of 14, 30, 90, 180 and 365 days respectively.

Example IV-8. BPH Human Clinical Subject E from Example IV-1: 35 mm by 45 mm Reinforce Fixed Wire Drug-Coated Balloon Catheter Human subject C had a 68 g prostate with a prostate width of 55 mm, a height of 54 mm, and a length of 43 mm. This was determined by conducting trans rectal ultrasound (TRUS). The human clinical subject had a baseline $Q_{max}$ of 7 mL/second, a baseline IPSS score of 25, and a baseline PVR of 65 mL. First a cystoscope was inserted into the urethra to survey for urethra stricture, view and assess prostatic obstruction due to BPH. This procedure was completed without the use of fluoroscopy. The cystoscope was removed, and the pre-dilation balloon was inserted into the urethra and tracked so the balloon was in the prostatic urethra. An inflation device with pressure monitoring capability was connected to the Luer hub at the proximal end of the device. Next the delivery sheath was removed to expose the balloon and the cystoscope was inserted side by side with the catheter shaft. Next the position of the balloon was slightly adjusted such that the proximal bond of the balloon was adjacent to the external sphincter. The balloon was inflated until a commissurotomy was created between the lateral lobes at about 1.5 atm. The commissurotomy was visually confirmed with the video image from the cystoscope. After a commissurotomy was achieved the balloon was deflated, the sheath was reinserted through the urethra, the balloon was recaptured in the sheath, and the pre-dilation balloon was removed. The drug-coated balloon was then inserted into the urethra and tracked to the prostatic urethra and the delivery sheath was removed. An inflation device with pressure monitoring capability was connected to the Luer hub at the proximal end of the device. The balloon was position as described above with a cystoscope. The balloon was held uninflated for at least 1 minute prior to inflating to hydrate the drug coating. Then the drug-coated balloon was inflated with a saline using the syringe with pressure gauge. The balloon was inflated to the rated burst pressure of 4 atmospheres and held at that pressure for 5 minutes. Then the balloon was deflated, the delivery sheath was re-inserted into the urethra, and the balloon was recaptured and removed from the subject. The stretch ratio for the 35 mm nominal diameter drug-coated balloon was 7.0 to 7.6. The residual drug remaining on the balloon after use was analyzed. The residual amount of paclitaxel left on the balloon was 2471 µg (12.6 percent of the initial drug load). The human clinical subject had follow-up visits at 14, 30, 90, 180, and 365 days to measure maximum urine flow rate, IPSS score, and PVR. The human clinical subject had a maximum urine flow rate improvement from 7 mL/second to 14, 16, 16, 11, and 14 mL/second at follow-up visits of 14, 30, 90, 180 and 365 days respectively. The human clinical subject had PVR improvement from 65 mL to 30, 7.5, 0, 32, and 9 mL at follow-up visits of 14, 30, 90, 180 and 365 days respectively. The human clinical subject had an IPSS improvement from 25 to 10, 22, 15, 10, and 14 at follow-up visits of 14, 30, 90, 180 and 365 days respectively.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

EXEMPLARY EMBODIMENTS

The following exemplary embodiments are provided, the numbering of which is not to be construed as designating levels of importance:

Embodiment 1 provides a method for treatment of a cancer treatment-induced non-vascular stricture, the method comprising:
  inserting a balloon catheter into a target site in a body lumen comprising the cancer treatment-induced non-vascular stricture, the balloon catheter comprising
    an elongated balloon, and
    a coating layer overlying an exterior surface of the balloon, wherein the coating layer comprises one or more water-soluble additives and an initial drug load of a therapeutic agent;
  inflating the balloon at the target site to contact the coating layer with walls of the body lumen at the location of the cancer treatment-induced non-vascular stricture until the balloon achieves an inflated balloon diameter for an inflation period;
  deflating the balloon after the inflation period; and
  withdrawing the balloon catheter from the body lumen.

Embodiment 2 provides the method of Embodiment 1, wherein the cancer treatment is radiation treatment.

Embodiment 3 provides the method of any one of Embodiments 1-2, wherein the stricture is a urethral stricture, ureteral stricture, esophageal stricture, sinus stricture, stomach stricture, small intestine stricture, colon stricture, rectum stricture, large intestine stricture, bladder neck stricture, or a biliary tract stricture.

Embodiment 4 provides the method of any one of Embodiments 1-3, wherein the cancer treatment is radiation treatment of the prostate, wherein the stricture is a bladder neck stricture.

Embodiment 5 provides a method for reducing the occurrence of or prevention of a cancer treatment-induced nonvascular stricture, or for reducing or preventing recurrence of cancer, the method comprising:
inserting a balloon catheter into a target site in a body lumen, wherein the target site is at, proximate to, proximal to, or distal to a site of a performed cancer treatment, the balloon catheter comprising
an elongated balloon, and
a coating layer overlying an exterior surface of the balloon, wherein the coating layer comprises one or more water-soluble additives and an initial drug load of a therapeutic agent;
inflating the balloon at the target site to contact the coating layer with walls of the body lumen at the target site until the balloon achieves an inflated balloon diameter for an inflation period;
deflating the balloon after the inflation period; and
withdrawing the balloon catheter from the body lumen.

Embodiment 6 provides the method of Embodiment 5, further comprising performing the cancer treatment of the body lumen at, proximate to, proximal to, or distal to the target site prior to the insertion of the balloon catheter into the target site.

Embodiment 7 provides the method of any one of Embodiments 5-6, wherein a cancer treatment-induced non-vascular stricture is present at the target site, further comprising performing a stricturotomy at the target site prior to the insertion of the balloon catheter into the target site.

Embodiment 8 provides the method of Embodiment 7, wherein the stricturotomy comprises needle knife electroincision, episiotomy, urethrotomy, direct vision internal urethrotomy (DVIU), endoscopic mucosal resection (EMR), or endoscopic sub-mucosal dissection (ESD).

Embodiment 9 provides the method of any one of Embodiments 5-7, wherein the cancer treatment is radiation treatment.

Embodiment 10 provides the method of any one of Embodiments 5-8, wherein the stricture is a urethral stricture, ureteral stricture, esophageal stricture, sinus stricture, stomach stricture, small intestine stricture, colon stricture, rectum stricture, large intestine stricture, a bladder neck stricture, or a biliary tract stricture.

Embodiment 11 provides the method of any one of Embodiments 5-9, wherein the cancer treatment is radiation treatment of the prostate, wherein the stricture is a bladder neck stricture.

Embodiment 12 provides a method for treatment of a surgical anastomosis-induced non-vascular stricture, the method comprising:
inserting a balloon catheter into a target site in a body lumen comprising the surgical anastomosis-induced non-vascular stricture, the balloon catheter comprising
an elongated balloon, and
a coating layer overlying an exterior surface of the balloon, wherein the coating layer comprises one or more water-soluble additives and an initial drug load of a therapeutic agent;
inflating the balloon at the target site to contact the coating layer with walls of the body lumen at the location of the surgical anastomosis-induced non-vascular stricture until the balloon achieves an inflated balloon diameter for an inflation period;
deflating the balloon after the inflation period; and
withdrawing the balloon catheter from the body lumen.

Embodiment 13 provides the method of Embodiment 12, wherein the stricture is a fibrotic stricture.

Embodiment 14 provides the method of any one of Embodiments 12-13, wherein the stricture is an esophageal stricture, stomach stricture, small intestine stricture, duodenum stricture, jejunum stricture, ileum stricture, colon stricture, rectum stricture, large intestine stricture, colorectal stricture, a stricture resulting from gastric bypass, ileocolonic stricture, gastrointestinal stricture, urethral stricture, ureteral stricture, J-pouch strictures, or a bladder neck stricture.

Embodiment 15 provides a method for reducing the occurrence of or prevention of a surgical anastomosis-induced non-vascular stricture, the method comprising:
inserting a balloon catheter into a target site in a body lumen, wherein the target site is at a site of a performed surgical anastomosis, the balloon catheter comprising
an elongated balloon, and
a coating layer overlying an exterior surface of the balloon, wherein the coating layer comprises one or more water-soluble additives and an initial drug load of a therapeutic agent;
inflating the balloon at the target site to contact the coating layer with walls of the body lumen at the target site until the balloon achieves an inflated balloon diameter for an inflation period;
deflating the balloon after the inflation period; and
withdrawing the balloon catheter from the body lumen.

Embodiment 16 provides the method of Embodiment 15, further comprising performing forming the surgical anastomosis at the target site prior to the insertion of the balloon catheter into the target site.

Embodiment 17 provides the method of any one of Embodiments 15-16, wherein a surgical anastomosis-induced non-vascular stricture is present at the target site, further comprising performing a stricturotomy at the target site prior to the insertion of the balloon catheter into the target site.

Embodiment 18 provides the method of Embodiment 17, wherein the stricturotomy comprises needle knife electroincision, episiotomy, urethrotomy, direct vision internal urethrotomy (DVIU), endoscopic mucosal resection (EMR), or endoscopic sub-mucosal dissection (ESD).

Embodiment 19 provides the method of any one of Embodiments 15-18, wherein the stricture is a fibrotic stricture.

Embodiment 20 provides the method of any one of Embodiments 15-19, wherein the stricture is an esophageal stricture, biliary stricture, stomach stricture, small intestine stricture, duodenum stricture, jejunum stricture, ileum stricture, colon stricture, rectum stricture, large intestine stricture, colorectal stricture, a stricture resulting from gastric bypass, ileocolonic stricture, gastrointestinal stricture, urethral stricture, ureteral stricture, J-pouch strictures, or a bladder neck stricture.

Embodiment 21 provides a method for treatment of an inflammatory disease-induced non-vascular stricture, the method comprising:
inserting a balloon catheter into a target site in a body lumen comprising the inflammatory disease-induced non-vascular stricture, the balloon catheter comprising
an elongated balloon, and
a coating layer overlying an exterior surface of the balloon, wherein the coating layer comprises one or more water-soluble additives and an initial drug load of a therapeutic agent;
inflating the balloon at the target site to contact the coating layer with walls of the body lumen at the location of the inflammatory disease-induced non-vascular stricture until the balloon achieves an inflated balloon diameter for an inflation period;

deflating the balloon after the inflation period; and
withdrawing the balloon catheter from the body lumen.

Embodiment 22 provides the method of Embodiment 21, wherein the inflammatory disease is Crohn's disease.

Embodiment 23 provides the method of any one of Embodiments 21-22, wherein the inflammatory disease is ulcerative colitis.

Embodiment 24 provides the method of any one of Embodiments 21-23, wherein the stricture is a small intestine stricture, duodenum stricture, jejunum stricture, ileum stricture, colon stricture, rectum stricture, large intestine stricture, colorectal stricture, ileocolonic stricture, or gastrointestinal stricture.

Embodiment 25 provides a method for reducing the occurrence of or prevention of an inflammatory disease treatment-induced non-vascular stricture, the method comprising:
 inserting a balloon catheter into a target site in a body lumen, wherein the target site is at a site of a performed inflammatory disease treatment, the balloon catheter comprising
  an elongated balloon, and
  a coating layer overlying an exterior surface of the balloon, wherein the coating layer comprises one or more water-soluble additives and an initial drug load of a therapeutic agent;
 inflating the balloon at the target site to contact the coating layer with walls of the body lumen at the target site until the balloon achieves an inflated balloon diameter for an inflation period;
 deflating the balloon after the inflation period; and
 withdrawing the balloon catheter from the body lumen.

Embodiment 26 provides the method of Embodiment 25, further comprising performing the inflammatory disease treatment at the target site prior to the insertion of the balloon catheter into the target site.

Embodiment 27 provides the method of any one of Embodiments 25-26, wherein an inflammatory disease treatment-induced stricture is present at the target site, further comprising performing a stricturotomy at the target site prior to the insertion of the balloon catheter into the target site.

Embodiment 28 provides the method of Embodiment 27, wherein the strictrotomy comprises needle knife electroincision, or endoscopic mucosal resection (EMR).

Embodiment 29 provides the method of any one of Embodiments 25-28, wherein the inflammatory disease is Crohn's disease.

Embodiment 30 provides the method of any one of Embodiments 25-29, wherein the inflammatory disease is ulcerative colitis.

Embodiment 31 provides the method of any one of Embodiments 25-30, wherein the stricture is a small intestine stricture, duodenum stricture, jejunum stricture, ileum stricture, colon stricture, rectum stricture, large intestine stricture, colorectal stricture, ileocolonic stricture, or gastrointestinal stricture.

Embodiment 32 provides a method for treatment of a gastrectomy-induced non-vascular stricture, the method comprising:
 inserting a balloon catheter into a target site in a body lumen comprising the gastrectomy-induced non-vascular stricture, the balloon catheter comprising
  an elongated balloon, and
  a coating layer overlying an exterior surface of the balloon, wherein the coating layer comprises one or more water-soluble additives and an initial drug load of a therapeutic agent;
 inflating the balloon at the target site to contact the coating layer with walls of the body lumen at the location of the gastrectomy-induced non-vascular stricture until the balloon achieves an inflated balloon diameter for an inflation period;
 deflating the balloon after the inflation period; and
 withdrawing the balloon catheter from the body lumen.

Embodiment 33 provides a method for reducing the occurrence of or prevention of a gastrectomy-induced non-vascular stricture, the method comprising:
 inserting a balloon catheter into a target site in a body lumen, wherein the target site is at a site of a performed gastrectomy, the balloon catheter comprising
  an elongated balloon, and
  a coating layer overlying an exterior surface of the balloon, wherein the coating layer comprises one or more water-soluble additives and an initial drug load of a therapeutic agent;
 inflating the balloon at the target site to contact the coating layer with walls of the body lumen at the target site until the balloon achieves an inflated balloon diameter for an inflation period;
 deflating the balloon after the inflation period; and
 withdrawing the balloon catheter from the body lumen.

Embodiment 34 provides the method of Embodiment 33, further comprising performing the gastrectomy at the target site prior to the insertion of the balloon catheter into the target site.

Embodiment 35 provides the method of any one of Embodiments 33-34, wherein a gastrectomy-induced non-vascular stricture is present at the target site, further comprising performing a stricturotomy at the target site prior to the insertion of the balloon catheter into the target site.

Embodiment 36 provides a method for treatment of a needle knife electroincision-, episiotomy-, urethrotomy-, direct vision internal urethrotomy (DVIU)-, endoscopic mucosal resection (EMR)-, or endoscopic sub-mucosal dissection (ESD)-induced non-vascular stricture, the method comprising:
 inserting a balloon catheter into a target site in a body lumen comprising the needle knife electroincision-, episiotomy-, urethrotomy-, direct vision internal urethrotomy (DVIU)-, endoscopic mucosal resection (EMR)-, or endoscopic sub-mucosal dissection (ESD)-induced non-vascular stricture, the balloon catheter comprising
  an elongated balloon, and
  a coating layer overlying an exterior surface of the balloon, wherein the coating layer comprises one or more water-soluble additives and an initial drug load of a therapeutic agent;
 inflating the balloon at the target site to contact the coating layer with walls of the body lumen at the location of the needle knife electroincision-, urethrotomy-, direct vision internal urethrotomy (DVIU)-, EMR (endoscopic mucosal resection)-, or endoscopic sub-mucosal dissection (ESD)-induced non-vascular stricture until the balloon achieves an inflated balloon diameter for an inflation period;
 deflating the balloon after the inflation period; and
 withdrawing the balloon catheter from the body lumen.

Embodiment 37 provides the method of Embodiment 36, wherein the electroincision, episiotomy, endoscopic mucosal resection (EMR), or endoscopic sub-mucosal dissection (ESD) is a treatment for esophageal cancer, biliary cancer, stomach cancer, small intestine cancer, duodenum cancer, jejunum cancer, ileum cancer, colon cancer, rectum cancer, colorectal cancer, ileocolonic cancer, or gastrointestinal cancers.

Embodiment 38 provides the method of any one of Embodiments 36-37, wherein the electroincision, episiotomy, endoscopic mucosal resection (EMR), or endoscopic sub-mucosal dissection (ESD) is a treatment for removing polyps from the colon, wherein the stricture is a colon stricture.

Embodiment 39 provides the method of any one of Embodiments 36-38, wherein the electroincision, episiotomy, urethrotomy, direct vision internal urethrotomy (DVIU), endoscopic mucosal resection (EMR), or endoscopic sub-mucosal dissection (ESD) is a treatment for Barrett's esophagus and wherein the stricture is an esophageal stricture.

Embodiment 40 provides the method of any one of Embodiments 36-39, wherein the stricture is an esophageal stricture, biliary stricture, small intestine stricture, duodenum stricture, jejunum stricture, ileum stricture, colon stricture, rectum stricture, colorectal stricture, ileocolonic stricture, or gastrointestinal stricture.

Embodiment 41 provides a method for reducing the occurrence of or prevention of a needle knife electroincision-, episiotomy-, urethrotomy-, direct vision internal urethrotomy (DVIU)-, endoscopic mucosal resection (EMR)-, or endoscopic sub-mucosal dissection (ESD)-induced non-vascular stricture, the method comprising:
  inserting a balloon catheter into a target site in a body lumen, wherein the target site is at a site of a performed needle knife electroincision, episiotomy, urethrotomy, DVIU, EMR, or ESD, the balloon catheter comprising an elongated balloon, and
    a coating layer overlying an exterior surface of the balloon, wherein the coating layer comprises one or more water-soluble additives and an initial drug load of a therapeutic agent;
  inflating the balloon at the target site to contact the coating layer with walls of the body lumen at the target site until the balloon achieves an inflated balloon diameter for an inflation period;
  deflating the balloon after the inflation period; and
  withdrawing the balloon catheter from the body lumen.

Embodiment 42 provides the method of Embodiment 41, further comprising performing the needle knife electroincision, episiotomy, urethrotomy, DVIU, EMR, or ESD at the target site prior to the insertion of the balloon catheter into the target site.

Embodiment 43 provides the method of any one of Embodiments 41-42, wherein the target site comprises a needle knife electroincision-, episiotomy-, urethrotomy-, direct vision internal urethrotomy (DVIU)-, endoscopic mucosal resection (EMR)-, or endoscopic sub-mucosal dissection (ESD)-induced non-vascular stricture, further comprising performing a stricturotomy at the target site prior to the insertion of the balloon catheter into the target site.

Embodiment 44 provides the method of any one of Embodiments 41-43, wherein the electroincision, episiotomy, urethrotomy, direct vision internal urethrotomy (DVIU), endoscopic mucosal resection (EMR), or endoscopic sub-mucosal dissection (ESD) is a treatment for esophageal cancer, biliary cancer, stomach cancer, small intestine cancer, duodenum cancer, jejunum cancer, ileum cancer, colon cancer, rectum cancer, colorectal cancer, ileocolonic cancer, or gastrointestinal cancers.

Embodiment 45 provides the method of any one of Embodiments 41-44, wherein the electroincision, episiotomy, urethrotomy, direct vision internal urethrotomy (DVIU), endoscopic mucosal resection (EMR), or endoscopic sub-mucosal dissection (ESD) is a treatment for Barrett's esophagus and wherein the stricture is an esophageal stricture.

Embodiment 46 provides the method of any one of Embodiments 41-45, wherein the stricture is an esophageal stricture, biliary stricture, small intestine stricture, duodenum stricture, jejunum stricture, ileum stricture, colon stricture, rectum stricture, colorectal stricture, ileocolonic stricture, or gastrointestinal stricture.

Embodiment 47 provides a method for treatment of a bladder neck stricture, the method comprising:
  inserting a balloon catheter into a target site in a body lumen comprising the bladder neck stricture, the balloon catheter comprising
    an elongated balloon, and
    a coating layer overlying an exterior surface of the balloon, wherein the coating layer comprises one or more water-soluble additives and an initial drug load of a therapeutic agent;
  inflating the balloon at the target site to contact the coating layer with walls of the body lumen at the location of the bladder neck stricture until the balloon achieves an inflated balloon diameter for an inflation period;
  deflating the balloon after the inflation period; and
  withdrawing the balloon catheter from the body lumen.

Embodiment 48 provides the method of Embodiment 47, wherein the bladder neck stricture is fibrotic.

Embodiment 49 provides a method for reducing the occurrence of or prevention of a prostate cancer treatment- or stricturotomy-induced bladder neck stricture, the method comprising:
  inserting a balloon catheter into a target site in a body lumen, wherein the target site is in a bladder neck and is at, proximate to, proximal to, or distal to a site of a prostate cancer treatment or stricturotomy, the balloon catheter comprising
    an elongated balloon, and
    a coating layer overlying an exterior surface of the balloon, wherein the coating layer comprises one or more water-soluble additives and an initial drug load of a therapeutic agent;
  inflating the balloon at the target site to contact the coating layer with walls of the body lumen at the target site until the balloon achieves an inflated balloon diameter for an inflation period;
  deflating the balloon after the inflation period; and
  withdrawing the balloon catheter from the body lumen.

Embodiment 50 provides the method of Embodiment 49, further comprising performing the prostate cancer treatment or stricturotomy prior to the insertion of the balloon catheter into the target site.

Embodiment 51 provides the method of any one of Embodiments 49-50, wherein the stricturotomy comprises needle knife electroincision, episiotomy, urethrotomy, direct vision internal urethrotomy (DVIU-, endoscopic mucosal resection (EMR), or endoscopic sub-mucosal dissection (ESD).

Embodiment 52 provides the method of any one of Embodiments 49-51, wherein the target site comprises a prostate cancer treatment- or stricturotomy-induced bladder neck stricture, further comprising performing a stricturotomy prior to the insertion of the balloon catheter into the target site.

Embodiment 53 provides the method of any one of Embodiments 49-52, wherein the prostate cancer treatment comprises radical prostatectomy (RP), radiotherapy, cryotherapy, or high intensity focused ultrasound (HIFU).

Embodiment 54 provides the method of any one of Embodiments 49-53, wherein the bladder neck stricture is fibrotic.

Embodiment 55 provides a method for treatment of an esophageal fibrostenotic stricture of eosinophilic esophagitis, the method comprising: inserting a balloon catheter into a target site in a body lumen comprising
- the esophageal fibrostenotic stricture of eosinophilic esophagitis, the balloon catheter comprising
  - an elongated balloon, and
    - a coating layer overlying an exterior surface of the balloon, wherein the coating layer comprises one or more water-soluble additives and an initial drug load of a therapeutic agent;
- inflating the balloon at the target site to contact the coating layer with walls of the body lumen at the location of the esophageal fibrostenotic stricture of eosinophilic esophagitis until the balloon achieves an inflated balloon diameter for an inflation period;
- deflating the balloon after the inflation period; and withdrawing the balloon catheter from the body lumen.

Embodiment 56 provides a method for treatment of achalasia, the method comprising:
- inserting a balloon catheter into a target site in a body lumen comprising the lower esophageal sphincter, the balloon catheter comprising
  - an elongated balloon, and
    - a coating layer overlying an exterior surface of the balloon, wherein the coating layer comprises one or more water-soluble additives and an initial drug load of a therapeutic agent;
- inflating the balloon at the target site to contact the coating layer with walls of the body lumen at the location of the lower esophageal sphincter until the balloon achieves an inflated balloon diameter for an inflation period;
- deflating the balloon after the inflation period; and withdrawing the balloon catheter from the body lumen.

Embodiment 57 provides a method for treatment of benign prostatic hyperplasia (BPH), the method comprising:
- inserting a balloon catheter into a target site in a body lumen comprising the prostatic urethra, the balloon catheter comprising
  - an elongated balloon, and
    - a coating layer overlying an exterior surface of the balloon, wherein the coating layer comprises one or more water-soluble additives and an initial drug load of a therapeutic agent;
- inflating the balloon at the target site to contact the coating layer with walls of the body lumen at the location of the prostatic urethra until the balloon achieves an inflated balloon diameter for an inflation period;
- deflating the balloon after the inflation period; and withdrawing the balloon catheter from the body lumen.

Embodiment 58 provides the method of Embodiment 57, wherein the BPH comprises median lobe hypertrophy.

Embodiment 59 provides the method of any one of Embodiments 57-58, wherein the BPH comprises lateral lobe hypertrophy.

Embodiment 60 provides the method of any one of Embodiments 57-59, wherein the BPH comprises both median lobe hypertrophy and lateral lobe hypertrophy.

Embodiment 61 provides a method for treatment of a urethral stricture that is a trauma-induced stricture, an idiopathic stricture, and/or an iatrogenic stricture, the method comprising:
- inserting a balloon catheter into a target site in a body lumen comprising the urethral stricture, the balloon catheter comprising
  - an elongated balloon, and
    - a coating layer overlying an exterior surface of the balloon, wherein the coating layer comprises one or more water-soluble additives and an initial drug load of a therapeutic agent;
- inflating the balloon at the target site to contact the coating layer with walls of the body lumen at the target site until the balloon achieves an inflated balloon diameter for an inflation period;
- deflating the balloon after the inflation period; and withdrawing the balloon catheter from the body lumen.

Embodiment 62 provides the method of any one of Embodiments 1-61, wherein the balloon catheter comprises one or more additional balloons in addition to the elongated balloon, wherein the additional balloons are elongated, wherein a spacing between balloons is about 0 to about 10 mm (e.g., 0 mm, or less than, equal to, or greater than about 0.5, 1, 2, 3, 4, 5, 6, 7, 8, 9, or 10 mm), wherein the additional balloons optionally comprise the same or similar coating layer as the coating layer on the elongated balloon.

Embodiment 63 provides the method of any one of Embodiments 1-62, wherein the elongated balloon has a main diameter.

Embodiment 64 provides the method of Embodiment 63, wherein the balloon comprises at least one neck section on the balloon comprising a smaller diameter than the main diameter when the balloon is inflated, the at least one neck section dividing the balloon into at least two main sections each having a diameter.

Embodiment 65 provides the method of Embodiment 64, wherein the balloon catheter comprises a catheter shaft on a longitudinal end of the balloon, wherein the at least one neck section is directly attached to the catheter shaft.

Embodiment 66 provides the method of any one of Embodiments 63-65, wherein the main diameter is at least 13 mm, or at least 15 mm, or at least 20 mm, or at least 30 mm, or at least 35 mm.

Embodiment 67 provides the method of any one of Embodiments 64-65, wherein the diameter of the at least two main sections is equal to the main diameter of the elongated balloon, or the at least one neck section has a diameter that is about 5% to about 99% of the diameter of at least one of the at least two main sections.

Embodiment 68 provides the method of any one of Embodiments 64-67, wherein the at least one neck section has a diameter that is independently about 2 mm to about 35 mm.

Embodiment 69 provides the method of any one of Embodiments 64-68, wherein the diameter of the at least one neck section is substantially static during inflation of the balloon.

Embodiment 70 provides the method of any one of Embodiments 64-69, wherein the at least one neck section comprises a substantially nonelastic portion of the balloon, a reinforced portion of the balloon, or a combination thereof.

Embodiment 71 provides the method of any one of Embodiments 64-70, wherein the at least one neck section comprises an inelastic material around a circumference of the neck section.

Embodiment 72 provides the method of Embodiment 71, wherein the inelastic material comprises ultra-high molecular weight polyethylene, a nylon, a polyamide, or a combination thereof.

Embodiment 73 provides the method of any one of Embodiments 1-72, wherein the elongated balloon has a length of about 20 mm to about 160 mm.

Embodiment 74 provides the method of any one of Embodiments 64-73, wherein the at least one neck section is one neck section and the balloon is free of other neck sections.

Embodiment 75 provides the method of any one of Embodiments 1-74, wherein the balloon catheter comprises a catheter shaft on a longitudinal end of the balloon, the catheter shaft comprising an interior lumen for delivery of a gas, liquid, or a combination thereof, to the balloon interior.

Embodiment 76 provides the method of Embodiment 75, wherein the proximal end of the catheter shaft comprises a hub that provides one or more connections to the interior lumen of the catheter shaft.

Embodiment 77 provides the method of any one of Embodiments 1-76, wherein the balloon catheter comprises a length-control mechanism that stretches and elongates the balloon while the balloon is in a deflated state.

Embodiment 78 provides the method of Embodiment 77, wherein the length-control mechanism stores energy during inflation of the balloon and wherein the stored energy is used to elongate the balloon once the balloon is in a deflated state.

Embodiment 79 provides the method of Embodiment 78, wherein the energy for the length control mechanism is stored in the catheter shaft during the inflation of the balloon.

Embodiment 80 provides the method of any one of Embodiments 1-79, wherein the balloon catheter comprises an elongated rigid component from a distal end of the elongated balloon to at least a proximal end of the elongated balloon.

Embodiment 81 provides the method of Embodiment 80, wherein the elongated rigid component is disposed inside or outside of a reinforcement tube that is continuous or discontinuous along a length of the elongated rigid component.

Embodiment 82 provides the method of any one of Embodiments 80-81, wherein a distal end of the elongated rigid component is mechanically coupled to a distal end of the elongated balloon, such that as the balloon is inflated force is transferred in a proximal direction along the elongated rigid component.

Embodiment 83 provides the method of any one of Embodiments 80-82, wherein a distal end of the elongated rigid component is attached to a distal end of the elongated balloon, or wherein the distal end of the elongated rigid component is attached to a catheter tip.

Embodiment 84 provides the method of any one of Embodiments 80-83, wherein the balloon catheter comprises a catheter shaft, wherein the proximal end of the elongated rigid component is attached to the catheter shaft at a proximal end of the elongated balloon or proximal to the proximal end of the elongated balloon.

Embodiment 85 provides the method of any one of Embodiments 80-84, wherein the balloon catheter comprises an elastic member attached to a proximal end of the elongated rigid component, such that as the elongated rigid component moves in a proximal direction force is stored in the elastic member, and such that as force is released from the elastic member force is applied from the elastic member to the elongated rigid component in a distal direction.

Embodiment 86 provides the method of any one of Embodiments 1-85, wherein the therapeutic agent is chosen from paclitaxel, docetaxel, taxol, their analogues, rapamycin, sirolimus, zotarolimus, everolimus, tacrolimus, mTOR inhibitors, their analogues, and combinations thereof.

Embodiment 87 provides the method of any one of Embodiments 1-86, wherein the water-soluble additive is chosen from N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, N-oleoyl-D-sphingosine, PEG caprylic/capric diglycerides, PEG8 caprylic/capric glycerides, PEG caprylate, PEG8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl)urea, pentaerythritol ethoxylate, pentaerythritol propoxylate, pentaerythritol propoxylate/ethoxylate, glycerol ethoxylate, glycerol propoxylate, trimethylolpropane ethoxylate, pentaerythritol, dipentaerythritol, crown ether, 18-crown-6, 15-crown-5, 12-crown-4, and combinations thereof.

Embodiment 88 provides the method of Embodiment 87, wherein the water-soluble additive is chosen from pentaerythritol ethoxylate, pentaerythritol propoxylate, and combinations thereof.

Embodiment 89 provides the method of any one of Embodiments 1-88, wherein the water-soluble additive comprises a first water-soluble additive that is a surfactant.

Embodiment 90 provides the method of Embodiment 89, wherein the first water-soluble additive is a PEG sorbitan monolaurate, a PEG sorbitan monooleate, or a combination thereof.

Embodiment 91 provides the method of any one of Embodiments 1-90, wherein the water-soluble additive comprises a second water-soluble additive that is a chemical compound with one or more moieties that are hydroxyl, amine, carbonyl, carboxyl, or ester.

Embodiment 92 provides the method of Embodiment 91, wherein the second water-soluble additive is sorbitol, sorbitan, xylitol, gluconolactone, or a combination thereof.

Embodiment 93 provides the method of any one of Embodiments 1-92, wherein after use the residual drug amount is about 70% or less of an initial drug load of the therapeutic agent on the balloon.

Embodiment 94 provides the method of any one of Embodiments 1-93, wherein an initial drug load of the therapeutic agent is from about 1 microgram to about 20 micrograms of the therapeutic agent per square millimeter of the balloon, measured when the balloon is at its nominal diameter.

Embodiment 95 provides the method of any one of Embodiments 1-94, wherein an initial drug load is from about 2 to about 6 micrograms of the therapeutic agent per square millimeter of the balloon, measured when the balloon is at its nominal diameter.

Embodiment 96 provides the method of any one of Embodiments 1-95, wherein the ratio by weight of the therapeutic agent in the coating layer to the total weight of the one or more water-soluble additives in the coating layer is from about 0.05 to about 20.

Embodiment 97 provides the method of any one of Embodiments 1-96, wherein the ratio by weight of the therapeutic agent in the coating layer to the total weight of the one or more water-soluble additives in the coating layer is from about 0.5 to about 8.

Embodiment 98 provides the method of any one of Embodiments 1-97, wherein the ratio by weight of the therapeutic agent in the coating layer to the total weight of the one or more water-soluble additives in the coating layer is from about 2 to about 6.

Embodiment 99 provides the method of any one of Embodiments 1-98, wherein the balloon catheter has a stretch ratio of about 1.0, 1.1, 1.2, 1.3, or 1.4 to 40 (e.g., 1, 1.1, 1.2, 1.3, 1.4, 1.5, 1.6, 1.7, 1.8, 1.9, 2, 2.2, 2.4, 2.6, 2.8, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or any value therebetween), or a combination thereof.

Embodiment 100 provides the method of any one of Embodiments 1-99, wherein the balloon catheter further comprises a sheath covering the elongated balloon.

Embodiment 101 provides the method of any one of Embodiments 1-100, wherein the balloon catheter is for delivering the therapeutic agent to the target site of the body lumen after the body lumen has been flushed with water, saline solution, or a water solution comprising at least one water soluble additive.

Embodiment 102 provides the method of any one of Embodiments 1-101, wherein the inflating comprises inflating the balloon to a pressure equal to or greater than a nominal pressure of the balloon catheter, and the stretch ratio at the target site (e.g., the ratio of the nominal diameter of the balloon in an unrestricted environment at the nominal pressure to the untreated diameter of the body lumen in the area being treated by the balloon catheter) is about 1.0 to about 40, or 1.4 to about 40.

Embodiment 103 provides the method of any one of Embodiments 1-102, wherein the inflating comprises inflating to a pressure greater than the nominal pressure of the balloon catheter, and the nominal diameter of the balloon catheter is less than the inflated balloon diameter.

Embodiment 104 provides the method of any one of Embodiments 1-103, wherein the inflating comprises inflating to a pressure less than the nominal pressure of the balloon catheter.

Embodiment 105 provides the method of any one of Embodiments 1-104, further comprising, prior to the insertion of the balloon to the target site, flushing the body lumen with water, saline solution, or a water solution comprising at least one water soluble additive.

Embodiment 106 provides the method of any one of Embodiments 1-105, wherein the inserting comprises positioning the at least one neck section of the balloon in the bladder neck.

Embodiment 107 provides the method of any one of Embodiments 1-106, wherein the inflating comprises increasing pressure within the balloon at a rate of about 0.1 to about 10 atm/minute.

Embodiment 108 provides the method of any one of Embodiments 1-107, wherein the inflating comprises observing pressure within the balloon.

Embodiment 109 provides the method of any one of Embodiments 1-108, wherein the inflating comprises inflating the balloon to a first pressure, allowing pressure within the balloon to stabilize while maintaining the first pressure in the balloon for a stabilization period, then resuming increasing pressure in the balloon until a desired inflation diameter is achieved.

Embodiment 110 provides the method of any one of Embodiments 1-109, wherein the inflation period is from about 0.1 minutes to about 7 days.

Embodiment 111 provides the method of any one of Embodiments 1-110, wherein the one or more water-soluble additives promote rapid release of the therapeutic agent from the balloon at the target site during the inflation period.

Embodiment 112 provides the method of any one of Embodiments 1-111, wherein the balloon has thereon a residual drug amount after the withdrawing.

Embodiment 113 provides the method of Embodiment 112, wherein the balloon has thereon a residual drug amount of less than about 70% of an initial drug load after the withdrawing.

Embodiment 114 provides the method of any one of Embodiments 1-113, wherein the balloon catheter further comprises a sheath covering the balloon and wherein the sheath is removed from the balloon prior to inflating the balloon.

Embodiment 115 provides the method of any one of Embodiments 1-114, wherein a scope is used to properly position the balloon catheter, visualize the inflation of the balloon, visualize the deflation of the balloon, visualize yielding of the target site, visualize released therapeutic agent on the wall of the target site, or a combination thereof.

Embodiment 116 provides the method of Embodiment 115, further comprising flushing the target site with water or saline solution through the scope before the inserting of the balloon catheter into the target site.

Embodiment 117 provides the method of any one of Embodiments 115-116, wherein the scope is an endoscope, enteroscope, colonoscope, sigmoidoscope, rectoscope, anoscope, rhinoscope, bronchoscope, or cystoscope.

Embodiment 118 provides the method of any one of Embodiments 115-117, wherein the balloon catheter is positioned within the lumen of the scope.

Embodiment 119 provides the method of any one of Embodiments 115-118, wherein the balloon catheter is positioned side by side with the scope when in the body lumen.

Embodiment 120 provides the method of any one of Embodiments 1-119, wherein the balloon catheter has a ratio of inflated balloon diameter to untreated body lumen diameter at the target site of 1.0, 1.1, 1.2, 1.3, or 1.4 to 40 (e.g., 1, 1.1, 1.2, 1.3, 1.4, 1.5, 1.6, 1.7, 1.8, 1.9, 2, 2.2, 2.4, 2.6, 2.8, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or any value therebetween) or the balloon catheter has a stretch ratio at the target site of 1.0, 1.1, 1.2, 1.3, or 1.4 to 40 (e.g., 1, 1.1, 1.2, 1.3, 1.4, 1.5, 1.6, 1.7, 1.8, 1.9, 2, 2.2, 2.4, 2.6, 2.8, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or any value therebetween), or a combination thereof.

Embodiment 121 provides the method of any one of Embodiments 1-120, further comprising pre-dilating the target site with another balloon catheter prior to the insertion of the drug-coated balloon into the target site.

Embodiment 122 provides the method of any one of Embodiments 1-121, wherein the balloon catheter used for the pre-dilation is substantially free of a drug coating.

Embodiment 123 provides the method of any one of Embodiments 1-122, wherein the balloon catheter used for the pre-dilation has a smaller nominal diameter than the drug-coated balloon.

Embodiment 124 provides the method of any one of Embodiments 1-123, wherein the balloon catheter comprises one or more markings to aid visually or radiologically in positioning or alignment.

Embodiment 125 provides a balloon catheter comprising the balloon catheter of any one of Embodiments 1-124.

Embodiment 126 provides the method or balloon catheter of any one or any combination of Embodiments 1-125 optionally configured such that all elements or options recited are available to use or select from.

What is claimed is:

1. A method for treatment of a anastomotic stricture, the method comprising:
   flushing the anastomotic stricture with a flushing media comprising water, saline solution, or a water solution comprising at least one water-soluble additive;
   inserting a balloon catheter into a target site in a body lumen comprising the anastomotic stricture, the balloon catheter comprising
      an elongated balloon, and
         a coating layer overlying an exterior surface of the balloon, wherein the coating layer comprises an initial drug load of a therapeutic agent;
   exposing the balloon catheter to a liquid comprising the flushing media in the anastomotic stricture for a soaking period prior to inflation to hydrate the coating layer;
   inflating the balloon at the target site to contact the coating layer with walls of the body lumen at the location of the anastomotic stricture until the balloon achieves an inflated balloon diameter for an inflation period;
   deflating the balloon after the inflation period; and
   withdrawing the balloon catheter from the body lumen.

2. The method of claim 1, wherein the anastomotic stricture is a non-vascular stricture.

3. The method of claim 1, wherein exposing the balloon catheter to the liquid comprises holding the balloon catheter in position for the soaking period prior to inflation to hydrate the coating layer.

4. The method of claim 1, wherein the balloon has thereon a residual drug amount after the withdrawing, wherein the residual drug amount is 70% or less of the initial drug load.

5. The method of claim 1, wherein the soaking period in combination with the contacting of the coating layer with the stricture is sufficient to release 37% to 97% of the initial drug load.

6. The method of claim 1, wherein the soaking period is predetermined prior to the exposing of the balloon catheter to the liquid.

7. The method of claim 1, wherein the soaking period comprises at least 1 minute.

8. The method of claim 1, wherein the inserting is prior to, during, or after the flushing of the anastomotic stricture.

9. The method of claim 1, wherein the flushing is prior to the inserting of the balloon catheter into the anastomotic stricture.

10. The method of claim 1, wherein the balloon catheter comprises an elongated balloon having a main diameter, the elongated balloon comprising at least one neck section, the balloon comprising a first main section and a second main section on opposite sides of the neck section.

11. The method of claim 10, wherein the at least one neck section comprises an inflated diameter that is smaller than the main diameter when the balloon is inflated, during the inflating the inflated diameter of the neck section is the smallest diameter of the balloon catheter between the first main section and the second main section, during the inflating the inflated diameter of the neck section is greater than a diameter of the neck section prior to the inflation, and the at least one neck section comprises an area of reduced compliance during inflation relative to the first main section and the second main section.

12. The method of claim 10, wherein the drug coating is on the first main section and the neck.

13. The method of claim 10, wherein the inflating comprises inflating the first section, the second section, and the neck section of the balloon simultaneously via a single inflation lumen.

14. The method of claim 10, wherein the at least one neck section comprises a reinforcing material around a circumference of the neck section to reduce compliance of the neck section during the inflation.

15. The method of claim 14, wherein the reinforcing material comprising a suture, monofilament, or multifilament, wherein the reinforcing material comprises nylon, a polyamide, an aromatic polyamide, ultra high molecular weight polyethylene (UHMWPE), a polyester, an aromatic polyester, polyethylene terephthalate (PET), or a combination thereof.

16. The method of claim 1, wherein inserting the balloon catheter into the target site in the body lumen comprises inserting the balloon catheter and a scope into the target site in the body lumen.

17. The method of claim 16, wherein the balloon catheter and the scope are positioned side-by-side or the balloon catheter is loaded into the scope.

18. The method of claim 16, wherein the balloon catheter and the scope are positioned side-by-side.

19. The method of claim 16, wherein the balloon catheter is loaded into the scope.

20. The method of claim 19, wherein the balloon is positioned within a working channel of the scope prior to inserting the scope into the body lumen.

21. The method of claim 19, wherein the balloon is positioned within a working channel of the scope after inserting the scope into the body lumen.

22. The method of claim 16, wherein balloon catheter is visualizable with the scope.

23. The method of claim 16, further comprising visualizing the balloon catheter with the scope before and/or during the inflating.

24. The method of claim 16, further comprising visualizing the therapeutic agent that deposits from the balloon onto the anastomotic stricture via the scope.

25. The method of claim 16, wherein the scope comprises an endoscope, enteroscope, colonoscope, sigmoidoscope, rectoscope, anoscope, rhinoscope, bronchoscope, or a cystoscope.

26. The method of claim 1, wherein the therapeutic agent is chosen from paclitaxel, docetaxel, taxol, rapamycin, sirolimus, zotarolimus, everolimus, tacrolimus, mTOR inhibitors, analogues thereof, and combinations thereof.

* * * * *

UNITED STATES PATENT AND TRADEMARK OFFICE
CERTIFICATE OF CORRECTION

PATENT NO. : 11,504,450 B2
APPLICATION NO. : 17/133088
DATED : November 22, 2022
INVENTOR(S) : Wang et al.

It is certified that error appears in the above-identified patent and that said Letters Patent is hereby corrected as shown below:

On the Title Page

In "Related U.S. Application Data", in Column 1, Line 1, delete "(60)" and insert --(63)-- therefor On page 5, in Column 1, under "Other Publications", Line 4, delete "Respone" and insert --Response-- therefor On page 5, in Column 1, under "Other Publications", Line 60, delete "Respone" and insert --Response-- therefor On page 6, in Column 1, under "Other Publications", Line 32, delete "alt uzosin" and insert --alfuzosin-- therefor In the Specification In Column 1, Line 8, delete "international" and insert --International-- therefor In Column 25, Line 44, delete "40," and insert --40;-- therefor In Column 50, in table-continued, Line 14, delete "1" and insert --7-- therefor In Column 50, Line 60 (Approx.), delete "Then" and insert --The-- therefor In Column 50, Line 64, after "has", insert --a--

In Column 74, Line 50, delete "(TAGA™ TO)," and insert --(TAGAT™ TO),-- therefor In Column 75, Line 11 (Approx.), delete "1-0)," and insert --1-O),-- therefor In Column 76, Lines 13-14 (Approx.), delete "$HO(C_2H_4O)_a(C_3H_6O)(C_2H_4O)_aH$" and insert Signed and Sealed this
Seventh Day of February, 2023

Katherine Kelly Vidal
*Director of the United States Patent and Trademark Office*

--HO(C₂H₄O)$_a$(C₃H₆O)$_b$(C₂H₄O)$_a$H-- therefor

In Column 77, Line 23, delete "Labrasol@)," and insert --Labrasol®),-- therefor

In Column 82, Lines 2-3, delete "n-decyl-p-D-maltopyranoside," and insert --n-decyl-β-D-maltopyranoside,-- therefor In Column 82, Lines 3-4, delete "n-dodecyl-o-D-maltoside," and insert --n-dodecyl-β-D-maltoside,-- therefor In Column 82, Lines 5-6, delete "n-heptyl-o-D-glucopyranoside, n-heptyl-o-D-thioglucoside, n-hexyl-O-D-glucopyranoside," and insert --n-heptyl-β-D-glucopyranoside, n-heptyl-β-D-thioglucoside, n-hexyl-β-D-glucopyranoside,-- therefor In Column 82, Line 7, delete "n-nonyl-o-D-glucopyranoside," and insert --n-nonyl-β-D-glucopyranoside,-- therefor In Column 82, Lines 8-9, delete "n-octyl-R-D-glucopyranoside, octyl-O-D-thioglucopyranoside" and insert --n-octyl-β-D-glucopyranoside, octyl-β-D-thioglucopyranoside-- therefor In Column 83, Lines 53-55, delete "n-decyl-p-D-glucopyranoside, n-decyl-o-D-maltopyranoside, n-dodecyl-p-D-glucopyranoside, n-dodecyl-p-D-maltoside," and insert --n-decyl-β-D-glucopyranoside, n-decyl-β-D-maltopyranoside, n-dodecyl-β-D-glucopyranoside, n-dodecyl-β-D-maltoside,-- therefor In Column 83, Lines 55-57, delete "n-heptyl-p-D-glucopyranoside, n-heptyl-o-D-thioglucoside, n-hexyl-o-D-glucopyranoside," and insert --n-heptyl-β-D-glucopyranoside, n-heptyl-β-D-thioglucoside, n-hexyl-β-D-glucopyranoside,-- therefor In Column 83, Lines 57-58, delete "n-nonyl-o-D-glucopyranoside," and insert --n-nonyl-β-D-glucopyranoside,-- therefor In Column 83, Lines 58-59, delete "n-octyl-o-D-glucopyranoside, octyl-p-D-thioglucopyranoside;" and insert --n-octyl-β-D-glucopyranoside, octyl-β-D-thioglucopyranoside;-- therefor In Column 88, Line 16, delete "3-sitosterin," and insert --β-sitosterin,-- therefor In Column 93, Line 10, after "stricture", insert --.--

In Column 93, Line 20, delete "mUs" and insert --mL/s-- therefor

In Column 93, Line 21, delete "mUs" and insert --mL/s-- therefor

In Column 93, Line 22, delete "mUs," and insert --mL/s,-- therefor

In Column 93, Line 27, delete "mUs," and insert --mL/s,-- therefor

CERTIFICATE OF CORRECTION (continued)
U.S. Pat. No. 11,504,450 B2

In Column 93, Line 28, delete "mUs," and insert --mL/s,-- therefor

In Column 93, Line 30, delete "Q," and insert --$Q_{max}$-- therefor

In Column 93, Line 32, delete "mUs," and insert --mL/s,-- therefor

In Column 93, Line 39, delete "mUs." and insert --mL/s.-- therefor

In Column 93, Line 44, delete "mUs" and insert --mL/s-- therefor

In Column 93, Line 48, delete "mUs," and insert --mL/s,-- therefor

In Column 93, Line 50, delete "mUs" and insert --mL/s-- therefor

In Column 93, Line 51, delete "mUs" and insert --mL/s-- therefor

In Column 93, Line 54, delete "mUs" and insert --mL/s-- therefor

In Column 101, Line 30, delete "1-1" and insert --I-1-- therefor

In Column 103, Line 33, after "groups", insert --.--

In Column 103, Line 39, delete "1-7." and insert --I-7.-- therefor

In Column 103, Line 47, delete "1-1" and insert --I-1-- therefor

In Column 109, Line 39, delete "that?Although" and insert --that? Although-- therefor In Column 111, Line 14, delete "a" and insert --A-- therefor In Column 113, Line 8, delete "structured" and insert --strictured-- therefor In Column 117, Line 52, delete "$Q_{max}$," and insert --$Q_{max}$-- therefor In Column 118, Line 5, delete "a" and insert --A-- therefor In Column 123, Line 21, delete "PSS" and insert --IPSS-- therefor In Column 130, Line 57, delete "(DVIU-," and insert --(DVIU)-,-- therefor In Column 131, Line 8, after "comprising:", insert a linebreak In Column 131, Line 9, after "comprising", delete a linebreak In the Claims In Column 137, Line 19, in Claim 1, after "comprising", insert --:--